United States Patent
Kodandapani et al.

(10) Patent No.: US 9,683,985 B2
(45) Date of Patent: Jun. 20, 2017

(54) METHODS FOR ASSESSING AND IDENTIFYING OR EVOLVING CONDITIONALLY ACTIVE THERAPEUTIC PROTEINS

(75) Inventors: Lalitha Kodandapani, San Diego, CA (US); Louis H. Bookbinder, San Diego, CA (US); Gregory I. Frost, Del Mar, CA (US); Philip Lee Sheridan, San Diego, CA (US); Harold Michael Shepard, San Diego, CA (US); Ge Wei, San Diego, CA (US); Lei Huang, San Diego, CA (US)

(73) Assignee: Halozyme, Inc., San Diego, CA (US)

( * ) Notice: Subject to any disclaimer, the term of this patent is extended or adjusted under 35 U.S.C. 154(b) by 7 days.

(21) Appl. No.: 13/200,666

(22) Filed: Sep. 27, 2011

(65) Prior Publication Data

US 2012/0108455 A1 May 3, 2012

Related U.S. Application Data

(63) Continuation-in-part of application No. PCT/US2011/050891, filed on Sep. 8, 2011.

(60) Provisional application No. 61/402,979, filed on Sep. 8, 2010.

(51) Int. Cl.
| | | |
|---|---|---|
| *G01N 33/50* | (2006.01) | |
| *C07K 16/28* | (2006.01) | |
| *C07K 16/30* | (2006.01) | |
| *C07K 16/44* | (2006.01) | |
| *G01N 33/53* | (2006.01) | |

(52) U.S. Cl.
CPC ...... *G01N 33/5011* (2013.01); *C07K 16/2863* (2013.01); *C07K 16/30* (2013.01); *C07K 16/44* (2013.01); *G01N 33/5014* (2013.01); *G01N 33/5088* (2013.01); *G01N 33/53* (2013.01); *C07K 2317/34* (2013.01); *G01N 2333/71* (2013.01)

(58) Field of Classification Search
CPC ........... G01N 33/5014; G01N 33/5011; G01N 33/50; G01N 33/5017; G01N 33/5088; G01N 33/53
See application file for complete search history.

(56) References Cited

U.S. PATENT DOCUMENTS

| | | | |
|---|---|---|---|
| 4,347,935 A | 9/1982 | Merrill | 209/3.2 |
| 5,464,581 A | 11/1995 | Van den Engh | 422/82.01 |
| 5,483,469 A | 1/1996 | Van den Engh | 702/21 |
| 5,571,894 A | 11/1996 | Wels et al. | 530/387.3 |
| 5,587,458 A | 12/1996 | King et al. | 530/387.3 |
| 5,602,039 A | 2/1997 | Van den Engh | 436/164 |
| 5,641,870 A | 6/1997 | Rinderknecht et al. | 530/417 |
| 5,643,796 A | 7/1997 | Van den Engh et al. | 436/50 |
| 5,654,182 A | 8/1997 | Wahl et al. | 435/462 |
| 5,677,177 A | 10/1997 | Wahl et al. | 435/322 |
| 5,679,640 A * | 10/1997 | Gaeta et al. | 514/13.5 |
| 5,804,387 A | 9/1998 | Cormack et al. | 435/6.12 |
| 5,885,836 A | 3/1999 | Wahl et al. | 435/455 |
| 5,968,738 A | 10/1999 | Anderson et al. | 435/6.2 |
| 6,211,477 B1 | 4/2001 | Cardott et al. | 209/127.4 |
| 6,248,516 B1 | 6/2001 | Winter et al. | 435/6.6 |
| 6,956,146 B2 | 10/2005 | Wahl et al. | 800/14 |
| 7,189,841 B2 | 3/2007 | Lerner et al. | 536/24.33 |
| 7,229,619 B1 | 6/2007 | Young et al. | 424/159.1 |
| 7,585,940 B2 * | 9/2009 | Skerra | C07K 14/47 530/350 |
| 7,781,405 B2 | 8/2010 | Szeto | 514/1.4 |
| 7,884,054 B2 | 2/2011 | Zhou et al. | 506/26 |
| 7,989,606 B2 | 8/2011 | Kranias et al. | 536/23.1 |
| 8,709,755 B2 | 4/2014 | Short et al. | 435/69.1 |
| 8,859,467 B2 | 10/2014 | Short | 506/7 |
| 2001/0012537 A1 | 8/2001 | Anderson et al. | 436/518 |
| 2002/0015970 A1 * | 2/2002 | Murray | C12Q 1/48 435/7.23 |
| 2004/0110294 A1 | 6/2004 | Bouayadi et al. | 435/455 |

(Continued)

FOREIGN PATENT DOCUMENTS

| | | |
|---|---|---|
| EP | 1975178 | 10/2008 |
| EP | 2275443 | 1/2011 |
| JP | A-2008-500833 | 1/2008 |
| JP | A-2009-542750 | 12/2009 |
| JP | 2010-068746 A | 4/2010 |
| WO | WO 93/16185 | 8/1993 |
| WO | WO 95/14710 | 6/1995 |
| WO | WO 96/07754 | 3/1996 |
| WO | WO 98/07408 | 2/1998 |
| WO | WO 03/105757 | 12/2003 |

(Continued)

OTHER PUBLICATIONS

Alberts et al. (Molecular Biology of the Cell. 4th edition, Isolating Cells and Growing Them in Culture, New York, Garland Science 2002, Table 8.1).*

(Continued)

*Primary Examiner* — Peter J Reddig
(74) *Attorney, Agent, or Firm* — Dentons US LLP; Stephanie Seidman

(57) ABSTRACT

Methods for evolving or selecting or producing therapeutic proteins that exhibit reduced adverse side-effects and the resulting proteins are provided. For example, provided herein is an in vitro assay to identify conditionally active therapeutic proteins that exhibit better activity within one in vivo environment compared to another in vivo environment. The methods include the steps of a) testing the activity of a protein under conditions in which normal or increased activity is desired; b) testing the activity of the protein under conditions in which reduced activity compared to normal is desired; and c) comparing the activity in a) with b) and selecting/identifying a protein that has greater activity in a) compared to b). The selected/identified protein is a conditionally active protein.

32 Claims, 1 Drawing Sheet

(56) References Cited

U.S. PATENT DOCUMENTS

| | | | |
|---|---|---|---|
| 2005/0191706 A1* | 9/2005 | Zhao et al. | 435/7.1 |
| 2005/0260711 A1 | 11/2005 | Datta et al. | 435/69.1 |
| 2006/0141456 A1* | 6/2006 | Edwards et al. | 435/6 |
| 2007/0009930 A1 | 1/2007 | Patten et al. | 435/6 |
| 2008/0044854 A1 | 2/2008 | Wang et al. | 435/69.1 |
| 2008/0131500 A1 | 6/2008 | Chang | 424/451 |
| 2008/0248028 A1 | 10/2008 | Lazar et al. | 424/133.1 |
| 2009/0042785 A1* | 2/2009 | Matschiner | C07K 14/47 514/1.1 |
| 2009/0075355 A1* | 3/2009 | Suzuki et al. | 435/183 |
| 2009/0130718 A1 | 5/2009 | Short et al. | 435/6 |
| 2009/0305982 A1* | 12/2009 | Jensen | C07K 14/47 514/21.2 |
| 2010/0003237 A1 | 1/2010 | Keller et al. | 424/94.62 |
| 2010/0260739 A1 | 10/2010 | Short et al. | 424/94.5 |
| 2010/0284995 A1 | 11/2010 | Bookbinder et al. | 424/94.62 |
| 2011/0111406 A1 | 5/2011 | Igawa et al. | 424/141.1 |
| 2012/0164127 A1 | 6/2012 | Short et al. | 435/69.1 |
| 2013/0266579 A1 | 10/2013 | Wei et al. | 424/158.1 |
| 2014/0105824 A1 | 4/2014 | Shepard et al. | 424/9.2 |
| 2014/0187748 A1 | 7/2014 | Short et al. | 435/69.1 |
| 2014/0199282 A1 | 7/2014 | Bookbinder et al. | |
| 2014/0356344 A1 | 12/2014 | Short et al. | 435/69.1 |
| 2014/0378660 A1* | 12/2014 | Short et al. | 530/350 |
| 2015/0071923 A1 | 3/2015 | Wei et al. | 424/133.1 |

FOREIGN PATENT DOCUMENTS

| | | |
|---|---|---|
| WO | WO 2005/058236 | 6/2005 |
| WO | WO 2005/090407 | 9/2005 |
| WO | WO 2005/118864 | 12/2005 |
| WO | WO/2006/031370 | 3/2006 |
| WO | WO 2007/087266 | 8/2007 |
| WO | WO 2007/095338 | 8/2007 |
| WO | WO 2008/006554 | 1/2008 |
| WO | WO 2009/125825 | 10/2009 |
| WO | WO 2010/104821 | 9/2010 |
| WO | WO 2012/033953 | 3/2012 |

OTHER PUBLICATIONS

Schmid et al. (Exp. Cell. Res. May 2007 313:2531-2549).*
Bauer et al. (HIV Medicine 2004 5:371-376).*
Carter et al. (Proc. Natl. Acad. Sci. USA May 1992 89:4285-4289).*
Gerdes et al. (Front. Oncol. Dec. 18, 2014 doi: 10.3389/fonc.2014.00366, pp. 1-12).*
Tate et al. (Thorax 2002; 57:926-929).*
Claverul et al. (In vitro Cell Dev. Biol.-Animal Jun. 16, 2009 45: 500-511).*
Adams et al., "The c-myc oncogene driven by immunoglobulin enhancers induces lymphoid malignancy in transgenic mice," Nature 318:533-538 (1985).
Alexander et al., "Expression of the c-myc oncogene under control of an immunoglobulin enhancer in E mu-myc transgenic mice," Mol. Cell Biol. 7:1436-1444 (1987).
Alexay et al., "Fluorescence scanner employing a macro scanning objective (Proceedings Paper)," Proceedings of SPIE, the International Society for Optical Engineering 2705:63-72 (1996).
Altschul, S., "Basic local alignment search tool," J Molec Biol 215(3):403-410 (1990).
Aluri et al., "Environmentally responsive peptides as anticancer drug carriers" Adv. Drug. Deliv. Rev. 61(11):940-952 (2009).
Arndt et al., "Helix-stabilized Fv (hsFv) antibody fragments: substituting the constant domains of a Fab fragment for a heterodimeric coiled-coil domain," J Mol Biol. 7:312:221-228 (2001).
Barbas et al., "In vitro evolution of a neutralizing human antibody to human immunodeficiency virus type 1 to enhance affinity and broaden strain cross-reactivity," Proc. Natl. Acad. Sci., 91(9):3809-3813 (1994).
Bas et al., "Very fast prediction and rationalization of pKa values for protein-ligand complexes," Proteins 73(3):765-783 (2008).
Basu et al., "Purification of specific cell population by fluorescence activated cell sorting (FACS)," J. Vis. Exp (41): Doi:10.3791/1546, 4 pages (2010).
Bernoist, C. and P. Chambon, "In vivo sequence requirements of the SV40 early promotor region," Nature 290:304-310 (1981).
Bhujwalla et al., "Combined vascular and extracellular pH imaging of solid tumors" NMR Biomed., 15(2):114-119 (2002).
Blick, S. and L. Scott, "Cetuximab: a review of its use in squamous cell carcinoma of the head and neck and metastatic colorectal cancer," Drugs 67(17):2585-2607 (2007).
Bonifer et al., "Tissue specific and position independent expression of the complete gene domain for chicken lysozyme in transgenic mice," EMBO J. 9(9):2843-2848 (1990).
Brennan et al., "Preparation of bispecific antibodies by chemical recombination of monoclonal immunoglobulin G1 fragments," Science, 229(4708):81-83 (1985).
Brinster et al., "Regulation of metallothionein—thymidine kinase fusion plasmids injected into mouse eggs," Nature 296:39-42 (1982).
Brooks, G., "What does glycolysis make and why is it important?," J. Appl. Physiol. 108(6):1450-1451 (2010).
Carrillo, H. and D. Lipman, "The multiple-sequence alignment problem in biology," SIAM J Applied Math 48:1073-1082 (1988).
Carroll, V. and M. Ashcroft, "Targeting the molecular basis for tumour hypoxia," Expert. Rev. Mol. Med. 7(6):1-16 (2005).
Carter et al., "High level *Escherichia coli* expression and production of a bivalent humanized antibody fragment," Biotechnology, 10(2):163-167 (1992).
Celej et al., "Differential scanning calorimetry as a tool to estimate binding parameters in multiligand binding proteins" Anal. Biochem. 350(2):277-284 (2006).
Chothia, C. and A. Lesk, "Canonical structures for the hypervariable regions of immunoglobulins," J. Mol. Biol. 196(4):901-917 (1987).
Chu et al., "Electroporation for the efficient transfection of mammalian cells with DNA," Nucl. Acid. Res. 15(3):1311-1326 (1987).
Ciardiello, F. and G. Tortora, "Interactions between the epidermal growth factor receptor and type I protein kinase A: biological significance and therapeutic implications," Clin Cancer Res. 4:821-828 (1998).
Clark-Curtiss, J. and R. Curtiss, "Analysis of recombinant DNA using *Escherichia coli* minicells," Methods Enzymol, 101:347-362 (1983).
Colley et al., "Conversion of a Golgi apparatus sialyltransferase to a secretory protein by replacement of the NH2-terminal signal anchor with a signal peptide," J. Biol. Chem., 264:17619-17622 (1989).
Coloma et al., "Novel vectors for the expression of antibody molecules using variable regions generated by polymerase chain reaction," J Immunol. Methods 152:89-104 (1992).
Cook et al., "Oxidative stress, redox, and the tumor microenvironment," Semin. Radiat. Oncol. 14(3):259-266 (2004).
Cryan et al, "Cell transfection with polycationic cyclodextrin vectors," Eur J Pharm Sci. 21(5):625-633 (2004).
Cumbers et al., "Generation and iterative affinity maturation of antibodies in vitro using hypermutating B-cell lines" Nat. Biotechnol., 20(11):1129-1134 (2002).
Dall'Acqua et al., "Increasing the affinity of a human IgG1 for the neonatal Fc receptor: biological consequences," J. Immunol. 169(91:5171-5780 (2002).
Davies et al., "Benchmarking pK(a) prediction," BMC Biochem. 7:18 (2006).
DeBoer et al., "The tac promoter: a functional hybrid derived from the trp and lac promoters," Proc. Natl. Acad. Sci. USA 80:21-25 (1983).
Deng et al., "Pharmacokinetics of humanized monoclonal antitumor necrosis factor-{alpha} antibody and its neonatal Fc receptor variants in mice and cynomolgus monkeys," Drug Metab. Dispos. 38(4):600-605 (2010).
Devereux et al, "A comprehensive set of sequence analysis programs for the VAX," Nucleic Acids Research 12:387-395 (1984).
Dubreuil et al., "Fine tuning of the specificity of an anti-progesterone antibody by first and second sphere residue engineering," J Bioll Chem 280(26):24880-24887 (2005).

(56) References Cited

OTHER PUBLICATIONS

Edidin, M., "Fluorescent labeling of cell surfaces," Methods Cell Biol 29:87-102 (1989).
Eng, C, "Toxic effects and their management: daily clinical challenges in the treatment of colorectal cancer," Nat. Rev. Clin. Oncol. 6:207-218 (2009).
Englebienne, P, "Use of colloidal gold surface plasmon resonance peak shift to infer affinity constants from the interactions between protein antigens and antibodies specific for single or multiple epitopes" Analyst 123:1599-1603 (1998).
Facciabene et al., "Tumour hypoxia promotes tolerance and angiogenesis via CCL28 and T(reg) cells," Nature 475(7355):226-230.
Fakih, M. and M. Vincent, "Adverse events associated with anti-EGFR therapies for the treatment of metastatic colorectal cancer," Curr. Oncol. 17(S1):S18-S30 (2010).
Favaro et al., "Gene expression and hypoxia in breast cancer," Genome Med. 3(8):55, 12 pages (2011).
Feau et al., "A high-throughput ligand competition binding assay for the androgen receptor and other nuclear receptors," J. Biomol. Screen. 14(1):43-48 (2009).
Fiers et al., "Complete nucleotide sequence of SV40 DNA," Nature 273(5658):113-120 (1978).
Flotte, T. and B. Carter, "Adeno-associated virus vectors for gene therapy," Gene Ther. 2(6):357-362 (1995).
Fogh-Andersen et al., "Composition of interstitial fluid," Clin. Chem., 41(10):1522-1525 (1995).
Fogolari et al., "The Poisson-Boltzmann equation for biomolecular electrostatics: a tool for structural biology," J. Mol. Recognit. 15(6):377-392 (2002).
Fox et al., "The epidermal growth factor receptor as a prognostic marker: results of 370 patients and review of 3009 patients" Breast Cancer Res. Treat., 29(1):41-49 (1994).
Francisco et al., "Production and fluorescence-activated cell sorting of *Escherichia coli* expressing a functional antibody fragment on the external surface" Proc. Natl. Acad. Sci. USA 90(22):10444-10448 (1993).
Friedman et al., "Combined measurements of blood lactate concentrations and gastric intramucosal pH in patients with severe sepsis," Crit. Care. Med 23(7):1184-1193 (1995).
Gao, X. and L. Huang, "Cationic liposome-mediated gene transfer,"Gene Ther. 2(10):710-722 (1995).
Gardner et al., "The complete nucleotide sequence of an infectious clone of cauliflower mosaic virus by M13mp7 shotgun sequencing," Nucleic Acids Res. 9:2871-2888 (1981).
Gerweck, L. and K. Seetharaman, "Cellular pH gradient in tumor versus normal tissue: potential exploitation for the treatment of cancer" Cancer Res. 56(6):1 194-1198 (1996).
Giepmans et al., "The fluorescent toolbox for assessing protein location and function," Science 312(5771):217-224 (2006).
Gilbert, W. and L. Villa-Komaroff, "Useful proteins from recombinant bacteria," Scientific American 242(4):74-94 (1980).
Gladden, L, "A lactatic perspective on metabolism," Med. Sci. Sports Exerc. 40(3):477-485 (2008).
Gladden, L, "Lactate metabolism: a new paradigm for the third millennium," J. Physiol.558(Pt 1):5-30 (2004).
Good et al., "Hydrogen ion buffers for biological research," Biochemistry 5(2):467-477 (1966).
Gribskov et al., "Sigma factors from *E. coli*, B. subtilis, phage SP01, and phage T4 are homologous proteins," Nucl. Acids Res. 14(16):6745-6763 (1986).
Grosschedl et al., "Introduction of a mu immunoglobulin gene into the mouse germ line: specific expression in lymphoid cells and synthesis of functional antibody," Cell 38:647-658 (1984).
Guo et al., "In vitro proton magnetic resonance spectroscopic lactate and choline measurements, 18F-FDG uptake, and prognosis in patients with lung adenocarcinoma," J Nucl Med 45(8):1334-1339 (2004).
Hahn, P. and E. Scanlan, "Gene delivery into mammalian cells: an overview on existing approaches employed in vitro and in vivo" Top. Curr. Chem. 296:1-13 (2010).
Hammer et al., "Diversity of alpha-fetoprotein gene expression in mice is generated by a combination of separate enhancer elements," Science 235:53-58 (1987).
Hanahan, D., "Heritable formation of pancreatic beta-cell tumours in transgenic mice expressing recombinant insulin/simian virus 40 oncogenes," Nature (3)15:115-122 (1985).
Hashimoto et al., "Hypoxia induces tumor aggressiveness and the expansion of CD133-positive cells in a hypoxia-inducible factor-1α-dependent manner in pancreatic cancer cells," Pathobiology 78(4):181-192 (2011).
Hawkins et al., "Selection of phage antibodies by binding affinity. Mimicking affinity maturation," J. Mol. Biol., 226:889-896 (1992).
Helmlinger et al., "Interstitial pH and pO2 gradients in solid tumors in vivo: high-resolution measurements reveal a lack of correlation," Nature Med., 3(2):177-182 (1997).
Herrera-Estrella et al., "Expression of chimaeric genes transferred into plant cells using a ti-plasmid-derived vector," Nature 303:209-213 (1984).
Herrera-Estrella et al., "Light-inducible and chloroplast-associated expression of a chimaeric gene introduced into Nicotiana tabacum using Ti plasmid vector," Nature 310(5973):115-120 (1984).
Herzenberg et al., "Fluorescence-activated cell sorting," Sci. Am. 234(3):108-117 (1976).
Higuchi et al., "A general method of in vitro preparation and specific mutagenesis of DNA fragments: study of protein and DNA interactions," Nucleic Acids Research 16(15):7351-7367 (1988).
Holdgate, G., "Making cool drugs hot: isothermal titration calorimetry as a tool to study binding energetics" Biotechniques 31(1):164-166, 168, 170 (2001).
Holroyde et al., "Lactate metabolism in patients with metastatic colorectal cancer," Cancer Research 39(12):4900-4904 (1979).
Hust et al., "Single chain Fab (scFab) fragment," BMC Biotechnol 7:14, 15 pages (2007).
IUPAC-IUB, "IUPAC-IUB Commission on Biochemical Nomenclature. A one-letter notation for amino acid sequences. Tentative rules," J. Biol. Chem. 243(13):3557-3559 (1968).
IUPAC-IUB, "Abbreviated nomenclature of synthetic poypeptides-polymerized amino acids-revised recommendations," Commission on Biochemical Nomenclature, Biochemistry 11:1726-1731 (1972).
Jackson et al., "In vitro antibody maturation. Improvement of a high affinity, neutralizing antibody against IL-1 beta," J. Immunol., 154:3310-3319 (1995).
Jay et al., "Construction of a general vector for efficient expression of mammalian proteins in bacteria: use of a synthetic ribosome binding site," Proc. Natl. Acad. Sci. USA 78:5543-5548 (1981).
Jecklin et al., "Label-free determination of protein-ligand binding constants using mass spectrometry and validation using surface plasmon resonance and isothermal titration calorimetry," J. Mol. Recognit. 22(4):319-329 (2009).
Juffer, A., "Theoretical calculations of acid-dissociation constants of proteins," Biochem. Cell Biol. 76(2-3):198-209 (1998).
Jung et al., "Aglycosylated IgG variants expressed in bacteria that selectively bind FcgammaRI potentiate tumor cell killing by monocyte-dendritic cells," Proc Natl Acad Sci U S A. 107(2):604-609 (2010).
Kahsay et al., "An improved hidden Markov model for transmembrane protein detection and topology prediction and its applications to complete genomes," Bioinformatics 21(9):1853-1858 (2005).
Kaufman, R., "Vectors used for expression in mammalian cells," Meth. In Enzymol. 185:487-511 (1990).
Kaunitz, J. and Y. Akiba, "Review article: duodenal bicarbonate—mucosal protection, luminal chemosensing and acid-base balance," Ailment Pharmacol. Ther. 24(S4):169-176 (2006).
Kegler-Ebo et al., "Codon cassette mutagenesis: a general method to insert or replace individual codons by using universal mutagenic cassettes," Nucleic Acids Research, 22(9):1593-1599 (1994).
Kelsey et al., "Species- and tissue-specific expression of human alpha 1-antitrypsin in transgenic mice," Genes and Devel. 1:161-171 (1987).

(56) References Cited

OTHER PUBLICATIONS

Kipriyanov, S., "Generation of antibody molecules through antibody engineering," *Methods in Molecular Biology*, vol. 207: Recombinant antibodies for cancer therapy methods and protocols, Chapter 1,3-25 (2003).
Kollias et al., "Regulated expression of human A gamma-, beta-, and hybrid gamma beta-globin genes in transgenic mice: manipulation of the developmental expression patterns," Cell 46:89-94 (1986).
Kozak J., "Structural features in eukaryotic mRNAs that modulate the initiation of translation," J Biol. Chem. 266:19867-19870 (1991).
Kozin, S. and L. Gerweck, "Cytotoxicity of weak electrolytes after the adaptation of cells to low pH: role of the transmembrane pH gradient," Br. J. Cancer 77(10):1580-1585 (1998).
Krumlauf et al., Developmental regulation of alpha-fetoprotein genes in transgenic mice, Mol. Cell. Biol. 5:1639-1648 (1985).
Kumon, et al., "Spatiotemporal effects of sonoporation measured by real-time calcium imaging" Ultrasound Med Biol. 35(3):494-506 (2009).
Leder et al., "Consequences of widespread deregulation of the c-myc gene in transgenic mice: multiple neoplasms and normal development," Cell 45:485-495 (1986).
Lefebvre, J., "Current clinical outcomes demand new treatment options for SCCHN," Ann. Oncol. 16(Suppl 6):vi7-vi12 (2005).
Li et al., "Very fast empirical prediction and rationalization of protein pKa values," Proteins, 61:704-721 (2005).
Macdonald, R., "Expression of the pancreatic elastase I gene in transgenic mice," Hepatology 7:425-515(1987).
Magram et al., "Developmental regulation of a cloned adult beta-globin gene in transgenic mice," Nature 315:338-340 (1985).
Malmqvist, M., "Biacore: an affinity biosensor system for characterization of biomolecular interactions" Biochem. Soc. Trans. 27:335-340 (2000).
Marks et al., "By-passing immunization: building high affinity human antibodies by chain shuffling," Biotechnolog (N Y), 10(7):779-783 (1992).
Martou et al., "Development of an in vitro model for study of the efficacy of ischemic preconditioning in human skeletal muscle against ischemia-reperfusion injury," J. Appl. Physiol. 101(5):1335-1342 (2006).
Mason et al., "The hypogonadal mouse: reproductive functions restored by gene therapy," Science 234:1372-1378 (1986).
Mathupala et al., "Lactate and malignant tumors: A therapeutic target at the end stage of glycolysis," J Bioenerg Biomembr 39(1):73-77 (2007).
Mayfield et al., "Expression and assembly of a fully active antibody in algae," PNAS 100:438-442 (2003).
McCall et al., "Isolation and characterization of an anti-CD16 single-chain Fv fragment and construction of an anti-HER2/neu/ anti-CD16 bispecific scFv that triggers CD16-dependent tumor cytolysis," Mol Immunol, 36(7):433-445 (1999).
McCord et al., "Physiologic oxygen concentration enhances the stem-like properties of CD133+ human glioblastoma cells in vitro," Mol. Cancer Res. 7:489-497 (2009).
McLauchlan et al., "Components required for in vitro cleavage and polyadenylation of eukaryotic mRNA," Nucleic Acids Res. 16(12):5323-5333 (1988).
Morimoto, K. and K. Inouye, "Single-step purification of F(ab')2 fragments of mouse monoclonal antibodies (immunoglobulins G1) by hydrophobic interaction high performance liquid chromatography using TSKgel Phenyl-5PW," J Biochem Biophys Methods, 24(1-2):107-117 (1992).
Morrison, D., "Transformation in *Escherichia coli*: cryogenic preservation of competent cells," J. Bact. 132:349-351 (1977).
Mosley et al., "The murine interleukin-4 receptor: molecular cloning and characterization of secreted and membrane bound forms," Cell 59:335-348 (1989).
Myburgh et al., "Plasma lactate concentrations for self-selected maximal effort lasting 1 h," Med. Sci. Sports Exer. 33(1):152-156 (2001).

Myers et al., "Competitive protein binding assay for methotrexate," Proc. Natl. Acad. Sci. USA 72(9):3683-3686 (1975).
Nayler et al., "A protective effect of a mild acidosis on hypoxic heart muscle," Journal of Molecular and Cellular Cardiology, 11(10):1053-1071 (1979).
Neal et al., "The epidermal growth factor receptor and the prognosis of bladder cancer," Cancer, 65(7):1619-1625 (1990).
Needleman, S. and C. Wunsch "A general method applicable to the search for similarities in the amino acid sequence of two proteins," J Mol Biol. 48:443 (1970).
Nguyen et al, "Biosensor-surface plasmon resonance: quantitative analysis of small molecule-nucleic acid interactions," Methods. 42(2):150-161 (2007).
Nielsen, J. and G. Vriend, "Optimizing the hydrogen-bond network in Poisson-Boltzmann equation-based pK(a) calculations," Proteins 43(4):403-412 (2001).
Nielsen; J., "Analysing the pH-dependent properties of proteins using pKa calculations," J. Mol. Graph. Model. 25(5):691-699 (2007).
O'Brien, J. and S. Lummis, "Biolistic and diolistic transfection: using the gene gun to deliver DNA and lipophilic dyes into mammalian cells," Methods 33(2):121-125 (2004).
O'Gorman et al., "Recombinase-mediated gene activation and site-specific integration in mammalian cells," Science 251:1351-1355 (1991).
Oller et al., "Growth of mammalian cells at high oxygen concentrations," J. Cell Sci. 94:43-49 (1989).
Ornitz et al., "Elastase I promoter directs expression of human growth hormone and SV40 T antigen genes to pancreatic acinar cells in transgenic mice," Cold Spring Harbor Symp. Quant. Biol. 50:399-409 (1986).
Parikh et al., "Cetuximab in head and neck cancer," Indian J Cancer 48:145-147 (2011).
Patiar, S. and A. Harris, "Role of hypoxia-inducible factor-1alpha as a cancer therapy target," Endocr. Relat Cancer S1:S61-S75 (2006).
Paterson et al., "Approaches to maximizing stable expression of alpha 1-antitrypsin in transformed CHO cells," Applied Microbiol. Biotechnol. 40(5):691-698 (1994).
Paul, W., ed., *Fundamental Immunology*, 2nd ed., Raven Press, New York, Chapter 12, pp. 332-336 (1989).
Pearson, W. and D. Lipman "Improved tools for biological sequence comparison," Proc. Natl. Acad. Sci. USA 85:2444-2448 (1988).
Perozzo et al., "Thermodynamics of protein-ligand interactions: history, presence, and future aspects," J. Recept Signal. Transduct Res. 24(1-2):1-52 (2004).
Perrotte et al., "Anti-epidermal growth factor receptor antibody C225 inhibits angiogenesis in human transitional cell carcinoma growing orthotopically in nude mice," Clin. Cancer Res., 5:257-264 (1999).
Petit et al., "Neutralizing antibodies against epidermal growth factor and ErbB-2/neu receptor tyrosine kinases down-regulate vascular endothelial growth factor production by tumor cells in vitro and in vivo: angiogenic implications for signal transduction therapy of solid tumors," Am. J. Pathol., 151:1523-1530 (1997).
Pham et al., "Large-scale transient transfection of serum-free suspension-growing HEK293 EBNA1 cells: peptone additives improve cell growth and transfection efficiency," Biotechnology and Bioengineering 84:332-342 (2003).
Phi-Van et al., "The chicken lysozyme 5' matrix attachment region increases transcription from a heterologous promoter in heterologous cells and dampens position effects on the expression of transfected genes," Mol. Cell. Biol. 10:2302-2307 (1988).
Piliarik et al., "Surface plasmon resonance biosensing," Methods Mol Biol. 503:65-88 (2009).
Pinkert et al., "An albumin enhancer located 10 kb upstream functions along with its promoter to direct efficient, liver-specific expression in transgenic mice," Genes and Devel. 1:268-276 (1987).
Prewett et al., "Mouse-human chimeric anti-epidermal growth factor receptor antibody C225 inhibits the growth of human renal cell carcinoma xenografts in nude mice," Clin. Cancer Res.4:2957-2966 (1998).

(56) References Cited

OTHER PUBLICATIONS

Quennet et al., "Tumor lactate content predicts for response to fractionated irradiation of human squamous cell carcinomas in nude mice," Radiother Oncol 81(2):130-135 (2006).
Raghavan et al., "Analysis of the pH dependence of the neonatal Fc receptor/immunoglobulin G interaction using antibody and receptor variants," Biochemistry, 34(45):14649-14657 (1995).
Readhead et al., "Expression of a myelin basic protein gene in transgenic shiverer mice: correction of the dysmyelinating phenotype," Cell 48:703-712 (1987).
Rich, R. and D. Myszka, "Advances in surface plasmon resonance biosensor analysis," Curr. Opin. Biotechnol 11(1):54-61 (2000).
Rosok et al., "Analysis of BR96 binding sites for antigen and anti-idiotype by codon-based scanning mutagenesis", J of Immunol 160(5):2353-2359 (1998).
Rostkowski et al., "Graphical analysis of pH-dependent properties of proteins predicted using PROPKA," BMC Struct. Biol. 11:6 (2011).
Rubin Grandis et al., "Levels of TGF-alpha and EGFR protein in head and neck squamous cell carcinoma and patient survival," (1998) J. Natl. Cancer Inst. 90(11):824-832 (1998).
Ryan, P. and B. Chabner, "On receptor inhibitors and chemotherapy," Clin. Cancer Res. 6(12):4607-4609 (2000).
Scatchard, G., "The attraction of proteins for small molecules and ions," Ann N.Y. Acad. Sci, 51:660-672 (1949).
Schafer, F. and G. Buettner, "Redox environment of the cell as viewed through the redox state of the glutathione disulfide/glutathione couple," Free Radic. Biol. Med. 30(11):1191-1212 (2001).
Schurr, A. and R. Payne, "Lactate, not pyruvate, is neuronal aerobic glycolysis end product: an in vitro electrophysiological study," Neuroscience 147:613-619 (2007).
Schwartz, R. and M. Dayhoff, eds., Atlas of Protein Sequence and structure, National Biomedical Research Foundation, pp. 353-358 (1979).
Schwickert et al., "Correlation of high lactate levels in human cervical cancer with incidence of metastasis," Cancer Research 55(21):4757-4759 (1995).
Semenza, G., "HIF-1 inhibitors for cancer therapy: from gene expression to drug discovery," Curr. Pharm. Des. 15(33):3839-3843 (2009).
Sham et al., "Consistent Calculations of pKa's of Ionizable Residues in Proteins: Semi-microscopic and Microscopic Approaches," J. Phys. Chem. B 101(22):4458-4472 (1997).
Shani, M., "Tissue-specific expression of rat myosin light-chain," Nature 314:283-286 (1985).
Smith, T. and M. Waterman, "Comparison of biosequences," Advances in Applied Mathematics 2:482-489 (1981).
Soliman, H, and J. Vincent, "Prognostic value of admission serum lactate concentrations in intensive care unit patients," Acta Clin. Belg. 65(3):176-181 (2010).
Spatola, A., "Peptide backbone modifications," pp. 267-357 in Chemistry and Biochemistry of Amino Acids, Peptides, and Proteins, Weistein, Ed. vol. 7, Marcel Dekker:New York (1983).
Stief et al., "A nuclear DNA attachment element mediates elevated and position-independent gene activity," Nature 341(6240):343-335 (1989).
Swift et al., "Tissue-specific expression of the rat pancreatic elastase I gene in transgenic mice," Cell 38(3):639-646 (1984).
Tan et al., "Engineering a novel secretion signal for cross-host recombinant protein expression," Protein Eng. 15(4):337-345 (2002).
Tanious et al., "Biosensor-surface plasmon resonance methods for quantitative analysis of biomolecular interactions," Methods Cell Biol. 84:53-77 (2008).
Tiller et al., "Efficient generation of monoclonal antibodies from single human B cells by single cell RT-PCR and expression vector cloning," J Immunol. Methods, 329(1-2):112-124 (2008).

Tiller et al., Corrigendum to 'Efficient generation of monoclonal antibodies from single human B cells by single cell RT-PCR and expression vector cloning,' [J Immunol. Methods, 329(1-2):112-124 (2008)].
Trédan et al., "Drug resistance and the solid tumor microenvironment," J. Natl. Cancer Inst. 99(19):1441-1454 (2007).
Trinh, K. and S. Morrison, "Site-specific and directional gene replacement mediated by Cre recombinase," J. Immunol. Methods 244(1-2):185-193 (2000).
Udenfriend, S. and K. Kodukula, "Prediction of omega site in nascent precursor of glycosylphosphatidylinositol protein," Methods Enzymol. 250:571-582 (1995).
Uhlman et al., "Epidermal growth factor receptor and transforming growth factor alpha expression in papillary and nonpapillary renal cell carcinoma: correlation with metastatic behavior and prognosis," Clin. Cancer Res. 1(8):913-920 (1995).
Wagner et al., "Nucleotide sequence of the thymidine kinase gene of herpes simplex virus type 1," Proc. Natl. Acad. Sci. USA 78:1441-1445 (1981).
Walenta et al., "Correlation of high lactate levels in head and neck tumors with incidence of metastasis," Am J of Pathol 150(2): 409-415 (1997).
Walenta et al., "High lactate levels predict likelihood of metastases, tumor recurrence, and restricted patient survival in human cervical cancers," Cancer Res. 60(4): 916-921 (2000).
Wilson, W. and M. Hay, Targeting hypoxia in cancer therapy, Nat Rev Cancer 11(6):393-410 (2011).
Wu et al., "Stepwise in vitro affinity maturation of Vitaxin, an alphav beta3-specific humanized mAb," Proc. Natl. Acad. Sci., 95: 6037-6042 (1998).
Wu, Y., "Study on the interaction between salicylic acid and catalase by spectroscopic methods," J. Pharm. Biomed. Anal.44(3):796-801 (2007).
Yamamoto et al., "Identification of a functional promoter in the long terminal repeat of Rous sarcoma virus," Cell 22:787-797 (1980).
Zhang et al., "Optical, structural and thermodynamic properties of the interaction between tradimefon and serum albumin," Spectrochim Acta a Biomol. Spectrosc. 72(3):621-626 (2009).
Zhou et al., "Development of a novel mammalian cell surface antibody display platform," MAbs 2(5):508-518 (2010).
Zhou et al., "Random mutagenesis of gene-sized DNA molecules by use of PCR with Taq DNA polymerase," Nucleic Acids Research 19(21):6052 (1991).
International Search Report and Written Opinion, issued Feb. 17, 2012, in connection with International Patent Application No. PCT/US2011/050891, 14 pages.
Letter/Written Disclosure of the Supplemental Information Disclosure Statement for the above-referenced application, mailed Sep. 17, 2013, 2 pages
Frost, G. I., "Halozyme Therapeutics, Inc. Thinking outside the cell," presented at J. P. Morgan Healthcare Conference on Jan. 10, 2013. Presentation. 23 pages.
Response to second Written Opinion, issued Oct. 8, 2012, in connection with International Patent Application No. PCT/US2011/050891, 33 pages.
International Preliminary Report on Patentability, mailed Dec. 19, 2012, in connection with International Patent Application No. PCT/US2011/050891, 14 pages.
Letter/Written Disclosure of the Supplemental Information Disclosure Statement for the above-referenced application, mailed on Nov. 1, 2012, 2 pages.
Barderas et al., "Affinity maturation of antibodies assisted by in silico modeling," Proc Natl Acad Sci U S A. 105(26):9029-9034 (2008). Epub Jan. 23, 2008.
Brunel et al., "Structure-function analysis of the epitope for 4E10, a broadly neutralizing human immunodeficiency virus type 1 antibody," J Virol. 80(4):1680-1687 (2006).
Chen et al., "Identification of key amino acid residues in a thyrotropin receptor monoclonal antibody epitope provides insight into its inverse agonist and antagonist properties," Endocrinology. 149(7):3427-3434 (2008). Epub Apr. 3, 2008.

(56) References Cited

OTHER PUBLICATIONS

Halozyme Website, "HTI-501," [online][retrieved on Apr. 23, 2012] Retrieved from :<URL: halozyme.com/Products-And-Pipeline/Pipeline/HTI-501/default.aspx [1 p.].
News Release, Halozyme Therapeutics, Inc., "HTI-501 data support commencement of phase 2 portion of clinical trial,", Published on Jan. 31, 2012 [online][retrieved on Apr. 23, 2012] Retrieved from:<URL: halozyme.com/Investors/News-Releases/News-Release-Details/2012/HTI-501-Data-Support-Commencement-of-Phase-2-Portion-of-Clinical-Trial1128090/default.aspx [3 pages].
Transcript, "Halozyme Therapeutics's Ceo Hosts Analyst/Investor Day Conference Call (Transcript)," Published on Oct. 02, 2012 [online] [Retrieved on Oct. 25, 2012] Retrieved from the Internet: URL:http://seekingalpha.com/article/901141-halozyme-therapeutics-s-ceo-hosts-analyst-investor-day-conference-call-transcript?part—single [49 pages].
Halozyme Therapeutics Investor Presentation, "Halozyme Therapeutics, Inc.: Thinking outside the cell," Presented on Oct. 11, 2012 [online][retrieved on Oct. 11, 2012] Retrieved from:<URL:sec.gov/Archives/edgar/data/1159036/000119312512412748/d419091dex991.htm [82 pages].
Kundu et al, "Temporal-spatial control of tissue contouring with extracellular pH-modulated rHuCathepsin-L," International Investigative Dermatology Conference, May 14-17, 2008, Kyoto Japan, poster, 3 pages.
Kundu et al, "Temporal-spatial control of tissue contouring with extracellular pH-modulated rHuCathepsin-L," Presentation in Lisbon, Jun. 2008, 15 pages.
Repsonse to Written Opinion, issued Feb. 17, 2012 in connection with International Patent Application No. PCT/US2011/050891, 45 pages.
Invitation to Restrict, mailed Aug. 2, 2012, in connection with International Patent Application No. PCT/US2011/050891, 5 pages.
Second Written Opinion, issued Oct. 8, 2012, in connection with International Patent Application No. PCT/US2011/050891, 11 pages.
Letter/Written Disclosure of the Supplemental Information Disclosure Statement for the above-referenced application, mailed May 6, 2014, 2 pages.
Kaar, J., "Using enzyme structure-environment-activity relationships to enhance biocatalyst utility," University of Pittsburgh, URN: etd-10152007-152622 (2008) [172 pages]. Dissertation.
Vaughn, D.E. and P.J. Bjorkman, "Structural basis of pH-dependent antibody binding by the neonatal Fc receptor," Structure; 6(1):63-73 (1998).
Letter/Written Disclosure of the Supplemental Information Disclosure Statement for the above-referenced application, filed Oct. 28, 2014, 2 pages.
Letter, dated Oct. 13, 2014, notifying Applicant of the filing of U.S. Appl. No. 14/483,980; the filing of a Second Preliminary Amendment stated to be copying claims of U.S. Appl. No. 13/200,666; and the filing of an Information Disclosure Statement and the accompanying enclosures. Part 1 of 5, 237 pages.
Letter, dated Oct. 13, 2014, notifying Applicant of the filing of U.S. Appl. No. 14/483,980; the filing of a Second Preliminary Amendment stated to be copying claims of U.S. Appl. No. 13/200,666; and the filing of an Information Disclosure Statement and the accompanying enclosures. Part 2 of 5, 284 pages.
Letter, dated Oct. 13, 2014, notifying Applicant of the filing of U.S. Appl. No. 14/483,980; the filing of a Second Preliminary Amendment stated to be copying claims of U.S. Appl. No. 13/200,666; and the filing of an Information Disclosure Statement and the accompanying enclosures. Part 3 of 5, 358 pages.
Letter, dated Oct. 13, 2014, notifying Applicant of the filing of U.S. Appl. No. 14/483,980; the filing of a Second Preliminary Amendment stated to be copying claims of U.S. Appl. No. 13/200,666; and the filing of an Information Disclosure Statement and the accompanying enclosures. Part 4 of 5, 163 pages.
Letter, dated Oct. 13, 2014, notifying Applicant of the filing of U.S. Appl. No. 14/483,980; the filing of a Second Preliminary Amendment stated to be copying claims of U.S. Appl. No. 13/200,666; and the filing of an Information Disclosure Statement and the accompanying enclosures. Part 5 of 5, 153 pages.
Letter/Written Disclosure of the Supplemental Information Disclosure Statement for the above-referenced application, filed Aug. 27, 2014, 2 pages.
Office Action, issued Jun. 5, 2014 (received Jul. 28, 2014), in connection with Chinese Patent Application No. 201180053564.6 [English translation and original document in Chinese], 10 pages.
Letter/Written Disclosure of the Supplemental Information Disclosure Statement for the above-referenced application, mailed Dec. 8, 2014, 2 pages.
BioAtla Advertisement Feature, "Conditionally active biologics: solving the problem of systemic toxicity," Nature Publishing Group Biopharma Dealmakers; published Aug. 2014 [Retrieved online from <URL:http ://www.google.com/url?sa=t&rct=j&q=&esrc=s&frm=1&source=web &cd=3 &ved=0CCs QFjAC &url=http%3A%2F%2Fbioatla.com%2Fwp-content%2Fuploads%2F2014%2F08%2Fbioatla_nature_feature.pdf&ei=9iqGVOPrMMexogTOioK4AQ &usg=AFQjCNHgjYOtEf9dTq5K5i7qPoqme4i0_w&bvm=bv.81449611,d.eGU, 1 page.
Fasciglione et al., "pH- and temperature-dependence of functional modulation in metalloproteinases. A comparison between neutrophil collagenase and gelatinases A and B," Biophys J. 79(4):2138-2149 (2000).
Ghetie et al., "Increasing the serum persistence of an IgG fragment by random mutagenesis," Nat Biotechnol. 15(7):637-40 (1997).
News Release, Halozyme Therapeutics Inc., "Halozyme Therapeutics, Inc. Announces Research Alliance with BioAtla, LLC for Conditionally Active Biologics" Jan. 19, 2010, retrieved from: <URL: http://www.halozyme.com/Investors/News-Releases/News-Release-Details/2010/Halozyme-Announces-Research-Alliance-with-BioAtla-for-Conditionally-Active-Biologics/default.aspx [retrieved on May 19, 2014 ][2 pages].
Response, dated Jun. 4, 2014, to Invitation Pursuant to Rule 137(4) EPC, issued May 16, 2014, in connection with European Patent Application No. 11778725.9, 4 pages.
Examination Report, dated Oct. 9, 2014, issued in connection with European Patent Application No. 11778725.9, 7 pages.
Instructions, dated Dec. 2, 2014 for response to Office Action, issued Jun. 5, 2014, in connection with Chinese Patent Application No. 201180053564.6, 31 pages.
U.S. Appl. No. 14/485,620, filed Sep. 12, 2014.
Letter/Written Disclosure of the Supplemental Information Disclosure Statement for the above-referenced application, filed herewith Aug. 18, 2015, 2 pages.
English language translation of Japanese Publication No. 2010-068746, published Apr. 2, 2010, 14 pages.
Yamagata et al., "The contribution of lactic acid to acidification of tumours: studies of variant cells lacking lactate dehydrogenase," Br J Cancer. 77(11):1726-1731 (1998).
Office Action, issued Jun. 4, 2015, in connection with Chinese Patent Application No. 201180053564.6 [English language translation and original document in Chinese], 5 pages.
Response, filed Apr. 20, 2015, to Examination Report, dated Oct. 9, 2014, issued in connection with European Patent Application No. 11778725.9, 12 pages.
Official Action, mailed Jan. 13, 2015, in connection with Japanese Patent Application No. 2013-528300 [English translation and original document in Japanese], 8 pages.
Response, filed Jun. 12, 2015, to Official Action, mailed Jan. 13, 2015, in connection with Japanese Patent Application No. 2013-528300 [English language instructions and response as filed in Japanese], 56 pages.
Official Action, issued May 20, 2015, in connection with Korean Patent Application No. 10-2013-7008951 [English translation and original document in Korean], 9 pages.
Letter/Written Disclosure of the Supplemental Information Disclosure Statement for the above-referenced application, filed herewith on Mar. 25, 2016, 3 pages.

(56) References Cited

OTHER PUBLICATIONS

Notice of Granting Patent Rights for an Invention, issued Feb. 5, 2016, in connection with Chinese Patent Application No. 201180053564.6 [Document as issued in Chinese and English language translation], 4 pages.
Official Action, issued Feb. 22, 2016, in connection with Mexican Patent Application No. MX/a/2013/002679 [English translation and original document in Spanish], 4 pages.
Letter/Written Disclosure of the Supplemental Information Disclosure Statement for the above-referenced application, filed herewith Jan. 15, 2016, 2 pages.
Engin et al., "Extracellular pH distribution in human tumours," Int J Hyperthermia 11(2):211-216 (1995).
Igawa et al., "Antibody recycling by engineered pH-dependent antigen binding improves the duration of antigen neutralization," Nat Biotechnol 28:1203-1207 (2010).
Murtaugh et al., "A combinatorial histidine scanning library approach to engineer highly pH-dependent protein switches," Protein Science 20:1619-1631 (2011).
Tawfik et al., "pH on-off switching of antibody-hapten binding by site-specific chemical modification of tyrosine," Prot Engineering 7(3):431-434 (1994).
News Release, "Halozyme Therapeutics to present at the 31st Annual J.P. Morgan Healthcare Conference," Published Jan. 3, 2013 [online][Retrieved Jan. 17, 2013][Retrieved from:<URL:halozyme.com/Investors/News-Release/News-Release-Details/2013/Halozyme-Therapeutics-to-Present-at-the-31st-Annual-JP-Morgan-Healthcare-Conference1132508/default.aspx, 2 pages.
Examiner's Report, dated Nov. 25, 2015, in connection with Canadian Patent Application No. 2,810,668, 5 pages.
Response, filed Aug. 11, 2015 to Office Action, issued Jun. 4, 2015, in connection with Chinese Patent Application No. 201180053564.6 [English instructions and Response as filed in Chinese], 26 pages.
Examination Report, dated Sep. 14, 2015, issued in connection with European Patent Application No. 11778725.9 [Examination Report as issued and cited document D1: International Publication No. WO 2003/105757], 113 pages.
Third Party Observations, issued Oct. 2, 2015, reported in connection with European Patent Application No. 11778725.9, 5 pages.
Office Action, issued Sep. 21, 2015, inconnection with Israeli Patent Application No. 224983 [English translation], 3 pages.
Official Action, mailed Nov. 10, 2015, in connection with Japanese Patent Application No. 2013-528300 [English translation and original document in Japanese], 9 pages.
Response, filed Aug. 20, 2015, to Official Action, issued May 20, 2015, in connection with Korean Patent Application No. 10-2013-7008951 [English instructions and document as filed in Korean], 119 pages.
Official Action, issued Dec. 29, 2015, in connection with Korean Patent Application No. 10-2013-7008951 [English translation and original document in Korean], 9 pages.
Letter/Written Disclosure of the Information Disclosure Statement for the above referenced application, filed herewith on Aug. 5, 2016, 2 pages.
Response, filed May 24, 2016 to Examiner's Report, issued Nov. 25, 2015, in connection with Canadian Patent Application No. 2,810,668, 51 pages.
Response, filed Mar. 23, 2016, to Examination Report, dated Sep. 14, 2015, issued in connection with European Patent Application No. 11778725.9, 28 pages.
Response, filed Apr. 5, 2016, to Office Action, issued Sep. 21, 2015, in connection with Israeli Patent Application No. 224983 [English translation], 16 pages.
Response, filed Mar. 9, 2016, and Appeal Brief, filed Apr. 15, 2016, to Official Action, mailed Nov. 10, 2015, in connection with Japanese Patent Application No. 2013-528300 [English instructions and document as filed in Japanese], 69 pages.
Response, filed Apr. 29, 2016, to Official Action, issued Dec. 29, 2015, in connection with Korean Patent Application No. 10-2013-7008951 [English instructions and document as filed in Korean], 47 pages.
Response, filed Jun. 23, 2016, to Official Action, issued Feb. 16, 2016, in connection with Mexican Patent Application No. MX/a/2013/002679 [English instructions and document as filed in Spanish], 48 pages.
Letter/Written Disclosure of the Supplemental Information Disclosure Statement for the above-referenced application, filed herewith on Jul. 27, 2016, 4 pages.
Examination Report, dated Apr. 22, 2016 and received Apr. 28, 2016, issued in connection with European Patent Application No. 11778725.9, 5 pages.
English translation of Office Action, dated May 19, 2016 and received Jul. 4, 2016, in connection with Israeli Patent Application No. 224983, 2 pages.
Examiner's pre-appeal Examination Report, issued Jun. 14, 2016 and received Jun. 28, 2016, in connection with Japanese Patent Application No. 2013-528300 [English translation], 6 pages.
Letter/Written Disclosure of the Supplemental Information Disclosure Statement for the above-referenced application, filed herewith on Mar. 1, 2017, 2 pages.
Notice of Rejection of Amendment and Notice of Final Rejection, each dated Jan. 26, 2017, issued in connection with Korean Patent Application No. 10-2013-7008951 [English translations, original documents in Korean and referenced document (Office Action dated Dec. 29, 2015)], 17 pages.
English translation of Notification Prior to Allowance, dated Jan. 31, 2017, in connection with Israeli Patent Application No. 224983, 2 pages.
Office Action, issued Feb. 14, 2017, in connection with Japanese Patent Application No. 2016-046184 [English translation and original document in Japanese], 3 pages.
Letter/Written Disclosure of the Supplemental Information Disclosure Statement for the above-referenced application, filed herewith Dec. 14, 2016, 2 pages.
Declaration of Dr. H. Michael Shepard, dated Jul. 28, 2014, 16 pages.
Examiner's Report, dated Nov. 7, 2016, in connection with Canadian Patent Application No. 2,810,668, 3 pages.
Response, filed Oct. 10, 2016, to Examination Report, dated Apr. 22, 2016, that issued in connection with European Patent Application No. 11778725.9, 20 pages.
English language translation of Response, filed Sep. 12, 2016, to Office Action, dated May 19, 2016, in connection with Israeli Patent Application No. 224983, 19 pages.
Response, filed Sep. 30, 2016, to Examiner's pre-appeal Examination Report, issued Jun. 14, 2016, in connection with Japanese Patent Application No. 2013-528300 [English instructions and document as filed in Japanese], 62 pages.
Official Action, issued Sep. 28, 2016, in connection with Korean Patent Application No. 10-2013-7008951 [English translation and original document in Korean], 6 pages.
Official Action, issued Oct. 12, 2016, in connection with Mexican Patent Application No. MX/a/2013/002679 [English translation and original document in Spanish], 5 pages.
Letter/Written Disclosure of the Supplemental Information Disclosure Statement for the above-referenced application, filed herewith on Apr. 6, 2017, 3 pages.
Examination Report, dated Mar. 9, 2017, issued in connection with European Patent Application No. 11778725.9, 6 pages.
English letter, dated Mar. 8, 2017, reporting Trial Decision to Grant a Patent, issued Mar. 7, 2017, in connection with Japanese Patent Application No. 2013-528300 [English letter and original document in Japanese], 3 pages.
Notice of Allowance, mailed Jan. 25, 2017, in connection with U.S. Appl. No. 14/483,980, 5 pages.
Issue Notification, mailed Mar. 29, 2017, in connection with U.S. Appl. No. 14/483,980, 1 page.
Letter/Written Disclosure of the Supplemental Information Disclosure Statement for the above-referenced application, filed herewith on May 4, 2017, 2 pages.

(56) References Cited

OTHER PUBLICATIONS

Office Action, issued Apr. 3, 2017, in connection with Mexican Patent Application No. MX/a/2013/002679 [English translation and original document in Spanish], 4 pages.

* cited by examiner

A. Erbitux Heavy Chain (SEQ ID NO:2)

```
         10         20         30         40         50         60
QVQLKQSGPG LVQPSQSLSI TCTVSGFSLT NYGVHWVRQS PGKGLEWLGV IWSGGNTDYN
         70         80         90        100        110        120
TPFTSRLSIN KDNSKSQVFF KMNSLQSNDT AIYYCARALT YYDYEFAYWG QGTLVTVSAA
        130        140        150        160        170        180
STKGPSVFPL APSSKSTSGG TAALGCLVKD YFPEPVTVSW NSGALTSGVH TFPAVLQSSG
        190        200        210        220        230        240
LYSLSSVVTV PSSSLGTQTY ICNVNHKPSN TKVDKRVEPK SPKSCDKTHT CPPCPAPELL
        250        260        270        280        290        300
GGPSVFLFPP KPKDTLMISR TPEVTCVVVD VSHEDPEVKF NWYVDGVEVH NAKTKPREEQ
        310        320        330        340        350        360
YNSTYRVVSV LTVLHQDWLN GKEYKCKVSN KALPAPIEKT ISKAKGQPRE PQVYTLPPSR
        370        380        390        400        410        420
DELTKNQVSL TCLVKGFYPS DIAVEWESNG QPENNYKTTP PVLDSDGSFF LYSKLTVDKS
        430        440        450
RWQQGNVFSC SVMHEALHNH YTQKSLSLSP GK
```

B. Erbitux Light Chain (SEQ ID NO:1)

```
         10         20         30         40         50         60
DILLTQSPVI LSVSPGERVS FSCRASQSIG TNIHWYQQRT NGSPRLLIKY ASESISGIPS
         70         80         90        100        110        120
RFSGSGSGTD FTLSINSVES EDIADYYCQQ NNNWPTTFGA GTKLELKRTV AAPSVFIFPP
        130        140        150        160        170        180
SDEQLKSGTA SVVCLLNNFY PREAKVQWKV DNALQSGNSQ ESVTEQDSKD STYSLSSTLT
        190        200        210
LSKADYEKHK VYACEVTHQG LSSPVTKSFN RGA
```

METHODS FOR ASSESSING AND IDENTIFYING OR EVOLVING CONDITIONALLY ACTIVE THERAPEUTIC PROTEINS

RELATED APPLICATIONS

This application is a continuation-in-part of International Application No. PCT/US11/50891, filed on Sep. 8, 2011, to Lalitha Kodandapani, Louis Howard Bookbinder, Gregory I. Frost, Philip Lee Sheridan, Harold Michael Shepard, Ge Wei and Lei Huang, entitled "METHODS FOR ASSESSING AND IDENTIFYING OR EVOLVING CONDITIONALLY ACTIVE THERAPEUTIC PROTEINS," which claims priority to U.S. Provisional Application Ser. No. 61/402,979, entitled "METHODS FOR ASSESSING AND IDENTIFYING OR EVOLVING CONDITIONALLY ACTIVE THERAPEUTIC PROTEINS AND CONDITIONALLY ACTIVE THERAPEUTIC PROTEINS," filed on Sep. 8, 2010, to Lalitha Kodandapani, Philip Lee Sheridan, Harold Michael Shepard, Louis H. Bookbinder and Gregory I. Frost. The subject matter of each of the above-noted applications is incorporated by reference in its entirety.

FIELD OF THE INVENTION

Methods for evolving or selecting therapeutic proteins with reduced adverse side-effects and the resulting proteins are provided.

BACKGROUND

Proteins have a role as pharmaceutical or therapeutic agents for the treatment of a wide range of human diseases, such as cancer, hemophilia, anemia and diabetes, and, for a number of diseases, are the only effective treatment. As such, there is a need to identify protein therapeutics with altered or improved activities or properties. It is an object herein to provide a method to identify or generate such proteins.

SUMMARY

Provided are methods for identifying/selecting conditionally active proteins. In the method, the activity of the protein is tested under conditions in which normal or increased activity is desired, and the activity of the protein is tested under conditions in which reduced activity compared to normal is desired. The activity of the protein under conditions in which normal or increased activity is desired can be compared to the activity of the protein under conditions in which reduced activity compared to normal is desired. Proteins can be selected and/or identified that have greater activity under conditions in which normal or increased activity is desired compared to conditions in which reduced activity compared to normal is desired. In some examples of the method herein, the therapeutic protein that treats tumors is not angiostatin.

In the methods, the activity of the protein under conditions in which reduced activity compared to normal is desired can be reduced compared to normal. In the methods, the conditions in which normal or increased activity is desired and the conditions in which reduced activity compared to normal is desired can be identical, except for a condition or conditions that render the protein conditionally active. In the methods herein, the activity that is tested can be binding to a target of the protein. The target can be immobilized on a solid support. In the methods herein, binding can be assessed by an immunoassay. Immunoassays include ELISA immunoassays, heterogeneous immunoassays and homogeneous immunoassays.

In the methods herein, the conditions in which normal or increased activity of the protein is desired can simulate a disease microenvironment, and the conditions in which reduced activity compared to normal is desired can simulate a healthy tissue environment. Exemplary of a healthy tissue environment is a non-tumor tissue environment, such as a systemic environment or a healthy tissue. Exemplary healthy tissues are the GI tract, the skin, the vasculature, the blood, and the extracellular matrix. Exemplary of diseased microenvironments is a tumor microenvironment. A tumor or disease microenvironment can have lower than neutral pH or lower pH than a healthy tissue microenvironment. A tumor or disease microenvironment can include one or more of increased vascularization, hypoxia, lowered pH, increased interstitial fluid pressure, altered metabolites or metabolism indicative of a tumor or other disease. For example, a tumor or other disease microenvironment can have elevated lactate concentration and/or increased pyruvate compared to a healthy microenvironment.

Also provided herein are methods in which conditions in which normal or increased activity of the protein is desired can include lower than neutral pH and elevated lactic acid compared to the conditions in which reduced activity compared to normal is desired.

In the methods herein, the protein tested can be a therapeutic protein and/or a protein with undesirable side effects manifested in healthy tissue. In the methods herein, reducing the activity of the protein under conditions in which reduced activity compared to normal is desired can ameliorate or prevent the undesirable side-effects.

In the methods provided herein, the activity of the protein can be tested in the presence of human serum. Human serum can be present in an amount that simulates physiological conditions, and the amount of serum present under conditions in which normal or increased activity is desired can be the same as the amount of serum present under conditions in which reduced activity compared to normal is desired. For example, the methods provided herein can be performed in the presence of human serum at least about or at any of 3%-30%, inclusive, or 5%-30%, inclusive, or 5%-25%, inclusive, 10%-30%, inclusive, or 15%-30%, inclusive, or 15%-25%, inclusive, of human serum by volume, including at or about 25% (plus or minus 10%) of human serum by volume.

In the methods provided herein, a plurality of proteins can be tested under conditions in which normal or increased activity is desired and under conditions in which reduced activity compared to normal is desired. In this particular method, each protein is tested under both conditions, and any proteins that have greater activity under conditions in which normal or increased activity is desired than under conditions in which reduced activity compared to normal is desired can be selected. In some examples, the activity is greater by a predetermined amount or ratio. For example, the activity is increased by at least 5%, 10%, 15%, 20%, 25%, 35%, 50%, 100%, 2-fold, 5-fold, 10-fold, 20-fold or more.

In the methods provided herein, the target protein can be a receptor or a portion thereof that binds to a ligand. Exemplary of a target protein is a receptor that is a tumor antigen. For example, the target protein is a member of the Her family of receptors or the target protein is the EGFR receptor or the extracellular domain thereof. In the methods provided herein, the protein whose activity is tested (the tested protein) can be a therapeutic protein that treats a tumor or other disease. In some examples, the therapeutic protein is an antibody, an enzyme, a hormone, a cytokine or active portion thereof, and reference to an antibody herein refers to an antibody or antigen-binding fragment thereof. In other examples of the method provided herein, the proteins can be modified variants of a therapeutic protein. Exemplary of a therapeutic protein is a ligand for a target receptor. In some examples of the method provided herein, the protein contains a multimerization domain, such as, for example, a multimerization domain that contains an Fc domain or modified Fc domain. In exemplary methods, the therapeutic protein is an antibody, an enzyme, a hormone or a cytokine. For example, the therapeutic protein can be an antibody.

In the methods provided herein, the protein tested in the method can be an anti-tumor antibody, selected from among those listed in Table 3. In some examples, the anti-tumor antibody exhibits undesirable side effects in healthy tissues. For example, the antibody is an anti-EGFR antibody or an anti-CTLA4 antibody that exhibits undesirable side effects in healthy tissues.

In other examples of the method provided herein, the proteins can be modified variants of a therapeutic protein. The modified variants can contain amino acid replacements, insertions and/or deletions. In some examples, a collection of variants are tested. In some examples, each variant differs from the wildtype or unmodified protein and all other variants by a single amino acid. In other examples, each variant contains two, three, four, five, six, seven, eight, nine or more different amino acids from the unmodified or wildtype protein. In the methods provided herein, in the collection of variants, the amino acid at each changed position is replaced by up to 1-19 amino acids other than the original amino acid. In other examples, histidine is a replacing amino acid or the histidines in the protein are replaced by a non-basic or uncharged amino acid. Each variant protein can be tested individually. For example, each variant protein can be tested in a high throughput format or an automated method.

In the methods provided herein, the selected protein can be conditionally active such that it has greater activity in the tumor or other disease microenvironment compared to the non-tumor environment. The methods provided herein can be repeated a plurality of times, wherein in each repetition, further variants of a selected protein or proteins are tested, whereby the therapeutic protein is evolved to exhibit reduced toxicity or adverse side-effects. In the methods provided herein, variant proteins can be produced by expression from a vector that contains a nucleic acid molecule encoding a variant protein.

In some examples of the methods provided herein, the protein that is tested is a variant antibody that contains one or more amino acid replacements in a complementarity determining region (CDR). In specific examples, every amino acid along the length of the protein or a selected portion thereof is replaced, one-by-one with up to 19 other amino acids. In other examples, the protein is an antibody and the selected portion is a CDR.

In one example, the therapeutic protein is an anti-EGFR antibody and the reduced adverse side effects are reduced dermal toxicities associated with systemic exposure to the antibody. In some examples of the methods provide herein, the pH of the tumor or other disease microenvironment is about or is 5.8-6.8, inclusive. In other examples, the selected protein is anti-EGFR antibody that preferentially binds to EGFR within the tumor microenvironment of reduced pH of 5.8-6.8 and lactate concentrations of about 12-20 mM compared to normal physiologic pH of 7.3-7.4 and normal lactate concentrations below 12 mM.

Provided herein is a method for identifying a conditionally active protein in which the method is performed by contacting a solid support coated with EGFR or the EGFR extracellular domain (ECD) with buffer at about pH 7.3-7.4 containing 1 mM lactic acid and about 25% human serum; contacting a second duplicate support with buffer at about pH 6 containing 12-20 mM, such as 16.6 mM, lactic acid and about 25% human serum; washing the supports with the corresponding buffer (pH 6.0 or pH 7.4); binding tagged anti-EGFR, such as FLAG-tagged anti-EGFR, standard in either the pH 7.4 buffer with lactic acid and human serum, or the pH 6.0 buffer with lactic acid and human serum to the corresponding support; and detecting binding of the anti-EGFR to the EGFR by adding goat-anti-Tag-enzyme, such as horseradish peroxidase (HRP), in the corresponding buffer and enzyme substrate to detect or quantitate binding of the anti-EGFR to each support.

Also provided herein are therapeutic proteins that are selected/identified or evolved by any of the methods provided herein. Also provided herein is a variant anti-tumor antibody that exhibits reduced dermal toxicity compared to an unmodified antibody. Also provided herein is an anti-EGFR antibody that exhibits reduced dermal toxicity compared to Erbitux.

Provided are methods for identifying/selecting a therapeutic protein that treats tumors and that is more active in low pH than at neutral pH. In the method, the activity of the protein is tested under conditions that contain a low pH, and the activity of the protein is tested under conditions that contain a neutral pH. The activity of the protein under conditions that contain low pH can be compared to the activity of the protein under conditions that contain neutral pH. Proteins can be selected and/or identified that are more active at low pH than at high pH. Low pH can be any pH that is less than 7.4, such as between or about between 5.8 to 6.8. Neutral pH can also be any pH that is or is about between 7.2 to 7.6, such as 7.4. In some examples of the method, the therapeutic protein that treats tumors is not angiostatin.

In the methods, the conditions also can include one or more conditions selected from among increased lactate concentration, increased pyruvate concentration and hypoxia. For example, the conditions can include an increased lactate concentration selected from among 10 mM to 20 mM lactic acid or 15 mM to 18 mM lactic acid; or at least about or 16 mM, 16.5 mM or 17 mM lactic acid. In the methods, conditions that contain neutral pH also can include other conditions, such as conditions where a lactate concentration is selected from among 0.5 to 5 mM or 0.2 mM to 4 mM lactic acid; or at or about 0.5, 1, 2, 3, 4, or 5 mM lactic acid.

Also provided herein are methods for identifying/selecting a therapeutic protein that is more active in a tumor microenvironment than in a non-tumor microenvironment. In the method, the activity of the protein is tested under a condition that exists in a tumor microenvironment but not a non-tumor environment in which activity is desired, and the activity of the protein is tested under a condition that exists in a non-tumor microenvironment. The activity of the protein under a condition that exists in a tumor microenvironment can be compared to the activity of the protein under a condition that exists in a non-tumor microenvironment. Proteins can be selected and/or identified that have greater activity under a condition that exists in a tumor microenvironment compared to under a condition that exists in a non-tumor microenvironment, thereby identifying a protein that is more active in a tumor microenvironment than in a non-tumor microenvironment. The condition that exists in a non-tumor microenvironment can be a condition in a systemic microenvironment and/or a healthy tissue, such as the gastrointestinal (GI) tract, the skin, the vasculature, the blood or the extracellular matrix. In some examples of the method, the therapeutic protein that treats tumors is not angiostatin.

The testing of the activity of the protein under conditions that contain low pH and under conditions that contain neutral pH can be performed under identical conditions, except for a condition or conditions that exists in a tumor microenvironment but not in a non-tumor microenvironment. Exemplary of conditions that exist in a tumor microenvironment include one or more properties such as increased vascularization, hypoxia, lowered pH, increased lactate concentration, increased pyruvate concentration, increased interstitial fluid pressure and altered metabolites or metabolism indicative of a tumor.

The conditions that exist in a tumor microenvironment can include lower than neutral pH or lower pH than the non-tumor microenvironment. For example, the condition that exists in a tumor microenvironment can be a pH below 7.4. In some examples, the pH of the tumor is about or is 5.8-6.8, inclusive, and the condition that exists in a tumor microenvironment is a pH between or about between 5.8 to 6.8. The conditions that exist in a tumor microenvironment can include elevated lactate concentration and/or increased pyruvate compared to the conditions that exist in a non-tumor microenvironment.

The condition in which the protein is tested that exists in a tumor microenvironment but not a non-tumor environment in which activity is desired, can include lower than neutral pH and elevated lactic acid concentration compared to the conditions in which the protein is tested that includes a condition that exists in a non-tumor microenvironment. For example, the lower than neutral pH can be between 5.8 and 6.8, inclusive, or 5.8 and 6.5, inclusive. The condition in which the protein is tested that exists in a tumor microenvironment but not a non-tumor environment in which activity is desired can include increased lactate concentration selected from among 10 mM to 20 mM lactic acid or 15 mM to 18 mM lactic acid; or at least about or 16 mM, 16.5 mM or 17 mM lactic acid. The condition in which the protein is tested that exists in a non-tumor microenvironment can include a lactate concentration selected from among 0.5 to 5 mM or 0.2 mM to 4 mM lactic acid; or at or about 0.5, 1, 2, 3, 4, or 5 mM lactic acid. In some examples of the methods, the protein is a therapeutic protein that treats a tumor. In some examples, a therapeutic protein is an antibody, an enzyme, a hormone, a cytokine or active portion thereof. Reference herein to an antibody herein includes an antibody or antigen-binding fragment thereof. In some examples, the therapeutic protein is a ligand for a target receptor, and/or an anti-tumor antibody. In some examples, administration of the anti-tumor antibody can be associated with one or more adverse side effects.

Anti-tumor antibodies for use in the methods provided herein include Cetuximab (Erbitux®), Trastuzumab (Herceptin®), Rituximab (Rituxan®, MabThera®), Bevacizumab (Avastin®), Alemtuzumab (Campath®), Panitumumab (Vectibix®), Ranibizumab (Lucentis®), Ibritumomab, Ibritumomab tiuxetan (Zevalin®), Tositumomab, Iodine I131 Tositumomab (BEXXAR®), Catumaxomab (Removab®), Gemtuzumab, Gemtuzumab ozogamicine (Mylotarg®), Abatacept (CTLA4-Ig, Orencia®), Belatacept (L104EA29YIg; LEA29Y; LEA), Ipilimumab (MDX-010, MDX-101), Tremelimumab (ticilimumab, CP-675,206), PRS-010, PRS-050, Aflibercept (VEGF Trap, AVE005), Volociximab (M200), F200, MORAb-009, SS1P (CAT-5001), Cixutumumab (IMC-A12), Matuzumab (EMD72000), Nimotuzumab (h-R3), Zalutumumab (HuMax-EGFR), Necitumumab IMC-11F8, mAb806/ch806, Sym004 and mAb-425. In some examples, the anti-tumor antibody is Cetuximab (Erbitux®). Exemplary antibodies include anti-EGFR antibodies and anti-CTLA4 antibodies.

The methods provided herein can be performed in vitro or in vivo.

In the methods provided, a plurality of proteins can be tested, and proteins that have greater activity in a low pH conditions compared to neutral pH can be selected. In the methods provided, a plurality of proteins can be tested, and proteins that have greater activity under a condition that exists in a tumor microenvironment than a non-tumor microenvironment can be selected. The plurality of proteins can include modified variants of a therapeutic protein, and a collection of variants can be tested.

The therapeutic proteins can include a multimerization domain, and the multimerization domain can include an Fc domain or modified Fc domain. A therapeutic protein can be an antibody (including an anti-tumor antibody), an enzyme, a hormone or a cytokine. In the methods provided, an anti-tumor antibody can be selected from among Cetuximab (Erbitux®), Trastuzumab (Herceptin®), Rituximab (Rituxan®, MabThera®), Bevacizumab (Avastin®), Alemtuzumab (Campath®), Panitumumab (Vectibix®), Ranibizumab (Lucentis®), Ibritumomab, Ibritumomab tiuxetan (Zevalin®), Tositumomab, Iodine I131 Tositumomab (BEXXAR®), Catumaxomab (Removab®), Gemtuzumab, Gemtuzumab ozogamicine (Mylotarg®), Abatacept (CTLA4-Ig, Orencia®), Belatacept (L104EA29YIg; LEA29Y; LEA), Ipilimumab (MDX-010, MDX-101), Tremelimumab (ticilimumab, CP-675,206), PRS-010, PRS-050, Aflibercept (VEGF Trap, AVE005), Volociximab (M200), F200, MORAb-009, SS1P (CAT-5001), Cixutumumab (IMC-A12), Matuzumab (EMD72000), Nimotuzumab (h-R3), Zalutumumab (HuMax-EGFR), Necitumumab IMC-11F8, mAb806/ch806, Sym004 and mAb-425.

Modified variants of a therapeutic protein or a plurality of therapeutic proteins can include amino acid replacements, insertions and/or deletions of an amino acid residue or residues compared to an unmodified form of the therapeutic protein. For example, each variant protein can contain a single amino acid replacement compared to an unmodified form of the therapeutic protein. Each variant protein can contain two, three, four, five, six, seven, eight, nine or more amino acid replacements compared to an unmodified form of a variant protein, such as a therapeutic antibody.

In some examples, the protein that is tested is a variant antibody that contains one or more amino acid replacements in a complementarity determining region (CDR) compared to an unmodified form of the antibody.

In the methods provided, variants of a therapeutic protein can be tested that include replacement of the amino acid at each changed position by up to 1-19 other amino acids than the original amino acid at the position, and every amino acid can be replaced along the length of the therapeutic protein, or a selected portion thereof. Provided are methods in which a modified protein is an antibody and the selected portion that is modified is a CDR.

Replacement amino acids can be selected from among Ala, Arg, Asn, Asp, Cys, Gln, Glu, Gly, H is, Ile, Leu, Lys, Met, Phe, Pro, Ser, Thr, Trp, Tyr and Val, with the proviso that the replacement amino acid differs from the amino acid at the corresponding position in the therapeutic protein. An example of a replacement amino acid is histidine. In some examples, the histidines in a protein are replaced by a non-basic or uncharged amino acid. In some methods, modifications contain amino acid replacement with an amino acid selected from among Arg, Asp, Glu, His and Lys, in some examples, replacement with His.

In the methods provided, each variant protein, such as a variant protein in a collection can be tested individually, such as, for example, in an array, including an addresible array. In some embodiments, the methods provided are performed in a high throughput format and/or are automated.

In the methods provided, the activity that is tested can be binding to a target protein of the therapeutic protein. Binding can be assessed by an immunoassay, such as, for example, an ELISA. Examples of an immunoassay is a heterogeneous immunoassay that can include immobilizing the target protein on a solid support; contacting the therapeutic protein with the target protein, wherein the therapeutic protein is detectably labeled; removing unbound therapeutic protein; and detecting or measuring the binding of the labeled therapeutic protein to the target protein. The immunoassay can be homogenous, comprising contacting the therapeutic protein with a target protein, wherein the therapeutic protein is detectably labeled; and detecting or measuring the binding of the labeled therapeutic protein to the target protein.

Provided are methods in which binding activity is assessed using a cell surface expression system comprising a cell or cells expressing therapeutic protein on the surface. The therapeutic protein can be expressed on the surface of cells, a target protein can be contacted with a population of the cells; and a cell or cells can be identified that binds to the target protein, thereby identifying a therapeutic protein that exhibits binding activity. The target protein can be detectably labeled or can be detected. The target protein can be fluorescently labeled or detected by a secondary reagent that is fluorescently labeled. Binding can be detected or measured by fluorescence activated cell sorting (FACS).

Binding activity can be tested in the methods using a cell surface expression system comprising cells expressing a therapeutic protein, and a cell or cells can be selected that bind to the target protein and a cell or cells can be selected that do not bind to the target protein. Cell or cells that are selected that do not bind to the target protein can be isolated and grown in a cell culture medium to generate a second population of cells expressing the therapeutic protein on the surface. In some examples binding activity is tested under conditions whereby cells from the second population of cells are contacted with the target protein, and a cell or cells is identified that binds to the target protein.

In the methods provided, binding activity can be tested under a condition or conditions, such as low pH, that exists in a tumor microenvironment but not in a non-tumor environment in which activity is desired, using a cell surface expression system comprising a population of cells expressing a therapeutic protein, whereby a cell or cells are selected that bind to the target protein and a cell or cells are selected that do not bind to the target protein. In some examples, the cells or cells that are selected that bind to the target protein are isolated and grown in a cell culture medium to generate a second population of cells. In some methods, cells from the second population of cells are contacted with the target protein, and binding activity is tested under a condition that exists in a non-tumor microenvironment, such as neutral pH. A cell or cells can be identified that do not bind to the target protein, and a cell or cells can be identified that binds to the target protein. The cell or cells that do not bind to the target protein can be selected. Thus, therapeutic proteins that exhibit binding activity can be identified.

In the methods provided, administration of the therapeutic protein to a subject can be associated with one or more adverse side-effects. Reducing the activity of the protein under a condition, such as neutral pH, that exists in a non-tumor microenvironment, compared to a condition that exists in a tumor microenvironment but not a non-tumor environment in which activity is desired, such as low pH, can ameliorate or prevent the adverse side-effects.

A target protein of the therapeutic protein can be a receptor or a portion thereof that binds to a ligand. In some examples, the target protein of the therapeutic protein is a receptor that is a tumor antigen, such as a member of the Her family of receptors. In some examples, the target protein of the therapeutic protein is the EGFR receptor or the extracellular domain thereof.

In the methods provided, the activities of the therapeutic protein can be tested in the presence of human serum, such as in the presence of human serum in an amount that is present in a physiological environment. The concentration of serum in a condition that exists in a tumor microenvironment but not a non-tumor environment in which activity is desired can be equal to the serum concentration in a condition that exists in a non-tumor microenvironment. For example, in the methods provided, a protein can be tested in the presence of at least about between or between or, by volume, human serum selected from among 3%-30%, inclusive; 5%-30%, inclusive; 5%-25%, inclusive; 10%-30%, inclusive; 15%-30%, inclusive; and 15%-25%, inclusive. In some examples, the concentration of human serum is at or about 25% (plus or minus 10%) or 15%-35% by volume.

In the methods provided, the selected protein can be conditionally active such that it has greater activity in a tumor microenvironment compared to a non-tumor environment. The activity of a protein under a condition that exists in a tumor microenvironment but not a non-tumor environment in which activity is desired, such as low pH, can be greater than under a condition that exists in a non-tumor microenvironment, such as neutral pH, by a predetermined amount or ratio. In some examples, the activity is greater by a ratio of at least or 1.2, 1.3, 1.4, 1.5, 1.6, 1.7, 1.8, 1.9, 2.0, 3, 4, 5, 6, 7, 8, 9, 10, 11, 12, 13, 14, 15, 16, 17, 18, 19, 20, 30, 40, 50 or more. In some examples, the activity is greater by at least 5%, 10%, 15%, 20%, 25%, 35%, 50%, 100%, 2-fold, 5-fold, 10-fold, 20-fold or more.

The methods provided can be repeated a plurality of times. In each repetition, further variants of a selected protein or proteins can be generated and tested. In some examples, a therapeutic protein is evolved to exhibit increased activity in a tumor environment than in a non-tumor environment. An evolved protein can exhibit reduced toxicity or reduced adverse side-effects. For example, the therapeutic protein can be an anti-EGFR antibody and the reduced adverse side effects can contain reduced dermal toxicities associated with systemic exposure to the antibody.

In some embodiments of the methods provided herein, the selected protein is an anti-EGFR antibody variant that preferentially binds to EGFR under conditions that exist in a tumor microenvironment but not a non-tumor environment, such as reduced pH of 5.8-6.8 and lactate concentrations of about 12-20 mM compared to that exists in a non-tumor microenvironment, such as normal physiologic pH of 7.3-7.4 and normal lactate concentrations below 12 mM.

In some examples of the methods herein, the methods further involve, prior to testing the activity of the protein, the steps of: 1) contacting a first solid support and a second duplicate solid support with EGFR or the EGFR extracellular domain (ECD) in a buffer comprising a pH at or about pH 7.4; 2) washing the first and second supports with a buffer comprising a pH at or about pH 7.4; 3) adding a buffer comprising 25% or about 25% human serum to the first and second solid supports; and 4) removing the buffer from the solid support.

In some examples of the methods herein, testing the activity of the protein under a condition that exists in a tumor microenvironment, such as under conditions that include low pH, can include: 1) adding a modified anti-EGFR antibody that is detectably labeled to the first support in a binding buffer that includes 12-20 mM lactic acid, 25% human serum, pH 6.0; 2) washing the first support with buffer comprising 12-20 mM lactic acid, at or about pH 6.0; and 3) adding a reagent to the first solid support to detect bound modified anti-EGFR, and detecting binding of the modified protein to the EGFR or EGFR ECD on the first solid support.

In some examples of the methods herein, testing the activity of the protein under a condition that exists in a non-tumor microenvironment, such as conditions that include neutral pH, can include: 1) adding a modified anti-EGFR antibody that is detectably labeled to the second support in a binding buffer that includes 1 mM lactic acid, 25% human serum, pH 7.4; 2) washing the second supports with buffer that includes 1 mM or about 1 mM lactic acid, at or about pH 7.4; and 3) adding a reagent to the second solid support to detect bound modified anti-EGFR, and detecting binding of the modified protein to the EGFR or EGFR ECD on the second solid supports. Binding can be detected by spectrophotometric measurement. An anti-EGFR antibody can include a FLAG-tag to facilitate detection with an anti-FLAG-TAG enzyme reagent.

Provided herein are methods for identifying/selecting a therapeutic protein that is more active in a first set of conditions than in a second set of conditions. The first set of conditions can include one or more conditions that exists in a tumor microenvironment compared to a non-tumor microenvironment selected from among low pH, increased lactate concentration, increased pyruvate concentration and hypoxia. The second set of conditions can include the corresponding condition that exists in the non-tumor microenvironment. In some examples, the method involves a) testing a plurality of proteins for activity under the first and second set of conditions; b) selecting/identifying proteins that have decreased activity under the first set of conditions compared to the unmodified therapeutic protein, and decreased activity under the second set of conditions compared to the unmodified therapeutic protein; c) analyzing proteins selected/identified in step b) to identify amino acid positions that are modified, whereby the amino acid is identified as a critical amino acid position; d) generating a second collection of variant proteins that includes substitution of an amino acid residue adjacent to or near to a critical amino acid position with a replacement amino acid, and each member of the library contains a single amino acid replacement compared to the therapeutic protein; e) testing the activity of members of the second collection of modified proteins under the first set of conditions and under the second set of conditions; and selecting/identifying members of the second collection that exhibit greater than or about equal to the activity compared to under the second set of conditions; f) analyzing proteins selected/identified in e) to identify amino acid positions that were substituted, wherein the identified positions are designated key residue positions; g) generating a third collection of variant proteins, wherein each member contains substitution of one or more key residue positions with a replacement amino acid; and h) testing the activity of members of the combinatorial library under the first set of conditions and under the second set of conditions, and selecting/identifying members of the second library that have greater activity under the first set of conditions compared to the second set of conditions, thereby identifying a therapeutic protein that is more active in a first set of conditions than in a second set of conditions. In some examples of the method, the plurality of proteins in step a) can include or are modified variants of a therapeutic protein; and a first collection of variants can be tested in each of the first and second set of conditions. In some examples of the method, step h) can include: 1) testing the activity of members of the third collection under the first set of conditions and selecting/identifying proteins that have an activity greater than a predetermined activity; and 2) testing the activity of proteins selected/identified in step 1) under the second set of conditions and selecting/identifying proteins that have an activity less than a predetermined activity. In some examples of the method, step h) can include: 1) testing the activity of members of the third collection library under the second set of conditions and selecting/identifying proteins that have an activity less than a predetermined activity; and 2) testing the activity of proteins selected/identified in step 1) under the first set of conditions and selecting/identifying proteins that have an activity greater than a predetermined activity. In some examples of the method, step g) is repeated a plurality of times, such as 1, 2, 3, or 4 times, wherein in each repetition, selected/identified proteins are tested.

In some examples of the methods, the therapeutic protein is an antibody, an enzyme, a hormone, a cytokine or active portion thereof, and reference to an antibody herein refers to an antibody or antigen-binding fragment thereof. For example, the therapeutic protein can be a ligand for a target receptor. In some examples, the therapeutic protein can be a protein that treats a tumor, such as an anti-tumor antibody. The anti-tumor antibody can be selected from among Cetuximab (Erbitux®), Trastuzumab (Herceptin®), Rituximab (Rituxan®, MabThera®), Bevacizumab (Avastin®), Alemtuzumab (Campath®), Panitumumab (Vectibix®), Ranibizumab (Lucentis®), Ibritumomab, Ibritumomab tiuxetan (Zevalin®), Tositumomab, Iodine I131 Tositumomab (BEXXAR®), Catumaxomab (Removab®), Gemtuzumab, Gemtuzumab ozogamicine (Mylotarg®), Abatacept (CTLA4-Ig, Orencia®), Belatacept (L104EA29YIg; LEA29Y; LEA), Ipilimumab (MDX-010, MDX-101), Tremelimumab (ticilimumab, CP-675,206), PRS-010, PRS-050, Aflibercept (VEGF Trap, AVE005), Volociximab (M200), F200, MORAb-009, SS1P (CAT-5001), Cixutumumab (IMC-A12), Matuzumab (EMD72000), Nimotuzumab (h-R3), Zalutumumab (HuMax-EGFR), Necitumumab IMC-11F8, mAb806/ch806, Sym004 and mAb-425. In some examples, the anti-tumor antibody is Cetuximab (Erbitux®).

In some embodiments of the methods, binding to a target protein is tested. Binding activity can be tested by spectrophotometric measurement; immunoassay, such as an immunoassay that includes an ELISA; and/or a cell based assay, such as in a cell surface expression system. For example, in some methods of identifying a protein that exhibits binding activity, members of the second library are expressed on the surface of cells, a target protein is contacted with a population of the cells; and a cell or cells is identified that binds to the target protein, thereby identifying a protein that exhibits binding activity. Cells that can be used in the assays described herein include Chinese Hamster Ovary (CHO)

cells. An example of a cell based assay for use in the methods provided is Fluorescence Activated Cell Sorting (FACS). For example, binding can be detected or measured by FACS.

In some methods provided herein, the target protein can be detectably labeled or can be detected. For example, the target protein can be fluorescently labeled or detected by a secondary reagent that is fluorescently labeled.

In the methods herein, the target protein can be a member of the Her family of receptors. An example of a target protein is the EGFR receptor or the extracellular domain thereof.

In some methods provided herein, the set of conditions that include one or more conditions that exists in a tumor microenvironment compared to a non-tumor microenvironment includes low pH below 7.4, and critical amino acids are selected such that protein variants include an amino acid replacement to a charged residue, such as Arg, Asp, Glu, His or Lys. An exemplary replacement amino acid is His. For example, amino acid replacement in the second and third collection can be a replacement amino acid to His.

In the methods provided, the first set of conditions can include a lower than neutral pH and/or elevated lactic acid concentration compared to the second set of conditions. For example, the first set of conditions can include a pH that is about or is 5.8-6.8, inclusive. In some embodiments, first set of conditions includes about 12-20 mM lactic acid, at or about pH 6.0; and the second set of conditions includes 1 mM or about 1 mM lactic acid, at or about pH 7.4.

BRIEF DESCRIPTION OF THE FIGURES

FIG. 1. Sequence of monoclonal antibody Erbitux®. FIG. 1 depicts the sequence of Eibitux® (SEQ ID NO:1 and 2). FIG. 1A depicts the sequence of the heavy chain. FIG. 1B depicts the sequence of the light chain. The variable chains are underlined and the residues selected for modification are in boldface, italic type.

DETAILED DESCRIPTION

Outline
A. DEFINITIONS
B. METHODS TO IDENTIFY CONDITIONALLY ACTIVE MOLECULES
  1. Therapeutic Proteins
    a. Tumor or Cancer Therapeutics
    b. Generating Libraries of Modified Proteins
      i. Modified therapeutic antibodies
        a) Modified Anti-EGFR Therapeutics
  2. Screening or Testing Activity Under Two Different Physiologic Conditions for Conditional Activity
    a. Tumor Microenvironments
      i. pH
      ii. lactate concentration
      iii. Hypoxia
  3. Detection and Identification of Conditionally Active Modified Proteins
  4. Iterative Methods
C. ASSAYS TO IDENTIFY CONDITIONALLY ACTIVE MOLECULES
  1. Assays that Detect Binding
    a. Solid Support Binding Assays
      i. Immobilization to a Solid Support
      ii. Contacting Under Simulated Conditions
      iii. Detection and Identification of Conditionally Active Test Molecules
    b. Solution Binding Assays
      i. isothermal titration calorimetry (ITC)
      ii. Spectroscopic assays
    c. Cell Based Assays
      i. Cell Surface Expression of Test Molecules
      ii. Binding And Detection by Fluorescence Activated Cell Sorting (FACS)
D. METHODS OF EXPRESSING PROTEINS
  1. Vectors
  2. Cells and Expression Systems
    a. Prokaryotic Expression
    b. Yeast
    c. Insects
    d. Mammalian Cells
    e. Plants
  3. Purification
E. EXAMPLES A. Definitions Unless defined otherwise, all technical and scientific terms used herein have the same meaning as is commonly understood by one of skill in the art to which the invention(s) belong. All patents, patent applications, published applications and publications, Genbank sequences, databases, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

As used herein, a conditionally active protein is more active in one environment, particularly one in vivo environment, compared to a second environment. For example, a conditionally active protein can be more active in a tumor environment than in a non-tumor environment, such as a non-tumor environment in the skin, GI tract or other non-tumor environment.

As used herein, a therapeutic protein is a protein that has been used for therapy to treat a subject having a disease or condition, can be used for therapy or is a candidate for therapy. For example, a candidate for therapy is a variant (e.g. containing amino acid modifications) of a therapeutic protein that has been used for therapy. For purposes herein, a therapeutic protein, including a protein that has been used for therapy, can be used for therapy or is a candidate for therapy, can be used in the practice of the method herein as a test protein to identify therapeutic proteins that exhibit more activity under one set of conditions than another, and hence are conditionally active.

As used herein, a "test protein," "tested protein," "binding molecule," "binding protein" or other variations thereof refer to molecules or proteins that are employed in the method herein. Any molecule or protein can be employed in the method herein to identify proteins that are conditionally active and exhibit activity under a condition or conditions that exist in a diseased microenvironments (e.g. tumor microenvironment) compared to a condition or condition that exists in a non-diseased microenvironments. Exemplary of tested proteins are therapeutic proteins in order to evolve the therapeutic as conditionally active. Exemplary tested proteins are set forth in Table 3.

As used herein, an antibody refers to immunoglobulins and immunoglobulin portions, whether natural or partially or wholly synthetic, such as recombinantly produced, including any portion thereof containing at least a portion of the variable region of the immunoglobulin molecule that is sufficient to form an antigen binding site. Hence, an antibody or portion thereof includes any protein having a binding domain that is homologous or substantially homologous to an immunoglobulin antigen binding site. For example, an antibody refers to an antibody that contains two heavy chains (which can be denoted H and H') and two light chains (which can be denoted L and L'), where each heavy chain can be a full-length immunoglobulin heavy chain or a portion thereof sufficient to form an antigen binding site (e.g. heavy chains include, but are not limited to, $V_H$ chains, $V_H$—$C_H1$ chains and $V_H$—$C_H1$-$C_H2$-$C_H3$ chains), and each light chain can be a full-length light chain or a portion thereof sufficient to form an antigen binding site (e.g. light chains include, but are not limited to, $V_L$ chains and $V_L$—$C_L$ chains). Each heavy chain (H and H') pairs with one light chain (L and L', respectively). Typically, antibodies minimally include all or at least a portion of the variable heavy ($V_H$) chain and/or the variable light ($V_L$) chain. The antibody also can include all or a portion of the constant region.

For purposes herein, the term antibody includes full-length antibodies and portions thereof including antibody fragments, such as, but not limited to, Fab, Fab', F(ab')$_2$, single-chain Fvs (scFv), Fv, dsFv, diabody, Fd and Fd' fragments, Fab fragments, Fd fragments and scFv fragments. Other known fragments include, but are not limited to, scFab fragments (Hust et al., *BMC Biotechnology* (2007), 7:14). Antibodies include members of any immunoglobulin class, including IgG, IgM, IgA, IgD and IgE.

As used herein, a full-length antibody is an antibody having two full-length heavy chains (e.g. $V_H$—$C_H1$-$C_H2$-$C_H3$ or $V_H$—$C_H1$-$C_H2$-$C_H3$-$C_H4$) and two full-length light chains ($V_L$—$C_L$) and hinge regions, such as human antibodies produced by antibody secreting B cells and antibodies with the same domains that are produced synthetically.

As used herein, antibody fragment or antibody portion with reference to a "portion thereof" or "fragment thereof" of an antibody refers to any portion of a full-length antibody that is less than full length but contains at least a portion of the variable region of the antibody sufficient to form an antigen binding site (e.g. one or more CDRs) and thus retains the a binding specificity and/or an activity of the full-length antibody; antibody fragments include antibody derivatives produced by enzymatic treatment of full-length antibodies, as well as synthetically, e.g. recombinantly produced derivatives. Examples of antibody fragments include, but are not limited to, Fab, Fab', F(ab')$_2$, single-chain Fvs (scFv), Fv, dsFv, diabody, Fd and Fd' fragments (see, for example, *Methods in Molecular Biology*, Vol 207: *Recombinant Antibodies for Cancer Therapy Methods and Protocols* (2003); Chapter 1; p 3-25, Kipriyanov). The fragment can include multiple chains linked together, such as by disulfide bridges and/or by peptide linkers. An antibody fragment generally contains at least about 50 amino acids and typically at least 200 amino acids.

Hence, reference to an "antibody or portion thereof that is sufficient to form an antigen binding site" means that the antibody or portion thereof contains at least 1 or 2, typically 3, 4, 5 or all 6 CDRs of the $V_H$ and $V_L$ sufficient to retain at least a portion of the binding specificity of the corresponding full-length antibody containing all 6 CDRs. Generally, a sufficient antigen binding site at least requires CDR3 of the heavy chain (CDRH3). It typically further requires the CDR3 of the light chain (CDRL3). As described herein, one of skill in the art knows and can identify the CDRs based on kabat or Chothia numbering (see e.g., Kabat, E. A. et al. (1991) *Sequences of Proteins of Immunological Interest*, Fifth Edition, U.S. Department of Health and Human Services, NIH Publication No. 91-3242, and Chothia, C. et al. (1987) *J. Mol. Biol.* 196:901-917).

As used herein, a complementary determining regions (CDRs; also called hypervariable regions) are regions within antibodies that determine the protein's affinity and specificity for specific antigens. Hence, a CDR is a restricted region within the variable region of antibodies that bind to antigenic determinants. The CDR of antibodies are known or can be determined based on Kabat or Chothia numbering as is known to one of skill in the art.

As used herein, "antigen-binding site" refers to the interface formed by one or more complementary determining regions (CDRs; also called hypervariable regions). Each antigen binding site contains three CDRs from the heavy chain variable region and three CDRs from the light chain variable region. An antibody molecule has two antigen combining sites, each containing portions of a heavy chain variable region and portions of a light chain variable region. The antigen combining sites can contain other portions of the variable region domains in addition to the CDRs.

As used herein, an Fv antibody fragment is composed of one variable heavy domain ($V_H$) and one variable light ($V_L$) domain linked by noncovalent interactions.

As used herein, a dsFv refers to an Fv with an engineered intermolecular disulfide bond, which stabilizes the $V_H$—$V_L$ pair.

As used herein, an Fd fragment is a fragment of an antibody containing a variable domain ($V_H$) and one constant region domain ($C_H1$) of an antibody heavy chain.

As used herein, "Fab fragment" is an antibody fragment that contains the portion of the full-length antibody that would results from digestion of a full-length immunoglobulin with papain, or a fragment having the same structure that is produced synthetically, e.g. recombinantly. A Fab fragment contains a light chain (containing a $V_L$ and $C_L$ portion) and another chain containing a variable domain of a heavy chain ($V_H$) and one constant region domain portion of the heavy chain ($C_H1$); it can be recombinantly produced.

As used herein, a F(ab')$_2$ fragment is an antibody fragment that results from digestion of an immunoglobulin with pepsin at pH 4.0-4.5, or a synthetically, e.g. recombinantly, produced antibody having the same structure. The F(ab')$_2$ fragment contains two Fab fragments but where each heavy chain portion contains an additional few amino acids, including cysteine residues that form disulfide linkages joining the two fragments; it can be recombinantly produced.

A Fab' fragment is a fragment containing one half (one heavy chain and one light chain) of the F(ab')$_2$ fragment.

As used herein, an Fd' fragment is a fragment of an antibody containing one heavy chain portion of a F(ab')$_2$ fragment.

As used herein, an Fv' fragment is a fragment containing only the $V_H$ and $V_L$ domains of an antibody molecule.

As used herein, a scFv fragment refers to an antibody fragment that contains a variable light chain ($V_L$) and variable heavy chain ($V_H$), covalently connected by a polypeptide linker in any order. The linker is of a length such that the two variable domains are bridged without substantial interference. Exemplary linkers are (Gly-Ser)$_n$ residues with some Glu or Lys residues dispersed throughout to increase solubility.

As used herein, diabodies are dimeric scFv; diabodies typically have shorter peptide linkers than scFvs, and they preferentially dimerize.

As used herein, hsFv refers to antibody fragments in which the constant domains normally present in a Fab fragment have been substituted with a heterodimeric coiled-coil domain (see, e.g., Arndt et al. (2001) *J Mol Biol.* 7:312:221-228).

As used herein, a "variable domain" with reference to an antibody is a specific Ig domain of an antibody heavy or light chain that contains a sequence of amino acids that varies among different antibodies. Each light chain and each heavy chain has one variable region domain ($V_L$ and $V_H$). The variable domains provide antigen specificity, and thus are responsible for antigen recognition. Each variable region contains CDRs that are part of the antigen binding site domain and framework regions (FRs).

As used herein, reference to a variable heavy ($V_H$) chain or a variable light ($V_L$) chain (also termed $V_H$ domain or $V_L$ domain) refers to the polypeptide chains that make up the variable domain of an antibody.

As used herein, framework regions (FRs) are the regions within the antibody variable region domains that are located within the beta sheets; the FR regions are comparatively more conserved, in terms of their amino acid sequences, than the hypervariable regions.

As used herein, a constant domain is a domain in an antibody heavy or light chain that contains a sequence of amino acids that is comparatively more conserved among antibodies than the variable region domain. Each light chain has a single light chain constant region ($C_L$) domain and each heavy chain contains one or more heavy chain constant region ($C_H$) domains, which include, $C_H1$, $C_H2$, $C_H3$ and $C_H4$. Full-length IgA, IgD and IgG isotypes contain $C_H1$, $C_H2$, $C_H3$ and a hinge region, while IgE and IgM contain $C_H1$, $C_H2$, $C_H3$ and $C_H4$. $C_H1$ and $C_L$ domains extend the Fab arm of the antibody molecule, thus contributing to the interaction with antigen and rotation of the antibody arms. Antibody constant regions can serve effector functions, such as, but not limited to, clearance of antigens, pathogens and toxins to which the antibody specifically binds, e.g. through interactions with various cells, biomolecules and tissues.

As used herein, a form of an antibody refers to a particular structure of an antibody. Antibodies herein include full length antibodies and portions thereof, such as, for example, a Fab fragment or other antibody fragment. Thus, a Fab is a particular form of an antibody.

As used herein, reference to a "corresponding form" of an antibody means that when comparing a property or activity of two antibodies, the property is compared using the same form of the antibody. For example, if it's stated that an antibody has less activity compared to the activity of the corresponding form of a first antibody, that means that a particular form, such as a Fab of that antibody, has less activity compared to the Fab form of the first antibody.

As used herein, corresponding with reference to corresponding residues, for example "amino acid residues corresponding to," refers to residues compared among or between two polypeptides that are related sequences (e.g. allelic variants, genes of the same family, species variants). One of skill in the art can readily identify residues that correspond between or among polypeptides. For example, by aligning two sequences, one of skill in the art can identify corresponding residues, using conserved and identical amino acids as guides. One of skill in the art can manually align a sequence or can use any of the numerous alignment programs available (for example, BLAST). Hence, amino acid residues or positions that correspond to each other are those residues that are determined to correspond to one another based on sequence and/or structural alignments with a specified reference polypeptide.

As used herein, "linker" or "spacer" peptide refers to short sequences of amino acids that join two polypeptide sequences (or nucleic acid encoding such an amino acid sequence). "Peptide linker" refers to the short sequence of amino acids joining the two polypeptide sequences. Exemplary of polypeptide linkers are linkers joining a peptide transduction domain to an antibody or linkers joining two antibody chains in a synthetic antibody fragment such as an scFv fragment. Linkers are well-known and any known linkers can be used in the provided methods. Exemplary of polypeptide linkers are (Gly-Ser)$_n$ amino acid sequences, with some Glu or Lys residues dispersed throughout to increase solubility. Other exemplary linkers are described herein; any of these and other known linkers can be used with the provided compositions and methods.

As used herein, "human serum" refers to normal serum that can be obtained by pooling approximately equal amounts of the liquid portion of coagulated whole blood from persons who are free from any disease transmissible by transfusion.

As used herein "angiostatin" refers to a 38 kD fragment of plasmin, which itself is a fragment of plasminogen. Angiostatin contains the kringles 1 to 3 of plasminogen (see e.g. Calbiochem® Angiostatin K1-3, Human, Recombinant, *E. coli*; Catalog No. 176708 available from EMD Millipore Bioscience, Billerica Mass.). Angiostatin is able to suppress tumor cell growth and metastiasis through inhibition of endothelial cell proliferation and migration, and hence is an angiogenesis inhibitor.

As used herein, reference to "detectable" or "detectably labeled" refers to an atom, molecule or composition, wherein the presence of the atom, molecule or composition can be directly or indirectly measured. Detectable labels can be used to identify one or more of proteins in the methods provided herein. Detectable labels can be used in any of the methods provided herein. Detectable labels include, for example, chemiluminescent moieties, bioluminescent moieties, fluorescent moieties, radionuclides, and metals. Methods for detecting labels are well known in the art. Such a label can be detected, for example, by visual inspection, by fluorescence spectroscopy, by reflectance measurement and by flow cytometry. Indirect detection refers to measurement of a physical phenomenon of an atom, molecule or composition that binds directly or indirectly to the detectable label, such as energy or particle emission or absorption, of an atom, molecule or composition that binds directly or indirectly to the detectable label. In a non-limiting example of indirect detection, a detectable label can be biotin, which can be detected by binding to avidin. Thus, included within the scope of a detectable label or detectable moiety is a bindable label or bindable moiety, which refers to an atom, molecule or composition, wherein the presence of the atom, molecule or composition can be detected as a result of the label or moiety binding to another atom, molecule or composition.

As used herein, a label is a detectable marker that can be attached or linked directly or indirectly to a molecule or associated therewith. The detection method can be any method known in the art.

As used herein, "screening" refers to identification or selection of a protein, such as an antibody or portion thereof from a plurality of antibodies, such as a collection or library of antibodies and/or portions thereof, based on determination of the activity or property of an antibody or portion thereof. Screening can be performed in any of a variety of ways and generally involves contacting members of the collection with a target protein or antigen and assessing a property or activity, for example, by assays assessing direct binding (e.g. binding affinity) of the antibody to a target protein or by functional assays assessing modulation of an activity of a target protein.

As used herein the term "assessing" or "testing" is intended to include quantitative and qualitative determination in the sense of obtaining an absolute value for the binding of an antibody or portion thereof with a target protein and/or modulation of an activity of a target protein by an antibody or portion thereof, and also of obtaining an index, ratio, percentage, visual or other value indicative of the level of the binding or activity. Assessment can be direct or indirect. For example, binding can be determined by directly labeling an antibody or portion thereof with a detectable label and/or by using a secondary antibody that itself is labeled. In addition, functional activities can be determined using any of a variety of assays known to one of skill in the art, for example, neutralization assays and others as described herein, and comparing the activity of the membrane-associated antigen (e.g. cell such as a virus) in the presence versus the absence of an antibody or portion thereof.

As used herein, "high-throughput" refers to a large-scale method or process that permits manipulation of large numbers of molecules or compounds, generally tens to hundreds to thousands of compounds. For example, methods of purification and screening can be rendered high-throughput. High-throughput methods can be performed manually. Generally, however, high-throughput methods involve automation, robotics or software.

As used herein, "target protein" or "target of the protein" is a protein, antigen or substrate that is capable of binding or interacting with a test molecule or protein.

As used herein, "disease" refers to a pathological condition in an organism resulting from cause or condition including, but not limited to, infections, acquired conditions, genetic conditions, and characterized by identifiable symptoms. Diseases include cancer and tumors. As used herein, a "diseased microenvironment" refers to the particular conditions in a particular microenvironment that is altered or changed in disease tissues compared to normal tissues. These conditions include, for example, altered or elevated or changed vascularization, hypoxia, altered pH, co-factors, interstitial fluid pressure, and altered metabolite levels such as altered lactate or pyruvate levels.

As used herein, conditions of a "non-diseased microenvironment" or "healthy tissue environment" refer to conditions that exist under normal physiologic conditions. For example, under normal physiologic conditions the pH of a non-diseased microenvironment, such as non-diseased tissues, can be neutral.

As used herein, "conditions that simulate" a diseased or non-diseased microenvironment, refer to in vitro or in vivo assay conditions that correspond to a condition or conditions that exist in the environment in vivo. For example, if a microenvironment is characterized by low pH, then a condition that simulates the microenvironment includes buffer or assay conditions having a low pH.

As used herein, conditions that exist in a tumor microenvironment include conditions that exist therein compared to a non-tumor microenvironment (e.g. a healthy or non-diseased cell or tissue). Conditions that exist in a tumor microenvironment include increased vascularization, hypoxia, low pH, increased lactate concentration, increased pyruvate concentration, increased interstitial fluid pressure and altered metabolites or metabolism indicative of a tumor. For example, a condition that exists in a tumor microenvironment is low pH less than 7.4, typically between or about between 5.6 to 6.8, such as less than or about or pH 5.6, 5.7, 5.8, 5.9, 6.0, 6.1, 6.2, 6.3, 6.4, 6.5, 6.6, 6.7, or 6.8. In another example, a condition that exists in a tumor microenvironment is high lactate concentration at or about between 5 mM to 20 mM lactic acid, for example 10 mM to 20 mM lactic acid such as 15 mM to 18 mM, and in particular at least or at least about or 16 mM, 16.5 mM or 17 mM lactic acid.

As used herein, conditions that exist in a non-tumor microenvironment include a condition or conditions that are not present in a tumor microenvironment. For purposes herein, the condition or conditions is the corresponding property or characteristic that is present in a tumor microenvironment and non-tumor environment, such as pH, lactate concentration or pyruvate concentration, but that differs between the two microenvironments. A condition that exists in a non-tumor microenvironment is pH from about 7.0 to about 7.8, such as at least or about or pH 7.1, 7.2, 7.3, 7.4, 7.5, 7.6, 7.7 or 7.8 (see, e.g., U.S. Pat. No. 7,781,405), in some examples pH 7.4. A condition that exists in a non-tumor microenvironment is lactate concentration that is 0.5 to 5 mM lactate, such as, for example 0.2 mM to 4 mM lactic acid, such as 0.5, 1, 2, 3, 4, or 5 mM lactic acid.

As used herein, a "collection of proteins" or "collection of antibodies" refers to a collection containing at least 10 different proteins and/or active portions thereof, and generally containing at least 50, 100, 500, 1000, $10^4$, $10^5$ or more members. The collections typically contain proteins to be screened for activity. Included in the collections are naturally occurring proteins (or active portions thereof) and/or modified proteins, in particular antibody variants or active fragments thereof. The modifications include random mutations along the length of the protein and/or modifications in targeted or selected regions (i.e., focused mutations). The modifications can be combinatorial and can include all permutations, by substitution of all amino acids at a particular locus or at all loci or subsets thereof. The collections can include proteins of full length or shorter. The size of the collection and particular collection is determined by the user. The term collection herein is used interchangeably with the term "library" and mean the same thing.

As used herein, a "template protein" or "protein not containing the mutations" refers to a protein having a sequence of amino acids that is used for mutagenesis thereof. A template protein can be the sequence of a wild-type protein, or it can be the sequence of a variant protein, for which additional mutations are made.

As used herein, "select" or grammatical variations thereof refers to picking or choosing a protein based on one or more activities of the protein. The selection can be based on the absolute activity of the protein, or selection can be based on a comparison of the relative activity of the protein compared to another protein under different conditions, the same protein under different conditions, or a different protein under different conditions.

As used herein, "identify" and grammatical variations thereof refer to the recognition of or knowledge of a protein that has a defined activity under desired conditions. Typically, in the methods herein, the protein is identified by its preferential binding under conditions that simulate a diseased environment compared to a non-diseased or normal physiologic environment.

As used herein, a molecule that is labeled for detection or separation means that the molecule, such as an antibody or protein, is associated with a detectable label, such as a fluorophore, or is associated with a tag or other moiety, such as for purification or isolation or separation. Detectably labeled refers to a molecule that is labeled for detection or separation.

As used herein, epitope tag refers to a short stretch of amino acid residues corresponding to an epitope to facilitate subsequent biochemical and immunological analysis of the epitope tagged protein or peptide. Epitope tagging can be achieved by adding the sequence of the epitope tag to a protein-encoding sequence in an appropriate expression vector. Epitope tagged proteins can be affinity purified using highly specific antibodies raised against the tags.

As used herein, homogeneous with reference to a reaction mixture means that the reactants are in the liquid phase as a mixture, including as a solution or suspension.

As used herein, heterogeneous with reference to a reaction mixture means that the reactants are in a solid phase or are in a liquid phase as a mixture, including as a solution or suspension. An example of a heterogeneous reaction mixture is an ELISA assay.

As used herein, a "variant protein" "modified protein," or "mutein protein", or variations thereof, refers to a polypeptide (protein) that has one or more modifications in primary sequence compared to a wild-type or template protein. The one or more mutations can be one or more amino acid replacements (substitutions), insertions, deletions and any combination thereof. A modified protein polypeptide includes those with 1, 2, 3, 4, 5, 6, 7, 8, 9, 10, 11, 12, 13, 14, 15, 16, 17, 18, 19, 20, or more modified positions. A modified protein can be a full-length protein, such as a full-length antibody or can be an antibody fragment thereof. A modified protein typically has 60%, 70%, 80%, 85%, 90%, 91%, 92%, 93%, 94%, 95%, 96%, 97%, 98%, 99% or more sequence identity to a corresponding sequence of amino acids of a wildtype or scaffold protein not containing the mutations.

As used herein, reference to a "critical amino acid residue" refers to a residue in a protein that, when changed (e.g. by amino acid replacement), reduces or ablates the activity of the protein. Typically, the activity is reduced less than 70%, 60%, 50%, 40%, 30%, 20%, 10% or less than the activity of the unmodified protein that does not contain the changed or replaced amino acid.

As used herein, reference to a "key residue" refers to a residue that is near to or adjacent to a critical amino acid position, and that when changed (e.g. by amino acid replacement) does not result in a protein that exhibits an undesired or predetermined activity or condition, for example, reduced or no expression of the protein or activity under a condition that is not desired (e.g. activity at pH 7.4 but no pH 6.0). Hence, key residues are residues that, when changed, are expressed and exhibit a desired activity.

As used herein, activity refers to a functional activity or activities of a polypeptide or portion thereof associated with a full-length (complete) protein. Functional activities include, but are not limited to, biological activity, catalytic or enzymatic activity, antigenicity (ability to bind to or compete with a polypeptide for binding to an anti-polypeptide antibody), immunogenicity, ability to form multimers, and the ability to specifically bind to a receptor or ligand for the polypeptide.

As used herein, binding activity refer to characteristics of a molecule, e.g., a polypeptide, relating to whether or not, and how, it binds one or more binding partners. Binding activities include the ability to bind the binding partner(s), the affinity with which it binds to the binding partner (e.g. high affinity), the avidity with which it binds to the binding partner, the strength of the bond with the binding partner and specificity for binding with the binding partner.

As used herein, "bind," "bound" or grammatical variations thereof refers to the participation of a molecule in any attractive interaction with another molecule, resulting in a stable association in which the two molecules are in close proximity to one another. Binding includes, but is not limited to, non-covalent bonds, covalent bonds (such as reversible and irreversible covalent bonds), and includes interactions between molecules such as, but not limited to, proteins, nucleic acids, carbohydrates, lipids, and small molecules, such as chemical compounds including drugs. Exemplary of bonds are antibody-antigen interactions and receptor-ligand interactions. When an antibody "binds" a particular antigen, bind refers to the specific recognition of the antigen by the antibody, through cognate antibody-antigen interaction, at antibody combining sites. Binding also can include association of multiple chains of a polypeptide, such as antibody chains which interact through disulfide bonds.

As used herein, "specifically bind" or "immunospecifically bind" with respect to an antibody or antigen-binding fragment thereof are used interchangeably herein and refer to the ability of the antibody or antigen-binding fragment to form one or more noncovalent bonds with a cognate antigen, by noncovalent interactions between the antibody combining site(s) of the antibody and the antigen. Typically, an antibody that immunospecifically binds (or that specifically binds) to an antigen is one that binds to the antigen with an affinity constant Ka of about or $1 \times 10^7$ $M^{-1}$ or $1 \times 10^8$ $M^{-1}$ or greater (or a dissociation constant ($K_d$) of $1 \times 10^{-7}$ M or $1 \times 10^{-8}$ M or less). Affinity constants can be determined by standard kinetic methodology for antibody reactions, for example, immunoassays, surface plasmon resonance (SPR) (Rich and Myszka (2000) Curr. Opin. Biotechnol 11:54; Englebienne (1998) Analyst. 123:1599), isothermal titration calorimetry (ITC) or other kinetic interaction assays known in the art (see, e.g., Paul, ed., Fundamental Immunology, 2nd ed., Raven Press, New York, pages 332-336 (1989); see also U.S. Pat. No. 7,229,619 for a description of exemplary SPR and ITC methods). Instrumentation and methods for real time detection and monitoring of binding rates are known and are commercially available (e.g., BiaCore 2000, Biacore AB, Upsala, Sweden and GE Healthcare Life Sciences; Malmqvist (2000) Biochem. Soc. Trans. 27:335).

As used herein, the term "bind selectively" or "selectively binds," in reference to a polypeptide or an antibody provided herein, means that the polypeptide or antibody binds with an epitope, antigen or substrate without substantially binding to another epitope, antigen or substrate. Typically, an antibody or fragment thereof that selectively binds to a selected epitope specifically binds to the epitope, such as with an affinity constant Ka of about or $1 \times 10^7$ $M^{-1}$ or $1 \times 10^8$ $M^{-1}$ or greater.

As used herein, "affinity" or "binding affinity" refers to the strength with which an antibody molecule or portion thereof binds to an epitope on a target protein or antigen. Affinity is often measured by equilibrium association constant ($K_A$) or equilibrium dissociation constant ($K_D$). Low-affinity antibody-antigen interaction is weak, and the molecules tend to dissociate rapidly, while high affinity antibody-antigen binding is strong and the molecules remain bound for a longer amount of time. A high antibody affinity means that the antibody specifically binds to a target protein with an equilibrium association constant ($K_A$) of greater than or equal to about $10^6$ $M^{-1}$, greater than or equal to about $10^7$ $M^{-1}$, greater than or equal to about $10^8$ $M^{-1}$, or greater than or equal to about $10^9$ M$^{-1}$, $10^{10}$ M$^{-1}$, $10^{11}$ M$^{-1}$ or $10^{12}$ M$^{-1}$. Antibodies also can be characterized by an equilibrium dissociation constant ($K_D$) $10^{-4}$ M, $10^{-6}$ M to $10^{-7}$ M, or $10^{-8}$ M, $10^{-10}$ M, $10^{-11}$ M or $10^{-12}$ M or lower. Generally, antibodies having a nanomolar or sub-nanomolar dissociation constant are deemed to be high affinity antibodies. Such affinities can be readily determined using conventional techniques, such as by equilibrium dialysis; by using the BIAcore 2000 instrument, using general procedures outlined by the manufacturer; by radioimmunoassay using radiolabeled target antigen; or by another method known to the skilled artisan. The affinity data can be analyzed, for example, by the method of Scatchard et al., Ann N.Y. Acad. ScL, 51:660 (1949).

As used herein, "addressable" means that members are identifiable or known a priori, for example, identifiable by their address, the position in a spatial array, such as a well of a microtiter plate, or on a solid phase support, or by virtue of an identifiable or detectable label, such as by color, fluorescence, electronic signal (i.e. RF, microwave or other frequency that does not substantially alter the interaction of the molecules of interest), bar code or other symbology, chemical or other such label.

As used herein, an addressable array is one in which the members of the array are located at identifiable loci on the surface of a solid phase or directly or indirectly linked to or otherwise associated with the identifiable label, such as affixed to a microsphere or other particulate support (herein referred to as beads) and suspended in solution or spread out on a surface.

As used herein, fluorescence activated cell sorting (FACs) refers to a method of identifying or sorting cells based on fluorescence. For example, in FACS, cells are stained with or express one or more fluorescent markers. In this method, cells are passed through an apparatus that excites and detects fluorescence from the marker(s). Upon detection of fluorescence in a given portion of the spectrum by the cell, the FACS apparatus allows the separation of that cell from those not expressing that fluorescence spectrum.

As used herein, reference to a "cell surface expression system" or "cell surface display system" refers to the display or expression of a protein or portion thereof on the surface of a cell. Typically, a cell is generated that expresses proteins of interest fused to a cell-surface protein. For example, a protein is expressed as a fusion protein with a transmembrane domain.

As used herein, a "multimerization domain" refers to a sequence of amino acids that promotes stable interaction of a polypeptide molecule with one or more additional polypeptide molecules, each containing a complementary multimerization domain, which can be the same or a different multimerization domain to form a stable multimer with the first domain. Generally, a polypeptide is joined directly or indirectly to the multimerization domain. Exemplary multimerization domains include the immunoglobulin sequences or portions thereof, leucine zippers, hydrophobic regions, hydrophilic regions, and compatible protein-protein interaction domains. The multimerization domain, for example, can be an immunoglobulin constant region or domain, such as, for example, the Fc domain or portions thereof from IgG, including IgG1, IgG2, IgG3 or IgG4 subtypes, IgA, IgE, IgD and IgM and modified forms thereof.

As used herein, a human protein is one encoded by a nucleic acid molecule, such as DNA, present in the genome of a human, including all allelic variants and conservative variations thereof. A variant or modification of a protein is a human protein if the modification is based on the wildtype or prominent sequence of a human protein.

As used herein, the residues of naturally occurring α-amino acids are the residues of those 20 α-amino acids found in nature which are incorporated into protein by the specific recognition of the charged tRNA molecule with its cognate mRNA codon in humans.

As used herein, non-naturally occurring amino acids refer to amino acids that are not genetically encoded.

As used herein, nucleic acids include DNA, RNA and analogs thereof, including peptide nucleic acids (PNA) and mixtures thereof. Nucleic acids can be single or double-stranded. When referring to probes or primers, which are optionally labeled, such as with a detectable label, such as a fluorescent or radiolabel, single-stranded molecules are contemplated. Such molecules are typically of a length such that their target is statistically unique or of low copy number (typically less than 5, generally less than 3) for probing or priming a library. Generally a probe or primer contains at least 14, 16 or 30 contiguous nucleotides of sequence complementary to or identical to a gene of interest. Probes and primers can be 10, 20, 30, 50, 100 or more nucleic acids long.

As used herein, a peptide refers to a polypeptide that is from 2 to 40 amino acids in length.

As used herein, the amino acids which occur in the various sequences of amino acids provided herein are identified according to their known, three-letter or one-letter abbreviations (Table 1). The nucleotides which occur in the various nucleic acid fragments are designated with the standard single-letter designations used routinely in the art.

As used herein, an "amino acid" is an organic compound containing an amino group and a carboxylic acid group. A polypeptide contains two or more amino acids. For purposes herein, amino acids include the twenty naturally-occurring amino acids, non-natural amino acids and amino acid analogs (i.e., amino acids wherein the α-carbon has a side chain).

As used herein, "amino acid residue" refers to an amino acid formed upon chemical digestion (hydrolysis) of a polypeptide at its peptide linkages. The amino acid residues described herein are presumed to be in the "L" isomeric form. Residues in the "D" isomeric form, which are so designated, can be substituted for any L-amino acid residue as long as the desired functional property is retained by the polypeptide. NH$_2$ refers to the free amino group present at the amino terminus of a polypeptide. COOH refers to the free carboxy group present at the carboxyl terminus of a polypeptide. In keeping with standard polypeptide nomenclature described in *J. Biol. Chem.*, 243: 3557-3559 (1968), and adopted 37 C.F.R. §§1.821-1.822, abbreviations for amino acid residues are shown in Table 1:

TABLE 1

Table of Correspondence

| SYMBOL | | |
|---|---|---|
| 1-Letter | 3-Letter | AMINO ACID |
| Y | Tyr | Tyrosine |
| G | Gly | Glycine |
| F | Phe | Phenylalanine |
| M | Met | Methionine |
| A | Ala | Alanine |
| S | Ser | Serine |
| I | Ile | Isoleucine |
| L | Leu | Leucine |

TABLE 1-continued

Table of Correspondence

| SYMBOL | | |
|---|---|---|
| 1-Letter | 3-Letter | AMINO ACID |
| T | Thr | Threonine |
| V | Val | Valine |
| P | Pro | Proline |
| K | Lys | Lysine |
| H | His | Histidine |
| Q | Gln | Glutamine |
| E | Glu | Glutamic acid |
| Z | Glx | Glu and/or Gln |
| W | Trp | Tryptophan |
| R | Arg | Arginine |
| D | Asp | Aspartic acid |
| N | Asn | Asparagine |
| B | Asx | Asn and/or Asp |
| C | Cys | Cysteine |
| X | Xaa | Unknown or other |

It should be noted that all amino acid residue sequences represented herein by formulae have a left to right orientation in the conventional direction of amino-terminus to carboxyl-terminus. In addition, the phrase "amino acid residue" is broadly defined to include the amino acids listed in the Table of Correspondence (Table 1) and modified and unusual amino acids, such as those referred to in 37 C.F.R. §§1.821-1.822, and incorporated herein by reference. Furthermore, it should be noted that a dash at the beginning or end of an amino acid residue sequence indicates a peptide bond to a further sequence of one or more amino acid residues, to an amino-terminal group such as $NH_2$ or to a carboxyl-terminal group such as COOH.

As used herein, "naturally occurring amino acids" refer to the 20 L-amino acids that occur in polypeptides.

As used herein, "non-natural amino acid" refers to an organic compound that has a structure similar to a natural amino acid but has been modified structurally to mimic the structure and reactivity of a natural amino acid. Non-naturally occurring amino acids thus include, for example, amino acids or analogs of amino acids other than the 20 naturally-occurring amino acids and include, but are not limited to, the D-isostereomers of amino acids. Exemplary non-natural amino acids are described herein and are known to those of skill in the art.

As used herein, an isokinetic mixture is one in which the molar ratios of amino acids has been adjusted based on their reported reaction rates (see, e.g., Ostresh et al., (1994) *Biopolymers* 34:1681).

As used herein, modification is in reference to modification of a sequence of amino acids of a polypeptide or a sequence of nucleotides in a nucleic acid molecule and includes deletions, insertions, and replacements of amino acids and nucleotides, respectively. Methods of modifying a polypeptide are routine to those of skill in the art, such as by using recombinant DNA methodologies.

As used herein, suitable conservative substitutions of amino acids are known to those of skill in this art and can be made generally without altering the biological activity of the resulting molecule. Those of skill in this art recognize that, in general, single amino acid substitutions in non-essential regions of a polypeptide do not substantially alter biological activity (see, e.g., Watson et al. Molecular Biology of the Gene, 4th Edition, 1987, The Benjamin/Cummings Pub. co., p. 224). Such substitutions can be made in accordance with those set forth in TABLE 2 as follows:

TABLE 2

| Original residue | Exemplary conservative substitution |
|---|---|
| Ala (A) | Gly; Ser |
| Arg (R) | Lys |
| Asn (N) | Gln; His |
| Cys (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

Other substitutions also are permissible and can be determined empirically or in accord with known conservative substitutions.

As used herein, a DNA construct is a single or double stranded, linear or circular DNA molecule that contains segments of DNA combined and juxtaposed in a manner not found in nature. DNA constructs exist as a result of human manipulation, and include clones and other copies of manipulated molecules.

As used herein, a DNA segment is a portion of a larger DNA molecule having specified attributes. For example, a DNA segment encoding a specified polypeptide is a portion of a longer DNA molecule, such as a plasmid or plasmid fragment, which, when read from the 5' to 3' direction, encodes the sequence of amino acids of the specified polypeptide.

As used herein, the term polynucleotide means a single- or double-stranded polymer of deoxyribonucleotides or ribonucleotide bases read from the 5' to the 3' end. Polynucleotides include RNA and DNA, and can be isolated from natural sources, synthesized in vitro, or prepared from a combination of natural and synthetic molecules. The length of a polynucleotide molecule is given herein in terms of nucleotides (abbreviated "nt") or base pairs (abbreviated "bp"). The term nucleotides is used for single- and double-stranded molecules where the context permits. When the term is applied to double-stranded molecules it is used to denote overall length and will be understood to be equivalent to the term base pairs. It will be recognized by those skilled in the art that the two strands of a double-stranded polynucleotide can differ slightly in length and that the ends thereof can be staggered; thus all nucleotides within a double-stranded polynucleotide molecule can not be paired. Such unpaired ends will, in general, not exceed 20 nucleotides in length.

As used herein, "similarity" between two proteins or nucleic acids refers to the relatedness between the sequence of amino acids of the proteins or the nucleotide sequences of the nucleic acids. Similarity can be based on the degree of identity and/or homology of sequences of residues and the residues contained therein. Methods for assessing the degree of similarity between proteins or nucleic acids are known to those of skill in the art. For example, in one method of assessing sequence similarity, two amino acid or nucleotide sequences are aligned in a manner that yields a maximal level of identity between the sequences. "Identity" refers to the extent to which the amino acid or nucleotide sequences are invariant. Alignment of amino acid sequences, and to some extent nucleotide sequences, also can take into account conservative differences and/or frequent substitutions in amino acids (or nucleotides). Conservative differences are those that preserve the physico-chemical properties of the residues involved. Alignments can be global (alignment of the compared sequences over the entire length of the sequences and including all residues) or local (the alignment of a portion of the sequences that includes only the most similar region or regions).

"Identity" per se has an art-recognized meaning and can be calculated using published techniques. (See, e.g.: *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and Sequence Analysis Primer, Gribskov, M. and Devereux, J., eds., M Stockton Press, New York, 1991). While there exists a number of methods to measure identity between two polynucleotide or polypeptides, the term "identity" is well known to skilled artisans (Carrillo, H. & Lipton, D., *SIAM J Applied Math* 48:1073 (1988)).

As used herein, homologous (with respect to nucleic acid and/or amino acid sequences) means about greater than or equal to 25% sequence homology, typically greater than or equal to 25%, 40%, 50%, 60%, 70%, 80%, 85%, 90% or 95% sequence homology; the precise percentage can be specified if necessary. For purposes herein the terms "homology" and "identity" are often used interchangeably, unless otherwise indicated. In general, for determination of the percentage homology or identity, sequences are aligned so that the highest order match is obtained (see, e.g.: *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; Carrillo et al. (1988) *SIAM J Applied Math* 48:1073). By sequence homology, the number of conserved amino acids is determined by standard alignment algorithms programs, and can be used with default gap penalties established by each supplier. Substantially homologous nucleic acid molecules would hybridize typically at moderate stringency or at high stringency all along the length of the nucleic acid of interest. Also contemplated are nucleic acid molecules that contain degenerate codons in place of codons in the hybridizing nucleic acid molecule.

Whether any two molecules have nucleotide sequences or amino acid sequences that are at least 60%, 70%, 80%, 85%, 90%, 95%, 96%, 97%, 98% or 99% "identical" or "homologous" can be determined using known computer algorithms such as the "FASTA" program, using for example, the default parameters as in Pearson et al. (1988) *Proc. Natl. Acad. Sci. USA* 85:2444 (other programs include the GCG program package (Devereux, J. et al., *Nucleic Acids Research* 12(I):387 (1984)), BLASTP, BLASTN, FASTA (Altschul, S. F. et al., *J Molec Biol* 215:403 (1990)); Guide to Huge Computers, Martin J. Bishop, ed., Academic Press, San Diego, 1994, and Carrillo et al. (1988) *SIAM J Applied Math* 48:1073). For example, the BLAST function of the National Center for Biotechnology Information database can be used to determine identity. Other commercially or publicly available programs include, DNAStar "MegAlign" program (Madison, Wis.) and the University of Wisconsin Genetics Computer Group (UWG) "Gap" program (Madison Wis.). Percent homology or identity of proteins and/or nucleic acid molecules can be determined, for example, by comparing sequence information using a GAP computer program (e.g., Needleman et al. (1970) *J. Mol. Biol.* 48:443, as revised by Smith and Waterman ((1981) *Adv. Appl. Math.* 2:482). Briefly, the GAP program defines simi-larity as the number of aligned symbols (i.e., nucleotides or amino acids), which are similar, divided by the total number of symbols in the shorter of the two sequences. Default parameters for the GAP program can include: (1) a unary comparison matrix (containing a value of 1 for identities and 0 for non-identities) and the weighted comparison matrix of Gribskov et al. (1986) *Nucl. Acids Res.* 14:6745, as described by Schwartz and Dayhoff, eds., *ATLAS OF PROTEIN SEQUENCE AND STRUCTURE*, National Biomedical Research Foundation, pp. 353-358 (1979); (2) a penalty of 3.0 for each gap and an additional 0.10 penalty for each symbol in each gap; and (3) no penalty for end gaps.

Therefore, as used herein, the term "identity" or "homology" represents a comparison between a test and a reference polypeptide or polynucleotide. As used herein, the term at least "90% identical to" refers to percent identities from 90 to 99.99 relative to the reference nucleic acid or amino acid sequence of the polypeptide. Identity at a level of 90% or more is indicative of the fact that, assuming for exemplification purposes a test and reference polypeptide length of 100 amino acids are compared. No more than 10% (i.e., 10 out of 100) of the amino acids in the test polypeptide differs from that of the reference polypeptide. Similar comparisons can be made between test and reference polynucleotides. Such differences can be represented as point mutations randomly distributed over the entire length of a polypeptide or they can be clustered in one or more locations of varying length up to the maximum allowable, e.g. 10/100 amino acid difference (approximately 90% identity). Differences are defined as nucleic acid or amino acid substitutions, insertions or deletions. At the level of homologies or identities above about 85-90%, the result should be independent of the program and gap parameters set; such high levels of identity can be assessed readily, often by manual alignment without relying on software.

As used herein, an aligned sequence refers to the use of homology (similarity and/or identity) to align corresponding positions in a sequence of nucleotides or amino acids. Typically, two or more sequences that are related by 50% or more identity are aligned. An aligned set of sequences refers to 2 or more sequences that are aligned at corresponding positions and can include aligning sequences derived from RNAs, such as ESTs and other cDNAs, aligned with genomic DNA sequence.

As used herein, "primer" refers to a nucleic acid molecule that can act as a point of initiation of template-directed DNA synthesis under appropriate conditions (e.g., in the presence of four different nucleoside triphosphates and a polymerization agent, such as DNA polymerase, RNA polymerase or reverse transcriptase) in an appropriate buffer and at a suitable temperature. It will be appreciated that certain nucleic acid molecules can serve as a "probe" and as a "primer." A primer, however, has a 3' hydroxyl group for extension. A primer can be used in a variety of methods, including, for example, polymerase chain reaction (PCR), reverse-transcriptase (RT)-PCR, RNA PCR, LCR, multiplex PCR, panhandle PCR, capture PCR, expression PCR, 3' and 5' RACE, in situ PCR, ligation-mediated PCR and other amplification protocols.

As used herein, "primer pair" refers to a set of primers that includes a 5' (upstream) primer that hybridizes with the 5' end of a sequence to be amplified (e.g. by PCR) and a 3' (downstream) primer that hybridizes with the complement of the 3' end of the sequence to be amplified.

As used herein, "specifically hybridizes" refers to annealing, by complementary base-pairing, of a nucleic acid molecule (e.g. an oligonucleotide) to a target nucleic acid molecule. Those of skill in the art are familiar with in vitro and in vivo parameters that affect specific hybridization, such as length and composition of the particular molecule. Parameters particularly relevant to in vitro hybridization further include annealing and washing temperature, buffer composition and salt concentration. Exemplary washing conditions for removing non-specifically bound nucleic acid molecules at high stringency are 0.1×SSPE, 0.1% SDS, 65° C., and at medium stringency are 0.2×SSPE, 0.1% SDS, 50° C. Equivalent stringency conditions are known in the art. The skilled person can readily adjust these parameters to achieve specific hybridization of a nucleic acid molecule to a target nucleic acid molecule appropriate for a particular application.

As used herein, substantially identical to a product means sufficiently similar so that the property of interest is sufficiently unchanged so that the substantially identical product can be used in place of the product.

As used herein, it also is understood that the terms "substantially identical" or "similar" varies with the context as understood by those skilled in the relevant art.

As used herein, an allelic variant or allelic variation references any of two or more alternative forms of a gene occupying the same chromosomal locus. Allelic variation arises naturally through mutation, and can result in phenotypic polymorphism within populations. Gene mutations can be silent (no change in the encoded polypeptide) or can encode polypeptides having an altered amino acid sequence. The term "allelic variant" also is used herein to denote a protein encoded by an allelic variant of a gene. Typically the reference form of the gene encodes a wildtype form and/or predominant form of a polypeptide from a population or single reference member of a species. Typically, allelic variants, which include variants between and among species typically have at least 80%, 90% or greater amino acid identity with a wildtype and/or predominant form from the same species; the degree of identity depends upon the gene and whether comparison is interspecies or intraspecies. Generally, intraspecies allelic variants have at least about 80%, 85%, 90% or 95% identity or greater with a wildtype and/or predominant form, including 96%, 97%, 98%, 99% or greater identity with a wildtype and/or predominant form of a polypeptide. Reference to an allelic variant herein generally refers to variations in proteins among members of the same species.

As used herein, "allele," which is used interchangeably herein with "allelic variant" refers to alternative forms of a gene or portions thereof. Alleles occupy the same locus or position on homologous chromosomes. When a subject has two identical alleles of a gene, the subject is said to be homozygous for that gene or allele. When a subject has two different alleles of a gene, the subject is said to be heterozygous for the gene. Alleles of a specific gene can differ from each other in a single nucleotide or several nucleotides, and can include substitutions, deletions and insertions of nucleotides. An allele of a gene also can be a form of a gene containing a mutation.

As used herein, species variants refer to variants in polypeptides among different species, including different mammalian species, such as mouse and human.

As used herein, a splice variant refers to a variant produced by differential processing of a primary transcript of genomic DNA that results in more than one type of mRNA.

As used herein, a peptidomimetic is a compound that mimics the conformation and certain stereochemical features of the biologically active form of a particular peptide. In general, peptidomimetics are designed to mimic certain desirable properties of a compound, but not the undesirable properties, such as flexibility, that lead to a loss of a biologically active conformation and bond breakdown. Peptidomimetics can be prepared from biologically active compounds by replacing certain groups or bonds that contribute to the undesirable properties with bioisosteres. Bioisosteres are known to those of skill in the art. For example the methylene bioisostere $CH_2S$ has been used as an amide replacement in enkephalin analogs (see, e.g., Spatola (1983) pp. 267-357 in Chemistry and Biochemistry of Amino Acids, Peptides, and Proteins, Weinstein, Ed. volume 7, Marcel Dekker, New York). Morphine, which can be administered orally, is a compound that is a peptidomimetic of the peptide endorphin. For purposes herein, cyclic peptides are included among peptidomimetics as are polypeptides in which one or more peptide bonds is/are replaced by a mimic.

As used herein, a polypeptide comprising a specified percentage of amino acids set forth in a reference polypeptide refers to the proportion of contiguous identical amino acids shared between a polypeptide and a reference polypeptide. For example, an isoform that comprises 70% of the amino acids set forth in a reference polypeptide having a sequence of amino acids set forth in SEQ ID NO:XX, which recites 147 amino acids, means that the reference polypeptide contains at least 103 contiguous amino acids set forth in the amino acid sequence of SEQ ID NO:XX.

As used herein, the term promoter means a portion of a gene containing DNA sequences that provide for the binding of RNA polymerase and initiation of transcription. Promoter sequences are commonly, but not always, found in the 5' non-coding region of genes.

As used herein, isolated or purified polypeptide or protein or biologically-active portion thereof is substantially free of cellular material or other contaminating proteins from the cell or tissue from which the protein is derived, or substantially free from chemical precursors or other chemicals when chemically synthesized. Preparations can be determined to be substantially free if they appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound, however, can be a mixture of stereoisomers. In such instances, further purification might increase the specific activity of the compound.

The term substantially free of cellular material includes preparations of proteins in which the protein is separated from cellular components of the cells from which it is isolated or recombinantly-produced. In one embodiment, the term substantially free of cellular material includes preparations of protease proteins having less that about 30% (by dry weight) of non-protease proteins (also referred to herein as a contaminating protein), generally less than about 20% of non-protease proteins or 10% of non-protease proteins or less that about 5% of non-protease proteins. When the protease protein or active portion thereof is recombinantly produced, it also is substantially free of culture medium, i.e., culture medium represents less than about or at 20%, 10% or 5% of the volume of the protease protein preparation.

As used herein, the term substantially free of chemical precursors or other chemicals includes preparations of protease proteins in which the protein is separated from chemical precursors or other chemicals that are involved in the synthesis of the protein. The term includes preparations of protease proteins having less than about 30% (by dry weight) 20%, 10%, 5% or less of chemical precursors or non-protease chemicals or components.

As used herein, synthetic, with reference to, for example, a synthetic nucleic acid molecule or a synthetic gene or a synthetic peptide refers to a nucleic acid molecule or polypeptide molecule that is produced by recombinant methods and/or by chemical synthesis methods.

As used herein, production by recombinant means by using recombinant DNA methods means the use of the well known methods of molecular biology for expressing proteins encoded by cloned DNA.

As used herein, vector (or plasmid) refers to discrete elements that are used to introduce a heterologous nucleic acid into cells for either expression or replication thereof. The vectors typically remain episomal, but can be designed to effect integration of a gene or portion thereof into a chromosome of the genome. Also contemplated are vectors that are artificial chromosomes, such as yeast artificial chromosomes and mammalian artificial chromosomes. Selection and use of such vehicles are well known to those of skill in the art.

As used herein, an expression vector includes vectors capable of expressing DNA that is operatively linked with regulatory sequences, such as promoter regions, that are capable of effecting expression of such DNA fragments. Such additional segments can include promoter and terminator sequences, and optionally can include one or more origins of replication, one or more selectable markers, an enhancer, a polyadenylation signal, and the like. Expression vectors are generally derived from plasmid or viral DNA, or can contain elements of both. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome.

As used herein, vector also includes "virus vectors" or "viral vectors." Viral vectors are engineered viruses that are operatively linked to exogenous genes to transfer (as vehicles or shuttles) the exogenous genes into cells.

As used herein, an adenovirus refers to any of a group of DNA-containing viruses that cause conjunctivitis and upper respiratory tract infections in humans. As used herein, naked DNA refers to histone-free DNA that can be used for vaccines and gene therapy. Naked DNA is the genetic material that is passed from cell to cell during a gene transfer processed called transformation. In transformation, purified or naked DNA is taken up by the recipient cell which will give the recipient cell a new characteristic or phenotype.

As used herein, operably or operatively linked when referring to DNA segments means that the segments are arranged so that they function in concert for their intended purposes, e.g., transcription initiates in the promoter and proceeds through the coding segment to the terminator.

As used herein, protein binding sequence refers to a protein or peptide sequence that is capable of specific binding to other protein or peptide sequences generally, to a set of protein or peptide sequences or to a particular protein or peptide sequence.

As used herein the term assessing is intended to include quantitative and qualitative determination in the sense of obtaining an absolute value for the activity of a protein, and also of obtaining an index, ratio, percentage, visual or other value indicative of the level of the activity. Assessment can be direct or indirect and the chemical species actually detected need not of course be the activity product itself but can for example be a derivative thereof or some further substance.

As used herein, a control refers to a sample that is substantially identical to the test sample, except that it is not treated with a test parameter, or, if it is a sample plasma sample, it can be from a normal volunteer not affected with the condition of interest. A control also can be an internal control.

As used herein, the singular forms "a," "an" and "the" include plural referents unless the context clearly dictates otherwise. Thus, for example, reference to a compound, comprising "an extracellular domain" includes compounds with one or a plurality of extracellular domains.

As used herein, ranges and amounts can be expressed as "about" a particular value or range. About also includes the exact amount. Hence "about 5 bases" means "about 5 bases" and also "5 bases."

As used herein, "optional" or "optionally" means that the subsequently described event or circumstance does or does not occur, and that the description includes instances where said event or circumstance occurs and instances where it does not. For example, an optionally substituted group means that the group is unsubstituted or is substituted.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:1726).

B. Methods to Identify Conditionally Active Molecules

Provided herein are methods for identifying or selecting a conditionally active molecule, such as a therapeutic protein, that is more active in a diseased microenvironment than a normal tissue microenvironment or vice versa. In particular, the method is for identifying a molecule, such as a therapeutic protein, that is more active in a tumor microenvironment than in a normal microenvironment or vice versa. In the methods, the activity of a molecule, such as a therapeutic protein, is tested under a first set of conditions, and the activity of the molecule is tested under a second set of conditions in which reduced activity is desired compared to the activity under the first set of conditions. A molecule, such as a protein, can be identified that is active or more active under the first set of conditions than the second set of conditions, such that a molecule is identified that is conditionally active under a predetermined set of conditions. Typically, in the method, the first set of conditions mimics or simulates conditions that exist in vivo in a diseased microenvironment, such as a tumor microenvironment. The second set of conditions mimics or simulates physiologic conditions in normal tissues or cells.

Hence, the methods herein are performed in an in vitro assay that is designed to simulate or mimic predetermined conditions that exist in a diseased microenvironment and a normal tissue microenvironment. Predetermined conditions include, for example, conditions such as pH, temperature, $O_2$ concentration and lactate concentration. For example, a predetermined first set of conditions can include conditions that exist in a tumor microenvironment, and a second set of conditions can include conditions that exist in a normal environment. Hence, molecules with biological efficacy, such as therapeutic proteins, can be identified that exhibit greater activity in a diseased environment, such as a tumor, than in surrounding normal tissue. Thus, the methods provided herein can be used to identify modified molecules, such as therapeutic proteins, with conditional activity under a set of conditions.

This can be advantageous by targeting therapy only to diseased tissues, such as tumor tissues, in order to reduce or prevent side effects, including local and systemic side effects. Identified therapeutic proteins can be used as cancer therapeutics while reducing side effects associated with systemic exposure. Therapeutic proteins that are associated with reduced side effects can be used at higher dosing regimens, and can have improved efficacy and safety. Side effects that can be reduced include any undesirable non-therapeutic effect, such as nausea, emesis, chest tightness, headache, and related cardiovascular effects such as blood pressure instability and arterial constriction, dermal toxicity, bone marrow suppression, cardiotoxicity, hair loss, renal dysfunctions, stomatitis, anemia, seizures, immune reactions such as acute anaphylaxis, serum sickness, generation of antibodies, infections, cancer, autoimmune disease and cardiotoxicity.

In the first step of the method, one or more molecules or proteins are selected to be tested in the methods provided herein. The molecule(s) can be any molecule(s) with biological efficacy or any modified molecule with biological efficacy, including a small molecule, peptide, protein, enzyme, antibody or other biomolecule. The molecule(s) can be unmodified or include any modifications described herein. In some examples, a library of modified molecules are prepared. Methods of preparing test molecules are known to the skilled artisan. Section D herein describes methods of cloning, modifying and preparing proteins, including antibodies. Further, methods of mutagenesis and generation of libraries or collections of variant molecules is described herein and is known to one of skill in the art using standard recombinant DNA techniques.

After a molecule or molecules, such as a protein or proteins, are selected and prepared, they are tested or screened for an activity or property under a first set of conditions and under a different second set of conditions. The first and second set of conditions are conditions that simulate or mimic those that exist physiologically in diseased or normal tissues or microenvironments, respectively. For example, diseased tissue or diseased microenvironment conditions can be those that exist in a tumor microenvironment. Exemplary of such conditions include, for example, chemical conditions, such as pH and chemical concentrations such as concentration of $O_2$ or lactate; and physical conditions, such as temperature and pressure. Hence, the first and second conditions can differ in any one or more of pH, concentration or level of $O_2$ or lactate or other chemical condition, temperature and/or pressure.

Testing of the molecules can be performed using any in vitro or in vivo method that can detect or distinguish an activity or property of the tested molecule or protein. Typically, testing is performed in vitro. The particular assay that is used is dependent on the tested molecule or protein. Examples of methods include any methods described herein or known to one of skill in the art, and include biochemical assays and/or cell based assays.

In one example, the molecules that are tested can be pooled and screened. In another example, the tested molecules can be physically separated and screened individually, such as by formatting in arrays, such as addressable arrays. Also testing of the molecule(s) under the second set of conditions can occur before, after, or simultaneously with the screening under the first set of conditions. For example, molecules can be screened and/or selected under the first set and second set of conditions simultaneously, or molecules can be screened and/or selected under the first set of conditions and then be screened and/or selected under a second set of conditions.

After molecules are tested under both sets of conditions, the activities of the molecules under one or both conditions are assessed in order to identify resulting molecules that are more active under a first condition than a second condition. The activity can include any observable biological, biochemical or biophysical phenomenon, such as, for example, luminescence, enzymatic activity or molecular interactions such as binding to a cognate biomolecule. The comparison of activities can be qualitative or quantitative.

In one example, after molecules are tested under both sets of conditions, the activities of each molecule under both set of conditions are compared to identify a molecule that is more active under the first condition than the second condition (i.e. that is conditionally active).

In other examples, conditionally active molecules are identified by screening and/or selection under the two different conditions in steps. For example, conditionally active molecules can be identified by first selecting molecules that are active under the first set of conditions and/or excluding molecules that are inactive under a first set of conditions (positive selection). Subsequent rounds of screening can be performed under the second set of conditions, and molecules identified that exhibit greater activity under the first set of conditions than the second set of conditions. In another example, conditionally active molecules can be identified by first excluding molecules that are active under the second set of conditions (negative selection). In an example of negative selection, molecules that do not meet a certain criteria, such as above or below a threshold for activity, are eliminated from subsequent rounds of screening and/or selection. Subsequent rounds of screening can be performed under the first set of conditions. Hence, molecules are identified that exhibit activity only under the first set of conditions. Thus, the molecules that are screened under first and/or second set of conditions can include all or a subset of the molecules that are screened under other set of conditions. Positive and negative selection can be repeated until a molecule with a predetermined conditional activity is identified.

The method can be performed a plurality of times, whereby the steps of the method are repeated 1, 2, 3, 4, or 5 times. For example, test molecules, for example protein variants, that are identified as exhibiting increased activity under the first set of conditions compared to the second set of conditions can be rescreened to confirm the activity. The method provided herein also is iterative. In one example, after the method is performed, any identified conditionally active molecules can be modified or further modified to increase or optimize the conditional activity. For example, a secondary library can be created by introducing additional modifications in a first identified conditionally active protein. For example, modifications that were identified as increasing conditional activity can be combined. The secondary library can be tested using the assays and methods described herein. In another example of an iterative aspect of the method, molecules that are identified as not exhibiting conditional activity, such that they are not active or do not have increased activity under the first set of conditions, can be further modified and retested for conditional activity. The further modifications can be targeted near particular regions (e.g. particular amino acid residues) associated with activity and/or stability of the molecule.

A description of the steps of the method and components of the method are provided in the subsections that follow.

1. Therapeutic Proteins

The tested molecule for use in practice of the method to identify a conditionally active molecule can be a therapeutic protein that is a protein known to treat or ameliorate one or more particular diseases or conditions. For example, the therapeutic protein is a protein known to treat or ameliorate a tumor or cancer. In some examples, the tested molecules are variants of a therapeutic protein that include one or more modifications, such as amino acid replacement(s), insertion(s) or deletion(s). Hence, the method can be used to identify variant therapeutic proteins that are conditionally active in a diseased microenvironment, such as a tumor environment, compared to a normal tissue or cell. Exemplary therapeutic proteins are tumor or cancer therapeutics, such that the method can be used to identify conditionally active therapeutics that are more active in a tumor microenvironment than a normal microenvironment.

In some examples of the method, the method is a high throughput screening method to identify molecules that exhibit altered activity in a tumor microenvironment compared to under normal physiologic conditions. Thus, the method can be used to evolve the activity, e.g. binding activity, of a therapeutic protein. In particular, the method can be used to screen for variants of existing therapeutic proteins to identify those that are preferentially active in the disease microenvironment of a tumor, but not in normal tissues. For example, therapeutic proteins that are associated with known toxicities can be mutagenized and screened in the assays provided herein to identify variant proteins with reduced side effects by virtue of the preferential activity in the tumor microenvironment only, compared to the therapeutic agent that does not contain the mutations. Thus, the method can be used to identify conditionally active biologics (CABs). The resulting identified CABs can be candidate cancer therapeutics.

a. Tumor or Cancer Therapeutics

In some examples, the test molecule is a therapeutic protein that is a variant of a known clinical candidate cancer therapeutic or of an existing cancer therapeutic. In some examples, the therapeutic protein is not angiostatin. Variants of known cancer therapeutic proteins can be screened in the methods provided herein to identify evolved therapeutic proteins that exhibit activity higher in a diseased microenvironment, such as a tumor microenvironment, than in a normal environment. For example, if the activity is binding activity, then the methods provided herein can be used to identify conditionally active cancer therapeutic proteins that preferentially bind in the tumor or cancer microenvironment compared to a normal microenvironment.

For example, the therapeutic protein used as a test molecule or as a scaffold to generate variants can be a protein that interacts with a target protein that is a point of intervention in the treatment of a tumor or cancer. Such cancer-promoting target proteins include any ligand, receptor, enzyme or other agent that is associated with proliferation, angiogenesis or cell growth properties of cancer cells and tumors. The target protein can be selected based on known targets of therapeutic intervention. The target can be a cognate binding partner or surrogate protein antigen for the therapeutic protein. Targets for known cancer therapeutics are known. Exemplary of such target proteins are any set forth in Table 3 under "protein" heading, including, but not limited to, EGFR, HER2, CD20, VEGF-A, EpCAM, CD3, CD33, CD80, CTLA-4, α5β1 integrin, Mesothelin, or IGF-1R. For example, an exemplary therapeutic molecule is a molecule or protein that interacts with or has a therapeutic effect associated with interaction with EGFR.

Exemplary tumor or cancer therapeutic proteins that can be used to generate modified proteins and screened in the assays herein are set forth in Table 3. The Table also sets forth the target protein, such as cognate or surrogate protein antigen, of the cancer therapeutic. Hence, in the methods provided herein the cancer therapeutic protein or modified cancer therapeutic protein(s) can be screened for binding to their cognate target protein, such as a surrogate protein ligand and/or can be screened for effecting altered activity of the target protein. Proteins, such as mutant proteins, identified or selected that are conditionally active in a tumor microenvironment, are those that exhibit preferential binding activity and/or other activity under in vitro conditions that simulate the tumor microenvironment compared to normal physiologic conditions. In some examples, modified proteins also can be identified that exhibit increased activity in the tumor microenvironment compared to the unmodified protein, for example a therapeutic or parent control antibody not containing the mutations.

TABLE 3

| | | Therapeutic | | | |
|---|---|---|---|---|---|
| | | Variable Domain | Full Length | Ligand | |
| Name | Format | (SEQ ID NO) | (SEQ ID NO) | Protein | SEQ ID NO |
| Cetuximab (IMC-C225; Erbitux ®) | Mouse/human chimeric IgG1 | | HC: 2 LC: 1 | EGFR (extracellular domain) | 50 |
| Trastuzumab (Herceptin ®) | Humanized IgG4 | HC: 29 LC: 30 | HC: 74 LC: 75 | HER2/Neu (extracellular domain) | 51 |

TABLE 3-continued

| Name | Format | Therapeutic Variable Domain (SEQ ID NO) | Full Length (SEQ ID NO) | Ligand Protein | SEQ ID NO |
|---|---|---|---|---|---|
| Rituximab (Rituxan ®; MabThera ®) | Mouse/human chimeric IgG1 | HC: 31 LC: 32 | HC: 76 LC: 77 | CD20 (large extracellular loop) | 52 |
| Bevacizumab (Avastin ®) | Humanized IgG1 | HC: 33 LC: 34 | HC: 78 LC: 79 | VEGF-A | 53 |
| Alemtuzumab (Campath ®; Campath-1H ®; Mabcampath ®) | Humanized IgG1 | HC: 35 LC: 36 | HC: 80 LC: 81 | CD52 (extracellular domain) | 54 |
| Panitumumab (ABX-EGF; Vectibix ®) | Human IgG2 | HC: 37 LC: 38 | HC: 82 LC: 83 | EGFR (extracellular domain) | 50 |
| Ranibizumab (Lucentis ®) | Humanized IgG1 Fab | HC: 39 LC: 40 | HC: 84 LC: 85 | VEGF-A | 53 |
| Ibritumomab | Mouse IgG1 | | HC: 41 LC: 42 | CD20 (large extracellular loop) | 52 |
| Ibritumomab tiuxetan (Zevalin ®) | Mouse IgG1 coupled to tiuxetan | | HC: 41 LC: 42 | CD20 (large extracellular loop) | 52 |
| Tositumomab | Mouse IgG2a | | HC: 43 LC: 44 | CD20 (large extracellular loop) | 52 |
| Iodine I 131 Tositumomab (BEXXAR ®) | Mouse IgG2a coupled to Iodine-131 | | HC: 43 LC: 44 | CD20 (large extracellular loop) | 52 |
| Catumaxomab (Removab ®) | Hybrid Ab: Mouse IgG2a Rat IgG2b | | | EpCAM(extracellular domain) CD3 (extracellular domain): γ chain ζ chain ε chain | 55 56 57 58 |
| Gemtuzumab | Humanized IgG4 | | | CD33 (extracellular domain) | 59 |
| Gemtuzumab ozogamicine (Mylotarg ®) | Humanized IgG4 coupled to calicheamicin | | | CD33 (extracellular domain) | 59 |
| Abatacept (CTLA4-Ig; Orencia ®) | Soluble fusion protein: Extracellular domain of human CTLA-4 linked to modified Fc human IgG1. | | 68 | CD80 (extracellular domain) CD86 (extracellular domain) | 60 61 |
| Belatacept (L104EA29YIg; LEA29Y; LEA) | Soluble fusion protein: Extracellular domain of human CTLA-4 linked to modified Fc human IgG1 | | 69 | CD80 (extracellular domain) CD86 (extracellular domain) | 60 61 |
| Ipilimumab (MDX-010; MDX-101) | Human IgG1 | | | CTLA-4 (extracellular domain) | 62 |
| Tremelimumab (ticilimumab; CP-675,206) | Human IgG4 | | | CTLA-4 (extracellular domain) | 62 |
| PRS-010 | Engineered human lipocalin protein (US20090042785) | | | CTLA-4 (extracellular domain) | 62 |
| PRS-050 | Engineered human lipocalin protein (U.S. Pat. No. 7,585,940; US20090305982) | | | VEGF-A | 53 |

TABLE 3-continued

| Name | Format | Variable Domain (SEQ ID NO) | Full Length (SEQ ID NO) | Therapeutic Ligand Protein | SEQ ID NO |
|---|---|---|---|---|---|
| Aflibercept (VEGF Trap, AVE005) | Soluble fusion protein: human extracellular domains of VEGFR-1 and VEGFR-2 with human IgG Fc (Holash et al., (2002) PNAS 99: 11393-11398) | | | VEGF-A<br>PLGF | 53<br>63 |
| Volociximab (M200) | Chimeric (82% human, 18% murine) IgG4 | | HC: 45<br>LC: 46 | α5β1 integrin (extracellular domain):<br>α5<br>β1 | <br><br><br>64<br>65 |
| F200 | Chimeric (human/murine) IgG4 Fab fragment of Volociximab (M200) | | HC: 47<br>LC: 46 | α5β1 integrin (extracellular domain):<br>α5<br>β1 | <br><br><br>64<br>65 |
| MORAb-009 | Mouse/human chimeric IgG1 (US20050054048) | | | Mesothelin (extracellular domain) | 66 |
| SS1P (CAT-5001) | Soluble fusion protein: Anti-mesothelin Fv linked to a truncated Pseudomonas exotoxin A (US20070189962) | | | Mesothelin (extracellular domain) | 66 |
| Cixutumumab (IMC-A12) | Human IgG1 | | HC: 48<br>LC: 49 | IGF-1R (extracellular domain) | 67 |
| Matuzumab (EMD72000) | Humanized IgG1 (Kim (2005) Curr Opin Mol Ther 6: 96-103) | | | EGFR (extracellular domain) | |
| Nimotuzumab (h-R3) | Humanized IgG2a (Spicer (2005) Curr Opin Mol Ther 7: 182-191) | | | EGFR (extracellular domain) | |
| Zalutumumab (HuMax-EGFR) | Human IgG1 (Lammerts van Bueren et al. (2008) PNAS 105: 6109-14) | | | EGFR (extracellular domain) | |
| Necitumumab IMC-11F8 | Human IgG1 (Li et al. (2008) Structure 16: 216-227) | | | EGFR (extracellular domain) | |
| mAb806/ch806 | IgG1 (Li et al., (2007) J Clin Invest 117: 346-352) | | | EGFR (extracellular domain) | |
| Sym004 | Chimeric/humanized IgG1 (Pederson et al. 2010 Cancer Res 70: 588-597) | | | EGFR (extracellular domain) | |
| mAb-425 | IgG2a | | | EGFR (extracellular domain) | | b. Generating Libraries of Modified Proteins

The therapeutic protein used in the method can be an unmodified protein that is an existing therapeutic. Libraries or collections of existing therapeutics also can be screened. In other examples, the therapeutic protein includes modified proteins, such as modified peptides, modified enzymes, modified antibodies or other modified polypeptides. In some examples, the modified therapeutic or library containing modified therapeutic protein is not or does not contain a modified angiostatin. In examples where modified therapeutics are used in practice of the methods, assays using an unmodified protein can be performed as positive controls, or to compare with results from assays performed with modified proteins.

Therapeutic proteins can be modified by any process known to one of skill in the art that can alter the structure of a protein. Examples of modifications include replacement, addition, and deletion of one or more amino acids of the protein to form libraries or collections of modified therapeutic proteins. The libraries or collections can be screened in assays provided herein under conditions that simulate a diseased microenvironment and a normal microenvironment to identify conditionally active therapeutic proteins.

It is within the level of one of skill in the art to generate modified or variant proteins for use in the methods herein. Methods of mutagenesis are well known in the art and include, for example, site-directed mutagenesis such as for example QuikChange (Stratagene) or saturation mutagenesis. Mutagenesis methods include, but are not limited to, site-mediated mutagenesis, PCR mutagenesis, cassette mutagenesis, site-directed mutagenesis, random point mutagenesis, mutagenesis using uracil containing templates, oligonucleotide-directed mutagenesis, phosphorothioate-modified DNA mutagenesis, mutagenesis using gapped duplex DNA, point mismatch repair, mutagenesis using repair-deficient host strains, restriction-selection and restriction-purification, deletion mutagenesis, mutagenesis by total gene synthesis, double-strand break repair, and many others known to persons of skill. In the methods herein, mutagenesis can be effected across the full length of a protein or within a region of a protein. The mutations can be made rationally or randomly.

If a test molecule is a protein, the modifications can include replacement of one or more amino acids of the protein. In some examples, the modifications are selected at random. In some examples, the modifications are selected to result in molecules with conditional activity. For example, rational mutagenesis includes mutation of amino acids known in the art or identified to be important for activity and/or structural stability of the therapeutic protein. Examples of residues that are known to be important include, for example, active site residues or amino acids in a binding pocket. For example, amino acids that are important for activity or structural stability of the therapeutic protein can be selected to be replaced to form a library of modified therapeutic proteins that can be screened to identify conditionally active therapeutic proteins. Also, residues to mutate can be empirically identified by any method known to the skilled artisan, including site-directed mutagenesis, alanine scanning, structure/function relationships, homology modeling, theoretical modeling and any assays described herein. In addition, a library can be formed by randomly selecting amino acids to be replaced. Libraries or collections of mutant proteins can be generated and tested or screened in the method herein.

For identifying conditionally active proteins that are more active under disease conditions, for example acidic conditions that exist in a tumor environment, one or more amino acids in the protein to be modified can be independently replaced with an amino acid that has an ionizable group that can change protonation states between two pH conditions. The particular choice of amino acid is dependent on the particular pH condition that is being tested for conditional activity. One of skill in the art can select one or more replacement amino acids that include ionizable groups that can change ionization states between two different pH values. For example, the Henderson-Hasselbalch equation ($pH=pK_a+\log([A^-]/[HA])$) can be used to determine the ratio of protonated and unprotonated side chains of an amino acid as a function of the side chain $pK_a$, which can be measured using any method known in the art (e.g., titration curves and/or Nuclear Magnetic Resonance), or can be calculated using any method known to one of skill in the art (Davies et al. (2006), *BMC Biochem.* 7:18; Juffer (1998), *Biochem. Cell Biol.* 76(2-3):198-209; Sham et al. (1997), *J. Phys. Chem. B* 101(22):4458-4472; Nielsen (2007) *J. Mol. Graph. Model.* 25(5):691-699; Bas et al. (2008), *Proteins* 73(3):765-783), such as molecular dynamics modeling (e.g., Li et al. (2005), *Proteins,* 61:704-721; Bas et al. (2008), *Proteins,* 73:765-783) or the Poisson-Boltzmann equation (Fogolari et al. (2002) *J. Mol. Recognit.* 15(6):377-392). In some examples, the $pK_a$ of an amino acid is determined using model values for amino acid side chains (see, e.g., Nielsen (2001), *Proteins* 43(4):403-12. The protonation states of ionizable residues in a protein can alter one or more activities of a protein (such as affinity, catalytic activity, solubility, charge and stability) in a pH-dependent manner. (Rostkowski et al. (2011), BMC Struct. Biol. 11:6). Exemplary of such residues are Asp, Glu, Lys, Arg, and His.

In particular, for the purpose of the methods provided herein to identify proteins with altered activity in a low pH tumor microenvironment, amino acid residues of a therapeutic molecule can be changed to a histidine. For example, histidine side chains have been identified as being involved in the pH-dependent affinity of an antibody at pH 6.0 compared to pH 7.0 (see e.g. Raghavan et al. (1995) Biochemistry, 34:14649-14657).

In some examples, the methods provided herein are performed such that the identity of each mutant protein is known a priori before the protein is tested. For example, the methods provided herein can be conducive to mutagenesis and screening or testing methods that are addressable. This can permit the ease of comparisons between the activity assay conditions, such as binding assay conditions, that simulate a diseased microenvironment and a normal microenvironment in a dual comparative assay method. For example, site-directed mutagenesis methods can be used to individually generate mutant proteins. Mutagenesis can be performed by the replacement of single amino acid residues at specific target positions, one-by-one such that each individual mutant generated is the single product of each single mutagenesis reaction. Mutant DNA molecules can be designed, generated by mutagenesis and cloned individually, such as in addressable arrays, such that they are physically separated from each other and each one is the single product of an independent mutagenesis reaction. The amino acids selected to replace the target positions on the particular protein being optimized can be either all of the remaining 19 amino acids, or a more restricted group containing only selected amino acids. In some methods provided herein, each amino acid that is replaced is independently replaced by 19 of the remaining amino acids or by less than 19 of the remaining amino acids, such as 10, 11, 12, 13, 14, 15, 16, 17 or 18 of the remaining amino acids.

Modified proteins, such as mutant protein molecules derived from the collection of mutant DNA molecules can be physically separated from each other, such as by formatting in arrays, such as addressable arrays. Thus, a plurality of modified protein molecules, such as mutant protein molecules, can be produced. For example, modified proteins used in the methods provided herein can contain a single amino acid replacement at a target position. The methods provided herein can be performed on each modified protein under one or more assay conditions described herein. Once modified proteins containing single mutations are identified that exhibit preferential activity in the diseased microenvironment, combination mutants can be generated containing some or all permutations of single amino acid mutations, such as 2, 3, 4, 5, 6, 7, 8, 9, 10, 11, 12, 13, 14, 15, 16, 17, 18, 19, 20 or more mutations.

i. Modified Therapeutic Antibodies

In some examples, the assays are performed using modified therapeutic proteins that are modified therapeutic antibodies. The antibodies for use in the methods provided herein typically contain a variable heavy chain and a variable light chain, or portion thereof sufficient to form an antigen binding site. It is understood, however, that the antibody also can include all or a portion of the constant heavy chain (e.g. one or more $C_H$ domains, such as $C_H1$, $C_H2$, $C_H3$ and $C_H4$, and/or a constant light chain (CO). Hence, the antibody can include those that are full-length antibodies, and also include fragments or portions thereof including, for example, Fab, Fab', F(ab')$_2$, single-chain Fvs (scFv), Fv, dsFv, diabody, Fd and Fd' fragments, Fab fragments, scFv fragments, and scFab fragments. It is understood that resulting modified antibodies can be produced as a full-length antibody or a fragment thereof, such as a Fab, Fab', F(ab')$_2$, single-chain Fvs (scFv), Fv, dsFv, diabody, Fd and Fd' fragments, Fab fragments, scFv fragments, and scFab fragments. Further, the constant region of any isotype can be used in the generation of full or partial antibody fragments, including IgG, IgM, IgA, IgD and IgE constant regions. Such constant regions can be obtained from any human or animal species. It is understood that activities and binding affinities can differ depending on the structure of an antibody. For example, generally a bivalent antibody, for example a bivalent F(ab')$_2$ fragment or full-length IgG, has a better binding affinity then a monovalent Fab antibody. As a result, where a Fab has a specified binding affinity for a particular target, it is expected that the binding affinity is even greater for a full-length IgG that is bivalent. Thus, comparison of binding affinities between antibodies are typically made between antibodies that have the same structure, e.g. Fab compared to Fab.

Antibody variants can be generated and screened in the methods provided herein. In particular, variants of existing antibody cancer therapeutics, such as mutants of anti-EGFR antibodies for example mutants of Erbitrux, can be generated. In some examples, the methods are performed with modified antibodies that contain one or more amino acid modifications located any position in the antibody. In some examples of the methods provided herein, modifications are made in the variable heavy chain and/or the variable light chain of an antibody.

Typically, amino acid mutations are introduced into an antibody in one or more of the CDRs. For example, amino acid mutations can be introduced within sequences encoding the CDR1, CDR2, and/or CDR3 regions of the heavy and/or light chain variable regions. In some examples, mutations also can be made in the framework region (FR) of an antibody, in particular in FR residues known to be involved in contact with an antigen. One of skill in the art knows and can identify the CDRs and FR based on Kabat or Chothia numbering (see e.g., Kabat, E. A. et al. (1991) *Sequences of Proteins of Immunological Interest*, Fifth Edition, U.S. Department of Health and Human Services, NIH Publication No. 91-3242, and Chothia, C. et al. (1987) *J. Mol. Biol.* 196:901-917). For example, based on Kabat numbering, CDR-L1 corresponds to residues L24-L34; CDR-L2 corresponds to residues L50-L56; CDR-L3 corresponds to residues L89-L97; CDR-H1 corresponds to residues H31-H35, 35a or 35b depending on the length; CDR-H2 corresponds to residues H50-H65; and CDR-H3 corresponds to residues H95-H102. For example, based on Kabat numbering, FR-L1 corresponds to residues L1-L23; FR-L2 corresponds to residues L35-L49; FR-L3 corresponds to residues L57-L88; FR-L4 corresponds to residues L98-L109; FR-H1 corresponds to residues H1-H30; FR-H2 corresponds to residues H36-H49; FR-H3 corresponds to residues H66-H94; and FR-H4 corresponds to residues H103-H113.

Methods of generating antibody libraries containing mutations are well known to one of skill in the art and include, for example, using a known antibody as a template by introducing mutations at random in vitro by using error-prone PCR (Zhou et al., (1991) *Nucleic Acids Research* 19(21):6052; and US2004/0110294); randomly mutating one or more CDRs or FRs (see e.g., WO 96/07754; Barbas et al. (1994) *Proc. Natl. Acad. Sci.*, 91:3809-3813; Cumbers et al. (2002) *Nat. Biotechnol.*, 20:1129-1134; Hawkins et al. (1992) *J. Mol. Biol.*, 226:889-896; Jackson et al., (1995) *J. Immunol.*, 154:3310-3319; Wu et al. (1998) *Proc. Natl. Acad. Sci.*, 95: 6037-6042; McCall et al. (1999) *Molecular Immunology*, 36:433-445); oligonucleotide directed mutagenesis (Rosok et al., (1998) *The Journal of Immunology*, 160:2353-2359); codon cassette mutagenesis (Kegler-Ebo et al., (1994) *Nucleic Acids Research*, 22(9):1593-1599); degenerate primer PCR, including two-step PCR and overlap PCR (U.S. Pat. Nos. 5,545,142, 6,248,516, and 7,189,841; Higuchi et al., (1988) *Nucleic Acids Research* 16(15): 7351-7367; and Dubreuil et al., (2005) *The Journal of Biological Chemistry* 280(26):24880-24887); domain shuffling by recombining the $V_H$ or $V_L$ domains selected by phage display with repertoires of naturally occurring V domain variants obtained from unimmunized donors and screening for higher affinity in several rounds of chain reshuffling as described in Marks et al., *Biotechnology*, 10: 779-783 (1992). For example, as discussed above, mutagenesis of residues in CDRs or FR can be effected one-by-one in an addressable format, thereby generating individual mutants that can be easily screened in the dual assay method herein.

a) Modified Anti-EGFR Therapeutics

In some examples of the methods provided herein, the therapeutic protein that is modified for use in the methods herein is one that interacts with all or a portion of Epidermal Growth Factor Receptor (EGFR). Thus, for example, a therapeutic protein for mutagenesis and screening in the methods herein is one that can interact with the extracellular domain of EGFR, the cytoplasmic domain of EGFR or with the internal tyrosine kinase domain of EGFR. In some examples, the unmodified therapeutic protein is one that inhibits EGFR-mediated signal transduction. For example, interaction of the a protein with EGFR can prevent EGFR from interacting with one or more ligands for EGFR including, for example, EGF, TGF-α, amphiregulin, heparin-binding EGF (HB-EGF) and betacellulin. In particular examples, a therapeutic protein against EGFR prevents EGFR from interacting with EGF and/or TGF-α. The therapeutic protein can interact with EGFR and inhibit EGFR dimerization with other EGFR receptor subunits (i.e., EGFR homodimers) or heterodimerization with other growth factor receptors (e.g., HER2).

In some examples, the protein that interacts with EGFR is an anti-EGFR antibody. The anti-EGFR antibody can be a humanized anti-EGFR antibody. Hence, exemplary of modified proteins, such as antibody variants provided herein, for use in the methods provided herein, are modified anti-EGFR antibodies. Examples of anti-EGFR antibodies that can be subjected to mutagenesis and used in the methods provided herein include the antibody designated 11F8 by Zhu (WO 2005/090407), EMD 72000 (matuzumab), Vectibix™ (panitumumab; ABX-EGF), TheraCIM (nimotuzumab), and HuMax-EGFR (zalutumumab) and any anti-EGFR antibody described herein. In particular, variants of the anti-EGFR antibody Erbitux® are provided for screening in the methods herein for a conditionally active protein that is more active in a tumor microenvironment than a normal environment.

Anti-EGFR antibodies, as well as small molecules, can specifically bind to the EGF receptor on both normal and tumor cells, and competitively inhibit the binding of epidermal growth factor (EGF) to its cognate receptor. The blockade can prevent receptor phosphorylation and activation of the receptor-associated kinase activity, ultimately shutting off receptor-mediated cell signaling which leads to cell death. Specifically, the anti-EGFR antibody Erbitux® (Cetuximab or C225) (SEQ ID NOS: 1 and 2) is a chimeric antibody against EGFR that is used for the treatment of colorectal carcinoma and squamous cell carcinoma. Erbitux® is a human-mousechimeric monoclonal EGFR antagonist antibody that can bind to the extracellular domain of EGFR and block ligand binding. Erbitux® binding to EGFR can inhibit dimerisation and, ultimately, inhibit tumor growth and metastasis (Blick et al., (2007) Drugs 67(17): 2585-2607). Erbitux® can also induce an antitumor effect through inhibition of angiogenesis. Erbitux® inhibits expression of VEGF, IL-8 and bFGF in the highly metastatic human TCC 253JB-V cells in a dose-dependent manner and decreases microvessel density (Perrotte et al. (1999), *Clin. Cancer Res.*, 5:257-264). Erbitux® can down-regulate VEGF expression in tumor cells in vitro and in vivo. (Petit et al. (1997), *Am. J. Pathol.*, 151:1523-1530; Prewett et al. (1998), *Clin. Cancer Res.* 4:2957-2966).

In the U.S., Erbitux® has been approved for use alone or in combination with radiation therapy to treat squamous cell cancer of the head and neck (SCCHN), which is the sixth leading cause for cancer deaths worldwide. Approximately 40% of patients with SCCHN present with metastatic disease, and in one study 5-year survival rates were 91% for stage I disease, 77% for stage II, 61% for stage III, 32% for stage IVa, 25% for stage IVb and less than 4% for stage IVc disease (Lefebvre (2005) *Ann. Oncol.* 16(Suppl 6):vi7-vi12). Cetuximab in combination with irinotecan has been approved to treat metastatic colorectal cancer (mCRC) in patients with EGFR-expressing tumors who are refractory to irinotecan-based therapy (Blick et al., (2007) Drugs 67(17): 2585-2607).

Anti-EGFR agents, such as the antibody Erbitux®, are associated with significant and characteristic adverse events such as skin toxicities and digestive disturbances (including nausea, vomiting, diarrhea), that often lead to interruption of dosing and discontinuation of treatment. Erbitux can prevent dermal EGFR ligands from binding to receptors on undifferentiated keratinocytes, leading to an accumulation of undifferentiated cells and a lack of mature cells to replenish epidermis. This can result in severe acne-like dermatologic rash (Eng C (2009) *Nat. Rev. Clin. Oncol.* 6:207-18). As a result of side effects, 76% of patients are associated with dosing interruptions, 60% with dose reductions and 32% with dose discontinuations. Other possible side effects of Erbitux® include deep vein and artery thrombosis, acne, dyspnea, fatigue, abdominal pain, asthenia and atrial fibrillation (Fakih and Vincent, (2010) *Curr. Oncol.* 17(S1):S18-S30). In some cases, side effects can prevent a patient from receiving further treatments with cetuximab. Hence, there exists a need for therapeutic molecules, such as therapeutic proteins that exhibit minimized or limited systemic side effects, yet retain their activity of target binding within the tumor microenvironment.

Antibody variants of an anti-EGFR antibody can be generated and screened in the assays provided herein, such as dual assays that are performed to simulate diseased and normal microenvironments. Provided herein are collections of antibody variants of anti-EGFR antibodies that contain single amino acid replacements in the variable heavy and light chain of the anti-EGFR antibody Erbitux® (see e.g. Example 8 and FIG. 1). In particular, each of 100 residues in the CDRL1, CDRL2, CDRL3, CDRH1, CDRH2 and CDRH3 and in framework residues that are associated with contact with EGFR can be independently replaced with up to 19 other amino acids, for example, 1, 2, 3, 4, 5, 6, 7, 8, 9, 10, 11, 12, 13, 14, 15, 16, 17, 18 or 19 amino acids, and in particular at least or about at least 15 other amino acid residues. In the anti-EGFR antibody Erbitux, CDR-H1 corresponds to amino acids 26-35 or 31-35 of SEQ ID NO:2, CDR-H2 corresponds to amino acids 50-65 of SEQ ID NO:2, CDR-H3 corresponds to amino acids 98-108 of SEQ ID NO:2, CDR-L1 corresponds to amino acids 24-34 of SEQ ID NO:1, CDR-L2 corresponds to amino acids 50-56 of SEQ ID NO:1 and CDR-L3 corresponds to amino acids 89-97 of SEQ ID NO:1. Amino acids selected for modification include heavy chain residues 23-37, 50-77, 93-94 and 96-112 of SEQ ID NO:2 and light chain residues 1-5, 24-34, 48-56, 86-87 and 89-100 of SEQ ID NO:1 (see FIG. 1). In the collections of variant anti-EGFR antibodies, all positions in the collection can contain amino acid replacement to histidine, except for those positions where histidine is present in the parent Erbitux antibody. The collection of anti-EGFR antibodies can be provided in an addressable array.

Antibody variants of anti-EGFR antibodies, for example variant Erbitux antibodies, can be generated and screened in the dual assay herein to identify an improved variant anti-EGFR analog for the treatment of cancer. For example, the method provided herein can be used to test anti-EGFR variant antibodies, for example variant Erbitux antibodies, and identify a variant or variants that binds to the EGFR within the tumor microenvironment of reduced pH and elevated lactate concentrations, but not at normal physiologic pH.

2. Screening or Testing Activity Under Two Different Physiologic Conditions for Conditional Activity In the methods provided herein, the activity of one or more molecules, such as any described above, is screened or tested under two different sets of conditions that simulate a condition or conditions in two different physiologic environments such as, for example, a diseased microenvironment and the normal physiologic condition of a non-diseased microenvironment. Typically, the conditions are conditions that can be simulated or replicated in vitro. A set of conditions can include one or more conditions to simulate a microenvironment associated with a disease. Disease can alter intracellular and extracellular homeostasis. For example, the diseased microenvironment can simulate one or more conditions in a tumor microenvironment or a cancer microenvironment. Typically, the difference or differences in activity under the two sets of conditions can result in the conditional activity of the molecule. Thus, a molecule that exhibits greater activity under the first set of conditions (e.g. simulating conditions in a tumor microenvironment) compared to the second set of conditions (e.g. simulating conditions in a normal or non-diseased environment) is identified as a candidate molecule that is conditionally active.

The two sets of conditions can be selected to vary by one or more parameters that differ in two physiologic environments, such as described herein or known to one of skill in the art, including but not limited to chemical conditions, biological conditions, or physical conditions. Parameters that can be varied between the two sets of conditions can include one or more conditions selected from among pressure, temperature, pH, ionic strength, turbidity, exposure to light (including UV, infrared or visible light), concentration of one or more solutes, such as electrolytes, concentration of lactic acid, concentration of $O_2$, and presence of oxidants or reductants. By varying the electrolyte and buffer systems in the calibration solutions, physiological conditions such as pH, buffer capacity, ionic environment, temperature, glucose concentration and ionic strength can be adjusted to those of the biological environment to be simulated. The set of conditions that simulate a normal physiologic environment can be selected to be different from the set of conditions that simulate a diseased microenvironment, such as a tumor microenvironment, by one or more conditions described herein.

For example, as discussed below, various parameters of the tumor microenvironment differ compared to a non-tumor microenvironment, including, but not limited to, oxygen concentration, pressure, presence of co-factors, pH, lactate concentration and pyruvate concentration. Any of these parameters can be replicated in vitro to simulate one or more conditions that exist in a tumor or cancer environment compared to conditions that exist in a non-tumor or a normal environment. The normal physiologic conditions that can be simulated include environments found in healthy or nondiseased tissue at any location of the body such as the GI tract, the skin, the vasculature, the blood, and extracellular matrix.

Typically, in the assays herein, physiologic conditions can be simulated in vitro by the choice of buffer that is used to assess the activity of the protein. For example, any one or more conditions of a diseased microenvironment (such as a tumor microenvironment) and a non-diseased environment can be simulated by differences in the assay buffer used to assess activity in the assay. Hence, in the methods herein to identify a conditionally active protein, a component or components or characteristic or characteristics of an assay buffer are altered or made to be different in a first assay to test activity under a first condition and in a second assay to test activity under a second condition. For example, as discussed herein, various parameters of the tumor microenvironment are different compared to a non-tumor environment including, but not limited to, oxygen, pressure, presence of co-factors, pH, lactate concentration (such as increased or decreased lactate concentration) and pyruvate concentration (including increased or decreased pyruvate concentration). Any one or more of these conditions can be simulated in vitro by choice of the particular assay buffer.

The composition of the assay buffer that simulates a diseased microenvironment can be selected to be identical to the composition of the assay buffer that simulate a normal environment, with the exception of one or more conditions known or described herein that is altered in the diseased microenvironment. Further, in screening or identifying the activity of one or more test molecules under two different sets of conditions, generally the only conditions that are varied in the assay relate to the buffer conditions simulating the in vivo microenvironment. The other conditions of the assay, such as time, temperature and incubation conditions, can be the same for both sets of conditions.

Typically, the same base buffer is used in the set of conditions that simulate a diseased microenvironment and conditions that simulate a normal microenvironment, but the design of the buffer composition can be made to differ in one or more parameters such as pH, oxygen, pressure, presence of co-factors, pH, lactate concentration (such as increased or decreased lactate concentration) and/or pyruvate concentration (including increased or decreased pyruvate concentration). In the conditions that simulate a diseased microenvironment and the conditions that simulate a normal microenvironment, any base buffer known to one of skill in the art that can be used, including TAPS ((N-Tris[hydroxymethyl]methyl-3-aminopropanesulfonic acid),), Tris (tris(hydroxymethyl)methylamine), Tricine (N-tris(hydroxymethyl) methylglycine, TAPSO (3-[N-Tris(hydroxymethyl) methylamino]-2-hydroxypropanesulfonic Acid, HEPES (4-2-hydroxyethyl-1-piperazineethanesulfonic acid), TES (2-{[tris(hydroxymethyl)methyl]amino}ethanesulfonic acid), MOPS (3-(N-morpholino)propanesulfonic acid), PIPES (piperazine-N,N'-bis(2-ethanesulfonic acid)), Cacodylate (dimethylarsinic acid), SSC (saline sodium citrate), MES (2-(N-morpholino)ethanesulfonic acid) and any of Good's buffers (MES, ADA, PIPES, ACES, Cholamine chloride, BES, TES, HEPES, Acetamidoglycine, Tricene, Glycinamide and Bicine (N,N-bis(2-hydroxyethyl)glycine)).

The skilled artisan can select an appropriate buffer by considering appropriate factors, such as buffer $pK_a$; solubility; membrane impermeability; minimal salt effects; minimum influence of buffer concentration, temperature and ionic composition of the medium on buffer dissociation; stability, low optical absorbance (see, e.g., Good et al., (1966) *Biochemistry* 5(2):467-477). The choice of buffer that is used can be empirically determined by one skilled in the art depending on the particular parameter or parameters that are being simulated. Buffers that can be used in an assay include any buffer that has an appropriate buffering capacity for the pH range. Typically, the higher the ionic strength or concentration of the buffer, the higher the buffer capacity. Typically, the buffer is selected to reflect the physiologic environment. Exemplary of physiologic buffers include, but are not limited to, phosphate buffered saline (PBS), Hank's balanced salt solution (HBSS), Ringers or Krebs.

In addition, in any conditions that are described herein, human serum can be added to simulate a physiological environment at a concentration that simulates physiological conditions, such as 1-40% human serum, in some examples 5-30% human serum, and in some examples 5%, 10%, 15%, 20%, 25% or 30% human serum.

a. Tumor Microenvironments

A set of conditions in an assay can be selected to, for example, simulate extracellular and/or intracellular conditions within a tumor microenvironment (such as conditions found in the extracellular matrix within a tumor microenvironment), compared to a non-tumor environment or normal physiologic conditions. In some examples, a set of conditions used in an assay simulates the conditions of the tumor microenvironment, such as due to the presence of a condition that is associated with, or specific to, tumors. For example, cancer is associated with numerous biomarkers, including altered pH and increased oxidative potential, altered vascularization, hypoxia, extracellular and cellular pH, increased interstitial fluid pressure (IFP), oxygen level, pressure, lactate concentration and pyruvate concentration as well as induced co-factors (see Table 4 below) (Aluri et al. (2009), *Adv. Drug. Deliv. Rev.* 61(11):940-952; Gerweck and Seetharaman (1996), Cancer Res. 56(6):1194-1198; Cook et al. (2004), *Semin. Radix. Oncol.* 14(3):259-266; Schafer and Buettner (2001); Free Radic. Biol. Med. 30(11): 1191-1212). Any one or more of these conditions can be simulated in an assay.

TABLE 4

Disease Microenvironments

| Micro-environment | Causes and Consequences |
| --- | --- |
| Vascularization | pH of normal tissue is highly regulated & well maintained (7.3-7.4) |
| Altered pH | Extracellular pH in tumor tissue is acidic ~5.6-7.2<br>Intracellular pH is aggressively maintained ~7.4<br>Normal $O_2$ levels is 80 mm Hg<br>(venus end of capillaries) |
| Interstitial Fluid Pressure (IFP) | Hyperglycolytic tumors results in acidic tumor ECM (Warburg effect)<br>LDH and $H^+$ ions are actively exported into the ECM |
| Hypoxia | Chaotic vascular causes hypoxic micro-gegions<br>Hyposia causes capillary leakage & inefficient $O_2$ diffusion<br>Increase in IFP due to vasucalal leakage causes hypoxic conditions<br>IFP due to capillary leak & loss of contractile characteristic of the ECM |
| Co-factors (disease associated) | Inflammation results in acidic pH (~6.5-7.2)<br>Select for cells with resistance apoptic signals<br>Induces drug resistance, radioresistance and metastasis ($O_2$ is a radiosensitizer) |
| Metabolic deficiencies | Upreguation of collagenases, uPA, cathepsins, VEGF, EGF, TNFα, IL-2, LOX<br>ECM degradation and metastasis<br>Asparagine synthase deficiency | i. pH

In some examples of a set of conditions to simulate a tumor microenvironment, the pH of one or more of the buffers is adjusted to simulate the microenvironment of a tumor. An altered pH microenvironment is the most common microenvironment found in disease states such as tumor microenvironments, and it is the most uniform within the disease microenvironment compared to other properties such as hypoxia (see e.g. Fogh Andersen et al. (1995) *Clin. Chem.*, 41:1522-1525; Bhujwalla et al. (2002) *NMR Biomed.*, 15:114-119; Helmlinger et al. (1997) *Nature Med.*, 3:177; Gerweck and Seetharaman (1996), Cancer Res. 56(6):1194-1198). For example, in many tumors the 'Warburg effect' creates a microenvironment with a pH ranging from 5.6 to 6.8. The conditions described herein include conditions that simulate the low pH extracellular microenvironment (ECM) compared to a normal physiologic pH environment. Thus, assays that measure activity under conditions that simulate low pH and under conditions that simulate normal physiologic pH (e.g. neutral pH) can be used to identify molecules with biological efficacy that are conditionally active in the tumor microenvironment.

For example, the pH of the normal microenvironment conditions can be any pH that exists under physiologic conditions, such as any pH from about 7.0 to about 7.8, such as at least or about or pH 7.1, 7.2, 7.3, 7.4, 7.5, 7.6, 7.7 or 7.8 (see, e.g., U.S. Pat. No. 7,781,405), in some examples pH 7.4.

The pH of the tumor microenvironment is selected to have a pH that is more acidic from the normal microenvironment, such as any pH from about 5.6 to 6.8, such as less than or about or pH 5.6, 5.7, 5.8, 5.9, 6.0, 6.1, 6.2, 6.3, 6.4, 6.5, 6.6, 6.7, or 6.8. Thus, the pH of the set of conditions that simulates a normal microenvironment can be more basic than the tumor conditions. Any buffer known to one of skill in the art or described herein can be adjusted to the desired pH.

In some examples, the pH environment of the tumor is simulated in the assay by altering the pH of a buffer used in the assay. The pH and buffering capacity is a function of the assay conditions and can be empirically determined or chosen by one of skill in the art. Any buffer known to one of skill in the art or described herein can be adjusted to the desired pH and used in an assay described herein. One of skill in the art can adjust the pH of a buffer by adding acid such as HCl, or a base such as NaOH. Typically, a buffer is allowed to equilibrate to the temperature of the assay conditions and the pH of the buffer is verified, and adjusted if necessary, before use.

For example, a physiologic buffer, such as Krebs-Ringer bicarbonate Buffer (KRB), can be adjusted to a low pH that is at or about between 5.6 to 6.8, for example 6.0 to 6.5, such as at or about 6.0. In some examples, the physiologic buffer, for example KRB, can be adjusted to a pH that is at or about 7.4. KRB buffer is a balanced salt solution that can maintain structural integrity of established cell lines and human primary cells. Furthermore, a bicarbonate buffering system is one of the major buffering systems used to maintain the pH of mammalian blood and is involved in mucosal protection and luminal buffering (Kaunitz and Akiba (2006), *Ailment Pharmacol. Ther.* 24(S4):169-176. Thus, KRB buffer is a physiologic buffer than can simulate conditions found within the body. Table 5 sets forth buffer components of Krebs-Ringer bicarbonate buffer as compared to PBS. Buffers can be adjusted to the final pH with 1 N HCl.

TABLE 5

Components per Liter for KRB buffer and 1X PBS

| Chemical | KRB | | | PBS |
| --- | --- | --- | --- | --- |
| | MW | Amount | Concentration | 1X |
| D-Glucose | 180.16 | 1.8 g | 10 mM | |
| $MgCl_2$ | 95.21 | 0.0468 g | 0.5 mM | |
| KCl | 74.55 | 0.34 g | 4.5 mM | 2.7 mM |
| NaCl | 58.44 | 7 g | 120 mM | 137 mM |
| $Na_2HPO_4$ (dibasic) | 141.96 | 0.1 g | 0.7 mM | 10 mM |
| $NaH_2PO_4$ (monobasic) | 199.98 | 0.18 g | 1.5 mM | |
| $NaHCO_3$ | 84.01 | 1.26 g | 15 mM | |
| $KH_2PO_4$ | | | | 1.76 mM | ii. Lactate Concentration

A condition that can differ between a normal environment and a diseased environment, such as a tumor environment, can include the concentration of lactate. In addition to being a gluconeogenic substrate for the liver (Gladden (2008), *Med. Sci. Sports Exerc.* 40(3):477-485), lactate is an important intermediary in numerous biochemical processes, including wound repair, regeneration, aerobic metabolism (Gladden (2004), *J. Physiol.* 558(Pt 1):5-30). One of skill in the art is familiar with the mechanisms for production and maintenance of lactate in healthy tissue in the body (see, e.g., Brooks (2010) *J. Appl. Physiol.* 108(6):1450-1451) and with exemplary lactate concentrations in both healthy and diseased tissue (see, e.g., Soliman and Vincent (2010), *Acta Clin. Belg.* 65(3):176-181; Friedman et al. (1995), *Crit. Care. Med.* 23(7):1184-1193; Myburgh et al. (2001), *Med. Sci. Sports Exer.* 33(1):152-156).

In many tumors, the 'Warburg effect' creates a microenvironment with lactate concentrations between 10 to 15 mM. Elevated lactate levels have been found associated with a variety of tumors including, but not limited to, head and neck, metastatic colorectal cancer, cervical cancer and squamous cell carcinoma (see e.g., Correlation of High Lactate Levels in Head and Neck Tumors with Incidence of Metastasis. Stefan Walenta, Ahmad Salameh, Heidi Lyng, Jan F. Evensen, Margarethe Mitze, Einar K. Rofstad, and Wolfgang Mueller-Klieser. (1997) *American Journal of Pathology* 150(2): 409-415; Correlation of High Lactate Levels in Human Cervical Cancer with Incidence of Metastasis. Georg Schwickert, Stefan Walenta, Kolbein Suiulfor. Einar K. Rofstad, and Wolfgang Mueller-Klieser. (1995) *Cancer Research* 55: 4757-4759; High Lactate Levels Predict Likelihood of Metastases, Tumor Recurrence, and Restricted Patient Survival in Human Cervical Cancers. Stefan Walenta, Michael Wetterling, Michael Lehrke, Georg Schwickert, Kolbein Sundfør, Einar K. Rofstad, and Wolfgang Mueller-Klieser. (2000) *Cancer Research* 60: 916-921; In Vitro Proton Magnetic Resonance Spectroscopic Lactate and Choline Measurements, 18F-FDG Uptake, and Prognosis in Patients with Lung Adenocarcinoma. JianFei Guo, Kotaro Higashi, Hajime Yokota, Yosinobu Nagao, Yoshimichi Ueda, Yuko Kodama, Manabu Oguchi, Suzuka Taki, Hisao Tonami, and Itaru Yamamoto. (2004) *J Nucl Med* 45: 1334-1339; Lactate and malignant tumors: A therapeutic target at the end stage of glycolysis. Saroj P. Mathupala, Chaim B. Colen, Prahlad Parajuli, Andrew E. Sloan (2007) *J Bioenerg Biomembr* 39: 73-77; Lactate Metabolism in Patients with Metastatic Colorectal Cancer. Christopher P. Holroyde, Rita S. Axelrod, Charles L. Skutches, Agnes C. Haff, Pavle Paul, and George A. Reichard. (1979) *Cancer Research* 39: 4900-4904; Lactate, not pyruvate, is neuronal aerobic glycolysis end product: an in vitro electrophysiological study. A Schurr and R. S. Payne. (2007) *Neuroscience* 147: 613-619; Tumor lactate content predicts for response to fractionated irradiation of human squamous cell carcinomas in nude mice. Verena Quennet, Ala Yarominab, Daniel Zipsb, Andrea Rosnerb, Stefan Walentaa, Michael Baumannb, Wolfgang Mueller-Kliesera. (2006) *Radiotherapy and Oncology* 81: 130-135).

A set of conditions described herein, that simulates a tumor microenvironment, can include increased levels of lactate in one or more buffers. The lactate concentration of a tumor can be simulated in an assay by adjusting concentrations of lactic acid in one or more buffers. For example, an assay can be performed using one or more buffers can contain at or about between 5 mM to 20 mM lactic acid, for example 10 mM to 20 mM lactic acid such as 15 mM to 18 mM, and in particular at least or at least about or 16 mM, 16.5 mM or 17 mM lactic acid. In some examples, the lactate concentration of one or more buffers that simulate a normal environment for use in the assays provided herein is adjusted to be at or about between 0.5 to 5 mM lactate, such as, for example 0.2 mM to 4 mM lactic acid, such as 0.5, 1, 2, 3, 4, or 5 mM lactic acid.

iii. Hypoxia

Another example of a set of conditions that can differ between a normal environment and a diseased environment, such as a tumor environment, can include hypoxia. Hypoxia, decreased availability of oxygen, is a feature of most solid tumors and is associated with poor prognosis in several cancer types, including breast cancer (Favaro et al., Genome Med. (2011), 3(8):55), due to contributions to chemoresistance, radioresistance, angiogenesis, vasculogenesis, invasiveness, metastasis, resistance to cell death, altered metabolism and genomic instability (Wilson and Hay (2011), *Nat. Rev. Cancer* 11(6):393-410). A factor implicated in the correlation between hypoxia and poor prognosis is the transcription factor hypoxia-inducible factor (HIF), which is activated in response to hypoxia and can activate genes which regulate cell proliferation and survival, pH, and migration, cell immortalization and de-differentiation, stem cell maintenance, genetic instability, glucose uptake and metabolism, autocrine growth/survival, angiogenesis, invasion/metastasis, and resistance to chemotherapy (Semenza (2009), *Curr. Pharm. Des.* 15(33):3839-3843; Patiar and Harris (2006), *Endocr. Relat Cancer* S1:S61-75). Hypoxia is associated with increased aggressiveness and distant metastasis (Hashimoto et al., (2011) *Pathobiology*, 78(4):181-192) and promotes tolerance and angiogenesis in tumors (Facciabene et al., *Nature* 475(7355):226-230). Tumor hypoxia can result from inadequate blood supply and disorganized tumor vasculature, impairing delivery of oxygen (Carroll and Ashcroft (2005), *Expert. Rev. Mol: Med.* 7(6):1-16).

Hypoxic conditions can be simulated in an assay by any method known to the skilled artisan, including buffer degassing. For example, inert gas can be bubbled through the buffer before use (see, e.g., Nayler et al., (1979), 11(10): 1053-1071). Hypoxic conditions can be simulated by bubbling a buffer with a mixture of $N_2:CO_2$ (19:1 vol/vol) (Martou et al., (2006) *J. Appl. Physiol.* 101(5):1335-1342). In addition, hypoxic conditions can be maintained during the assay by performing the reaction in an atmosphere with an oxygen ($O_2$) concentration lower than atmospheric oxygen, for example, less than 21% $O_2$ (McCord et al. (2009), *Mol. Cancer. Res.* 7:489-497) or by bubbling air with less than 21% $O_2$ into the reaction. Hypoxic conditions include any conditions in which oxygen concentration is less than the equilibrium concentration of oxygen from atmospheric exposure, and can include, for example, 0-20% oxygen, including 0-10% oxygen, such as 0%, 1%, 2%, 3%, 4%, 5%, 6%, 7%, 8%, 9%, 10% or 15% oxygen.

In addition, the conditions that simulate a normal microenvironment can include an $O_2$ concentration that corresponds to an $O_2$ concentration typically found under physiologic conditions. For example, an assay performed under conditions that simulate a healthy environment can be performed in a reaction that is exposed to air (approximately 21% gas phase oxygen). Under these conditions, cells can be exposed to dissolved oxygen concentrations of 200 μM or less. However, cells can grow at oxygen concentrations above or below 200 μM such as, for example 40 μM-400 μM. Thus, the conditions that simulate a normal microenvironment can include an oxygen concentration within a range of between or about between 40 μM to 400 μM, in some instances 40 μM to 200 μM, and in some instances 40 μM to 140 μM. If necessary, dissolved oxygen concentrations can be increased by aerating with either atmospheric air or an air/oxygen mixture. (see, e.g., Oller et al. (1989), *J. Cell Sci.* 94:43-49).

3. Detection and Identification of Conditionally Active Modified Proteins

In the method, after selecting a condition or conditions, the test molecule, such as a therapeutic protein or modified therapeutic protein, for example a modified anti-EGFR antibody, is assessed for activity under the first condition and second condition. Various assays to assess activity of the molecule or protein are known to one of skill in the art and are dependent on the particular molecule or protein. For example, assays include binding assays or functional assays. Exemplary assays are described in Section C below. For example, to assess the activity of an anti-EGFR antibody, binding to EGFR can be assessed.

The resulting activity under each of the conditions is then compared. Molecules or proteins are identified or selected that exhibit greater activity under the first set of conditions, which typically are the conditions that simulate or replicate a diseased condition such as exists in a tumor environment. For example, activity (e.g. binding activity) under conditions that simulate a tumor microenvironment is compared to the same activity (e.g. binding activity) under conditions that simulate a non-tumor or normal physiologic environment. For comparison, the activity can be represented as a ratio of activity under the second condition (e.g. conditions of a disease microenvironment) compared to under the first set of conditions (e.g. of a non-diseased normal microenvironment). For example, where the parameter that differs between the first and second condition is pH, activity can be represented as a ratio of activity observed at an acidic pH versus a more neutral pH, such as a ratio of activity at pH 6.0/7.4. A test molecule, such as a therapeutic protein or modified therapeutic protein, such as antibodies or variant antibodies for example a modified anti-EGFR antibody, are identified or selected that exhibit a ratio that is greater than 1 such that the molecule exhibits greater activity in the diseased or tumor microenvironment. For example, the ratio is at or about between 1.5 to 100, such as 2 to 50, for example 5 to 30 or more. Hence, in the methods, a conditionally active protein or variant can be identified.

In addition, activity can be compared to a control, such as a protein not containing mutations, in order to identify proteins that exhibit increased activity in the diseased or tumor microenvironment compared to the protein not containing the mutation or mutations. In some examples, the activity of modified proteins can be normalized to the activity of the unmodified protein. Thus, conditional activity of a modified protein can be determined based on a normalized activity. As an illustrative example, if an unmodified protein has activities of 10 and 1 in a normal microenvironment and a diseased microenvironment, respectively; and a modified protein has activities of 2 and 1 in a normal microenvironment and a diseased microenvironment, respectively, the normalized activities of the modified protein in the normal and diseased environment are 0.2 (2/10) and 1 (1/1), respectively. Thus, in this hypothetical example, the modified protein is twice as active in the normal microenvironment as in the diseased microenvironment, but can be conditionally active for the diseased microenvironment, because the normalized activity of the modified protein in the diseased environment is five times the normalized activity in the normal environment (1/0.2=5). Thus, the methods provided herein can be used to identify modifications that can alter the ratio of normalized activities of a modified protein.

4. Iterative Methods

In one example, after the method is performed, any identified conditionally active molecules can be modified or further modified to increase or optimize the conditional activity. For example, a secondary library can be created using the identified therapeutic protein or variant as a template and by introducing additional modifications in the first identified conditionally active protein. For example, modifications that were identified as increasing conditional activity can be combined. The secondary library can be tested using the assays and methods described herein.

In another example of an iterative aspect of the method, optionally, molecules that are identified as not exhibiting conditional activity, such that they are not active or do not have increased activity under the first set of conditions, can be further modified and retested for conditional activity. The further modifications can be targeted near particular regions (e.g. particular amino acid residues) associated with activity and/or stability of the molecule. For example, residues that are associated with activity and/or stability of the molecule generally are critical residues and are involved in the structural folding or other activities of the molecule, such as binding.

Critical residues can be identified because, when mutated, a normal activity of the protein is ablated or reduced. For example, critical residues can be identified that, when mutated, exhibit reduced or ablated binding activity of the therapeutic protein to its cognate binding partner. Critical residues can include residues that reside in the binding pocket. In particular, for purposes herein where the conditional activity is dependent on pH differences (e.g. acidic pH environment of a tumor environment), a charge effect on protein interaction can be determined by identifying critical residues that when mutated to a charged amino acid residue (e.g. Asp, Glu, Lys, Arg, and His) ablate or reduce binding to a cognate binding partner. Critical residues are then identified as residues that should not be targeted for mutagenesis to generate a conditionally active protein, since they are required for activity. Nevertheless, residues that are adjacent to or near to the identified critical residues can be particular targets that can be changed and that can affect the particular activity, such as binding. For example, mutation of an adjacent residue can affect the pocket of binding, and thereby alter binding activity.

Hence, in an example of an optional step to the method, amino acid residues that are important for protein activity and/or stability, and in particular binding (e.g. at an acidic pH), designated herein as critical residues, can be identified. Then, a further library of modified proteins can be generated with amino acid mutations targeted near to the identified critical amino acid residues, such as adjacent to the identified critical amino acid residues. In some examples, the mutations can be amino acid replacement to any other of up to 19 other amino acid residues at the adjacent position. In other examples, the mutation can be made rationally or empirically, for example, depending on the particular conditional activity that is being evolved. For example, where conditional activity under a pH condition is being evolved, the mutation at an amino acid residue near to or adjacent to a critical residue can be to a charged residue, and in particular to a histidine (H) residue, which is a weakly charged and has a pK of around 6.5 to 6.8. For example, a library of protein mutants can be generated in which a plurality of mutant or variant proteins are generated that each contain a single amino acid replacement to a histidine at an amino acid residue that is adjacent to or near to a critical amino acid residue.

The activity of each of the new plurality of mutants containing a mutation at a residue adjacent to a critical residue can be assessed or determined. For example, each member of the further library can be individually expressed and individually tested for activity at a first condition and a second condition as described herein above. Following testing under both conditions, protein variants that are not expressed or that exhibit preferential binding under the second condition (e.g. the non-desired environment, such as the physiologic or neutral pH environment of a normal tissue) are excluded. Hence, only variants that exhibit similar activity under either condition (i.e. don't affect activity, such as binding), are expressed, and/or exhibit preferential activity at the first condition are selected. The identity of the mutated residue can be determined and are designated key residues.

Then, a further combinatorial library is generated that includes combinations of mutations at the key residue positions. The mutations at the key residues can be amino acid replacement to any other of up to 19 other amino acid residues. In other examples, the mutation can be made rationally or empirically depending on the particular conditional activity that is being evolved. For example, where conditional activity under a pH condition is being evolved, the mutation at a key amino acid residue can be to a charged residue, and in particular to a histidine (H) residue. For example, if 11 key residues are identified, a combinatorial library can be generated containing protein variants having 1, 2, 3, 4, 5, 6, 7, 8, 9, 10 or all 11 residues varied, in any combination. As an example, where a combinatorial library is generated where only the key residue is mutated to a histidine (H) residue, the number of mutants in the library (size of library) can be calculated as $2^{11}$ members or 2048 combination mutants, since each position can be a wildtype amino acid or a histidine and there are 11 sites that can be mutated and combined. It is understood that excluding the wildtype and the 11 single His mutations (already tested above), the library contains 2036 combinations. It also is understood that the size of the library can be increased or decreased depending on the number of key residues identified, and the number of amino acid replacements made at each key residue position. The further library then can be screened in the methods herein described above to identify a conditionally active protein at a predetermined condition, such as increased activity in a tumor environment than in a non-tumor or healthy environment.

For example, to select for conditionally active modified therapeutic proteins, such as therapeutic antibodies for example Erbitux, with increased activity under conditions that simulate a tumor microenvironment (e.g., pH 6.0) compared to a normal microenviroment (e.g., pH 7.4), the amino acids in the therapeutic protein can be mutated to form a library of single amino acid modified therapeutic proteins. This library can be assayed in an in vitro assay under conditions that simulate a tumor microenvironment and a normal environment to identify critical residues that, when mutated, result in loss of activity under both conditions. For example, one or more members of the library include modified proteins that can be independently replaced with an amino acid that has an ionizable group that can change protonation states between the two pH conditions (such as, for example, Asp, Glu, Lys, Arg, His). The protonation states of ionizable residues in a protein can alter one or more activities of a protein (such as affinity, catalytic activity, solubility, charge and stability) in a pH-dependent manner (Rostkowski et al. (2011), BMC Struct. Biol. 11:6). Critical residues can be defined as amino acid positions that, when mutated to a charged amino acid, result is no activity under both conditions. Hence, the residue is one that resides in the binding pocket and/or is otherwise associated with a charge effect to binding to its cognate binding partner. From an activity screen, such as an ELISA screen, critical residues can be identified that, when mutated to charged residues, lose binding at pH 6.0 and 7.4.

In the second step, after critical residues are identified, the activity of protein variants containing replacement of amino acids adjacent to the critical residues can be determined or assessed. The replacement amino acid can be randomly selected from all possible amino acids, or from a subset of all possible amino acids. For example, replacement amino acids can include amino acids that can change ionization states between the tumor and normal conditions as discussed above, such as an amino acid residue that is charged. In particular examples, the amino acid that is replaced at adjacent residues is a histidine. The activity of each of the new plurality of mutants containing a mutation at a residue adjacent to a critical residue can be assessed or determined at a first condition that mimics or simulates a condition of a tumor environment (e.g. a condition of acidic pH and/or high lactic acid) and at a second condition that mimics or simulates a non-tumor environment (e.g. a condition of neutral pH, 7.4 and/or lower lactic acid concentration). Variants that exhibit similar activity under either condition (i.e. don't affect activity, such as binding), are expressed, and/or exhibit preferential activity at the first condition are selected. The identity of the mutated residue of the selected mutants is determined and designated key residues.

Then, as a final step, a further combinatorial library is generated containing all combinations of mutants at the identified key residue positions. To select for conditionally active modified therapeutic proteins, such as therapeutic antibodies for example Erbitrux, with increased activity under conditions that simulate a tumor microenvironment (e.g., pH 6.0) compared to a normal microenviroment (e.g., pH 7.4), the replacing amino acid is one that has an ionizable group that can change protonation states between the two pH conditions (such as, for example, Asp, Glu, Lys, Arg, H is). For example, a combinatorial library is generated where the replacing amino acid at each key residue is a histidine. The activity of each member of the combinatorial library can be assessed or determined at a first condition that mimics or simulates a condition of a tumor environment (e.g. a condition of acidic pH, such as pH 6.0 and/or high lactic acid) and at a second condition that mimics or simulates a non-tumor environment (e.g. a condition of neutral pH, 7.4 and/or lower lactic acid concentration). Variants that exhibit increased activity at the first condition are identified or selected as conditionally active proteins.

C. Assays to Identify Conditionally Active Molecules

The steps of the method provided in Section B above to select or identify a conditionally active therapeutic molecule, for example a therapeutic protein such as an antibody therapeutic (e.g. a variant anti-EGFR antibody such as a variant Erbitrux antibody) can be performed in any in vitro or in vivo assay that is amenable to changing or altering one or more condition parameters associated with a physiologic environment. Typically, the assay is an in vitro assay. The assay can be any assay that can test or assess an activity of a therapeutic molecule in a detectable or otherwise measurable manner so that the activity as determined under a first condition and an activity as determined under a second condition can be compared. Hence, the assay or method is performed twice (i.e. in a dual format), whereby the only difference in the assay in the first iteration and the second iteration is a parameter or condition that differs between a first condition (e.g. diseased or tumor environment) compared to a second condition (non-diseased or normal physiologic environment). For example, a first assay can be performed where an activity is assessed at an acidic pH and/or high lactate concentration as exists in a tumor environment and a second assay is performed that is identical to the first assay except that the activity is assessed at a higher pH (e.g. neutral pH) and/or a lower lactate concentration as exists in a non-tumor or normal physiologic environment.

Any assay described herein can be used to assess an activity of a protein in order to generate and identify a protein that is more active in one environment than another environment. For example, exemplary assays are those that measure binding activity of a therapeutic molecule to its cognate binding partner or a functional activity of a therapeutic molecule. The assays provided herein can be developed in a high throughput format in order to assess an activity of numerous test molecules, for example protein variants, at one time in dual format. Provided herein are exemplary assays that can be used in the methods provided herein. The assays are not meant to be limiting. Any assay known to one of skill in the art is contemplated for use in the methods provided herein, including assays that detect binding, and functional assays.

1. Assays that Detect Binding

In some examples, the assays for use in the methods provided herein measure binding of a test molecule, such as a therapeutic protein or variants thereof for example an antibody variant (e.g. anti-EGFR) to a cognate binding partner, such as a receptor, ligand or an antigen. Hence, provided herein is an in vitro physiologic sensitive method to identify and distinguish activity, such as binding activity of ligand-binding pair, between two different physiologic microenvironments. The method is a comparative method to identify a protein that exhibits higher activity, for example binding activity, in one environment than another environment. For example, an in vitro assay provided herein is a binding assay performed separately (e.g. in parallel or sequentially) under conditions that 1) simulate binding conditions found in the extracellular matrix within a tumor microenvironment and 2) simulate physiologic binding conditions, such as found at non-diseased sites. The method can be used to identify any test molecule that preferentially binds to its ligand or receptor under the diseased state of the tumor microenvironment compared to normal physiologic conditions of a non-tumor microenvironment, such as exists in the skin, GI tract or other tissue. The method is a dual assay comparative method, whereby the cognate binding partner (e.g. target antigen or ligand) is separately contacted with a test molecule under the two different binding conditions.

In the assay, each binding molecule (e.g. therapeutic protein or variant) is screened individually and separately for binding to its congnate binding partner (e.g. target antigen) under both simulated conditions. For example, a therapeutic protein can be contacted with a cognate binding partner, such as a target antigen, and the binding activity of the therapeutic protein for the cognate binding partner can be assessed and compared. Examples of assays that measure binding include solution binding assays and solid support binding assays, such as surface plasmon resonance and immunoassays, such as ELISA.

Exemplary cognate binding partners for use in the binding assays described herein include small molecules, peptides, proteins, enzymes, antibodies or other biomolecules. In some examples, the cognate binding partner is a point of intervention in the treatment of a tumor or cancer, such as any ligand, receptor, enzyme or other protein that is associated with proliferation, angiogenesis or cell growth properties of cancer cells and tumors. Hence, reference to a cognate binding partner and target protein are used interchangeably herein. The target protein can be selected based on known targets of therapeutic intervention. For example, surrogate targets for known cancer therapeutics can be selected as target proteins in the method herein. It is understood that the choice of target protein used in the binding assays herein is dependent on the test molecule target protein that is screened. Table 3 sets forth the cognate binding partners or target proteins for exemplary therapeutic proteins. Exemplary of such target proteins are set forth in Table 3 above, and include, for example, EGFR (including full length protein or extracellular domain), HER2/Neu, CD20 (full length or large extracellular loop), VEGF-A, CD52 (full length or extracellular domain), EpCAM (full length or extracellular domain) CD3 (full length, extracellular domain, γ chain, ζ chain or ∈ chain), CD33 (full length or extracellular domain), CD80 (full length or extracellular domain), CD86 (full length or extracellular domain), CTLA-4 (full length or extracellular domain), PLGF, α5β1 integrin (full length, extracellular domain, α5 or β1), Mesothelin (full length or extracellular domain) and IGF-1R (full length or extracellular domain).

In addition, a fragment of a target protein can be used in the assays provided herein. For example, target proteins, such as target antigens, can be expressed as soluble proteins. For example, a soluble EGFR for use as a target protein is the soluble EGF receptor extracellular domain (sECD). Cognate binding partners also include the extracellular domain or intracellular domain of any cognate binding partners described herein that include an extracellular domain and/or an intracellular domain.

In some examples of the methods provided herein, the test molecule is an anti-EGFR antibody or variant thereof and the cognate binding partner is a ligand or soluble fragment thereof, such as, for example, soluble EGFR receptor. The epidermal growth factor receptor (EGFR, HER1, c-ErbB-1; SEQ ID NO:10) is a target for intervention and treatment of various cancers. EGFR is a transmembrane glycoprotein that is a member of a subfamily of type I receptor tyrosine kinases, including EGFR, HER2, HER3 and HER4. EGFR is constitutively expressed in many normal epithelial tissues, including skin and hair follicles. EGFR is overexpressed in a several cancers of epidermal origin. Expression of EGFR is detected in many human cancers including those of the head and neck, colon and rectum. For example, squamous cell carcinoma of the head and neck is associated with overexpression of EGFR (Parikh et al., (2011) *Indian J Cancer* 48:145-147). EGFR is associated with poor patient prognosis and resistance to cytotoxic chemotherapy (Ryan and Chabner (2000), *Clin. Cancer Res.* 6:4607-4609; Fox et al., (1994) *Breast Cancer Res. Treat.,* 29:41-49; Grandis et al., (1998) J. Natl. Cancer Inst. (Bethesda), 90: 824-832; Uhlman et al., (1995) Clin. Cancer Res., 1:913-920; Neal et al., (1990) Cancer (Phila.), 65:1619-1625). EGFR is frequently overexpressed in epithelial tumors and EGFR expression can correlate with tumor resistance to cytotoxic agents and chemotherapy (Ryan and Chabner (2000), *Clin. Cancer Res.* 6:4607-4609).

Binding of a ligand to the extracellular domain of EGFR can stimulate dimerization, activate an internal tyrosine kinase domain, and can activate several downstream signals, including, for example, protein kinase A, which can phosphorylate bcl-2. (Ryan and Chabner (2000), *Clin. Cancer Res.* 6:4607-4609; Ciardiello and Tortora (1998), Clin Cancer Res. 4:821-828).

In particular examples herein, binding activity of an anti-EGFR antibody or variants thereof to EGFR or a soluble EGFR can be assessed under conditions of low pH (<7.4) and elevated lactic acid concentrations, and under conditions of physiologic pH of about 7.3 to 7.4 and low lactate concentrations. In addition, human serum also can be included in the binding assay to further mimic the natural environments. Binding activity can be compared between the two conditions to identify biomolecule binding agents that exhibit greater binding activity under the tumor microenvironment conditions compared to under the normal physiologic conditions. Anti-EGFR antibodies can be identified that exhibit greater binding for its EGFR cognate binding partner under conditions that simulate the tumor microenvironment as compared to conditions that simulate normal physiologic conditions.

Typically, the test molecule or cognate binding partner is detectably labeled so that the binding activity can be assessed and determined. For example, to detect binding, the test molecules, such as therapeutic proteins for example antibody variants (e.g. anti-EGFR antibody variants), can be labeled with a detectable moiety or tag in order to facilitate detection. The skilled artisan can select an appropriate detectable moiety or tag for assay conditions. For example, some secondary reagents, such as anti-Ig antibodies cannot be used to detect binding of a modified protein that is an antibody in a solution that contains human serum. In addition, an anti-IgG antibody cannot be used to detect binding of a biomolecule that is an antibody.

Any detectable moiety or other moiety known to one of skill in the art that is capable of being detected or identified can be used. The moiety or tag can be linked to the test molecule, such as a therapeutic protein or antibody, directly or indirectly, for example using a linker. Linkage can be at the N- or C-terminus of the therapeutic antibody. Exemplary tags and moieties that can be used in the method herein, include but are not limited to, any set forth in Table 6.

TABLE 6

| Name | Sequence | # of Residues | Size (Da) | SEQ ID NO |
|---|---|---|---|---|
| c-Myc | EQKLISEEDL | 10 | 1200 | 5 |
| FLAG | DYKDDDDK | 8 | 1012 | 3 |
| HA | YPYDVPDYA | 9 | 1102 | 15 |
| VSV-G | YTDIEMNRLGK | 11 | 1339 | 16 |
| HSV | QPELAPEDPED | 11 | 1239 | 17 |
| V5 | GKPIPNPLLGLDST | 14 | 1421 | 18 |
| Poly Arg | RRRRR | 5-6 | 800 | 19 |
| Strep-tag-II | WSHPQFEK | 8 | 1200 | 20 |
| S- | KETAAAKFERQHMDS | 15 | 1750 | 21 |
| 3x FLAG | DYKDHDGDYKDHDIDYKDDDDK | 22 | 2730 | 22 |
| HAT- | KDHLIHNVHKEFHAHAHNK | 19 | 2310 | 23 |
| SBP- | MDEKTTGWRGGHVVEGLAGELE QLRARLEHHPQGQREP | 38 | 4306 | 24 |

Any linker known to one of skill in the art that is capable of linking the detectable moiety to the therapeutic antibodies described herein can be used. Exemplary linkers include the glycine rich flexible linkers (-G$_4$S—)$_n$, where n is a positive integer, such as 1 (SEQ ID NO:4), 2 (SEQ ID NO:70), 3 (SEQ ID NO: 71), 4 (SEQ ID NO: 72), 5 (SEQ ID NO: 73), or more.

Binding assays can be performed in solution or by affixing the test molecule or cognate binding partner to a solid support. In some examples, cognate binding molecules or test molecules can be expressed from cells and binding can be assessed in a cell-based assay.

a. Solid Support Binding Assays

The assays for use in the methods provided herein include binding assays in which binding of a test molecule, such as a therapeutic target protein or variant thereof, to a cognate binding partner is measured under conditions in which one or both is attached to a solid support. For example, a cognate binding partner in solution can interact with a test molecule immobilized on a solid support, or a test molecule in solution can interact with a cognate binding partner immobilized on a solid support. Solid support binding assays can be advantageous compared to solution binding assays because immobilization on the solid phase can facilitate separation of bound protein from unbound protein. Any solid support binding assay known to the skilled artisan is contemplated for use in the methods provided herein, including surface plasmon resonance and ELISA.

For example, Surface Plasmon resonance (SPR) can be used to detect binding of unlabeled molecules in highly sensitive assays by measuring refractive index changes that occur upon molecular binding of analyte molecules in a sample to immobilized molecules (Piliarik et al. (2009) *Methods Mol. Biol.* 503:65-88). SPR occurs when surface plasmon waves, which are collective oscillations of electrons in a metal, are excited at a metal/dielectric interface. SPR reduces reflected light intensity at a specific combination of angle and wavelength. Molecular binding can change the refractive index and thickness of an ultra-thin organic (dielectric) layer on the metal film, which changes the SPR resonance conditions. A solution with the cognate binding partner can be passed over an immobilized therapeutic protein or a solution with therapeutic protein can be passed over immobilized cognate binding partner. Association rates can be measured by measuring SPR signal as a function of time. After association, a blank solution can be passed over immobilized therapeutic protein or cognate binding partner and dissociation rates can be measured as a function of time. From the association and dissociation rates, an equilibrium binding constant can be calculated. (Jecklin et al. (2009), *J. Mol. Recognit.* 22(4):319-29; Nguyen et al. (2007) *Methods.* 42(2):150-61; Tanious et al. (2008), *Methods Cell Biol.* 84:53-77). Thus, SPR can be used to measure kinetics and thermodynamics of interactions between therapeutic proteins and cognate binding partners.

In another example, binding between a therapeutic protein and a cognate binding partner can be detected by Enzyme-linked immunosorbent Assay (ELISA). ELISA is an immunological assay that can be used to detect protein/ligand interactions, such as antibody/antigen interacts. Typically, in an ELISA, the antibody/antigen interactions are detected by measuring a signal from an enzyme marker linked directly or indirectly to the antibody/antigen complex. Several ELISA methods are known to the skilled artisan, and any ELISA method known to one of skill in the art or described herein can be used, including direct ELISA and indirect ELISA. In a direct ELISA, a labeled primary antibody that interacts with an immobilized molecule is detected. A direct ELISA can include steps of: 1) coating a solid phase with a cognate binding partner (i.e., a ligand or antigen) of a test molecule, such as an antibody; 2) incubating the solid phase with a blocking reagent to block non-specific binding sites on the solid phase; 3) incubating the solid phase with a detectabletest molecule that binds to the cognate binding partner; and 4) detecting the bound detectabletest molecule. In an indirect ELISA, a labeled secondary antibody that interacts with the primary antibody is detected. An indirect ELISA can include steps of: 1) coating a solid phase with a cognate binding partner (i.e., a ligand or antigen) of a test molecule, such as an antibody; 2) incubating the solid phase with a blocking reagent to block non-specific binding sites on the solid phase; 3) incubating the solid phase with a test molecule that binds to the cognate binding partner; 4) incubating with a secondary detection agent, such as a labeled secondary antibody capable of detecting the test molecule, but not human serum components contained in the assay buffers, that can bind to the therapeutic antibody; and 5) detecting the secondary detection agent. Furthermore, for the direct or indirect ELISA methods, one or more washing steps (e.g., 1, 2, 3, 4 or more washing steps) can be included between any steps of the method.

It is within the level of one of skill in the art to empirically determine the precise assay or assay conditions depending on the cognate binding protein and biomolecule being screened. The steps of the method performed in a solid support binding assay includes 1) immobilizing a cognate binding protein to a solid support; 2) contacting a test molecule or molecules (e.g. antibody variants) with the cognate binding protein; and 3) detecting and identifying bound test molecules that exhibit binding activity to the cognate binding protein. It is understood that the steps of the method can be performed such that the test molecule is immobilized to the solid support and the cognate binding molecule is contacted therewith. Any of the steps can be performed under conditions to simulate two in vivo physiologic conditions. For example, where the assay is an ELISA, any of the steps of an ELISA, such as coating, blocking, incubation with test molecule (e.g. therapeutic antibody or variants thereof), or detection, can be performed under conditions described herein, such as conditions that simulate a tumor microenvironment (e.g., pH 6.0) or under conditions that simulate a normal microenvironment (e.g., pH 7.4) or other suitable conditions known to one of skill in the art.

A description of the general assay method is provided below with reference to an immunoassay-based format. One of skill in the art can adapt a step or steps to perform a binding assay in other solid support format, such as by surface plasmonan resonance. Any test molecule, such as a therapeutic protein or variants, described in Section B above can be tested for binding activity for its cognate binding protein as described herein. In particular, antibody variants of anti-EGFR antibodies, for example variant Erbitux antibodies, can be generated and screened in the dual assay herein to identify an improved variant anti-EGFR analog for the treatment of cancer that binds to the EGFR within the tumor microenvironment of reduced pH and elevated lactate concentrations, but not at normal physiologic pH.

i. Immobilization to a Solid Support

As a first step of the method, a cognate binding protein (e.g. ligand or antigen) of interest is adapted for use to facilitate capture of bound molecules such that detection or identification of the bound molecules can later be achieved. To facilitate capture, the cognate binding protein for screening against can be provided in solution, in suspension or can be attached to a solid support as appropriate for the assay method. For example, the cognate binding protein is immobilized to a solid support. Alternatively or in addition, the test molecule can be modified to facilitate capture. For example, the test molecule can be immobilized to a solid support or otherwise detectably labeled. Generally, the binding assay is effected on a solid support.

Solid supports that can be used in the binding assays provided herein include any carrier that is capable of being affixed with a molecule, for example a test molecule or a cognate binding partner of a protein such as a ligand, receptor or antigen. Typically, to facilitate high throughput screening of variant test molecules (e.g. a library or collection of antibody variants such as anti-EGFR antibody variants), a cognate binding partner is affixed to the solid support. Examples of carriers for use as solid supports in the methods provided herein include, but are not limited to, glass, polystyrene, polypropylene, polyethylene, dextran, nylon, amyloses, natural and modified celluloses, polyacrylamides, agaroses and magnetic solid supports, such as solid supports that include magnetite. The solid support can be one or more beads or particles, microspheres, a surface of a tube or plate, a filter membrane, and other solid supports known in the art. Exemplary solid support systems include, but are not limited to, a flat surface constructed, for example, of glass, silicon, metal, nylon, cellulose, plastic or a composite, including multiwell plates or membranes; or can be in the form of a bead such as a silica gel, a controlled pore glass, a magnetic (Dynabead) or cellulose bead. Further, such methods can be adapted for use in suspension or in the form of a column.

It is within the level of one of skill in the art to select a suitable solid support depending on the particular assay conditions. For example, nickel coated microplates can be less suitable for binding of His-tagged proteins, since buffer pH can affect antigen coating to Ni-coated but not high-bind plates. It is within the level of one of skill in the art to determine whether a solid support is suitable for use with varying pH conditions.

Test molecules or cognate binding partners can be immobilized to the solid support by any method known to one of skill in the art. Covalent or non-covalent methods for attachment can be used. Typically, the test molecule or cognate binding partner (such as a ligand or antigen) is immobilized by adsorption from an aqueous medium. In some examples, adsorption can be carried out under conditions that simulate a diseased microenvironment (such as a tumor or cancer microenvironment), under conditions that simulate a normal microenvironment, or under standard conditions known to one of skill in the art. For example, adsorption can be carried out using a buffer with a pH range of at or about between 6.0 to 7.4, in some examples at or about pH 7.4. In particular, to effect adsorption, a high binding microplate can be used as a solid support. High binding plates are known to those of skill in the art and readily available from various manufacturers (see e.g., Nunc Maxisorp flat-bottom plates available from eBioscience, San Diego, Calif., Cat. No. 44-2404-21; Costar 96-well EIA/RIA Stripwell plate, Costar 2592).

Other modes of affixation, such as covalent coupling or other well known methods of affixation of the target protein to the solid matrix can also be used. Covalent methods of attachment of therapeutic proteins and/or cognate binging partners include chemical crosslinking methods. Reactive reagents can create covalent bonds between the support and functional groups on the protein or cognate binding partner. Examples of functional groups that can be chemically reacted are amino, thiol, and carboxyl groups. N-ethylmaleimide, iodoacetamide, N-hydrosuccinimide, and glutaraldehyde are examples of reagents that react with functional groups. In other examples, test molecules and/or cognate binding partners can be indirectly attached to a solid support by methods such as, but not limited to, immunoaffinity or ligand-receptor interactions (e.g. biotin-streptavidin or glutathione S-transferase-glutathione). For example, a test molecules can be coated to an ELISA plate, or other similar addressable array.

In one example, a solid support, such as the wells of a microplate can be coated with an affinity capture agent, which binds to and captures the test molecule or cognate binding partner to affix it to the solid support. The test molecule and/or cognate binding partner can be modified to contain a tag that is compatible with any chosen affinity capture agent. Exemplary tags or moieties that can be used in the assays herein include, but are not limited to, a His, T7, Myc, HA, VSV-G, or Flag Tag (see e.g. SEQ ID NOS:3, 5, 7, 15-16, 25). Such tags are well-known to one of skill in the art. For example, a biotinylated anti-His antibody can be coated onto a streptavidin containing plate to facilitate capture of a cognate binding partner or test molecule protein containing a His-tag. Streptavidin and affinity capture agent-coated plates are available from manufacturers (see e.g. Thermo Fisher Scientific, Rockford, Ill.; Catalog No. 15500) or can be prepared by one of skill in the art. As noted above, the choice of adsorption or immobilization technique is generally selected to be compatible with varying pH environments.

In examples herein where the cognate binding partner is affixed to the solid support, attachment of a cognate binding partner (e.g. sEGFR) to a solid support can be performed either before, during, or subsequent to contact with a screened test molecule or library of test molecules. For example, one or more cognate binding partners can be pre-absorbed to a solid support, such as a chromatography column or a well of a Microplate, prior to incubation with a test molecule. In other examples, the cognate binding partner and test molecule are contacted in solution followed by capture of the cognate binding partner on a solid support.

In the dual format or duplicate assay, the immobilized agent, typically the cognate binding partner is immobilized under standard conditions that are the same. Typically, the buffer that is used to facilitate adsorption or immobilization under both conditions is a neutral or physiologic buffer. Exemplary of physiologic buffers include, but are not limited to, phosphate buffered saline (PBS), Hank's balanced salt solution (HBSS), Ringers or Krebs. The pH and buffering capacity is a function of the assay conditions and can be empirically determined or chosen by one of skill in the art. Exemplary of a physiologic buffer is Krebs-Ringer Bicarbonate (KRB) buffer (Sigma Aldrich, Catalog No. K4002). Further, adsorption or immobilization of the immobilized agent, typically the cognate binding partner, on a solid support is effected in a buffer that does not contain human serum, since human serum is used in the contacting step or screen to simulate natural environment conditions.

For example, varying concentrations of a cognate binding partner, such as an antigen, in KRB buffer or other similar physiologic buffer can be adsorbed onto a solid support. For example, from at or about between 1 and 50 nM, for example, 3 and 30 nM, such as 5-20 nM, for example, at or about 3, 6, 9, 12, 13, 14, 15, 16, 17, 18, 19, 20, 25, 30, 35, 40 or 50 nM of cognate binding partner (e.g. antigen such as a sEGFR) in KRB buffer or other similar physiologic buffer can be adsorbed. The amount of target antigen to be adsorbed is a function of the binding agent and can be empirically determined, such as by using a control known to bind the target antigen. Adsorption can proceed for any desired length of time and temperature to allow the cognate binding protein to bind to binding sites on the solid support. For example, adsorption is generally performed at 4° C.-37° C., such as 4° C., room temperature (i.e., 22° C.) or 37° C. The time for adsorption is generally 30 minutes to 48 hours or more, and can vary as a function of the temperature. For example, a cognate binding protein can be adsorbed to a solid support, such as a high-binding microwell plate, at 4° C. for 6 hours to 48 hours, such as 12 hours to 36 hours, and typically overnight, for example, 12 hours to 24 hours. In another example, a cognate binding protein is adsorbed to a solid support, such as a high-binding microwell plate at room temperature for 30 minutes to 4 hours, such as 1 hour to 2 hours, in particular 2 hours. The solid support can be washed one or more times, such as 1, 2, 3, 4 or more times with the same buffer used for adsorption to remove any unbound target antigen.

ii. Contacting Under Simulated Conditions

In the assay, binding of a binding partner and agent is effected under conditions that simulate two different physiologic conditions, a diseased microenvironment and the normal physiologic condition of a non-diseased microenvironment. For example, the diseased microenvironment can simulate conditions in a tumor microenvironment. Thus, following affixation of the target antigen to a support, the subsequent steps of the method are generally performed as two separate assays. Thus, for each target antigen, the antigen is adsorbed, attached or immobilized as described above onto duplicate solid supports. Subsequently, the duplicate supports are treated separately for performance of the binding assay under two varied assay conditions, one simulating the tumor microenvironment and the other simulating the normal physiologic environment. Such conditions are described above in Section B. As discussed above in Section B, it is understood that in performing the separate assays, the only conditions that are varied relate to the buffer conditions simulating the in vivo microenvironment. Time and temperature incubation conditions are generally the same between the parallel assays.

For example, in the method provided herein, a test molecule is contacted with a cognate binding protein in two separate assays to test for binding activity. In one assay, the test molecule is contacted or incubated with the cognate binding protein in the presence of a buffer that simulates the tumor microenvironment as described above. In the second assay, the test binding molecule is contacted or incubated with the cognate binding protein in the presence of a buffer that simulates the normal physiologic conditions as described above. Typically, the incubation reaction can proceed for any desired length of time and temperature to allow the test molecule or protein to bind to the cognate binding partner (e.g. antigen). For example, binding is generally performed at 4° C.-37° C., such as 4° C., room temperature or 37° C. The time for binding is generally 30 minutes to 48 hours or more, and can be a function of the temperature. Typically, binding of the binding molecule or protein is at room temperature at or about between 30 minutes to 4 hours, such as 1 hour to 2 hours, for example about 1 hour. The solid support can be washed in the same buffer used for binding to remove any unbound target antigen.

For example, contacting can be performed with 1 mM lactic acid, pH 7.4, and 25% human serum to simulate a non-tumor or microenvironment. Separately, the contacting step is performed with 16.5 mM lactic acid, pH 6.0, 25% human serum to simulate a tumor microenvironment. In each contacting reaction, contacting can be for 1 hour at room temperature (i.e., 22° C.).

Hence, in each of the assay conditions, a test molecule, such as a therapeutic antibody or antibody variants (e.g. anti-EGFR antibody variants) can be incubated with the cognate binding partner, such as a target antigen, for an appropriate length of time and temperature to allow binding to occur in the presence of the requisite buffer conditions (e.g. diseased or normal microenvironment). Except for the buffer conditions that simulate the microenvironment, the assay conditions (time and temperature) are the same. The assay can be performed in the presence of varying concentrations of test molecule. The amount of test molecule that is contacted with a cognate binding protein (e.g. antigen) is a function of, for example, the cognate binding protein and test molecule (e.g. EGFR and anti-EGFR or variants), and the particular binding conditions, and can be empirically determined. Generally, varying concentrations are tested in serial dilutions. Whole supernatant, diluted supernatant or purified protein can be tested. As discussed above, the test molecule is labeled with a detectable moiety or tag in order to facilitate detection of bound antigen-binding molecule complexes to assess binding activity.

In some examples, prior to contacting a test molecule (e.g. modified therapeutic protein) with a cognate binding protein (e.g. target antigen), non-specific protein binding sites on the surface of the solid phase support are typically blocked. Hence, the step of contacting the therapeutic antibody or variants thereof (e.g. anti-EGFR variants) and cognate binding partner (e.g. EGFR or sEGFR) typically can be performed after a blocking step. Blocking of the solid support can reduce nonspecific binding to the solid support, reduce background signal, reduce nonspecific binding to adsorbed proteins, and stabilize the adsorbed protein. The selection of conditions for blocking is within the ability of one of skill in the art. Any blocking conditions described in the art can be used in the methods provided herein.

Thus, for example, after adsorption of solid-phase bound cognate binding partner, such as a target antigen, an aqueous solution of a protein free from interference with the assay can be admixed with the solid phase to absorb the admixed protein onto the surface of the antigen-containing solid support at protein binding sites on the surface that are not occupied by the antigen molecule. For example, blocking solutions include those containing human, bovine, horse or other serum albumin. Typically, the blocking solution contains human serum. Blocking of a solid support, such as a plate, can be performed using a binding assay buffer to which one or more blocking agents are added. Exemplary blocking agents include 1-5% Bovine Serum Albumin, 1-5% non-fat dry milk and 25% human serum. Detergents, such as Tween-20, and preservatives, such as thimerisol, can be added to the blocking solution. Binding assay buffers include i.e. the tumor microenvironment buffer or the normal physiologic buffer. The aqueous protein solution-solid support mixture is typically maintained for a time period of 30 minutes, 1 hour, or longer, and can vary as a function of the temperature. The blocking reaction can be performed at any temperature, and generally can be performed 4° C.-37° C., such as 4° C., room temperature (i.e., 22° C.) or 37° C. In some examples, the reaction is allowed to proceed for at least one hour at a temperature of about 4° C.-37° C. For example, blocking can be achieved at room temperature for one hour. After incubation and blocking, the resulting solid phase can be thereafter rinsed free of unbound protein prior to contact with the test molecule (e.g. therapeutic protein or antibody or variants thereof).

iii. Detection and Identification of Conditionally Active Test Molecules

Test molecules, such as therapeutic proteins for example antibody variants (e.g. anti-EGFR antibodies) that specifically bind to the cognate binding partner can be selected or identified. After washing away unbound protein, the therapeutic proteins can be detected using any assay or method known to one of skill in the art. For example, detection can be facilitated by the presence of a fluorescent, radioactive or other detectable moiety. Typically, because the test molecules (e.g. therapeutic proteins, such as antibody variants) are tagged, detection is effected using an anti-tag reagent. The choice of anti-tag reagent is a function of the tag that is employed with the binding molecule or protein. In addition, an anti-tag reagent is chosen that is compatible with the environment conditions (e.g. pH) used in the assay. It is within the level of one of skill in the art to identify or select such reagents, and test their compatibility with the assay conditions. For example, the Examples exemplify such procedures.

Anti-tag reagents are readily available such as from commercial sources or other sources. Exemplary anti-tag reagents that can be used for detection in the methods herein include, but are not limited to an anti-FLAG antibody or anti-Myc antibody (available from vendors such as Abcam, Cambridge, Mass.; GeneTex, Irvine, Calif.).

Typically, in the methods herein, the method of detection of the bound complex is one that is capable of being quantitated such that the level of activity can be assessed. For example, a label can produce a signal, such as a colorimetric signal, a chemiluminescent signal, a chemifluorescent signal or a radioactive signal. Depending upon the nature of the label, various techniques can be employed for detecting or detecting and quantitating the label. For example, methods of quantitation include, but are not limited to, spectrophotometric, fluorescent and radioactive methods.

Examples of enzyme labels include horse radish peroxidase, alkaline phosphatase, and beta-D-galactosidase. Examples of enzyme substrates that can be added to develop the signal include PNPP (p-Nitrophenyl Phosphate, Disodium Salt), ABTS (2,2'-Azinobis[3-ethylbenzothiazoline-6-sulfonic acid]-diammonium salt), OPD (o-phenylenediamine dihydrochloride), and TMB (3,3',5,5'-tetramethylbenzidine) (SOMA Labs, Romeo, Mich.), including Sureblue TMB Microwell Peroxidase Substrate 1-component (KPL, #52-00-03). The reaction can be stopped by adding a stopping reagent (e.g. TMB stop solution). The absorbance at a suitable wavelength (i.e. 450 nm) can be determined.

For fluorescence, a large number of fluorometers are available. For chemiluminescers, such as horse radish peroxidase (HRP), luminometers or films are available. With enzymes, a fluorescent, chemiluminescent, or colored product can be determined or measured fluorometrically, luminometrically, spectrophotometrically or visually. For example, an anti-tag reagent can be conjugated to horse radish peroxidase (HRP) or other detectable agent.

Typically, the incubation reaction can proceed for any desired length of time and temperature to allow detection of the binding molecule or protein. For example, detection is generally performed at 4° C.-37° C., such as 4° C., room temperature or 37° C. The time for binding is generally 30 minutes to 48 hours or more, and is a function of the temperature. Typically, binding of the binding molecule or protein is at room temperature at or about between 30 minutes to 4 hours, such as 1 hour to 2 hours, for example about 1 hour. The solid support can be washed in the same buffer used for binding to remove any unbound target antigen.

Once binding activity is determined under each assay condition, the binding activity under the first condition (e.g. the diseased environment for example tumor environment) and the second condition (e.g. non-diseased or normal environment) are compared as described in Section B.3 above. Conditionally active molecules are identified that exhibit greater activity under the first condition than the second condition, for example, a ratio of activity that is at or about between 1.5 to 100, such as 2 to 50, for example 5 to 30 or more.

b. Solution Binding Assays

The assays for use in the methods provided herein include assays in which binding of a therapeutic protein to a cognate binding partner is measured in solution. The skilled artisan can select a solution binding assay for use in the methods provided herein. Below is a brief description of exemplary solution binding assays that can be used in the methods provided herein. However, these are not meant to be limiting, and any solution binding assay known to the skilled artisan is contemplated for use in the methods provided herein, including equilibrium dialysis, competitive binding assays (e.g., Myers et al., (1975) *Proc. Natl. Acad. Sci. USA* 72:3683-3686), radiolabeled binding assays (e.g., Feau et al., (2009) *J. Biomol. Screen.* 14(1):43-48), calorimetry (including isothermal titration calorimetry (ITC) and differential scanning calorimetry (e.g., Perozzo et al., (2004) *J. Recept Signal. Transduct Res.* 24(1-2):1-52; Holdgate (2001) *Biotechniques* 31(1):164-166, 168, 170), Celej et al. (2006) *Anal. Biochem.* 350(2):277-284)), and spectroscopic fluorescence assays, including fluorescence resonance energy transfer assays. The conditions for the method herein where binding activity is determined in solution can be determined by one of skill in the art based on the description herein. For example, the conditions can be adapted from conditions discussed above for binding assays performed on a solid support.

i. Isothermal Titration Calorimetry (ITC)

In ITC, one binding partner is titrated into a solution containing the other binding partner, thereby generating or absorbing heat, which is quantified by the calorimeter. ITC can be used to detect heat effects from reactants in quantities of nanomoles or less. For example, isothermal titration calorimetry assays can be performed to measure all thermodynamic parameters, including free energy of binding ($\Delta G$), enthalpy ($\Delta H$), and entropy ($\Delta S$) of binding, and the heat capacity change ($\Delta Cp$), involved in binding of a therapeutic protein to a cognate binding partner. Analysis of these features can help elucidate the mechanism and thermodynamic parameters of binding between a therapeutic protein and a cognate binding partner (Perozzo et al., (2004) *J. Recept. Signal. Transduce. Res.* 24(1-2):1-52)

ii. Spectroscopic Assays

Any spectroscopic assay known to one of skill in the art can be used to detect binding of a therapeutic protein in the methods provided herein. Interaction between a modified protein and a cognate binding partner can be detected by any spectroscopic assay known to one of skill in the art, including UV-vis spectroscopic techniques, fluorescence assays such as fluorescence resonance energy transfer assays and fluorescence quenching assays (Wu (2007), *J. Pharm. Biomed. Anal.* 44(3):796-801). For example, changes in fluorescence or UV/vis absorption as a result of a therapeutic protein binding to a cognate binding partner, such as quenching of inherent fluorescence, can be detected. In some examples, the therapeutic protein and/or the cognate binding partner can be labeled with a fluorescent label or a UV/vis label. After measuring a spectroscopic signal, the observed binding constant can be calculated (e.g., Zhang et al. (2009) *Spectrochim Acta A Biomol. Spectrosc.* 72(3):621-626).

c. Cell Based Assays

Assays for use in the methods provided herein to detect binding of a therapeutic protein to a cognate binding partner include cell based assays, and in particular assays performed using cell surface display systems, such as mammalian cell surface display systems. In an exemplary method, nucleic acids encoding a therapeutic protein or a library of variant therapeutic proteins, including a library of modified therapeutic proteins, can be introduced into a vector suitable for expression in cells, such as mammalian cells. Cells are then transfected with the vector, and the therapeutic protein(s) are expressed by the cells. The library of cells containing surface-expressed therapeutic proteins can be contacted with a solution containing a soluble or surface-bound cognate binding partner. Binding activity can be detected using any assay that can detect the binding to the surface of the cells. Activity also can be assessed by assessing a functional activity of the test molecule or therapeutic protein. Any cell based assay known to the skilled artisan is contemplated for use in the methods provided herein, including cell proliferation assays, cell death assays, flow cytometry, cell separation techniques, fluorescence activated cell sorting (FACS), phase microscopy, fluorescence microscopy, receptor binding assays, cell signaling assays, immunocytochemistry and reporter gene assays. In some examples, the assays are fluorescence activated cell sorting (FACS) assays.

Proteins can be expressed by mammalian cells as secreted, soluble molecules, cell surface molecules, or intracellular antibodies. In an exemplary method, cells can be transfected with a library of proteins under conditions whereby most or all of the cells display a member of the protein library anchored on the cell surface. Optionally, an expression system can be used in which most of mammalian cell transfectants have only one plasmid integrated in their genome. Therefore, most (i.e., at least about 70% or about 80% or about 90%) of the transfectants express one or more molecules of one therapeutic protein. This can be verified, for example, by isolating and culturing individual transfectants; and amplifying and sequencing the expressed sequences to determine whether they have a single sequence.

In some examples of the methods provided herein, the therapeutic proteins are antibodies displayed on the surface of mammalian cells. Any antibody described herein can be expressed on the surface of mammalian cells, including full length, bivalent, functional antibodies, such as IgG antibodies. The antibody can be a fragment, for example, Fab fragments or scFv fragments. Antibodies can include an Fc region, such as a scFv-Fc or a full length antibody, which comprises two heavy and two light chains. The skilled artisan can select a suitable antibody fragment. For example, scFv-Fcs and full length antibodies made in mammalian cells can have several advantages over scFvs or Fab fragments including their multimeric nature and their longer in vivo half-lives, higher affinities for antigens, and lesser tendencies to form aggregates. For example, anti-EGFR variant antibodies are displayed on the surface of cells, and activity to a cognate binding partner (e.g. and EGFR or soluble EGFR) is assessed.

i. Cell Surface Expression of Test Molecules

Test molecules, such as a therapeutic protein for example antibody variants (e.g. anti-EGFR antibody variants) can be expressed on the surface of cells. Nucleic acids encoding test molecules, such as therapeutic proteins, can be inserted into a suitable vector, such as a vector described herein, and used to transfect cells. Cell lines that can be used include any cell lines described in the art or that can be obtained from repositories such as the American Type Culture Collection. The skilled artisan can select cell lines with desired properties. For example, an antibody made in mammalian cells is more likely to be properly folded and glycosylated than one made in prokaryotic cells. In some examples, the therapeutic proteins are expressed in mammalian cells, such as chinese hamster ovary (CHO) cells.

Any vectors known in the art for displaying proteins, such as antibodies, on the surface of mammalian cells can be used in the methods provided herein (see, e.g., Zhou et al. (2010), MAbs 2(5):508-518). For example, the vectors can express the nucleic acids encoding therapeutic proteins as secreted proteins, soluble proteins or as cell surface proteins. Optionally, the vector is suitable for expression in cells for the purpose of producing nucleic acids of adequate purity and quantity for a mammalian transfection. These cells can be, for example, bacterial cells, such as *Escherichia coli* or *Bacillus subtilus*, or fungal cells such as *Saccharomyces cerevisiae*. The vector can be selected so that only one type of therapeutic protein from the transformed library is expressed by the host cell. Methods of transfection of cells are known to one of skill in the art (e.g., Hahn and Scanlan (2010) *Top. Curr. Chem.* 296:1-13), and include, for example, chemical methods such as polycationic cyclodextrin vectors (e.g., Cryan et al., (2004) *Eur J Pharm Sci.* 21(5):625-33) and liposome complexes, including cationic liposomes (e.g., Gao and Huang (1995) *Gene Ther.* 2(10): 710-722). Exemplary cationic liposomes which may be used include those described in U.S. Pat. No. 7,989,606, including 3-beta-[N—(N',N'-dimethyl-aminoethane)-1-carbamoyl]-cholesterol (DC-Chol), 1,2-bis(oleoyloxy-3-trimethyl-ammonio-propane (DOTAP) (see, for example, WO 98/07408), lysinylphosphatidylethanol amine (L-PE), lipopolyamines such as lipospermine, N-(2-hydroxyethyl)-N,N-d-dimethyl-2,3-bis(dodecyloxy) 1-propanaminium bromide, dimethyl dioctadecyl ammonium bromide (DDAB), dioleoylphosphatidyl ethanolamine (DOPE), dioleoylphosphatidyl choline (DOPC), N(1,2,3-dioleyloxy) propyl-N,N,N-triethylammonium (DOTMA), DOSPA, DMRIE, GL-67, GL-89, Lipofectin, and Lipofectamine (Thiery et al. Gene Ther. (1997); Feigner et al., Annals N.Y. Acad. Sci. (1995); Eastman et al., Hum. Gene Ther. (1997)). Methods of transfection also include nonchemical methods, such as electroporation (Chu et al. (1987), *Nucl. Acid. Res.* 15(3) 1311-1326.), sonoportation (e.g., Kumon et al (2009), *Ultrasound Med. Biol.* 35(3):494-506), gene gun (e.g., O'Brien and Lummis (2004) *Methods* 33(2):121-125) and viral transduction (e.g., Flotte and Carter (1995), *Gene Ther.* 2(6):357-362).

In some examples the transfectants can express therapeutic proteins as cell surface proteins. The skilled artisan can select a vector to express the modified proteins described herein. For example, a vector can be used that integrates into a specific site in the genome of a mammalian cell line. One example of a vector that can be used is a FLP-IN™ vector (Invitrogen), that can be transfected into cells that contain an appropriate site for site-specific chromosomal integration. The FLP-IN™ vector can integrate into a specific site in the genome of a mammalian cell line that has been genetically engineered to contain a FLP recombination target (FRT) site, using the FLP recombinase of *Saccharomyces cerevisiae* (see, e.g., U.S. Pat. Nos. 5,654,182; 5,677,177; 5,885,836; 6,956,146; and 7,884,054; and O'Gorman et al. (1991), Science 251:1351-1355). Other vector systems that can be used are a Cre-LoxP system (Trinh and Morrison (2000), J. Immunol. Methods 244:185-193). Cre recombinase, can catalyze recombination between two LoxP sites. In some embodiments, two LoxP sites with slightly different sequences (such that recombination between the two different sites cannot be catalyzed by the Cre recombinase) may be present in a mammalian cell that is transfected with modified antibody-encoding sequences that are flanked by the same two different LoxP sites. In this situation, an antibody-encoding sequence can be inserted between the two different LoxP sites without the possibility of also being excised by Cre recombinase. In other embodiments, the LoxP sites may be identical. In another aspect, the expression or activity of Cre recombinase may be conditionally controllable.

Regulatory sequences used in vectors are typically derived from mammalian, microbial, viral, and/or insect genes. Examples of regulatory sequences include transcriptional promoters, operators, and enhancers, a ribosomal binding site (see e.g. Kozak (1991), *J. Biol. Chem.* 266: 19867-19870), an internal ribosome entry site, appropriate sequences to control transcriptional and translational initiation and termination, polyadenylation signals (see e.g. McLauchlan et al. (1988), *Nucleic Acids Res.* 16:5323-5333), and matrix and scaffold attachment sites (see Phi-Van et al. (1988), *Mol. Cell. Biol.* 10:2302-2307; Stief et al. (1989), *Nature* 341:343-345; Bonifer et al. (1990), *EMBO J.* 9:2843-2848). Nucleotide sequences are operably linked when the regulatory sequence functionally relates to the polypeptide coding sequence. Thus, a promoter nucleotide sequence can be operably linked to a polypeptide coding sequence if the promoter nucleotide sequence controls the transcription of the coding sequence.

An expression vector will typically comprise a promoter that can direct transcription in a mammalian cell operably linked to the nucleic acids encoding a therapeutic protein. Often the promoters will be capable of a high level of transcription. Expression vectors may be advantageous in comparison with FLP-IN™-type vectors in situations where a high level of expression is required to detect binding. Examples of such promoters include the CMV and SV40 viral promoters, mammalian actin promoters, the promoter contained within the 3' long terminal repeat of Rous Sarcoma virus, the herpes thymidine kinase promoter, or the promoter of the metallothionine gene. For example, the human CMV promoter/enhancer of immediate early gene 1 may be used (see e.g. Paterson et al. (1994), *Applied Microbiol. Biotechnol.* 40:691-698). DNA sequences derived from the SV40 viral genome, for example, SV40 origin, early and late promoter, enhancer, splice, and polyadenylation sites can be used to provide other genetic elements for expression of a structural gene sequence in a mammalian host cell. Viral early and late promoters are particularly useful because both are easily obtained from a viral genome as a fragment, which can also contain a viral origin of replication (Fiers et al. (1978), *Nature* 273:113; Kaufman (1990), *Meth. in Enzymol.* 185:487-511). Smaller or larger SV40 fragments can also be used, provided the approximately 250 bp sequence extending from the Hind III site toward the Bgl I site located in the SV40 viral origin of replication site is included.

Promoters from other highly expressed mammalian genes could also be used. An expression vector also typically comprises a bacterial origin of DNA replication, sequences encoding a gene product that can be positively selected for in bacteria, a polyadenylation site, a ribosome binding site, and, optionally, sequences encoding a gene product that can be positively selected for in mammalian cells, such as a sequences conferring resistance to hygromycin, neomycin, or G418. An example of an expression vector is pDC302 (Mosley et al. (1989), *Cell* 59:335-348). Other examples of expression vectors include commercially available vectors such as pTriE™-4 Ek/LIC vector (Novagen, Wis., USA) or the pGEN vectors (Promega, Wis., USA).

In some examples, the therapeutic protein is expressed with one or more transmembrane domain(s) for display on the surface of cells, such as by attachment of the transmembrane domain to the N-terminus and/or the C-terminus of the protein. Transmembrane domains that can be used as membrane association sequences in the methods provided herein include any transmembrane domain described herein, known in the art, or that can be predicted (see, e.g., Kahsay et al. (2005) *Bioinformatics* 21(9):1853-1858). Exemplary membrane association sequences include transmembrane domains and glycophosphatidylinositol (GPI) anchor sequences known to one of skill in the art (see, e.g., Udenfriend and Kodukula (1995), *Methods Enzymol.* 250: 571-582). Exemplary vectors that can attach a trans-membrane domain to a therapeutic protein include the vector FVTM (Zhou et al. (2010), MAbs 2(5):508-518).

The skilled artisan can select other expression systems that provide for expression of the therapeutic protein. For example, if the therapeutic protein is an antibody, a vector can be selected that is suited for expression of antibodies. Many vectors for mammalian expression of antibodies on the surface of cells are known to one of skill in the art. For example, a vector can be selected in which the heavy and light chain coding sequences can be transcribed and translated separately or a vector can be selected in which the heavy and light chain coding sequences can be transcribed and translated together. A membrane association sequence, such as a trans-membrane domain can be attached to the heavy chain or to the light chain, or a trans-membrane domain can be attached to the heavy chain and light chain. The membrane association sequence can be attached to the N-terminus or the C-terminus of the heavy chain and/or light chain.

ii. Binding And Detection by Fluorescence Activated Cell Sorting (FACS)

Fluorescence Activated Cell Sorting (FACS) is a cell separation technique that distinguishes fluorescent cells from non-fluorescent cells (Current Protocols in Cytometry, Robinson et al., eds., John Wiley & Sons (2004); Edidin (1989), Methods in Cell Biology 29:87-102; Herzenberg et al., (1976) *Sci. Am* 234:108-117; U.S. Pat. Nos. 5,968,738 and 5,804,387). Flow sorters are capable of rapidly examining a large number of individual cells that contain library inserts (e.g., 10-100 million cells per hour) (Shapiro et al., Practical Flow Cytometry, 1995). Briefly, cells in suspension are passed in front of a laser in droplets, each containing a single cell. A charge is applied to the droplet and an electrostatic deflection system collects charged droplets into appropriate collection tubes (Basu et, al. (2010), J. Vis. Exp (41):1546). Flow cytometers for sorting and examining biological cells are well known in the art. Known flow cytometers are described, for example, in U.S. Pat. Nos. 4,347,935; 5,464,581; 5,483,469; 5,602,039; 5,643,796; and 6,211,477. Other known flow cytometers are the FACS Vantage™ system manufactured by Becton Dickinson and Company, and the COPAS™ system manufactured by Union Biometrica.

FACS can be used to select for cells that display a protein with desirable binding properties. In the methods provided herein, conditionally active test molecules, such as a proteins, can be identified by FACS assay by screening proteins for binding to a cognate binding partner under different conditions. In an exemplary method, cells are transfected with vectors encoding for proteins that are displayed on the cell surface. The cells are then contacted with a cognate binding partner. Binding of a protein displayed on a cell surface to a cognate binding partner can result in cell-associated fluorescence. Fluorescent cells are separated from non-fluorescent cells, thus separating cells that display an active protein that binds to a cognate binding partner from cells that display a protein that does not bind to a cognate binding partner. Nucleic acid encoding active and/or inactive proteins can be isolated and sequenced to identify the protein that interacts with a cognate binding partner. In addition, separated cells can be subjected to further assays, such as assays described herein, including further FACS assays.

Typically, the cognate binding partner is detectably labeled to aid in detection. Alternatively, the cognate binding partner is not labeled, but can be detected by the use of a secondary agent. Labels for the cognate binding partner of secondary reagent include a fluorescent label (e.g., Francisco et al. (1993), *Proc. Natl. Acad. Sci. USA* 90:10444-10448) or a label that interacts with a fluorescent secondary label. Any fluorophore known to one of skill in the art can be used as a fluorescent label, such as, for example, a fluorescent label on the cognate binding partner or the secondary label. Exemplary fluorophores include fluorescein, rhodamine or Texas Red, FLUOR X®, ALEXA FLUOR, OREGON GREEN, TMR (tetramethylrhodamine), ROX (X-rhodamine), BODIPY 630/650 and Cy5 (available from Amersham Pharmacia Biotech of Piscataway, N.J. or from Molecular Probes Inc. of Eugene, Oreg.), or any other fluorescent label known to one of skill in the art (see, e.g., Giepmans et al. (2006), *Science* April 14; 312(5771):217-24). Criteria for consideration when analyzing fluorescent samples are summarized by Alexay et al. (1996) *Proceedings of SPIE, the International Society of Optical Engineering* 2705:63-72.

In further examples, to aid in interaction with the secondary reagent, the cognate binding partner can include a label that interacts with a fluorescent secondary label. Any secondary label can be used that interacts with a label on the cognate binding partner. In some examples, the cognate binding partner, such as EGFR or EGFR sECD, is labeled with Biotin with a linker known to one of skill in the art or described herein, and the cells are mixed with a fluorescent secondary label attached to a molecule that interacts with biotin, such as streptavidin. In some examples, the secondary label is Streptavidin attached to fluorescein.

In one example, the FACS analysis can be performed as two separate assays under different sets of conditions performed simultaneously or in parallel. In one example, the assays are performed in parallel and a population of cells expressing the test molecule or therapeutic protein is divided into two populations. One population is contacted with the test molecule or therapeutic protein in an assay buffer that simulates a first condition in which activity is desired (e.g. a diseased microenvironment or tumor environment). A second population is contacted with the test molecule in an assay buffer that simulates a condition in which activity is not desired (e.g., a physiologically normal environment). In the FACS assay, any of the steps, such as contacting can be performed under conditions that simulate a diseased microenvironment, such as a tumor, or conditions that simulate a normal microenvironment. Exemplary conditions that simulate a tumor microenvironment is a set of conditions such as 16.5 mM lactic acid, pH 6.0, 25% human serum. An exemplary set of conditions that simulates a normal microenvironment is a set of conditions such as 1 mM lactic acid, pH 7.4, and 25% human serum to simulate a non-tumor or microenvironment.

For example, the cells expressing therapeutic proteins can be contacted with a labeled cognate binding partner, for example, by mixing with a solution or buffer containing the cognate binding partner, where the binding buffer is one that mimics or simulates a desired condition (either a first condition or second condition as described herein). Separately (performed simultaneously or as an iterative step after positive or negative selection as described herein), a second identical population of cells expressing the assayed therapeutic proteins can be contacted with a labeled cognate binding partner, for example, by mixing with a solution or buffer containing the cognate binding partner, where the binding buffer is one that mimics or simulates the other condition. In each step the contacting steps are identical, except for the particular binding buffer or solution. The contacting step can be performed for any desired length of time and temperature to allow the cell-surface protein to bind to the cognate binding partner (e.g. antigen). For example, binding is generally performed at 4° C.-37° C., such as 4° C., room temperature or 37° C. The time for binding is generally 30 minutes to 48 hours or more, and can be a function of the temperature. Typically, binding of the binding molecule or protein is at room temperature at or about between 30 minutes to 4 hours, such as 1 hour to 2 hours, for example about 1 hour. The cells can be washed in the same buffer used for binding to remove any unbound cognate binding partner. Additionally, specific parameters that can be varied for optimization include, but are not limited to, the concentration of cognate binding partner, kinetic competition time, and FACS stringency. In addition, FACS screening can be performed under equilibrium or kinetic conditions.

If a secondary reagent is used in the detection step, after washing the cells to remove unbound cognate binding partner, the cells are contacted with appropriate secondary reagents. This further contacting step can be performed for any desired length of time and temperature to allow the secondary reagent to bind to the cognate binding protein. For example, binding is generally performed at 4° C.-37° C., such as 4° C., room temperature or 37° C. The time for binding is generally 5 minutes to 2 hours or more, and can be a function of the temperature. Typically, binding of the secondary reagent and cells is at room temperature at or about between 30 minutes to 4 hours, such as 1 hour to 2 hours, for example about 1 hour. The cells can be washed in the same buffer used for binding to remove any unbound secondary reagent.

Fluorescent cells can be separated from non fluorescent cells to separate cells that display proteins that bind to the cognate binding partner from cells that display proteins that do not bind to the cognate binding partner. Nucleic acid can be isolated from the separated fluorescent cells and non fluorescent cells, and the nucleic acid can be sequenced to identify expressed proteins that interact or do not interact with the cognate binding partner.

Typically, the binding assays are performed by first performing a positive or negative selection step. The flow sorter can collect or sort cells that have specified fluorescent properties. This feature can be employed to select or exclude a first population of cells that are identified as exhibiting binding and/or not exhibiting binding, depending on the particular binding characteristic that is desired. For example, in a positive selection step, the contacting and binding reaction is performed as described above, and cells are separated to enrich cells that display proteins that bind to a cognate binding partner under a set of conditions. Typically, in a positive selection step, contacting, labeling, and sorting are performed under a set of conditions that simulates physiological conditions in which activity of the protein is desired. Examples of conditions for a positive selection step are conditions that simulate physiological conditions of a tumor microenvironment. In a negative selection step, cells are separated to separate and/or enrich cells that do display proteins that have little or no binding to a cognate binding partner under a set of conditions. Typically, in a negative selection step, contacting, labeling, and sorting are performed under a set of conditions that simulates a physiological conditions in which activity of the protein is not desired. Examples of conditions for a negative selection step are conditions that simulate physiological conditions of a normal microenvironment.

A selection step or a series of alternative selection steps can be performed once or multiple times, for example, at least about 2, 3, 4, 5, 6, or 7 times. If desired, two or more different selection steps can be performed either simultaneously or in succession. For example, a positive selection step can be followed by a negative selection step, and the combination of a positive selection step and a negative selection step can be repeated as often as necessary to isolate cells that display conditionally active proteins. In some examples, any FACS selection parameters known to one of skill in the art or described herein can be attuned to increase or decrease the stringency of selection. For example, the stringency of selection can be low in initial rounds of selection and increased in later rounds as the cells become enriched with a population of cells that display conditionally active proteins. Sort gates can be established to select for cells that show the highest affinity or lowest affinity for a cognate binding partner. Sort gates can be established empirically by one skilled in the art. In addition, libraries can be oversampled by at least 10-fold to improve the probability of isolating rare clones.

Between each round of selection cells can be regrown and/or induced to allow cells to recover and/or increase protein expression on cell surfaces. Although not intending to be bound by a particular mode of action, this iterative process helps enrich the population of the cells that express conditionally active proteins.

D. Methods of Expressing Proteins

Test molecules, and in particular therapeutic proteins or antibodies, for use in the screening assay herein can be expressed using standard cell culture and other expression systems known in the art. Prior to use in the screening methods, the proteins can be purified. Alternatively, whole supernatant or diluted supernatant can be screened in the dual assay herein.

The binding molecules, proteins and target antigens used in the methods herein can be produced recombinantly or can be purchased from commercial vendors. For example, binding molecules such as antibodies, can be made by recombinant DNA methods that are within the purview of those skilled in the art. DNA encoding a protein of interest can be synthetically produced or can be readily isolated and sequenced using conventional procedures (e.g. by using oligonucleotide probes that are capable of binding specifically to genes encoding the heavy and light chains of the antibody). For example, any cell source known to produce or express the protein or antibody of interest can serve as a preferred source of such DNA. In another example, once the sequence of the DNA encoding the antibodies is determined, nucleic acid sequences can be constructed using gene synthesis techniques.

Further, mutagenesis techniques also can be employed to generate variant forms of any protein. The DNA also can be modified. For example, gene synthesis or routine molecular biology techniques can be used to effect insertion, deletion, addition or replacement of nucleotides. For example, additional nucleotide sequences can be joined to a nucleic acid sequence. In one example linker sequences can be added, such as sequences containing restriction endonuclease sites for the purpose of cloning the synthetic gene into a vector, for example, a protein expression vector. Furthermore, additional nucleotide sequences specifying functional DNA elements can be operatively linked to a nucleic acid molecule. Examples of such sequences include, but are not limited to, promoter sequences designed to facilitate intracellular protein expression, and leader peptide sequences designed to facilitate protein secretion.

Proteins, such as antibodies, can be expressed as full-length proteins or less then full length proteins. For example, antibody fragments can be expressed. Nucleic acid molecules and proteins provided herein can be made by any method known to one of skill in the art. Such procedures are routine and are well known to the skill artisan. They include routine molecular biology techniques including gene synthesis, PCR, ligation, cloning, transfection and purification techniques. A description of such procedures is provided below.

Once isolated, the DNA can be placed into expression vectors, which are then transfected into host cells. Choice of vector can depend on the desired application. For example, after insertion of the nucleic acid, the vectors typically are used to transform host cells, for example, to amplify the protein genes for replication and/or expression thereof. In such examples, a vector suitable for high level expression is used.

For expression of antibodies, generally, nucleic acid encoding the heavy chain of an antibody is cloned into a vector and the nucleic acid encoding the light chain of an antibody is cloned into a vector. The genes can be cloned into a single vector for dual expression thereof, or into separate vectors. If desired, the vectors also can contain further sequences encoding additional constant region(s) or hinge regions to generate other antibody forms. The vectors can be transfected and expressed in host cells. Expression can be in any cell expression system known to one of skill in the art. For example, host cells include cells that do not otherwise produce immunoglobulin protein, to obtain the synthesis of antibodies in the recombinant host cells. For example, host cells include, but are not limited to, simian COS cells, Chinese hamster ovary (CHO) cells, 293FS cells, HEK293-6E cells. NSO cells or other myeloma cells. Other expression vectors and host cells are described below.

In one example, nucleic acid encoding the heavy chain of an antibody, is ligated into a first expression vector and nucleic acid encoding the light chain of an antibody, is ligated into a second expression vector. The expression vectors can be the same or different, although generally they are sufficiently compatible to allow comparable expression of proteins (heavy and light chain) therefrom. The first and second expression vectors are generally co-transfected into host cells, typically at a. 1:1 ratio. Exemplary of vectors include, but are not limited to, pγ1HC and pκLC (Tiller et al. (2008) *J Immunol. Methods*, 329:112-24). Other expression vectors include the light chain expression vector pAG4622 and the heavy chain expression vector pAH4604 (Coloma et al. (1992) *J Immunol. Methods*, 152:89-104). The pAG4622 vector contains the genomic sequence encoding the C-region domain of the human κ L chain and the gpt selectable marker. The pAH4604 vectors contains the hisD selectable marker and sequences encoding the human H chain γ1 C-region domain. In another example, the heavy and light chain can be cloned into a single vector that has expression cassettes for both the heavy and light chain.

Hence, antibodies provided herein can be generated or expressed as full-length antibodies or as antibodies that are less than full length, including, but not limited to Fabs, Fab hinge fragment, scFv fragment, scFv tandem fragment and scFv hinge and scFv hinge (ΔE) fragments. Various techniques have been developed for the production of antibody fragments. Traditionally, these fragments were derived via proteolytic digestion of intact antibodies (see e.g. Morimoto et al. (1992) *Journal of Biochemical and Biophysical Methods*, 24:107-117; Brennan et al. (1985) *Science*, 229:81). Fragments also can be produced directly by recombinant host cells. Fab, Fv and scFv antibody fragments can all be expressed in and secreted from host cells, such as *E. coli*, thus allowing the facile production of large amounts of these fragments. Also, Fab'-SH fragments can be chemically coupled to form F(ab')$_2$ fragments (Carter et al. (1992) *Biotechnology*, 10:163-167). According to another approach, F(ab')$_2$ fragments can be isolated directly from recombinant host cell culture. In other examples, the antibody of choice is a single chain Fv fragment (scFv) (see e.g. WO93/16185; U.S. Pat. No. 5,571,894 and U.S. Pat. No. 5,587,458). Fv and sFv are the only species with intact combining sites that are devoid of constant regions; thus, they are suitable for reduced nonspecific binding during in vivo use. sFv fusion proteins can be constructed to yield fusion of an effector protein at either the amino or the carboxy terminus of an sFv. The antibody fragment can also be a linear antibody (see e.g. U.S. Pat. No. 5,641,870). Such linear antibody fragments can be monospecific or bispecific. Other techniques for the production of antibody fragments are known to one of skill in the art.

For example, upon expression, antibody heavy and light chains pair by disulfide bond to form a full-length antibody or fragments thereof. For example, for expression of a full-length Ig, sequences encoding the $V_H$—$C_H1$-hinge-$C_H2$-$C_H3$ can be cloned into a first expression vector and sequences encoding the $V_L$—$C_L$ domains can be cloned into a second expression vector. Upon co-expression with the second expression vector encoding the $V_L$—$C_L$ domains, a full-length antibody is expressed. In another example, to generate a Fab, sequences encoding the $V_H$—$C_H1$ can be cloned into a first expression vector and sequences encoding the $V_L$—$C_L$ domains can be cloned into a second expression vector. The heavy chain pairs with a light chain and a Fab monomer is generated. Sequences of $C_H1$, hinge, $C_H2$ and/or $C_H3$ of various IgG sub-types are known to one of skill in the art (see e.g. U.S. Published Application No. 20080248028). Similarly, sequences of $C_L$, lambda or kappa, also are known (see e.g. U.S. Published Application No. 20080248028).

Exemplary sequences that can be inserted into vectors for expression of whole antibodies and antibody fragments include sequences of antibody fragments provided in Table 3. For example, the heavy chain and light chain sequences of Erbitux® (Cetuximab) (SEQ ID NOs: 2 and 1, respectively) or the heavy chain and light chain sequences of any other antibody (i.e, SEQ ID NOs: 74 and 75, respectively (Herceptin®); SEQ ID NOs: 76 and 77, respectively (Rituxan®); SEQ ID NOS: 78 and 79, respectively (Avastin®); SEQ ID NOS: 80 and 81, respectively (Cempath®); SEQ ID NOs: 82 and 83, respectively (Vectibix®); SEQ ID NOS: 41 and 42, respectively (Ibritumomab®); SEQ ID NOs: 43 and 44, respectively (Tositumomab®); SEQ ID NOS: 45 and 46, respectively (Volociximab); SEQ ID NOS: 47 and 46, respectively (F200); or SEQ ID NOS:48 and 49, respectively (Cixutumumab) can be inserted into a suitable expression vector described herein or known to one of skill in the art for expression of IgG antibodies. In addition, VH—CH1 and VL-CL sequences, such as SEQ ID NOs 84 and 85, respectively (Lucentis®) can be inserted into a suitable expression vector for expression of Fab molecules. Variable heavy chain and variable light chain domains of an antibody (i.e., SEQ ID NOS: 29 and 30, respectively (Herceptin®); SEQ ID NOS: 31 and 32, respectively (Rituxin®); SEQ ID NOS: 33 and 34, respectively (Avastin®); SEQ ID NOS: 35 and 36, respectively (Campath®); SEQ ID NOS: 37 and 38, respectively (Vectibix®); and SEQ ID NOS: 39 and 40, respectively (Lucentis®) can also be expressed in a suitable expression vector, such as a vector encoding for a linker between the variable heavy chain and variable light chain. Exemplary linkers include the glycine rich flexible linkers ($-G_4S-)_n$, where n is a positive integer, such as 1 (SEQ ID NO:4), 2 (SEQ ID NO:70), 3 (SEQ ID NO: 71), 4 (SEQ ID NO: 72), 5 (SEQ ID NO: 73), or more.

1. Vectors

Choice of vector can depend on the desired application. Many expression vectors are available and known to those of skill in the art for the expression of recombined antibodies or portions thereof. The choice of an expression vector is influenced by the choice of host expression system. Such selection is well within the level of skill of the skilled artisan. In general, expression vectors can include transcriptional promoters and optionally enhancers, translational signals, and transcriptional and translational termination signals. Expression vectors that are used for stable transformation typically have a selectable marker which allows selection and maintenance of the transformed cells. In some cases, an origin of replication can be used to amplify the copy number of the vectors in the cells. Vectors also generally can contain additional nucleotide sequences operably linked to the ligated nucleic acid molecule (e.g. His tag, Flag tag). For applications with antibodies, vectors generally include sequences encoding the constant region. Thus, antibodies or portions thereof also can be expressed as protein fusions. For example, a fusion can be generated to add additional functionality to a polypeptide. Examples of fusion proteins include, but are not limited to, fusions of a signal sequence, an epitope tag such as for localization, e.g. a $his_6$ tag or a myc tag, or a tag for purification, for example, a GST fusion, and a sequence for directing protein secretion and/or membrane association.

For example, expression of the proteins can be controlled by any promoter/enhancer known in the art. Suitable bacterial promoters are well known in the art and described herein below. Other suitable promoters for mammalian cells, yeast cells and insect cells are well known in the art and some are exemplified below. Selection of the promoter used to direct expression of a heterologous nucleic acid depends on the particular application. Promoters which can be used include but are not limited to eukaryotic expression vectors containing the SV40 early promoter (Bernoist and Chambon, Nature 290:304-310 (1981)), the promoter contained in the 3' long terminal repeat of Rous sarcoma virus (Yamamoto et al. Cell 22:787-797 (1980)), the herpes thymidine kinase promoter (Wagner et al., Proc. Natl. Acad. Sci. USA 78:1441-1445 (1981)), the regulatory sequences of the metallothionein gene (Brinster et al., Nature 296:39-42 (1982)); prokaryotic expression vectors such as the β-lactamase promoter (Jay et al., (1981) Proc. Natl. Acad. Sci. USA 78:5543) or the tac promoter (DeBoer et al., Proc. Natl. Acad. Sci. USA 80:21-25 (1983)); see also "Useful Proteins from Recombinant Bacteria": in Scientific American 242: 79-94 (1980); plant expression vectors containing the nopaline synthetase promoter (Herrera-Estrella et al., Nature 303:209-213 (1984)) or the cauliflower mosaic virus 35S RNA promoter (Gardner et al., Nucleic Acids Res. 9:2871 (1981)), and the promoter of the photosynthetic enzyme ribulose bisphosphate carboxylase (Herrera-Estrella et al., Nature 310:115-120 (1984)); promoter elements from yeast and other fungi such as the Gal4 promoter, the alcohol dehydrogenase promoter, the phosphoglycerol kinase promoter, the alkaline phosphatase promoter, and the following animal transcriptional control regions that exhibit tissue specificity and have been used in transgenic animals: elastase I gene control region which is active in pancreatic acinar cells (Swift et al., Cell 38:639-646 (1984); Ornitz et al., Cold Spring Harbor Symp. Quant. Biol. 50:399-409 (1986); MacDonald, Hepatology 7:425-515 (1987)); insulin gene control region which is active in pancreatic beta cells (Hanahan et al., Nature 315:115-122 (1985)), immunoglobulin gene control region which is active in lymphoid cells (Grosschedl et al., Cell 38:647-658 (1984); Adams et al., Nature 318:533-538 (1985); Alexander et al., Mol. Cell. Biol. 7:1436-1444 (1987)), mouse mammary tumor virus control region which is active in testicular, breast, lymphoid and mast cells (Leder et al., Cell 45:485-495 (1986)), albumin gene control region which is active in liver (Pinckert et al., Genes and Devel. 1:268-276 (1987)), alpha-fetoprotein gene control region which is active in liver (Krumlauf et al., Mol. Cell. Biol. 5:1639-1648 (1985); Hammer et al., Science 235:53-58 (1987)), alpha-1 antitrypsin gene control region which is active in liver (Kelsey et al., Genes and Devel. 1:161-171 (1987)), beta globin gene control region which is active in myeloid cells (Magram et al., Nature 315:338-340 (1985); Kollias et al., Cell 46:89-94 (1986)), myelin basic protein gene control region which is active in oligodendrocyte cells of the brain (Readhead et al., Cell 48:703-712 (1987)), myosin light chain-2 gene control region which is active in skeletal muscle (Shani, Nature 314:283-286 (1985)), and gonadotrophic releasing hormone gene control region which is active in gonadotrophs of the hypothalamus (Mason et al., Science 234:1372-1378 (1986)).

In addition to the promoter, the expression vector typically contains a transcription unit or expression cassette that contains all the additional elements required for the expression of the antibody, or portion thereof, in host cells. A typical expression cassette contains a promoter operably linked to the nucleic acid sequence encoding the protein and signals required for efficient polyadenylation of the transcript, ribosome binding sites and translation termination. Additional elements of the cassette can include enhancers. In addition, the cassette typically contains a transcription termination region downstream of the structural gene to provide for efficient termination. The termination region can be obtained from the same gene as the promoter sequence or can be obtained from different genes.

Some expression systems have markers that provide gene amplification such as thymidine kinase and dihydrofolate reductase. Alternatively, high yield expression systems not involving gene amplification are also suitable, such as using a baculovirus vector in insect cells, with a nucleic acid sequence encoding a protein under the direction of the polyhedron promoter or other strong baculovirus promoter.

For purposes herein with respect to expression of antibodies or antibody variants, vectors are provided that contain a sequence of nucleotides that encodes a constant region of an antibody operably linked to the nucleic acid sequence encoding the r variable region of the antibody. The vector can include the sequence for one or all of a $C_H1$, $C_H2$, hinge, $C_H3$ or $C_H4$ and/or $C_L$. Generally, such as for expression of Fabs, the vector contains the sequence for a $C_H1$ or $C_L$ (kappa or lambda light chains). The sequences of constant regions or hinge regions are known to one of skill in the art (see e.g. U.S. Published Application No. 20080248028).

Exemplary expression vectors include any mammalian expression vector such as, for example, pCMV. For bacterial expression, such vectors include pBR322, pUC, pSKF, pET23D, and fusion vectors such as MBP, GST and LacZ. Other eukaryotic vectors, for example any containing regulatory elements from eukaryotic viruses can be used as eukaryotic expression vectors. These include, for example, SV40 vectors, papilloma virus vectors, and vectors derived from Epstein-Bar virus. Other exemplary eukaryotic vectors include pMSG, pAV009/A+, pMT010/A+, pMAMneo-5, baculovirus pDSCE, and any other vector allowing expression of proteins under the direction of the CMV promoter, SV40 early promoter, SV40 late promoter, metallothionein promoter, murine mammary tumor virus promoter, Rous sarcoma virus promoter, polyhedron promoter, or other promoters shown effective for expression in eukaryotes.

Any methods known to those of skill in the art for the insertion of DNA fragments into a vector can be used to construct expression vectors containing a nucleic acid encoding a protein or an antibody chain. These methods can include in vitro recombinant DNA and synthetic techniques and in vivo recombinants (genetic recombination). The insertion into a cloning vector can, for example, be accomplished by ligating the DNA fragment into a cloning vector which has complementary cohesive termini. If the complementary restriction sites used to fragment the DNA are not present in the cloning vector, the ends of the DNA molecules can be enzymatically modified. Alternatively, any site desired can be produced by ligating nucleotide sequences (linkers) onto the DNA termini; these ligated linkers can contain specific chemically synthesized nucleic acids encoding restriction endonuclease recognition sequences.

2. Cells and Expression Systems

Cells containing the vectors also are provided. Generally, any cell type that can be engineered to express heterologous DNA and has a secretory pathway is suitable. Expression hosts include prokaryotic and eukaryotic organisms such as bacterial cells (e.g. *E. coli*), yeast cells, fungal cells, Archea, plant cells, insect cells and animal cells including human cells. Expression hosts can differ in their protein production levels as well as the types of post-translational modifications that are present on the expressed proteins. Further, the choice of expression host is often related to the choice of vector and transcription and translation elements used. For example, the choice of expression host is often, but not always, dependent on the choice of precursor sequence utilized. For example, many heterologous signal sequences can only be expressed in a host cell of the same species (i.e., an insect cell signal sequence is optimally expressed in an insect cell). In contrast, other signal sequences can be used in heterologous hosts such as, for example, the human serum albumin (hHSA) signal sequence which works well in yeast, insect, or mammalian host cells and the tissue plasminogen activator pre/pro sequence which has been demonstrated to be functional in insect and mammalian cells (Tan et al., (2002) *Protein Eng.* 15:337). The choice of expression host can be made based on these and other factors, such as regulatory and safety considerations, production costs and the need and methods for purification. Thus, the vector system must be compatible with the host cell used.

Expression in eukaryotic hosts can include expression in yeasts such as *Saccharomyces cerevisiae* and *Pichia pastoris*, insect cells such as *Drosophila* cells and lepidopteran cells, plants and plant cells such as tobacco, corn, rice, algae, and lemna. Eukaryotic cells for expression also include mammalian cells lines such as Chinese hamster ovary (CHO) cells or baby hamster kidney (BHK) cells. Eukaryotic expression hosts also include production in transgenic animals, for example, including production in serum, milk and eggs.

Recombinant molecules can be introduced into host cells via, for example, transformation, transfection, infection, electroporation and sonoporation, so that many copies of the gene sequence are generated. Generally, standard transfection methods are used to produce bacterial, mammalian, yeast, or insect cell lines that express large quantities of antibody chains, which is then purified using standard techniques (see e.g., Colley et al. (1989) *J. Biol. Chem.*, 264: 17619-17622; Guide to Protein Purification, in Methods in Enzymology, vol. 182 (Deutscher, ed.), 1990). Transformation of eukaryotic and prokaryotic cells are performed according to standard techniques (see, e.g., Morrison (1977) *J. Bact.* 132:349-351; Clark-Curtiss and Curtiss (1983) *Methods in Enzymology*, 101, 347-362). For example, any of the well-known procedures for introducing foreign nucleotide sequences into host cells can be used. These include the use of calcium phosphate transfection, polybrene, protoplast fusion, electroporation, biolistics, liposomes, microinjection, plasma vectors, viral vectors and any other the other well known methods for introducing cloned genomic DNA, cDNA, synthetic DNA or other foreign genetic material into a host cell. Generally, for purposes of expressing an antibody, host cells are transfected with a first vector encoding at least a $V_H$ chain and a second vector encoding at least a $V_L$ chain. Thus, it is only necessary that the particular genetic engineering procedure used be capable of successfully introducing at least both genes into the host cell capable of expressing antibody polypeptide, or modified form thereof.

Transformation of host cells with recombinant DNA molecules that incorporate cDNA, or synthesized DNA sequence enables generation of multiple copies of the gene. Thus, the gene can be obtained in large quantities by growing transformants, isolating the recombinant DNA molecules from the transformants and, when necessary, retrieving the inserted gene from the isolated recombinant DNA.

Proteins, including antibodies and portions thereof, can be produced using a high throughput approach by any methods known in the art for protein production including in vitro and in vivo methods such as, for example, the introduction of nucleic acid molecules encoding proteins into a host cell or host animal and expression from nucleic acid molecules encoding recombined antibodies in vitro. Prokaryotes, especially *E. coli*, provide a system for producing large amounts of recombined antibodies or portions thereof, and are particularly desired in applications of high-throughput expression and purification of proteins. Transformation of *E. coli* is a simple and rapid technique well known to those of skill in the art. *E. coli* host strains for high throughput expression include, but are not limited to, BL21 (EMD Biosciences) and LMG194 (ATCC). Exemplary of such an *E. coli* host strain is BL21. Vectors for high throughput expression include, but are not limited to, pBR322 and pUC vectors.

a. Prokaryotic Expression

Prokaryotes, especially *E. coli*, provide a system for producing large amounts of recombined antibodies or portions thereof. Transformation of *E. coli* is a simple and rapid technique well known to those of skill in the art. Expression vectors for *E. coli* can contain inducible promoters that are useful for inducing high levels of protein expression and for expressing proteins that exhibit some toxicity to the host cells. Examples of inducible promoters include the lac promoter, the trp promoter, the hybrid tac promoter, the T7 and SP6 RNA promoters and the temperature regulated $\lambda P_L$ promoter.

Proteins, including antibodies or portions thereof can be expressed in the cytoplasmic environment of *E. coli*. The cytoplasm is a reducing environment and for some molecules, this can result in the formation of insoluble inclusion bodies. Reducing agents such as dithiothreitol and β-mercaptoethanol and denaturants (e.g., such as guanidine-HCl and urea) can be used to resolubilize the proteins. An exemplary alternative approach is the expression of recombined antibodies or fragments thereof in the periplasmic space of bacteria which provides an oxidizing environment and chaperonin-like and disulfide isomerases leading to the production of soluble protein. Typically, a leader sequence is fused to the protein to be expressed which directs the protein to the periplasm. The leader is then removed by signal peptidases inside the periplasm. There are three major pathways to translocate expressed proteins into the periplasm, namely the Sec pathway, the SRP pathway and the TAT pathway. Examples of periplasmic-targeting leader sequences include the pelB leader from the pectate lyase gene, the StII leader sequence, and the DsbA leader sequence. An exemplary leader sequence is a DsbA leader sequence. In some cases, periplasmic expression allows leakage of the expressed protein into the culture medium. The secretion of proteins allows quick and simple purification from the culture supernatant. Proteins that are not secreted can be obtained from the periplasm by osmotic lysis. Similar to cytoplasmic expression, in some cases proteins can become insoluble and denaturants and reducing agents can be used to facilitate solubilization and refolding. Temperature of induction and growth also can influence expression levels and solubility. Typically, temperatures between 25° C. and 37° C. are used. Mutations also can be used to increase solubility of expressed proteins. Typically, bacteria produce aglycosylated proteins. Thus, if proteins require glycosylation for function, glycosylation can be added in vitro after purification from host cells.

b. Yeast

Yeasts such as *Saccharomyces cerevisiae, Schizosaccharomyces pombe, Yarrowia lipolytica, Kluyveromyces lactis,* and *Pichia pastoris* are useful expression hosts for recombined antibodies or portions thereof. Yeast can be transformed with episomal replicating vectors or by stable chromosomal integration by homologous recombination. Typically, inducible promoters are used to regulate gene expression. Examples of such promoters include AOX1, GAL1, GAL7, and GAL5 and metallothionein promoters such as CUP1. Expression vectors often include a selectable marker such as LEU2, TRP1, HIS3, and URA3 for selection and maintenance of the transformed DNA. Proteins expressed in yeast are often soluble. Co-expression with chaperonins such as Bip and protein disulfide isomerase can improve expression levels and solubility. Additionally, proteins expressed in yeast can be directed for secretion using secretion signal peptide fusions such as the yeast mating type alpha-factor secretion signal from *Saccharomyces cerevisae* and fusions with yeast cell surface proteins such as the Aga2p mating adhesion receptor or the *Arxula adeninivorans* glucoamylase. A protease cleavage site such as for the Kex-2 protease, can be engineered to remove the fused sequences from the expressed polypeptides as they exit the secretion pathway. Yeast also is capable of glycosylation at Asn-X-Ser/Thr motifs.

c. Insects

Insect cells, particularly using baculovirus expression, are useful for expressing antibodies or portions thereof. Insect cells express high levels of protein and are capable of most of the post-translational modifications used by higher eukaryotes. Baculovirus have a restrictive host range which improves the safety and reduces regulatory concerns of eukaryotic expression. Typical expression vectors use a promoter for high level expression such as the polyhedrin promoter and p10 promoter of baculovirus. Commonly used baculovirus systems include the baculoviruses such as *Autographa californica* nuclear polyhedrosis virus (AcNPV), and the *Bombyx mori* nuclear polyhedrosis virus (BmNPV) and an insect cell line such as Sf9 derived from *Spodoptera frugiperda* and TN derived from *Trichoplusia ni*. For high-level expression, the nucleotide sequence of the molecule to be expressed is fused immediately downstream of the polyhedrin initiation codon of the virus. To generate baculovirus recombinants capable of expressing human antibodies, a dual-expression transfer, such as pAcUW51 (PharMingen) is utilized. Mammalian secretion signals are accurately processed in insect cells and can be used to secrete the expressed protein into the culture medium An alternative expression system in insect cells is the use of stably transformed cells. Cell lines such as Sf9 derived cells from *Spodoptera frugiperda* and TN derived cells from *Trichoplusia ni* can be used for expression. The baculovirus immediate early gene promoter IE1 can be used to induce consistent levels of expression. Typical expression vectors include the pIE1-3 and pI31-4 transfer vectors (Novagen). Expression vectors are typically maintained by the use of selectable markers such as neomycin and hygromycin.

d. Mammalian Cells

Mammalian expression systems can be used to express modified proteins, including antibodies or portions thereof. Expression constructs can be transferred to mammalian cells by viral infection such as adenovirus or by direct DNA transfer such as liposomes, calcium phosphate, DEAE-dextran and by physical means such as electroporation and microinjection. Expression vectors for mammalian cells typically include an mRNA cap site, a TATA box, a translational initiation sequence (Kozak consensus sequence) and polyadenylation elements. Such vectors often include transcriptional promoter-enhancers for high-level expression, for example the SV40 promoter-enhancer, the human cytomegalovirus (CMV) promoter and the long terminal repeat of Rous sarcoma virus (RSV). These promoter-enhancers are active in many cell types. Tissue and cell-type promoters and enhancer regions also can be used for expression. Exemplary promoter/enhancer regions include, but are not limited to, those from genes such as elastase I, insulin, immunoglobulin, mouse mammary tumor virus, albumin, alpha fetoprotein, alpha 1 antitrypsin, beta globin, myelin basic protein, myosin light chain 2, and gonadotropic releasing hormone gene control. Selectable markers can be used to select for and maintain cells with the expression construct. Examples of selectable marker genes include, but are not limited to, hygromycin B phosphotransferase, adenosine deaminase, xanthine-guanine phosphoribosyl transferase, aminoglycoside phosphotransferase, dihydrofolate reductase and thymidine kinase. Antibodies are typically produced using a NEO$^R$/G418 system, a dihydrofolate reductase (DHFR) system or a glutamine synthetase (GS) system. The GS system uses joint expression vectors, such as pEE12/pEE6, to express both heavy chain and light chain. Fusion with cell surface signaling molecules such as TCR-ζ and Fc$_\varepsilon$RI-γ can direct expression of the proteins in an active state on the cell surface.

Many cell lines are available for mammalian expression including mouse, rat human, monkey, chicken and hamster cells. Exemplary cell lines include but are not limited to CHO, Balb/3T3, HeLa, MT2, mouse NS0 (nonsecreting) and other myeloma cell lines, hybridoma and heterohybridoma cell lines, lymphocytes, fibroblasts, Sp2/0, COS, NIH3T3, HEK293, 293S, 2B8, and HKB cells. Cell lines also are available adapted to serum-free media which facilitates purification of secreted proteins from the cell culture media. One such example is the serum free EBNA-1 cell line (Pham et al., (2003) *Biotechnol. Bioeng.* 84:332-42.)

e. Plants

Transgenic plant cells and plants can be used to express proteins such as any antibody or portion thereof described herein. Expression constructs are typically transferred to plants using direct DNA transfer such as microprojectile bombardment and PEG-mediated transfer into protoplasts, and with *agrobacterium*-mediated transformation. Expression vectors can include promoter and enhancer sequences, transcriptional termination elements and translational control elements. Expression vectors and transformation techniques are usually divided between dicot hosts, such as *Arabidopsis* and tobacco, and monocot hosts, such as corn and rice. Examples of plant promoters used for expression include the cauliflower mosaic virus CaMV $^{35}$S promoter, the nopaline synthase promoter, the ribose bisphosphate carboxylase promoter and the maize ubiquitin-1 (ubi-1) promoter promoters. Selectable markers such as hygromycin, phosphomannose isomerase and neomycin phosphotransferase are often used to facilitate selection and maintenance of transformed cells. Transformed plant cells can be maintained in culture as cells, aggregates (callus tissue) or regenerated into whole plants. Transgenic plant cells also can include algae engineered to produce proteases or modified proteases (see for example, Mayfield et al. (2003) *PNAS* 100:438-442). Because plants have different glycosylation patterns than mammalian cells, this can influence the choice of protein produced in these hosts.

3. Purification

Proteins, including antibodies and antigen binding portions thereof are purified by any procedure known to one of skill in the art. Proteins can be purified to substantial purity using standard protein purification techniques known in the art including but not limited to, SDS-PAGE, size fraction and size exclusion chromatography, ammonium sulfate precipitation, chelate chromatography, ionic exchange chromatography or column chromatography. For example, antibodies can be purified by column chromatography. Exemplary of a method to purify antibodies is by using column chromatography, wherein a solid support column material is linked to Protein G, a cell surface-associated protein from *Streptococcus*, that binds immunoglobulins with high affinity. The antibodies can be purified to 60%, 70%, 80% purity and typically at least 90%, 91%, 92%, 93%, 94%, 95%, 96%, 97%, 98% or 99% purity. Purity can be assessed by standard methods such as by SDS-PAGE and coomassie staining.

Methods for purification of proteins, including antibodies or portions thereof from host cells depend on the chosen host cells and expression systems. For secreted molecules, proteins are generally purified from the culture media after removing the cells. For intracellular expression, cells can be lysed and the proteins purified from the extract. When transgenic organisms such as transgenic plants and animals are used for expression, tissues or organs can be used as starting material to make a lysed cell extract. Additionally, transgenic animal production can include the production of polypeptides in milk or eggs, which can be collected, and if necessary further the proteins can be extracted and further purified using standard methods in the art.

When proteins are expressed by transformed bacteria in large amounts, typically after promoter induction, although expression can be constitutive, the polypeptides can form insoluble aggregates. There are several protocols that are suitable for purification of polypeptide inclusion bodies known to one of skill in the art. Numerous variations will be apparent to those of skill in the art.

For example, in one method, the cell suspension is generally centrifuged and the pellet containing the inclusion bodies resuspended in buffer which does not dissolve but washes the inclusion bodies, e.g., 20 mM Tris-HCL (pH 7.2), 1 mM EDTA, 150 mM NaCl and 2% Triton-X 100, a non-ionic detergent. It can be necessary to repeat the wash step to remove as much cellular debris as possible. The remaining pellet of inclusion bodies can be resuspended in an appropriate buffer (e.g., 20 mM sodium phosphate, pH 6.8, 150 mM NaCl). Other appropriate buffers are apparent to those of skill in the art.

Alternatively, proteins can be purified from bacteria periplasm. Where the polypeptide is exported into the periplasm of the bacteria, the periplasmic fraction of the bacteria can be isolated by cold osmotic shock in addition to other methods known to those of skill in the art. For example, in one method, to isolate recombinant polypeptides from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM MgSO$_4$ and kept in an ice bath for approximately 10 minutes. The cell suspension is centrifuged and the supernatant decanted and saved. The recombinant polypeptides present in the supernatant can be separated from the host proteins by standard separation techniques well known to those of skill in the art. These methods include, but are not limited to, the following steps: solubility fractionation, size differential filtration, and column chromatography.

E. Examples

The following examples are included for illustrative purposes only and are not intended to limit the scope of the invention.

EXAMPLE 1

Vectors and Expression Plasmids

In this example, expression constructs to allow for the production of EGF receptor antigen in CHO mammalian cells, and Erbitux® anti-EGFR antibody in CHO mammalian cells, were generated. The use of CHO cells allows production of μg/mL quantities of antibodies and relevant post-translational modifications (e.g. glycosylation).

The EGFR antigen (SEQ ID NO:10) was produced as a soluble extracellular domain (sECD) encompassing the complete ECD (N-terminal 640 amino acids, SEQ ID NO:13, DNA set forth in SEQ ID NO:12). A histidine tag (His-tag, SEQ ID NO:7) was incorporated at the C-terminal domain to allow purification. The plasmids additionally contain either a native (SEQ ID NO:11) or IgG HC (SEQ ID NO:6) leader sequence, a Kozak consensus sequence and optionally a Gly$_4$Ser linker (SEQ ID NO:4) between the EGFR extracellular domain and the tag.

Erbitux® anti-EGFR antibody (SEQ ID NOS:1 and 2, DNA set forth in SEQ ID NOS:9 and 8, light and heavy chains, respectively) plasmids were generated in which an affinity tag (c-Myc, SEQ ID NO:5 or FLAG, SEQ ID NO:3) is linked to the C-terminal end of the Fc domain of Erbitux® anti-EGFR antibody. The plasmids contain genes for both the heavy chain and the light chain, such that upon expression, an IgG antibody was produced. The plasmids optionally contain a Gly$_4$Ser linker (SEQ ID NO:4) between the Fc domain and the affinity tag. The plasmid descriptions are set forth in Table 7 below.

TABLE 7

EGFR sECD and Erbitux Plasmids

| Plasmid description | Affinity Tag |
|---|---|
| EGFR Extracellular Domain (aa 1-640; native leader) with His-tag | His |
| EGFR Extracellular Domain (aa 1-640; native leader) with Gly$_4$Ser linker and His-tag | His |
| EGFR Extracellular Domain (aa 25-640; IgG HC Leader) with His-tag | His |
| EGFR Extracellular Domain (aa 25-640; IgG HC Leader) with Gly$_4$Ser linker and His-tag | His |
| Erbitux ® anti-EGFR antibody with C-terminal FLAG-tag | FLAG |
| Erbitux ® anti-EGFR antibody with C-terminal Gly$_4$Ser linker and FLAG-tag | FLAG |
| Erbirux ® anti-EGFR antibody with C-terminal cMyc-tag | cMyc |
| Erbirux ® anti-EGFR antibody with C-terminal Gly$_4$Ser linker and cMyc-tag | cMyc |

EXAMPLE 2

Binding Assay Development

In this example, an ELISA assay was developed as a preliminary binding assay using commercially available reagents. In this assay, soluble EGFR receptor was bound to a 96-well plate, Erbitux® anti-EGFR antibody was added and allowed to bind, and binding was detected using a rabbit anti-human-Fc-HRP conjugated secondary antibody. Buffer pH was evaluated for its effect on binding of 1) the soluble EGFR receptor to either Hi-bind or Ni-coated plates, 2) secondary antibody binding and 3) soluble EGFR receptor-Erbitux® anti-EGFR antibody binding.

Standard Direct ELISA Protocol Using Commercial Reagents:

A 96-well Hi-bind plate (Hi bind, Costar #2592) was coated overnight at 4° C. with 100 µL sEGFR-H6 antigen (Sino Biologics, Cat #10001-H08H) at 12 nM (1.32 µg/mL) in PBS. The plate was then washed 3× with 250 µL/well of PBS and subsequently blocked for 1 hour at RT with 250 µL of PBS/BSA (PBS, pH 7.4, 5 mg/mL BSA). Serial dilutions (3×, starting concentration 500 ng/mL, followed by 1:3 dilutions) of Erbitux® anti-EGFR antibody were prepared in PBS/BSA and 100 µL was added per well and the plate was incubated at RT for 1 hr. The plate was then washed 3× with 250 µL/well PBS/BSA. 100 µL/well rabbit anti-human-Fc-HRP conjugated secondary antibody (diluted 1:5000 in PBS/BSA) was added to each well and the plate was incubated for 1 hr at RT. The plate was then washed 3× with 250 µL/well of PBS/BSA. Finally, 100 µL HRP substrate was added to each well and the plate was allowed to develop for 15 minutes at RT (away from light). The reaction was stopped by adding 100 µL stop solution to each well and the plate was read within 30 min at OD$_{450}$ nM using a Microplate Spectrophotometer (Molecular Devices, Spectra Max M2). The dynamic range was ~3 logs and sensitivity was ~50 pg (in PBS, pH 7.4, with 5 mg/mL BSA)

Effect of Buffer pH on Coating of EGFR sECD-H6 Antigen to 96-Well Plates

The assay described above was performed with the following modifications: (1) either Hi Bind or Ni coated plates were used; (2) the sEGFR-H6 antigen was coated at 3, 6, 12 and 24 nM in either PBS or KRB (Krebs-Ringer bicarbonate buffer), pH 7.4; (3) the plates were blocked with 5 mg/mL BSA in PBS or KRB, pH 7.4, 6.5 or 6.0; and (4) Erbitux® anti-EGFR antibody was added at 250 ng/mL in 5 mg/mL BSA in PBS or KRB, pH 7.4.

The results show that buffer pH had no effect on the ability of EGFR sECD-H6 to bind to a Hi-Bind plate but impacted binding through the His tag (H6) to the nickel plates.

Effect of Buffer pH on Secondary Antibody Detection

The effect of buffer pH on secondary antibody binding was assessed in an assay modified from that described above in which Erbitux® anti-EGFR antibody was coated directly on the Hi-bind plate and then secondary antibody binding was assessed in the presence of 5 mg/mL BSA with PBS, pH 7.4, or KRB, pH 7.4, 6.5 or 6.0. The results indicated that secondary antibody detection of Erbitux® anti-EGFR antibody was unaffected at pH 6.0 to 7.4.

Effect of Buffer pH of EGFR sECD-Erbitux® Anti-EGFR Antibody Binding

To assess the effect of buffer pH of EGFR sECD-Erbitux® anti-EGFR antibody binding, the concentration of Erbitux® anti-EGFR antibody in the assay was varied as well as the buffer pH. Three times (3×) serial dilutions of Erbitux® anti-EGFR antibody, starting at 100 ng/mL, in KRB, pH 7.4, 6.5 or 6.0, were used in the assay described above. The results indicated that at high Erbitux® anti-EGFR antibody concentrations (i.e., greater than 3 ng/mL), variations in binding occur for each pH, with pH 7.4 having better binding than pH 6.0.

EXAMPLE 3

Effect of Addition of Human Serum on ELISA

In this example, the effect of the addition of human serum on the ELISA binding assay was determined. Human serum was added to mimic the tumor microenvironment. The ELISA was performed as described in Example 2 above. Normal human serum was added at a level of 5% of the buffer. IgG-depleted human serum was added at 1% or 5% of the buffer. Five (5) mg/mL BSA was added as a control. All experiments were performed in KRB, pH 7.4.

The results indicated that the addition of normal or IgG-depleted human serum significantly affected the ELISA assay. The addition of 5% human serum resulted in an increased K$_D$, as human serum contains IgG and thus the goat anti-human-Fc-HRP conjugated secondary antibody binds to the serum as well as the Erbitux® anti-EGFR antibody. The addition of IgG-depleted human serum resulted in a 30% reduced dynamic range for the assay.

EXAMPLE 4

Effect of Use of Anti-mouse Fab Secondary Antibodies

In this example, 6 different anti-mouse Fab antibodies were evaluated for use as the secondary antibody in the assay described in Example 2 above. Erbitux® anti-EGFR antibody is a chimeric antibody that was originally generated in mouse. These secondary antibodies were evaluated to determine if a different secondary antibody could be used to avoid the interaction of the goat anti-human-Fc secondary when human serum is used in the assay.

It was observed that none of the anti-mouse secondary antibodies recognized Erbitux® anti-EGFR antibody in the ELISA assay.

EXAMPLE 5

Tagged-surrogate Protein Indirect ELISA

In this example, a tagged-surrogate protein indirect ELISA assay was used as model for development of an epitope-tag specific indirect ELISA. The use of an epitope-tag specific indirect ELISA was evaluated in order to allow the use of human serum as a reagent/buffer in the assay. Human serum contains antibodies and thus, the use of an anti-human-Fc secondary antibody would result in signal from binding to the antibody, i.e., Erbitux, as well as the serum. In this assay, Erbitux® anti-EGFR antibody was conjugated to a protein tag directly at its c-terminus and an anti-Epitope Tag antibody that binds the tag on Erbitux® anti-EGFR antibody was used as the secondary antibody. Common protein epitope tags are set forth in Table 8 below. Assay reagents and conditions, i.e., buffer pH, and feasibility were evaluated.

TABLE 8

Common protein epitope tags

| Name | Sequence | # of Residues | Size (Da) | SEQ ID NO |
|---|---|---|---|---|
| c-Myc | EQKLISEEDL | 10 | 1200 | 5 |
| FLAG | DYKDDDDK | 8 | 1012 | 3 |
| HA | YPYDVPDYA | 9 | 1102 | 15 |
| VSV-G | YTDIEMNRLGK | 11 | 1339 | 16 |
| HSV | QPELAPEDPED | 11 | 1239 | 17 |
| V5 | GKPIPNPLLGLDST | 14 | 1421 | 18 |
| Poly Arg | RRRRR | 5-6 | 800 | 19 |
| Strep-tag-II | WSHPQFEK | 8 | 1200 | 20 |
| S- | KETAAAKFERQHMDS | 15 | 1750 | 21 |
| 3x FLAG | DYKDHDGDYKDHDIDYKDDDDK | 22 | 2730 | 22 |
| HAT- | KDHLIHNVHKEFHAHAHNK | 19 | 2310 | 23 |
| SBP- | MDEKTTGWRGGHVVEGLAGELEQLRARLEHHPQGQREP | 38 | 4306 | 24 |

Assay reagents and conditions were evaluated using a simplified tagged-surrogate protein indirect ELISA, in which a 96-well plate was coated directly with a tagged-surrogate protein and binding of the secondary anti-tag antibody to the tagged-surrogate protein was detected. Three epitope tagged surrogate proteins were used (see Table 9 below). Six epitope tags were evaluated, using commercially available anti-tag antibodies, including an anti-myc antibody (GenScript, #A00173, Abcam, #ab1326 or Abcam, #1261), an anti-FLAG antibody (GenScript, #A01428), an anti-HA antibody (GenScript, #A00169) and an anti-VSV-G antibody (GenScript, #A00872).

TABLE 9

Surrogate tagged proteins

| Protein | Tag(s) | Alpha Diagnostic Cat # | Concentration for ELISA |
|---|---|---|---|
| Multifusion-tagged marker | His, T7, Myc, HA and VSV-G | MFPM20-C | 10 µg/mL |
| Myc-tag marker | Myc | Myc15-R | 5 µg/mL |
| FLAG-tag marker | FLAG | FLAG15-R | 5 µg/mL |

Testing of Tag Detection Antibodies

In order to test detection by anti-tag antibodies, Hi bind 96-well plates were coated with a surrogate tagged protein diluted in PBS, according to Table 8 above. The plates were blocked with 5 mg/mL BSA. Epitope tags were then detected with an anti-tag antibody diluted in PBS with 5 mg/mL BSA to concentrations of 1000, 500, 250, 120 and 0 ng/mL.

The results demonstrated that anti-HA and anti-FLAG antibodies gave a higher signal than anti-Myc antibodies.

Effect of Buffer pH on Coating Tagged Protein on Hi Bind Plates

In order to test the effect of buffer pH on coating tagged proteins on Hi bind plates, the c-Myc-, FLAG and multifusion-tagged proteins were coated at concentrations of 10, 5, 2.5 and 1 µg/mL in either PBS, pH 7.4 or Krebs-Ringers Buffer (KRB), pH 7.4. The plates were then blocked with 5 mg/mL BSA in either PBS or KRB, pH 7.4, 6.5 and 6.0. Epitope tags were detected with anti-tag Ab (500 ng/mL with 5 mg/mL BSA) diluted in PBS or KRB, pH 7.4.

The results demonstrated that buffer pH has no effect on coating stability of tagged proteins on Hi bind plates, as no difference was observed between plates blocked with PBS or KRB at pH 7.4, 6.5 or 6.0.

Effect of Buffer pH on Detection of Tagged Protein on Hi Bind Plates

In order to test the effect of buffer pH on detection of tagged protein, Hi bind plates were coated with c-Myc- and FLAG-tagged proteins serially diluted 2×, starting concentration of 10 µg/mL in PBS or KRB, pH 7.4. Plates were blocked with 5 mg/mL BSA in either PBS or KRB, pH 7.4, 6.5 and 6.0. Epitope tags were detected with anti-tag Ab (1 µg/mL for anti-c-Myc-tag Ab, 0.5 µg/mL for anti-FLAG-tag Ab, with 5 mg/mL BSA) diluted in PBS or KRB, pH 7.4, 6.5 and 6.0.

The results demonstrated that buffer pH has a small effect on epitope tag detection by the anti-FLAG-tag antibody, as binding was slightly reduced at pH 7.4 compared to pH 6.5 and 6.0. The same overall effect was observed for the anti-c-Myc-tag antibody.

pH Sensitivity of Anti-Myc-Tag Antibodies

The three anti-Myc-tag antibodies (GenScript, #A00173, Abcam, #ab1326 or Abcam, #1261) were further evaluated for their pH sensitivity. Hi bind plates were coated with the multifusion tag protein in 4× serial dilutions starting at a concentration of 250 ng/mL, in either PBS or KRB, pH 7.4. Plates were blocked with 5 mg/mL BSA in either PBS or KRB, pH 7.4, 6.5 and 6.0. Tagged protein was detected with goat or rabbit anti-c-Myc tag Ab (200 or 500 ng/mL) in either PBS or KRB, pH 7.4, 6.5 and 6.0.

The results show that the Abcam antibodies are more sensitive than the GenScript antibody. Additionally, buffer pH had only a minimal effect on epitope tag detection by the goat or rabbit anti-c-myc antibodies from Abcam.

Effect of Buffer pH on Anti-Myc-Tag Antibodies

Buffer pH was further evaluated for its effect on binding of Abcam anti-Myc-tag antibodies (Abcam, #ab1326 or Abcam, #1261). Hi bind plates were coated with the multifusion tag protein in 3× serial dilutions starting at a concentration of 250 ng/mL in PBS, pH 7.4. Plates were blocked with 5 mg/mL BSA in KRB, pH 7.4, 6.5 and 6.0. Tagged protein was detected with goat or rabbit anti-c-Myc tag Ab (250 or 500 ng/mL) in KRB, pH 7.4, 6.5 and 6.0.

The results demonstrated that buffer pH had only a minimal effect on epitope tag detection by the goat or rabbit anti-c-myc antibodies from Abcam.

Evaluation of Additional Anti-Myc-Tag Antibodies

Three additional anti-Myc-tag antibodies were evaluated and compared to the Abcam anti-Myc-tag antibodies (Abcam, #ab1326 or Abcam, #1261) and to the anti-VSV-G antibody (Genscript, #A00872). The antibodies were goat anti-c-Myc tag Ab (GeneTex, Cat # GTX21261), rabbit anti-c-Myc tag Ab (GeneTex, Cat # GTX 19312) and goat anti-c-Myc tag Ab (Alpha Diagnostics, Cat #MYC13-HRP). Hi bind plates were coated with the multifusion tag protein at a concentration of 250 ng/mL, in PBS, pH 7.4. Plates were blocked with 5 mg/mL BSA in PBS pH 7.4. Tagged protein was detected with goat or rabbit anti-c-Myc tag Ab (serial dilutions, starting at 250 ng/mL) in PBS pH 7.4.

The results demonstrated that the Abcam antibodies and the goat anti-c-Myc tag Ab from GeneTex all bind the multifusion tag protein with similar affinity with the rabbit anti-c-Myc tag Ab from GeneTex having a slightly lower affinity. The anti-VSV-G antibody and the goat anti-c-Myc tag Ab from Alpha Diagnostics both have about 5 times lower affinity than the other antibodies tested.

Effect of Human Serum as a Blocking Agent on Anti-c-Myc Versus Anti-HA Antibodies The five anti-c-myc antibodies (see above) were compared to the anti-HA-tag antibody (GenScript, #A00169) for binding in the presence of 5% human serum. Hi bind plates were coated with the Multifusion-tagged marker protein in 3× serial dilutions starting at a concentration of 250 ng/mL in PBS, pH 7.4. The plates were blocked with 5% human serum in KRB, pH 7.4. Tagged protein was detected with goat or rabbit anti-c-Myc tag Ab or goat anti-HA antibody (3× serial dilutions, starting at 250 ng/mL) in KRB, pH 7.4.

The results indicated that the anti-HA antibody did not bind as well as the anti-c-Myc antibody in the presence of 5% human serum. The Abcam and GeneTex anti-c-myc antibodies all had similar affinity. The results also indicated that human serum did not interfere with detection of tagged-protein by the secondary antibody.

Tagged Protein Detection in the Presence of 25% Human Serum

The anti-FLAG antibody (Abcam, ab1238) was evaluated for its detection of FLAG-tag protein in the presence of 25% human serum in KRB buffer, pH 6.0 and 7.4. The $K_D$ at pH 7.4 was approximately 224 ng/mL whereas the $K_D$ at pH 6.0 was approximately 135 ng/mL.

The anti-myc antibody (Abcam, ab1326) also was evaluated for its detection of myc-tag protein in the presence of 25% human serum in KRB buffer, pH 6.0 and 7.4. The $K_D$ at pH 7.4 was approximately 7.98 ng/mL whereas the $K_D$ at pH 6.0 was approximately 7.73 ng/mL.

The anti-Myc antibody (Abcam, ab1326) was evaluated for its detection of the multifusion tag protein in the presence of 25% human serum in KRB buffer, pH 7.4. The $K_D$ was approximately 20 ng/mL.

EXAMPLE 6

Effect of Human Serum on Anti-EGFR-FL MAb pH Sensitive ELISA

In this example, the effect of increasing the amount of human serum was evaluated using FLAG-tagged Erbitux® anti-EGFR antibody and goat anti-FLAG-HRP conjugated secondary antibody. The experiments were performed using KRB at either pH 7.4 or 6.0 with either 5% or 25% human serum and differing amounts of lactic acid (see Table 9 below). Human serum and lactic acid were added to mimic the tumor microenvironment.

Briefly, a 96-well Hi-bind plate (Costar #2592) was coated overnight at 4° C. with 100 µL sEGFR-HG antigen (Sino Biologics, Cat #10001-H08H) at 12 nM (1.32 µg/mL) in KRB, pH 7.4. The plate was then washed 3× with 250 µL/well of KRB, pH 7.4 and subsequently blocked for 1 hour at RT with 250 µL of KRB with human serum and lactic acid at pH 7.4 and 6.0 (set forth in Table 9 below). Serial dilutions (3×, starting concentration 100 ng/mL, followed by 1:3 dilutions) of FLAG-EGFR MAb standard or test standards were prepared in KRB with human serum and lactic acid at pH 7.4 and 6.0 and 100 µL was added per well and the plate was incubated at RT for 1 hr. The plate was then washed 3× with 250 µL/well KRB with human serum and lactic acid at pH 7.4 and 6.0. 100 µL/well goat anti-FLAG-HRP conjugated secondary antibody (diluted 1:2000 in KRB with 25% human serum and lactic acid at pH 7.4 and 6.0) was added to each well and the plate was incubated for 1 hr at RT. The plate was then washed 3× with 250 µL/well of KRB with human serum and lactic acid at pH 7.4 and 6.0. Finally, 100 µL Sureblue TMB Microwell Peroxidase Substrate 1-component (KPL, #52-00-03) solution was added to each well and the plate was allowed to develop for 15-20 minutes at RT (away from light). The reaction was stopped by adding 100 µL TMB stop solution (KPL, #50-85-06) to each well and the plate was read within 30 min at $OD_{450}$ nM using a Microplate Spectrophotometer (Molecular Devices, Spectra Max M2).

TABLE 10

| ELISA Assay Buffer Conditions | | | |
|---|---|---|---|
| Buffer | Lactic Acid | Human Serum | pH |
| KRB | 1 mM | 5% | 7.4 |
| KRB | 16.5 mM | 5% | 6.0 |
| KRB | 1 mM | 25% | 7.4 |
| KRB | 16.5 mM | 25% | 6.0 |

The results were consistent for each tested pH regardless of human serum concentration. For example, the $K_D$ for binding of the anti-EGFR antibody in 25% human serum, pH 6.0 was 2.21 ng/mL whereas for assays utilizing 5% human serum, pH 6.0, the $K_D$ was 2.12 ng/mL. The same effect was observed for pH 7.4. The results were confirmed for three experiments each run by three different operators. Since the results indicate no difference between the two percentages of human serum, and 25% more closely mimics physiological conditions, 25% was selected for future experiments. The suitability criteria for robustness for both 5% and 25% human serum are set forth in Tables 11-12 below.

TABLE 11

Suitability Criteria for Robustness - 5% human serum

| Buffer pH | Buffer components | LLOQ | ULOQ | $K_D$ | S/N Ratio |
|---|---|---|---|---|---|
| 7.4 | 1 mM lactate, 5% human serum | 2.7 pM | 74 pM | 15.4 pM ± 30% | ≥20 |
| 6.0 | 16.5 mM lactate, 5% human serum | 2.7 pM | 74 pM | 11.1 pM ± 30% | ≥20 |

Change in concentration of (α-EGFR-FLAG antibody) 1.0 Log corresponds to change in OD ~2.5.

TABLE 12

Suitability Criteria for Robustness - 25% human serum

| Buffer pH | Buffer components | LLOQ | ULOQ | $K_D$ | S/N Ratio |
|---|---|---|---|---|---|
| 7.4 | 1 mM lactate, 25% human serum | 2.7 pM | 74 pM | 16.6 pM ± 30% | ≥20 |
| 6.0 | 16.5 mM lactate, 25% human serum | 2.7 pM | 74 pM | 10.1 pM ± 30% | ≥20 |

LLOQ: lower limit of quantification; ULOQ: upper limit of quantification; Change in concentration of (α-EGFR-FLAG antibody) 1.0 Log corresponds to change in OD ~2.5.

EXAMPLE 7

ELISA Simulating a Tumor Microenvironment and Normal Physiological Conditions

In this example, a parallel, high throughput pH sensitive indirect ELISA was developed and used to test binding conditions that simulate binding conditions in the extracellular matrix within a tumor microenvironment, such as low pH (pH<7.4, e.g. 6.0), elevated lactic acid concentrations (12-20 mM) and the presence of human serum. Simultaneously, conditions that simulate normal physiology (e.g. pH 7.4, 1 mM lactic acid, 25% human serum) also were tested. In this way, antibodies, such as variant antibodies produced using the methods described elsewhere and below in Example 8 that preferentially bind a target protein in conditions that represent a tumor microenvironment, rather than normal physiological conditions, can be identified.

Krebs-Ringer bicarbonate buffer was selected for the screen as it most closely reflects a physiologic buffer. Lactic acid was included in the assay buffer at specified concentrations, and the pH of the buffers were adjusted to either 7.4 or 6.0 using 1 N HCl. Furthermore, since human serum was used in the screen, standard and readily available anti-human IgG1 Fc antibodies cannot be used due to the amount of IgG found in human serum (see Example 3 above). Therefore, a FLAG-tagged anti-EGFR parental antibody was used as a standard in the assay.

Briefly, the extracellular domain of the EGF receptor (EGFR sECD) was immobilized on 96 well plates. This antigen coating step is carried out using a pH 7.4 buffer. The bound antigen was then incubated with pre-determined dilutions of cell culture supernatant containing the FLAG-tagged anti-EGFR antibody variants. The tagged antibody variants were detected following binding of an HRP-conjugated anti-FLAG antibody. The initial blocking, binding of the FLAG-antibody variants, washing and the detection by the conjugated anti-FLAG secondary antibody were carried out under parallel conditions with pH 7.4 or pH 6.0 buffers as described below.

Assay:

A 96-well Hi-bind plate (Costar #2592) is coated overnight at 4° C. or for 2 hours at room temperature (RT) with 100 µL EGFR sECD-H6 antigen (prepared as described in Example 1 or sEGFR-H6 (Sino Biologics, Cat #10001-H08H)) at 12 nM (1.32 µg/mL) in Buffer A (Krebs-Ringer Buffer (KRB, Sigma Aldrich, #K4002), pH 7.4, no human serum). The plate was then washed 3× with 250 µL/well of Buffer A and subsequently blocked for 1 hour at RT with 250 µL of either pH 7.4 Buffer B (1 mM lactic acid/25% human serum) or pH 6.0 Buffer C (16.6 mM lactic acid/25% human serum), while covered. Serial dilutions (3×, starting concentration 100 ng/mL, followed by 1:3 dilutions) of anti-EGFR-FLAG antibody standards were prepared in either pH 7.4 Buffer B (KRB, pH 7.4, 1 mM lactic acid/25% human serum) or pH 6.0 Buffer C (KRB, pH 6.0, 16.6 mM lactic acid/25% human serum) and 100 µL was added per well. After dilution, concentrations of anti-EGFR-FLAG antibody were 666.67 pM (100 ng/mL), 222.22 pM (33.33 ng/mL), 74.07 pM (11.11 ng/mL), 24.69 pM (3.70 ng/mL), 8.23 pM (1.23 ng/mL), 2.74 pM (0.41 ng/mL), 0.91 pM (0.137 ng/mL) and 0. Test sample dilutions were prepared, as described above for the antibody standards, and 100 µL was added per well. The anti-EGFR-FLAG antibody standards and test samples were covered and incubated at RT for 1 hr. The plate was then washed 3× with 250 µL/well of either pH 7.4 Buffer B or pH 6.0 Buffer C. 100 µL/well goat anti-FLAG-HRP detection antibody (Abcam, #ab 1238) at 500 ng/mL in either pH 7.4 Buffer B or pH 6.0 Buffer C was added to each well and the plate was covered and incubated for 1 hr at RT. The plate was then washed 3× with 250 µL/well of either pH 7.4 Buffer B or pH 6.0 Buffer C. Finally, 100 µL Sureblue TMB Microwell Peroxidase Substrate 1-component (KPL, #52-00-03) solution was added to each well and the plate was allowed to develop for 15-20 minutes at RT (away from light). The reaction was stopped by adding 100 µl TMB stop solution (KPL, #50-85-06) to each well and the plate was read within 30 min at $OD_{450}$ nM using a Microplate Spectrophotometer (Molecular Devices, Spectra Max M2).

Each plate included an anti-EGFR-FLAG antibody standard, a positive control (parental antibody) and negative control transfections. The ELISA was performed in triplicate.

Selection criteria for identifying antibodies, such as variant antibodies, that preferentially bind a target protein in conditions that simulate a tumor microenvironment rather than normal physiological conditions was determined as ratio of antibody variant binding at pH 6.0/7.4 and specific fold increase over parent control antibody. Those antibodies, such as variant antibodies, that have strong binding activity at pH 6.0 and diminished binding at neutral pH 7.4 as compared to the parental control antibody, such as a tagged-Erbitux® anti-EGFR antibody control antibody, are antibodies of interest.

EXAMPLE 8

Generation of Anti-EGFR Antibody Mutants

In this example, a comprehensive positional evolution (CPE) library of single point mutants of the Erbitux® anti-EGFR antibody was constructed and generated. The positions for CPE library construction were focused in the variable region CDRs of the light and heavy chains of the Erbitux® anti-EGFR antibody, with the inclusion of additional amino acids that may play a role in antigen recognition. A library of single point variants was created that contains at least 15 amino acid variants at each of one hundred amino acid positions within the variable regions of either the heavy chain or light chain of Erbitux® (SEQ ID NOS:2 and 1, respectively) (see FIG. 1). The amino acid histidine was included among the 15 variants at each position. Glycerol stocks of members of the library were prepared and stored at −80° C.

Each member of the library was sequenced, expressed in CHO cells as IgG antibodies, arrayed in an addressable array in 96-well plates, and tested by ELISA for binding to soluble extracellular domain of EGFR antigen under conditions that simulate a tumor microenvironment and under conditions that simulate normal physiological conditions, as described in Example 7 to identify antibodies that have binding activity at the lower pH of 6.0, and diminished binding activity at pH 7.4 as compared to the parental tagged-Erbitux® anti-EGFR control antibody.

Additionally, a SEAP or quantitative assay will be used. In this assay, the activity of secreted alkaline phosphatase (SEAP) in the cell culture supernatant will be measured. SEAP activity/antibody protein concentration will be used to compensate for transfection/expression efficiency variations and to normalized antibody variant binding activities to the wild type. Positive clones identified from the CPE screen will be considered for further evolution through construction of a CPS library to screen for muteins with increased binding to the EGFR sECD under low pH (6.0) conditions.

EXAMPLE 9

Conditional Activity of anti-EGFR Antibody Mutants

Members of the CPE library of single point mutants of the Erbitux® anti-EGFR antibody described in Example 8 was assessed by ELISA to measure binding to EGFR sECD-H6 antigen at pH 6.0 and pH 7.4 to identify conditionally active mutants as described in Example 7. The results are set forth in Table 13. Out of 1501 Erbitux® mutants tested, 248 mutants were conditionally active (209 mutants with normalized specific activity >0.4 at pH 7.4 and <0.4 at pH 6.0; and 39 mutants with normalized specific activity >0.4 at pH 6.0 and <0.4 at pH 7.4). Out of the remaining mutants, 283 had low expression levels (<20 ng/ml), 149 did not have binding activity at pH 6.0 or pH 7.4, and 737 mutants had a normalized specific activity >0.4 at pH 6.0 and pH 7.4.

TABLE 13

| Categories | Criteria | # of Clones Total | Light Chain | Heavy Chain | % Total Clones |
|---|---|---|---|---|---|
| Low Expression | Expression level <20 ng/ml | 283 | 78 | 205 | 18.9 |
| Non-active clones | No binding activity at pH 6.0 or pH 7.4 | 149 | 43 | 106 | 10.0 |
| Active at pH 6.0 and 7.4 | Normalized specific activity >0.4 at pH 6.0 and pH 7.4 | 737 | 315 | 422 | 49.1 |
| Active at pH 7.4 only | Normalized specific activity >0.4 at pH 7.4 and <0.4 at pH 6.0 | 209 | 134 | 75 | 13.9 |
| Active at pH 6.0 only | Normalized specific activity >0.4 at pH 6.0 and <0.4 at pH 7.4 | 39 | 3 | 36 | 2.6 |
| Others | | 84 | 12 | 72 | 5.5 |

Since modifications will be apparent to those of skill in this art, it is intended that this invention be limited only by the scope of the appended claims.

The invention claimed is:

1. An in vitro method for identifying/selecting a modified therapeutic protein that treats tumors and that has greater activity in a tumor microenvironment in a subject compared to a non-tumor environment in the subject, comprising:
1) testing the binding activity of a plurality of modified therapeutic anti-tumor proteins to the target of the therapeutic anti-tumor proteins under conditions a) and under conditions b), wherein:
the modified therapeutic anti-tumor proteins are anti-tumor antibodies or antigen-binding portions thereof;
the conditions in a) comprise low pH that is between 5.8 and 6.8, and human serum;
the conditions in b) comprise pH that is between about 7.2 and 7.8, and human serum at the same concentration as in a);
the serum concentration in both conditions is the same and is 15%-35% by volume;
optionally, the conditions in a) compared to the conditions in b) comprise one or more properties in addition to lower pH selected from among hypoxia, higher lactate concentration and higher pyruvate concentration;
all other conditions in a) and b) are the same;
the activity tested is binding to a target protein of the therapeutic protein;
each modified therapeutic protein contains an amino acid replacement, insertion, and/or deletion of an amino acid residue or residues compared to the unmodified form of the therapeutic protein; and
each modified protein is tested in each of conditions a) and b);
2) comparing the binding activity of the modified therapeutic proteins in a) to the binding activity in b); and
3) selecting/identifying a modified therapeutic protein that has greater binding activity for the target protein in a) compared to b), thereby identifying a modified therapeutic antibody or antigen-binding portion thereof that is conditionally active such that it has greater binding activity in the low pH conditions of a tumor microenvironment compared to the pH conditions of a non-tumor environment.

2. The method of claim 1, wherein the conditions in b) comprise pH between about 7.2 to about 7.6.

3. The method of claim 1, wherein the pH in b) is the pH of a healthy tissue.

4. The method of claim 3, wherein the healthy tissue is the gastrointestinal (GI) tract, the skin, the vasculature, the blood or the extracellular matrix.

5. The method of claim 1, wherein the modified therapeutic proteins comprise an antigen-binding portion of an anti-tumor antibody.

6. The method of claim 1, wherein the therapeutic protein is selected from among Cetuximab, Trastuzumab, Rituximab, Bevacizumab, Alemtuzumab, Panitumumab, Ranibizumab, Ibritumomab, Ibritumomab tiuxetan, Tositumomab, I131Tositumomab, Catumaxomab, Gemtuzumab, Gemtuzumab ozogamicine, Abatacept, Belatacept, Ipilimumab, Tremelimumab, Volociximab, F200, MORAb-009, SS1P, Cixutumumab, Matuzumab, Nimotuzumab, Zalutumumab, Necitumumab IMC-11F8, mAb806/ch806, Sym004 and mAb-425.

7. The method of claim 1, wherein the modified therapeutic protein that is tested is an antibody that comprises one or more amino acid replacements in a complementarity determining region (CDR) compared to an unmodified form of the antibody.

8. The method of claim 1, wherein each modified therapeutic protein contains a single amino acid replacement or two, three, four, five, six, seven, eight, nine or more amino acid replacements compared to an unmodified form of the therapeutic protein.

9. The method of claim 1, wherein:
a plurality of therapeutic proteins are modified to generate a collection of modified therapeutic proteins, wherein:
each modified protein in the collection is tested in each of a) and b);
each modified therapeutic protein in the collection contains a single amino acid replacement compared to an unmodified form of the therapeutic protein;
in the collection, the amino acid at each modified position is replaced by up to 1-19 other amino acids other than the original amino acid at the position, whereby each modified therapeutic protein contains a different amino acid replacement; and
in the collection, every amino acid along the length of the therapeutic protein, or a selected portion thereof, is replaced.

10. The method of claim 1, wherein:
the modified therapeutic protein comprises an amino acid replacement; and
histidine is a replacing amino acid and/or the histidines in the protein is/are replaced by a non-basic or uncharged amino acid.

11. The method of claim 1, wherein:
the modified therapeutic protein comprises an amino acid replacement; and
the amino acid replacement is replacement with an amino acid selected from among Arg, Asp, Glu, His and Lys.

12. The method of claim 1, wherein:
the modified protein comprises an amino acid replacement; and
the amino acid replacement is replacement with His.

13. The method of claim 1, wherein binding is assessed by an immunoassay.

14. The method of claim 13, wherein the immunoassay comprises an ELISA.

15. The method of claim 1, wherein the modified therapeutic protein is expressed on the surface of a cell.

16. The method of claim 15, wherein:
the activity assessed is binding of the target protein to the modified therapeutic protein on the surface of the cell;
the target protein is contacted with a population of the cells that each express different modified therapeutic proteins; and
a cell or cells is/are identified that bind(s) to the target protein, thereby identifying a modified therapeutic protein that exhibits binding activity.

17. The method of claim 16, wherein the target protein is detectably labeled or can be detected.

18. The method of claim 17, wherein the target protein is fluorescently labeled or is detected by a secondary reagent that is fluorescently labeled.

19. The method of claim 17, wherein detecting or measuring the binding is by fluorescence activated cell sorting (FACS).

20. The method of claim 1, wherein the target protein is a receptor or a portion thereof that binds to a ligand.

21. The method of claim 20, wherein the target protein of the therapeutic protein is a receptor that is a tumor antigen.

22. The method of claim 21, wherein the target protein of the therapeutic protein is a member of the Her family of receptors.

23. The method of claim 22, wherein the target protein of the therapeutic protein is the EGFR receptor or the extracellular domain thereof.

24. The method of claim 1, wherein the activity in a) is greater than in b) by a ratio of at least 1.2, 1.3, 1.4, 1.5, 1.6, 1.7, 1.8, 1.9, 2.0, 3, 4, 5, 6, 7, 8, 9, 10, 11, 12, 13, 14, 15, 16, 17, 18, 19, 20, 30, 40, 50 or more.

25. The method of claim 1, further comprising repeating steps 1)-3) a plurality of times, wherein in each repetition, further modified proteins of a selected modified protein or proteins are generated and tested, whereby the therapeutic protein is evolved to exhibit increased activity at the lower pH in a).

26. The method of claim 1, wherein the therapeutic protein is an anti-EGFR antibody.

27. The method of claim 1, wherein:
the conditions that exist in the tumor microenvironment a) compared to the non-tumor environment b) comprise one or more properties in addition to lower pH selected from among hypoxia, increased lactate concentration, increased pyruvate concentration, increased interstitial fluid pressure, and altered metabolites or metabolism indicative of a tumor compared to the non-tumor environment.

28. The method of claim 1, wherein the conditions in a) further comprise a lactate concentration that is 10 mM to 20 mM and/or the conditions in b) further comprise lactate concentration that is 0.5 to 5 mM.

29. The method of claim 1, wherein the conditions in a) further comprise elevated lactic acid concentration compared to the conditions in b).

30. The method of claim 1, wherein the concentration of human serum is 15% to 30% by volume, inclusive.

31. The method of claim 1, wherein the concentration of human serum is 15% to 25% by volume, inclusive.

32. The method of claim 1, wherein
the conditions in a) further comprise a lactate concentration that is 10mM to 20 mM; and the conditions in b) further comprise lactate concentration that is 0.2 mM to 4 mM.

* * * * *

UNITED STATES PATENT AND TRADEMARK OFFICE
CERTIFICATE OF CORRECTION

| | |
|---|---|
| PATENT NO. | : 9,683,985 B2 |
| APPLICATION NO. | : 13/200666 |
| DATED | : June 20, 2017 |
| INVENTOR(S) | : Kodandapani et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 154 days.

Signed and Sealed this
Twenty-first Day of November, 2017

Joseph Matal
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 85

<210> SEQ ID NO 1
<211> LENGTH: 213
<212> TYPE: PRT
<213> ORGANISM: Artificial Sequence
<220> FEATURE:
<223> OTHER INFORMATION: Erbitux LC (Cetuximab, IMC-C225)

<400> SEQUENCE: 1

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60
```

```
Ser Gly Ser Gly Thr Asp Phe Thr Leu Ser Ile Asn Ser Val Glu Ser
 65                  70                  75                  80

Glu Asp Ile Ala Asp Tyr Tyr Cys Gln Gln Asn Asn Asn Trp Pro Thr
                 85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Ala
    210
```

<210> SEQ ID NO 2
<211> LENGTH: 449
<212> TYPE: PRT
<213> ORGANISM: Artificial Sequence
<220> FEATURE:
<223> OTHER INFORMATION: Erbitux HC (Cetuximab, IMC-C225)

<400> SEQUENCE: 2

```
Gln Val Gln Leu Lys Gln Ser Gly Pro Gly Leu Val Gln Pro Ser Gln
  1               5                  10                  15

Ser Leu Ser Ile Thr Cys Thr Val Ser Gly Phe Ser Leu Thr Asn Tyr
             20                  25                  30

Gly Val His Trp Val Arg Gln Ser Pro Gly Lys Gly Leu Glu Trp Leu
         35                  40                  45

Gly Val Ile Trp Ser Gly Gly Asn Thr Asp Tyr Asn Thr Pro Phe Thr
     50                  55                  60

Ser Arg Leu Ser Ile Asn Lys Asp Asn Ser Lys Ser Gln Val Phe Phe
 65                  70                  75                  80

Lys Met Asn Ser Leu Gln Ser Asn Asp Thr Ala Ile Tyr Tyr Cys Ala
                 85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205
```

```
Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445
Lys

<210> SEQ ID NO 3
<211> LENGTH: 8
<212> TYPE: PRT
<213> ORGANISM: Artificial Sequence
<220> FEATURE:
<223> OTHER INFORMATION: FLAG Tag

<400> SEQUENCE: 3

Asp Tyr Lys Asp Asp Asp Asp Lys
1               5

<210> SEQ ID NO 4
<211> LENGTH: 5
<212> TYPE: PRT
<213> ORGANISM: Artificial Sequence
<220> FEATURE:
<223> OTHER INFORMATION: Gly4Ser Linker

<400> SEQUENCE: 4

Gly Gly Gly Gly Ser
1               5

<210> SEQ ID NO 5
<211> LENGTH: 10
<212> TYPE: PRT
<213> ORGANISM: Artificial Sequence
```

```
<220> FEATURE:
<223> OTHER INFORMATION: cMyc Tag

<400> SEQUENCE: 5

Glu Gln Lys Leu Ile Ser Glu Glu Asp Leu
 1               5                  10

<210> SEQ ID NO 6
<211> LENGTH: 29
<212> TYPE: PRT
<213> ORGANISM: Artificial Sequence
<220> FEATURE:
<223> OTHER INFORMATION: IgG HC Leader

<400> SEQUENCE: 6

Met Glu Phe Gly Leu Ser Trp Leu Phe Leu Val Ala Ile Leu Lys Gly
 1               5                  10                  15

Val Gln Cys Glu Val Gln Leu Leu Glu Ser Gly Gly Gly
             20                  25

<210> SEQ ID NO 7
<211> LENGTH: 6
<212> TYPE: PRT
<213> ORGANISM: Artificial Sequence
<220> FEATURE:
<223> OTHER INFORMATION: 6xHis Tag

<400> SEQUENCE: 7

His His His His His His
 1               5

<210> SEQ ID NO 8
<211> LENGTH: 414
<212> TYPE: DNA
<213> ORGANISM: Artificial Sequence
<220> FEATURE:
<223> OTHER INFORMATION: Erbitux HC Variable DNA

<400> SEQUENCE: 8
atggctgtct tggcgctgct cttctgcctg gtgacattcc caagctgtgt cctatcccag      60
gtgcagctga agcagtcagg acctggccta gtgcagccct cacagagcct gtccatcacc     120
tgcacagtct ctggtttctc attaactaac tatggtgtac actgggttcg ccagtctcca     180
ggaaagggtc tggagtggct gggagtgata tggagtggtg aaacacaga ctataataca      240 cctttcacat ccagactgag catcaacaag acaattcca agagccaagt tttctttaaa      300
atgaacagtc tgcaatctaa tgacacagcc atatattact gtgccagagc cctcacctac     360
tatgattacg agtttgctta ctggggccaa gggactctgg tcactgtctc tgca            414

<210> SEQ ID NO 9
<211> LENGTH: 400
<212> TYPE: DNA
<213> ORGANISM: Artificial Sequence
<220> FEATURE:
<223> OTHER INFORMATION: Erbitux LC Variable DNA

<400> SEQUENCE: 9
atgagggccc ctgctcagtt tcttggcttc ttgcttttct ggattccagc ctccagaagt      60
gacatcttgc tgactcagtc tccagtcatc ctgtctgtga gtccaggaga aagagtcagt     120
ttctcctgca gggccagtca gagtattggc acaaacatac actggtatca gcaaagaaca     180
aatggttctc caaggcttct cataaagtat gcttctgagt ctatctctgg gatcccttcc     240
```

```
aggtttagtg gcagtggatc agggacagat tttactctta gcatcaacag tgtggagtct    300
gaagatattg cagattatta ctgtcaacaa aataataact ggccaaccac gttcggtgct    360
gggaccaagc tggagctgaa acgtgagtgg atccttctag                          400
```

<210> SEQ ID NO 10
<211> LENGTH: 1210
<212> TYPE: PRT
<213> ORGANISM: Artificial Sequence
<220> FEATURE:
<223> OTHER INFORMATION: EGFR Receptor

<400> SEQUENCE: 10

```
Met Arg Pro Ser Gly Thr Ala Gly Ala Ala Leu Leu Ala Leu Leu Ala
 1               5                  10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335
```

```
Cys Asn Gly Ile Gly Ile Gly Glu Phe Lys Asp Ser Leu Ser Ile Asn
                340                 345                 350

Ala Thr Asn Ile Lys His Phe Lys Asn Cys Thr Ser Ile Ser Gly Asp
            355                 360                 365

Leu His Ile Leu Pro Val Ala Phe Arg Gly Asp Ser Phe Thr His Thr
        370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
        450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
        530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
        610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
        690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
```

-continued

```
            755                 760                 765
Val Asp Asn Pro His Val Cys Arg Leu Leu Gly Ile Cys Leu Thr Ser
770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                    805                 810                 815

Trp Cys Val Gln Ile Ala Lys Gly Met Asn Tyr Leu Glu Asp Arg Arg
                    820                 825                 830

Leu Val His Arg Asp Leu Ala Ala Arg Asn Val Leu Val Lys Thr Pro
                    835                 840                 845

Gln His Val Lys Ile Thr Asp Phe Gly Leu Ala Lys Leu Leu Gly Ala
850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                    885                 890                 895

Val Trp Ser Tyr Gly Val Thr Val Trp Glu Leu Met Thr Phe Gly Ser
                    900                 905                 910

Lys Pro Tyr Asp Gly Ile Pro Ala Ser Glu Ile Ser Ser Ile Leu Glu
                    915                 920                 925

Lys Gly Glu Arg Leu Pro Gln Pro Pro Ile Cys Thr Ile Asp Val Tyr
                    930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                    965                 970                 975

Arg Tyr Leu Val Ile Gln Gly Asp Glu Arg Met His Leu Pro Ser Pro
                    980                 985                 990

Thr Asp Ser Asn Phe Tyr Arg Ala Leu Met Asp Glu Glu Asp Met Asp
                    995                 1000                1005

Asp Val Val Asp Ala Asp Glu Tyr Leu Ile Pro Gln Gln Gly Phe Phe
1010                1015                1020

Ser Ser Pro Ser Thr Ser Arg Thr Pro Leu Leu Ser Ser Leu Ser Ala
1025                1030                1035                1040

Thr Ser Asn Asn Ser Thr Val Ala Cys Ile Asp Arg Asn Gly Leu Gln
                    1045                1050                1055

Ser Cys Pro Ile Lys Glu Asp Ser Phe Leu Gln Arg Tyr Ser Ser Asp
                    1060                1065                1070

Pro Thr Gly Ala Leu Thr Glu Asp Ser Ile Asp Asp Thr Phe Leu Pro
                    1075                1080                1085

Val Pro Glu Tyr Ile Asn Gln Ser Val Pro Lys Arg Pro Ala Gly Ser
                    1090                1095                1100

Val Gln Asn Pro Val Tyr His Asn Gln Pro Leu Asn Pro Ala Pro Ser
1105                1110                1115                1120

Arg Asp Pro His Tyr Gln Asp Pro His Ser Thr Ala Val Gly Asn Pro
                    1125                1130                1135

Glu Tyr Leu Asn Thr Val Gln Pro Thr Cys Val Asn Ser Thr Phe Asp
                    1140                1145                1150

Ser Pro Ala His Trp Ala Gln Lys Gly Ser His Gln Ile Ser Leu Asp
                    1155                1160                1165

Asn Pro Asp Tyr Gln Gln Asp Phe Phe Pro Lys Glu Ala Lys Pro Asn
                    1170                1175                1180
```

```
Gly Ile Phe Lys Gly Ser Thr Ala Glu Asn Ala Glu Tyr Leu Arg Val
1185               1190                1195                1200

Ala Pro Gln Ser Ser Glu Phe Ile Gly Ala
            1205                1210

<210> SEQ ID NO 11
<211> LENGTH: 24
<212> TYPE: PRT
<213> ORGANISM: Artificial Sequence
<220> FEATURE:
<223> OTHER INFORMATION: EGFR Receptor Signal

<400> SEQUENCE: 11

Met Arg Pro Ser Gly Thr Ala Gly Ala Ala Leu Leu Ala Leu Leu Ala
 1               5                  10                  15

Ala Leu Cys Pro Ala Ser Arg Ala
            20

<210> SEQ ID NO 12
<211> LENGTH: 3633
<212> TYPE: DNA
<213> ORGANISM: Artificial Sequence
<220> FEATURE:
<223> OTHER INFORMATION: EGFR Receptor cDNA

<400> SEQUENCE: 12
atgcgaccct ccgggacggc cggggcagcg ctcctggcgc tgctggctgc gctctgcccg    60
gcgagtcggg ctctggagga aagaaaagtt tgccaaggca cgagtaacaa gctcacgcag   120
ttgggcactt ttgaagatca ttttctcagc ctccagagga tgttcaataa ctgtgaggtg   180
gtccttggga atttggaaat tacctatgtg cagaggaatt atgatctttc cttcttaaag   240
accatccagg aggtggctgg ttatgtcctc attgccctca acacagtgga gcgaattcct   300
ttggaaaacc tgcagatcat cagaggaaat atgtactacg aaaattccta tgccttagca   360
gtcttatcta actatgatgc aaataaaacc ggactgaagg agctgcccat gagaaattta   420
caggaaatcc tgcatggcgc cgtgcggttc agcaacaacc ctgccctgtg caacgtggag   480
agcatccagt ggcgggacat agtcagcagt gactttctca gcaacatgtc gatggacttc   540
cagaaccacc tgggcagctg ccaaaagtgt gatccaagct gtcccaatgg gagctgctgg   600
ggtgcaggag aggagaactg ccagaaactg accaaaatca tctgtgccca gcagtgctcc   660
gggcgctgcc gtggcaagtc ccccagtgac tgctgccaca accagtgtgc tgcaggctgc   720
acaggccccc gggagagcga ctgcctggtc tgccgcaaat tccgagacga agccacgtgc   780
aaggacacct gccccccact catgctctac aaccccacca cgtaccagat ggatgtgaac   840
cccgagggca aatacagctt tggtgccacc tgcgtgaaga agtgtccccg taattatgtg   900
gtgacagatc acggctcgtg cgtccgagcc tgtggggccg acagctatga gatggaggaa   960
gacggcgtcc gcaagtgtaa gaagtgcgaa gggccttgcc gcaaagtgtg taacggaata  1020
ggtattggtg aatttaaaga ctcactctcc ataaatgcta cgaatattaa acacttcaaa  1080
aactgcacct ccatcagtgg cgatctccac atcctgccgg tggcatttag gggtgactcc  1140
ttcacacata ctcctcctct ggatccacag gaactggata ttctgaaaac cgtaaaggaa  1200
atcacagggt ttttgctgat tcaggcttgg cctgaaaaca ggacggacct ccatgccttt  1260
gagaacctag aaatcatacg cggcaggacc aagcaacatg gtcagttttc tcttgcagtc  1320
gtcagcctga acataacatc cttgggatta cgctccctca aggagataag tgatggagat  1380
```

-continued

| | |
|---|---|
| gtgataattt caggaaacaa aaatttgtgc tatgcaaata caataaactg gaaaaaactg | 1440 |
| tttgggacct ccggtcagaa aaccaaaatt ataagcaaca gaggtgaaaa cagctgcaag | 1500 |
| gccacaggcc aggtctgcca tgccttgtgc tcccccgagg gctgctgggg cccggagccc | 1560 |
| agggactgcg tctcttgccg gaatgtcagc cgaggcaggg aatgcgtgga caagtgcaag | 1620 |
| cttctggagg gtgagccaag ggagtttgtg gagaactctg agtgcataca gtgccaccca | 1680 |
| gagtgcctgc ctcaggccat gaacatcacc tgcacaggac ggggaccaga caactgtatc | 1740 |
| cagtgtgccc actacattga cggcccccac tgcgtcaaga cctgcccggc aggagtcatg | 1800 |
| ggagaaaaca cacccctggt ctggaagtac gcagacgccg ccatgtgtg ccacctgtgc | 1860 |
| catccaaact gcacctacgg atgcactggg ccaggtcttg aaggctgtcc aacgaatggg | 1920 |
| cctaagatcc cgtccatcgc cactgggatg gtggggggccc tcctcttgct gctggtggtg | 1980 |
| gccctgggga tcggcctctt catgcgaagg cgccacatcg ttcggaagcg cacgctgcgg | 2040 |
| aggctgctgc aggagaggga gcttgtggag cctcttacac ccagtggaga agctcccaac | 2100 |
| caagctctct tgaggatctt gaaggaaact gaattcaaaa agatcaaagt gctgggctcc | 2160 |
| ggtgcgttcg gcacggtgta taagggactc tggatcccag aaggtgagaa agttaaaatt | 2220 |
| cccgtcgcta tcaaggaatt aagagaagca acatctccga aagccaacaa ggaaatcctc | 2280 |
| gatgaagcct acgtgatggc cagcgtggac aaccccccacg tgtgccgcct gctgggcatc | 2340 |
| tgcctcaccc ccaccgtgca actcatcacg cagctcatgc ccttcggctg cctcctggac | 2400 |
| tatgtccggg aacacaaaga caatattggc tcccagtacc tgctcaactg gtgtgtgcag | 2460 |
| atcgcaaagg gcatgaacta cttggaggac cgtcgcttgg tgcaccgcga cctggcagcc | 2520 |
| aggaacgtac tggtgaaaac accgcagcat gtcaagatca cagattttgg gctggccaaa | 2580 |
| ctgctgggtg cggaagagaa agaataccat gcagaaggag gcaaagtgcc tatcaagtgg | 2640 |
| atggcattgg aatcaatttt acacagaatc tatacccacc agagtgatgt ctggagctac | 2700 |
| ggggtgaccg tttgggagtt gatgaccttt ggatccaagc catatgacgg aatccctgcc | 2760 |
| agcgagatct cctccatcct ggagaaagga gaacgcctcc ctcagccacc catatgtacc | 2820 |
| atcgatgtct acatgatcat ggtcaagtgc tggatgatag acgcagatag tcgcccaaag | 2880 |
| ttccgtgagt tgatcatcga attctccaaa atggcccgag accccagcg ctaccttgtc | 2940 |
| attcaggggg atgaaagaat gcatttgcca agtcctacag actccaactt ctaccgtgcc | 3000 |
| ctgatggatg aagaagacat ggacgacgtg gtggatgccg acgagtacct catcccacag | 3060 |
| cagggcttct tcagcagccc ctccacgtca cggactcccc tcctgagctc tctgagtgca | 3120 |
| accagcaaca attccaccgt ggcttgcatt gatagaaatg ggctgcaaag ctgtcccatc | 3180 |
| aaggaagaca gcttccttgca gcgatacagc tcagacccca caggcgcctt gactgaggac | 3240 |
| agcatagacg acaccttcct cccagtgcct gaatacataa accagtccgt tcccaaaagg | 3300 |
| cccgctggct ctgtgcagaa tcctgtctat cacaatcagc ctctgaaccc cgcgcccagc | 3360 |
| agagacccac actaccagga cccccacagc actgcagtgg caaccccga gtatctcaac | 3420 |
| actgtccagc ccacctgtgt caacagcaca ttcgacagcc ctgcccactg ggcccagaaa | 3480 |
| ggcagccacc aaattagcct ggacaaccct gactaccagc aggacttctt tcccaaggaa | 3540 |
| gccaagccaa atggcatctt taagggctcc acagctgaaa atgcagaata cctaagggtc | 3600 |
| gcgccacaaa gcagtgaatt tattggagca tga | 3633 |

<210> SEQ ID NO 13
<211> LENGTH: 641

```
<212> TYPE: PRT
<213> ORGANISM: Artificial Sequence
<220> FEATURE:
<223> OTHER INFORMATION: EGFR ECD 1-640

<400> SEQUENCE: 13

Met Arg Pro Ser Gly Thr Ala Gly Ala Ala Leu Leu Ala Leu Leu Ala
 1               5                  10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380
```

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
            405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
            435                 440                 445

Gly Leu Arg Ser Leu Lys Glu Ile Ser Asp Gly Asp Val Ile Ile Ser
            450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
            485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
            515                 520                 525

Val Ser Arg Gly Arg Glu Cys Val Asp Lys Cys Asn Leu Leu Glu Gly
530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
            565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
            595                 600                 605

Lys Tyr Ala Asp Ala Gly His Val Cys His Leu Cys His Pro Asn Cys
            610                 615                 620

Thr Tyr Gly Cys Thr Gly Pro Gly Leu Glu Gly Cys Pro Thr Asn Gly
625                 630                 635                 640

Pro

<210> SEQ ID NO 14
<211> LENGTH: 617
<212> TYPE: PRT
<213> ORGANISM: Artificial Sequence
<220> FEATURE:
<223> OTHER INFORMATION: EGFR ECD 25-640

<400> SEQUENCE: 14

Leu Glu Glu Lys Lys Val Cys Gln Gly Thr Ser Asn Lys Leu Thr Gln
1                   5                   10                  15

Leu Gly Thr Phe Glu Asp His Phe Leu Ser Leu Gln Arg Met Phe Asn
            20                  25                  30

Asn Cys Glu Val Val Leu Gly Asn Leu Glu Ile Thr Tyr Val Gln Arg
            35                  40                  45

Asn Tyr Asp Leu Ser Phe Leu Lys Thr Ile Gln Glu Val Ala Gly Tyr
50                  55                  60

Val Leu Ile Ala Leu Asn Thr Val Glu Arg Ile Pro Leu Glu Asn Leu
65                  70                  75                  80

Gln Ile Ile Arg Gly Asn Met Tyr Tyr Glu Asn Ser Tyr Ala Leu Ala
            85                  90                  95

Val Leu Ser Asn Tyr Asp Ala Asn Lys Thr Gly Leu Lys Glu Leu Pro

-continued

```
               100                 105                 110
Met Arg Asn Leu Gln Glu Ile Leu His Gly Ala Val Arg Phe Ser Asn
            115                 120                 125
Asn Pro Ala Leu Cys Asn Val Glu Ser Ile Gln Trp Arg Asp Ile Val
            130                 135                 140
Ser Ser Asp Phe Leu Ser Asn Met Ser Met Asp Phe Gln Asn His Leu
145                 150                 155                 160
Gly Ser Cys Gln Lys Cys Asp Pro Ser Cys Pro Asn Gly Ser Cys Trp
                165                 170                 175
Gly Ala Gly Glu Glu Asn Cys Gln Lys Leu Thr Lys Ile Ile Cys Ala
                180                 185                 190
Gln Gln Cys Ser Gly Arg Cys Arg Gly Lys Ser Pro Ser Asp Cys Cys
            195                 200                 205
His Asn Gln Cys Ala Ala Gly Cys Thr Gly Pro Arg Glu Ser Asp Cys
            210                 215                 220
Leu Val Cys Arg Lys Phe Arg Asp Glu Ala Thr Cys Lys Asp Thr Cys
225                 230                 235                 240
Pro Pro Leu Met Leu Tyr Asn Pro Thr Thr Tyr Gln Met Asp Val Asn
                245                 250                 255
Pro Glu Gly Lys Tyr Ser Phe Gly Ala Thr Cys Val Lys Lys Cys Pro
                260                 265                 270
Arg Asn Tyr Val Val Thr Asp His Gly Ser Cys Val Arg Ala Cys Gly
            275                 280                 285
Ala Asp Ser Tyr Glu Met Glu Glu Asp Gly Val Arg Lys Cys Lys Lys
            290                 295                 300
Cys Glu Gly Pro Cys Arg Lys Val Cys Asn Gly Ile Gly Ile Gly Glu
305                 310                 315                 320
Phe Lys Asp Ser Leu Ser Ile Asn Ala Thr Asn Ile Lys His Phe Lys
                325                 330                 335
Asn Cys Thr Ser Ile Ser Gly Asp Leu His Ile Leu Pro Val Ala Phe
            340                 345                 350
Arg Gly Asp Ser Phe Thr His Thr Pro Pro Leu Asp Pro Gln Glu Leu
            355                 360                 365
Asp Ile Leu Lys Thr Val Lys Glu Ile Thr Gly Phe Leu Leu Ile Gln
            370                 375                 380
Ala Trp Pro Glu Asn Arg Thr Asp Leu His Ala Phe Glu Asn Leu Glu
385                 390                 395                 400
Ile Ile Arg Gly Arg Thr Lys Gln His Gly Gln Phe Ser Leu Ala Val
                405                 410                 415
Val Ser Leu Asn Ile Thr Ser Leu Gly Leu Arg Ser Leu Lys Glu Ile
            420                 425                 430
Ser Asp Gly Asp Val Ile Ile Ser Gly Asn Lys Asn Leu Cys Tyr Ala
            435                 440                 445
Asn Thr Ile Asn Trp Lys Lys Leu Phe Gly Thr Ser Gly Gln Lys Thr
            450                 455                 460
Lys Ile Ile Ser Asn Arg Gly Glu Asn Ser Cys Lys Ala Thr Gly Gln
465                 470                 475                 480
Val Cys His Ala Leu Cys Ser Pro Glu Gly Cys Trp Gly Pro Glu Pro
                485                 490                 495
Arg Asp Cys Val Ser Cys Arg Asn Val Ser Arg Gly Arg Glu Cys Val
            500                 505                 510
Asp Lys Cys Asn Leu Leu Glu Gly Glu Pro Arg Glu Phe Val Glu Asn
            515                 520                 525
```

-continued

```
Ser Glu Cys Ile Gln Cys His Pro Glu Cys Leu Pro Gln Ala Met Asn
        530                 535                 540

Ile Thr Cys Thr Gly Arg Gly Pro Asp Asn Cys Ile Gln Cys Ala His
545                 550                 555                 560

Tyr Ile Asp Gly Pro His Cys Val Lys Thr Cys Pro Ala Gly Val Met
                565                 570                 575

Gly Glu Asn Asn Thr Leu Val Trp Lys Tyr Ala Asp Ala Gly His Val
            580                 585                 590

Cys His Leu Cys His Pro Asn Cys Thr Tyr Gly Cys Thr Gly Pro Gly
        595                 600                 605

Leu Glu Gly Cys Pro Thr Asn Gly Pro
    610                 615

<210> SEQ ID NO 15
<211> LENGTH: 9
<212> TYPE: PRT
<213> ORGANISM: Artificial Sequence
<220> FEATURE:
<223> OTHER INFORMATION: hemagglutinin (HA) tag

<400> SEQUENCE: 15

Tyr Pro Tyr Asp Val Pro Asp Tyr Ala
1               5

<210> SEQ ID NO 16
<211> LENGTH: 11
<212> TYPE: PRT
<213> ORGANISM: Artificial Sequence
<220> FEATURE:
<223> OTHER INFORMATION: VSV-G

<400> SEQUENCE: 16

Tyr Thr Asp Ile Glu Met Asn Arg Leu Gly Lys
1               5                   10

<210> SEQ ID NO 17
<211> LENGTH: 11
<212> TYPE: PRT
<213> ORGANISM: Artificial Sequence
<220> FEATURE:
<223> OTHER INFORMATION: HSV

<400> SEQUENCE: 17

Gln Pro Glu Leu Ala Pro Glu Asp Pro Glu Asp
1               5                   10

<210> SEQ ID NO 18
<211> LENGTH: 14
<212> TYPE: PRT
<213> ORGANISM: Artificial Sequence
<220> FEATURE:
<223> OTHER INFORMATION: V5 tag

<400> SEQUENCE: 18

Gly Lys Pro Ile Pro Asn Pro Leu Leu Gly Leu Asp Ser Thr
1               5                   10

<210> SEQ ID NO 19
<211> LENGTH: 5
<212> TYPE: PRT
<213> ORGANISM: Artificial Sequence
<220> FEATURE:
<223> OTHER INFORMATION: Poly-arginine tag
```

```
<400> SEQUENCE: 19

Arg Arg Arg Arg Arg
 1               5

<210> SEQ ID NO 20
<211> LENGTH: 8
<212> TYPE: PRT
<213> ORGANISM: Artificial Sequence
<220> FEATURE:
<223> OTHER INFORMATION: Strep-tag-II

<400> SEQUENCE: 20

Trp Ser His Pro Gln Phe Glu Lys
 1               5

<210> SEQ ID NO 21
<211> LENGTH: 15
<212> TYPE: PRT
<213> ORGANISM: Artificial Sequence
<220> FEATURE:
<223> OTHER INFORMATION: S-tag

<400> SEQUENCE: 21

Lys Glu Thr Ala Ala Ala Lys Phe Glu Arg Gln His Met Asp Ser
 1               5                  10                  15

<210> SEQ ID NO 22
<211> LENGTH: 22
<212> TYPE: PRT
<213> ORGANISM: Artificial Sequence
<220> FEATURE:
<223> OTHER INFORMATION: 3x FLAG

<400> SEQUENCE: 22

Asp Tyr Lys Asp His Asp Gly Asp Tyr Lys Asp His Asp Ile Asp Tyr
 1               5                  10                  15

Lys Asp Asp Asp Asp Lys
                20

<210> SEQ ID NO 23
<211> LENGTH: 19
<212> TYPE: PRT
<213> ORGANISM: Artificial Sequence
<220> FEATURE:
<223> OTHER INFORMATION: HAT tag

<400> SEQUENCE: 23

Lys Asp His Leu Ile His Asn Val His Lys Glu Phe His Ala His Ala
 1               5                  10                  15

His Asn Lys

<210> SEQ ID NO 24
<211> LENGTH: 38
<212> TYPE: PRT
<213> ORGANISM: Artificial Sequence
<220> FEATURE:
<223> OTHER INFORMATION: Streptavidin binding peptide (SBP) tag

<400> SEQUENCE: 24

Met Asp Glu Lys Thr Thr Gly Trp Arg Gly Gly His Val Val Glu Gly
 1               5                  10                  15

Leu Ala Gly Glu Leu Glu Gln Leu Arg Ala Arg Leu Glu His His Pro
                20                  25                  30

Gln Gly Gln Arg Glu Pro
```

<210> SEQ ID NO 25
<211> LENGTH: 11
<212> TYPE: PRT
<213> ORGANISM: Artificial Sequence
<220> FEATURE:
<223> OTHER INFORMATION: T7

<400> SEQUENCE: 25

Met Ala Ser Met Thr Gly Gly Gln Gln Met Gly
1               5                   10

<210> SEQ ID NO 26
<211> LENGTH: 51
<212> TYPE: PRT
<213> ORGANISM: Artificial Sequence
<220> FEATURE:
<223> OTHER INFORMATION: Chitin-binding domain

<400> SEQUENCE: 26

Thr Asn Pro Gly Val Ser Ala Trp Gln Val Asn Thr Ala Tyr Thr Ala
1               5                   10                  15

Gly Gln Leu Val Thr Tyr Asn Gly Lys Thr Tyr Lys Cys Leu Gln Pro
            20                  25                  30

His Thr Ser Leu Ala Gly Trp Glu Pro Ser Asn Val Pro Ala Leu Trp
        35                  40                  45

Gln Leu Gln
    50

<210> SEQ ID NO 27
<211> LENGTH: 220
<212> TYPE: PRT
<213> ORGANISM: Artificial Sequence
<220> FEATURE:
<223> OTHER INFORMATION: Glutathione S-transferase (GST) tag

<400> SEQUENCE: 27

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

-continued

```
Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
            195                 200                 205

Thr Phe Gly Gly Gly Asp His Pro Pro Lys Ser Asp
            210                 215                 220

<210> SEQ ID NO 28
<211> LENGTH: 396
<212> TYPE: PRT
<213> ORGANISM: Artificial Sequence
<220> FEATURE:
<223> OTHER INFORMATION: Maltose binding protein (MBP) tag

<400> SEQUENCE: 28

Met Lys Ile Lys Thr Gly Ala Arg Ile Leu Ala Leu Ser Ala Leu Thr
 1               5                  10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320
```

```
Lys Asp Lys Pro Leu Gly Ala Val Ala Leu Lys Ser Tyr Glu Glu Glu
            325                 330                 335

Leu Ala Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
            355                 360                 365

Val Arg Thr Ala Val Ile Asn Ala Ala Ser Gly Arg Gln Thr Val Asp
            370                 375                 380

Glu Ala Leu Lys Asp Ala Gln Thr Arg Ile Thr Lys
385                 390                 395

<210> SEQ ID NO 29
<211> LENGTH: 120
<212> TYPE: PRT
<213> ORGANISM: Artificial Sequence
<220> FEATURE:
<223> OTHER INFORMATION: Trastuzumab variable HC

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 30
<211> LENGTH: 107
<212> TYPE: PRT
<213> ORGANISM: Artificial Sequence
<220> FEATURE:
<223> OTHER INFORMATION: Trastuzumab variable LC

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
```

-continued

```
                100                 105

<210> SEQ ID NO 31
<211> LENGTH: 121
<212> TYPE: PRT
<213> ORGANISM: Artificial Sequence
<220> FEATURE:
<223> OTHER INFORMATION: Rituximab variable HC

<400> SEQUENCE: 31

Gln Val Gln Leu Gln Gln Pro Gly Ala Glu Leu Val Lys Pro Gly Ala
  1               5                  10                  15

Ser Val Lys Met Ser Cys Lys Ala Ser Gly Tyr Thr Phe Thr Ser Tyr
             20                  25                  30

Asn Met His Trp Val Lys Gln Thr Pro Gly Arg Gly Leu Glu Trp Ile
         35                  40                  45

Gly Ala Ile Tyr Pro Gly Asn Gly Asp Thr Ser Tyr Asn Gln Lys Phe
     50                  55                  60

Lys Gly Lys Ala Thr Leu Thr Ala Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala
        115                 120

<210> SEQ ID NO 32
<211> LENGTH: 106
<212> TYPE: PRT
<213> ORGANISM: Artificial Sequence
<220> FEATURE:
<223> OTHER INFORMATION: Rituximab variable LC

<400> SEQUENCE: 32

Gln Ile Val Leu Ser Gln Ser Pro Ala Ile Leu Ser Ala Ser Pro Gly
  1               5                  10                  15

Glu Lys Val Thr Met Thr Cys Arg Ala Ser Ser Ser Val Ser Tyr Ile
             20                  25                  30

His Trp Phe Gln Gln Lys Pro Gly Ser Ser Pro Lys Pro Trp Ile Tyr
         35                  40                  45

Ala Thr Ser Asn Leu Ala Ser Gly Val Pro Val Arg Phe Ser Gly Ser
     50                  55                  60

Gly Ser Gly Thr Ser Tyr Ser Leu Thr Ile Ser Arg Val Glu Ala Glu
 65                  70                  75                  80

Asp Ala Ala Thr Tyr Tyr Cys Gln Gln Trp Thr Ser Asn Pro Pro Thr
                 85                  90                  95

Phe Gly Gly Gly Thr Lys Leu Glu Ile Lys
            100                 105

<210> SEQ ID NO 33
<211> LENGTH: 123
<212> TYPE: PRT
<213> ORGANISM: Artificial Sequence
<220> FEATURE:
<223> OTHER INFORMATION: Bevacizumab variable HC

<400> SEQUENCE: 33

Glu Val Gln Leu Val Glu Ser Gly Gly Gly Leu Val Gln Pro Gly Gly
  1               5                  10                  15
```

```
Ser Leu Arg Leu Ser Cys Ala Ala Ser Gly Tyr Thr Phe Thr Asn Tyr
         20                  25                  30

Gly Met Asn Trp Val Arg Gln Ala Pro Gly Lys Gly Leu Glu Trp Val
         35                  40                  45

Gly Trp Ile Asn Thr Tyr Thr Gly Glu Pro Thr Tyr Ala Ala Asp Phe
     50                  55                  60

Lys Arg Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
            115                 120
```

<210> SEQ ID NO 34
<211> LENGTH: 107
<212> TYPE: PRT
<213> ORGANISM: Artificial Sequence
<220> FEATURE:
<223> OTHER INFORMATION: Bevacizumab variable LC

<400> SEQUENCE: 34

```
Asp Ile Gln Met Thr Gln Ser Pro Ser Ser Leu Ser Ala Ser Val Gly
 1               5                  10                  15

Asp Arg Val Thr Ile Thr Cys Ser Ala Ser Gln Asp Ile Ser Asn Tyr
             20                  25                  30

Leu Asn Trp Tyr Gln Gln Lys Pro Gly Lys Ala Pro Lys Val Leu Ile
         35                  40                  45

Tyr Phe Thr Ser Ser Leu His Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Thr Val Pro Trp
                 85                  90                  95

Thr Phe Gly Gln Gly Thr Lys Val Glu Ile Lys
            100                 105
```

<210> SEQ ID NO 35
<211> LENGTH: 121
<212> TYPE: PRT
<213> ORGANISM: Artificial Sequence
<220> FEATURE:
<223> OTHER INFORMATION: Alemtuzumab variable HC

<400> SEQUENCE: 35

```
Gln Val Gln Leu Gln Glu Ser Gly Pro Gly Leu Val Arg Pro Ser Gln
 1               5                  10                  15

Thr Leu Ser Leu Thr Cys Thr Val Ser Gly Phe Thr Phe Thr Asp Phe
             20                  25                  30

Tyr Met Asn Trp Val Arg Gln Pro Pro Gly Arg Gly Leu Glu Trp Ile
         35                  40                  45

Gly Phe Ile Arg Asp Lys Ala Lys Gly Tyr Thr Thr Glu Tyr Asn Pro
     50                  55                  60

Ser Val Lys Gly Arg Val Thr Met Leu Val Asp Thr Ser Lys Asn Gln
 65                  70                  75                  80

Phe Ser Leu Arg Leu Ser Ser Val Thr Ala Ala Asp Thr Ala Val Tyr
```

```
                 85                  90                  95
Tyr Cys Ala Arg Glu Gly His Thr Ala Ala Pro Phe Asp Tyr Trp Gly
                100                 105                 110

Gln Gly Ser Leu Val Thr Val Ser Ser
        115                 120

<210> SEQ ID NO 36
<211> LENGTH: 107
<212> TYPE: PRT
<213> ORGANISM: Artificial Sequence
<220> FEATURE:
<223> OTHER INFORMATION: Alemtuzumab variable LC

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asp Lys Tyr
            20                  25                  30

Leu Asn Trp Tyr Gln Gln Lys Pro Gly Lys Ala Pro Lys Leu Leu Ile
        35                  40                  45

Tyr Asn Thr Asn Asn Leu Gln Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln His Ile Ser Arg Pro Arg
                85                  90                  95

Thr Phe Gly Gln Gly Thr Lys Val Glu Ile Lys
            100                 105

<210> SEQ ID NO 37
<211> LENGTH: 118
<212> TYPE: PRT
<213> ORGANISM: Artificial Sequence
<220> FEATURE:
<223> OTHER INFORMATION: Panitumumab variable HC

<400> SEQUENCE: 37

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Asp Tyr Tyr Trp Thr Trp Ile Arg Gln Ser Pro Gly Lys Gly Leu Glu
        35                  40                  45

Trp Ile Gly His Ile Tyr Tyr Ser Gly Asn Thr Asn Tyr Asn Pro Ser
    50                  55                  60

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
                85                  90                  95

Cys Val Arg Asp Arg Val Thr Gly Ala Phe Asp Ile Trp Gly Gln Gly
            100                 105                 110

Thr Met Val Thr Ser Ser
        115

<210> SEQ ID NO 38
<211> LENGTH: 107
<212> TYPE: PRT
<213> ORGANISM: Artificial Sequence
<220> FEATURE:
```

<223> OTHER INFORMATION: Panitumumab variable LC

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Phe Asp His Leu Pro Leu
                85                  90                  95

Ala Phe Gly Gly Gly Thr Lys Val Glu Ile Lys
            100                 105

<210> SEQ ID NO 39
<211> LENGTH: 123
<212> TYPE: PRT
<213> ORGANISM: Artificial Sequence
<220> FEATURE:
<223> OTHER INFORMATION: Ranibizumab variable HC

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser
        115                 120

<210> SEQ ID NO 40
<211> LENGTH: 107
<212> TYPE: PRT
<213> ORGANISM: Artificial Sequence
<220> FEATURE:
<223> OTHER INFORMATION: Ranibizumab variable LC

<400> SEQUENCE: 40

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly

```
                    50                    55                   60
Ser Gly Ser Gly Thr Asp Phe Thr Leu Thr Ile Ser Ser Leu Gln Pro
 65                  70                   75                   80

Glu Asp Phe Ala Thr Tyr Tyr Cys Gln Gln Tyr Ser Thr Val Pro Trp
                 85                   90                   95

Thr Phe Gly Gln Gly Thr Lys Val Glu Ile Lys
            100                 105
```

<210> SEQ ID NO 41
<211> LENGTH: 443
<212> TYPE: PRT
<213> ORGANISM: Artificial Sequence
<220> FEATURE:
<223> OTHER INFORMATION: Ibritumomab HC

<400> SEQUENCE: 41

```
Gln Ala Tyr Leu Gln Gln Ser Gly Ala Glu Leu Val Arg Pro Gly Ala
  1               5                   10                  15

Ser Val Lys Met Ser Cys Lys Ala Ser Gly Tyr Thr Phe Thr Ser Tyr
                 20                  25                  30

Asn Met His Trp Val Lys Gln Thr Pro Arg Gln Gly Leu Glu Trp Ile
             35                  40                  45

Gly Ala Ile Tyr Pro Gly Asn Gly Asp Thr Ser Tyr Asn Gln Lys Phe
 50                  55                  60

Lys Gly Lys Ala Thr Leu Thr Val Asp Lys Ser Ser Ser Thr Ala Tyr
 65                  70                  75                   80

Met Gln Leu Ser Ser Leu Thr Ser Glu Asp Ser Ala Val Tyr Phe Cys
                 85                  90                   95

Ala Arg Val Val Tyr Tyr Ser Asn Ser Tyr Trp Tyr Phe Asp Val Trp
                100                 105                 110

Gly Thr Gly Thr Thr Val Thr Val Ser Ala Pro Ser Val Tyr Pro Leu
            115                 120                 125

Ala Pro Val Cys Gly Asp Thr Thr Gly Ser Ser Val Thr Leu Gly Cys
        130                 135                 140

Leu Val Lys Gly Tyr Phe Pro Glu Pro Val Thr Leu Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Thr Ser Ser Thr Trp
            180                 185                 190

Pro Ser Gln Ser Ile Thr Cys Asn Val Ala His Pro Ala Ser Ser Thr
        195                 200                 205

Lys Val Asp Lys Lys Ile Glu Pro Arg Gly Pro Thr Ile Lys Pro Cys
    210                 215                 220

Pro Pro Cys Lys Cys Pro Ala Pro Asn Leu Leu Gly Gly Pro Ser Val
225                 230                 235                 240

Phe Ile Phe Pro Pro Lys Ile Lys Asp Val Leu Met Ile Ser Leu Ser
                245                 250                 255

Pro Ile Val Thr Cys Val Val Val Asp Val Ser Glu Asp Asp Pro Asp
            260                 265                 270

Val Gln Ile Ser Trp Phe Val Asn Asn Val Glu Val His Thr Ala Gln
        275                 280                 285

Thr Gln Thr His Arg Glu Asp Tyr Asn Ser Thr Leu Arg Val Val Ser
    290                 295                 300

Ala Leu Pro Ile Gln His Gln Asp Trp Met Ser Gly Lys Glu Phe Lys
```

```
                305                 310                 315                 320
Cys Lys Val Asn Asn Lys Asp Leu Pro Ala Pro Ile Glu Arg Thr Ile
                325                 330                 335

Ser Lys Pro Lys Gly Ser Val Arg Ala Pro Gln Val Tyr Val Leu Pro
                340                 345                 350

Pro Pro Glu Glu Met Thr Lys Lys Gln Val Thr Leu Thr Cys Met
                355                 360                 365

Val Thr Asp Phe Met Pro Glu Asp Ile Tyr Val Glu Trp Thr Asn Asn
    370                 375                 380

Gly Lys Thr Glu Leu Asn Tyr Lys Asn Thr Glu Pro Val Leu Asp Ser
385                 390                 395                 400

Asp Gly Ser Tyr Phe Met Tyr Ser Lys Leu Arg Val Glu Lys Lys Asn
                405                 410                 415

Trp Val Glu Arg Asn Ser Tyr Ser Cys Ser Val Val His Glu Gly Leu
                420                 425                 430

His Asn His His Thr Thr Lys Ser Phe Ser Arg
                435                 440

<210> SEQ ID NO 42
<211> LENGTH: 209
<212> TYPE: PRT
<213> ORGANISM: Artificial Sequence
<220> FEATURE:
<223> OTHER INFORMATION: Ibritumomab LC

<400> SEQUENCE: 42

Gln Ile Val Leu Ser Gln Ser Pro Ala Ile Leu Ser Ala Ser Pro Gly
  1               5                  10                  15

Glu Lys Val Thr Met Thr Cys Arg Ala Ser Ser Ser Val Ser Tyr Met
                 20                  25                  30

His Trp Tyr Gln Gln Lys Pro Gly Ser Ser Pro Lys Pro Trp Ile Tyr
             35                  40                  45

Ala Pro Ser Asn Leu Ala Ser Gly Val Pro Ala Arg Phe Ser Gly Ser
         50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Phe Asn Pro Pro Thr
                 85                  90                  95

Phe Gly Ala Gly Thr Lys Leu Glu Leu Lys Arg Ala Asp Ala Ala Pro
                100                 105                 110

Thr Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn

<210> SEQ ID NO 43
```

<211> LENGTH: 447
<212> TYPE: PRT
<213> ORGANISM: Artificial Sequence
<220> FEATURE:
<223> OTHER INFORMATION: Tositumomab HC

<400> SEQUENCE: 43

```
Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Arg Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Val Val Tyr Tyr Ser Asn Ser Tyr Trp Tyr Phe Asp Val Trp
            100                 105                 110

Gly Thr Gly Thr Thr Val Thr Val Ser Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Ala Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380
```

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
        420                 425                 430

His Asn His Tyr Thr Gln Lys Ser Leu Ser Leu Ser Pro Gly Lys
        435                 440                 445

<210> SEQ ID NO 44
<211> LENGTH: 210
<212> TYPE: PRT
<213> ORGANISM: Artificial Sequence
<220> FEATURE:
<223> OTHER INFORMATION: Tositumomab LC

<400> SEQUENCE: 44

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
        35                  40                  45

Ala Pro Ser Asn Leu Ala Ser Gly Val Pro Ala Arg Phe Ser Gly Ser
50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Phe Asn Pro Pro Thr
                85                  90                  95

Phe Gly Ala Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg
    210

<210> SEQ ID NO 45
<211> LENGTH: 451
<212> TYPE: PRT
<213> ORGANISM: Artificial Sequence
<220> FEATURE:
<223> OTHER INFORMATION: Volociximab M200 HC

<400> SEQUENCE: 45

Gln Val Gln Leu Lys Glu Ser Gly Pro Gly Leu Val Ala Pro Ser Gln
1               5                   10                  15

Ser Leu Ser Ile Thr Cys Thr Ile Ser Gly Phe Ser Leu Thr Asp Tyr

-continued

```
             20                  25                  30
Gly Val His Trp Val Arg Gln Pro Gly Lys Gly Leu Glu Trp Leu
             35                  40                  45
Val Val Ile Trp Ser Asp Gly Ser Ser Thr Tyr Asn Ser Ala Leu Lys
 50                  55                  60
Ser Arg Met Thr Ile Arg Lys Asp Asn Ser Lys Ser Gln Val Phe Leu
 65                  70                  75                  80
Ile Met Asn Ser Leu Gln Thr Asp Asp Ser Ala Met Tyr Tyr Cys Ala
                 85                  90                  95
Arg His Gly Thr Tyr Tyr Gly Met Thr Thr Thr Gly Asp Ala Leu Asp
                100                 105                 110
Tyr Trp Gly Gln Gly Thr Ser Val Thr Val Ser Ser Ala Ser Thr Lys
                115                 120                 125
Gly Pro Ser Val Phe Pro Leu Ala Pro Cys Ser Arg Ser Thr Ser Glu
            130                 135                 140
Ser Thr Ala Ala Leu Gly Cys Leu Val Lys Asp Tyr Phe Pro Glu Pro
145                 150                 155                 160
Val Thr Val Ser Trp Asn Ser Gly Ala Leu Thr Ser Gly Val His Thr
                165                 170                 175
Phe Pro Ala Val Leu Gln Ser Ser Gly Leu Tyr Ser Leu Ser Ser Val
                180                 185                 190
Val Thr Val Pro Ser Ser Ser Leu Gly Thr Lys Thr Tyr Thr Cys Asn
                195                 200                 205
Val Asp His Lys Pro Ser Asn Thr Lys Val Asp Lys Arg Val Glu Ser
            210                 215                 220
Lys Tyr Gly Pro Pro Cys Pro Ser Cys Pro Ala Pro Glu Phe Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser Gln
                260                 265                 270
Glu Asp Pro Glu Val Gln Phe Asn Trp Tyr Val Asp Gly Val Glu Val
            275                 280                 285
His Asn Ala Lys Thr Lys Pro Arg Glu Glu Gln Phe Asn Ser Thr Tyr
        290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Gly Leu Pro Ser Ser Ile
                325                 330                 335
Glu Lys Thr Ile Ser Lys Ala Lys Gly Gln Pro Arg Glu Pro Gln Val
                340                 345                 350
Tyr Thr Leu Pro Pro Ser Gln Glu Glu Met Thr Lys Asn Gln Val Ser
            355                 360                 365
Leu Thr Cys Leu Val Lys Gly Phe Tyr Pro Ser Asp Ile Ala Val Glu
        370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Arg Leu Thr Val
                405                 410                 415
Asp Lys Ser Arg Trp Gln Glu Gly Asn Val Phe Ser Cys Ser Val Met
                420                 425                 430
His Glu Ala Leu His Asn His Tyr Thr Gln Lys Ser Leu Ser Leu Ser
            435                 440                 445
```

-continued

```
Leu Gly Lys
    450

<210> SEQ ID NO 46
<211> LENGTH: 215
<212> TYPE: PRT
<213> ORGANISM: Artificial Sequence
<220> FEATURE:
<223> OTHER INFORMATION: Volociximab M200 LC

<400> SEQUENCE: 46

Gln Ile Val Leu Thr Gln Ser Pro Ala Ile Met Ser Ala Ser Leu Gly
1               5                   10                  15

Glu Arg Val Thr Met Thr Cys Thr Ala Ser Ser Ser Val Ser Ser Asn
            20                  25                  30

Tyr Leu His Trp Tyr Gln Gln Lys Pro Gly Ser Ala Pro Asn Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Tyr Leu Arg Ser Pro
                85                  90                  95

Pro Thr Phe Gly Gly Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 47
<211> LENGTH: 232
<212> TYPE: PRT
<213> ORGANISM: Artificial Sequence
<220> FEATURE:
<223> OTHER INFORMATION: Volociximab F200 (Fab of M200) HC

<400> SEQUENCE: 47

Gln Val Gln Leu Lys Glu Ser Gly Pro Gly Leu Val Ala Pro Ser Gln
1               5                   10                  15

Ser Leu Ser Ile Thr Cys Thr Ile Ser Gly Phe Ser Leu Thr Asp Tyr
            20                  25                  30

Gly Val His Trp Val Arg Gln Pro Pro Gly Lys Gly Leu Glu Trp Leu
        35                  40                  45

Val Val Ile Trp Ser Asp Gly Ser Ser Thr Tyr Asn Ser Ala Leu Lys
    50                  55                  60

Ser Arg Met Thr Ile Arg Lys Asp Asn Ser Lys Ser Gln Val Phe Leu
```

```
              65                  70                  75                  80
Ile Met Asn Ser Leu Gln Thr Asp Asp Ser Ala Met Tyr Tyr Cys Ala
                    85                  90                  95

Arg His Gly Thr Tyr Tyr Gly Met Thr Thr Gly Asp Ala Leu Asp
                100                 105                 110

Tyr Trp Gly Gln Gly Thr Ser Val Thr Val Ser Ser Ala Ser Thr Lys
                115                 120                 125

Gly Pro Ser Val Phe Pro Leu Ala Pro Cys Ser Arg Ser Thr Ser Glu
130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

Val Thr Val Pro Ser Ser Ser Leu Gly Thr Lys Thr Tyr Thr Cys Asn
                195                 200                 205

Val Asp His Lys Pro Ser Asn Thr Lys Val Asp Lys Arg Val Glu Ser
        210                 215                 220

Lys Tyr Gly Pro Pro Cys Pro Ser
225                 230
```

<210> SEQ ID NO 48
<211> LENGTH: 460
<212> TYPE: PRT
<213> ORGANISM: Artificial Sequence
<220> FEATURE:
<223> OTHER INFORMATION: Cixutumumab (IMC-A12) HC

<400> SEQUENCE: 48

```
Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Pro Leu Arg Phe Leu Glu Trp Ser Thr Gln Asp His Tyr
                100                 105                 110

Tyr Tyr Tyr Tyr Met Asp Val Trp Gly Lys Gly Thr Thr Val Thr Val
            115                 120                 125

Ser Ser Ala Ser Thr Lys Gly Pro Ser Val Phe Pro Leu Ala Pro Ser
130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
                180                 185                 190

Tyr Ser Leu Ser Ser Val Val Thr Val Pro Ser Ser Ser Leu Gly Thr
```

```
                195                 200                 205
Gln Thr Tyr Ile Cys Asn Val Asn His Lys Pro Ser Asn Thr Lys Val
210                 215                 220

Asp Lys Lys Val Glu Pro Lys Ser Cys Asp Lys Thr His Thr Cys Pro
225                 230                 235                 240

Pro Cys Pro Ala Pro Glu Leu Leu Gly Gly Pro Ser Val Phe Leu Phe
                245                 250                 255

Pro Pro Lys Pro Lys Asp Thr Leu Met Ile Ser Arg Thr Pro Glu Val
                260                 265                 270

Thr Cys Val Val Val Asp Val Ser His Glu Asp Pro Glu Val Lys Phe
            275                 280                 285

Asn Trp Tyr Val Asp Gly Val Glu Val His Asn Ala Lys Thr Lys Pro
            290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Ala Leu Pro Ala Pro Ile Glu Lys Thr Ile Ser Lys Ala
                340                 345                 350

Lys Gly Gln Pro Arg Glu Pro Gln Val Tyr Thr Leu Pro Pro Ser Arg
                355                 360                 365

Glu Glu Met Thr Lys Asn Gln Val Ser Leu Thr Cys Leu Val Lys Gly
            370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Lys Leu Thr Val Asp Lys Ser Arg Trp Gln Gln
                420                 425                 430

Gly Asn Val Phe Ser Cys Ser Val Met His Glu Ala Leu His Asn His
                435                 440                 445

Tyr Thr Gln Lys Ser Leu Ser Leu Ser Pro Gly Lys
            450                 455                 460

<210> SEQ ID NO 49
<211> LENGTH: 214
<212> TYPE: PRT
<213> ORGANISM: Artificial Sequence
<220> FEATURE:
<223> OTHER INFORMATION: Cixutumumab (IMC-A12) LC

<400> SEQUENCE: 49

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
                20                  25                  30

Thr Trp Tyr Gln Gln Lys Pro Gly Gln Ala Pro Ile Leu Val Ile Tyr
            35                  40                  45

Gly Glu Asn Lys Arg Pro Ser Gly Ile Pro Asp Arg Phe Ser Gly Ser
50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Lys Ser Arg Asp Gly Ser Gly Gln His
                85                  90                  95

Leu Val Phe Gly Gly Gly Thr Lys Leu Thr Val Leu Gly Gln Pro Lys
```

```
                100                 105                 110
Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
        130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Ala Glu Cys Ser
        210

<210> SEQ ID NO 50
<211> LENGTH: 621
<212> TYPE: PRT
<213> ORGANISM: Artificial Sequence
<220> FEATURE:
<223> OTHER INFORMATION: EGFR extracellular (ec) domain

<400> SEQUENCE: 50

Leu Glu Glu Lys Lys Val Cys Gln Gly Thr Ser Asn Lys Leu Thr Gln
  1               5                  10                  15

Leu Gly Thr Phe Glu Asp His Phe Leu Ser Leu Gln Arg Met Phe Asn
            20                  25                  30

Asn Cys Glu Val Val Leu Gly Asn Leu Glu Ile Thr Tyr Val Gln Arg
        35                  40                  45

Asn Tyr Asp Leu Ser Phe Leu Lys Thr Ile Gln Glu Val Ala Gly Tyr
    50                  55                  60

Val Leu Ile Ala Leu Asn Thr Val Glu Arg Ile Pro Leu Glu Asn Leu
65                  70                  75                  80

Gln Ile Ile Arg Gly Asn Met Tyr Tyr Glu Asn Ser Tyr Ala Leu Ala
                85                  90                  95

Val Leu Ser Asn Tyr Asp Ala Asn Lys Thr Gly Leu Lys Glu Leu Pro
            100                 105                 110

Met Arg Asn Leu Gln Glu Ile Leu His Gly Ala Val Arg Phe Ser Asn
        115                 120                 125

Asn Pro Ala Leu Cys Asn Val Glu Ser Ile Gln Trp Arg Asp Ile Val
    130                 135                 140

Ser Ser Asp Phe Leu Ser Asn Met Ser Met Asp Phe Gln Asn His Leu
145                 150                 155                 160

Gly Ser Cys Gln Lys Cys Asp Pro Ser Cys Pro Asn Gly Ser Cys Trp
                165                 170                 175

Gly Ala Gly Glu Glu Asn Cys Gln Lys Leu Thr Lys Ile Ile Cys Ala
            180                 185                 190

Gln Gln Cys Ser Gly Arg Cys Arg Gly Lys Ser Pro Ser Asp Cys Cys
        195                 200                 205

His Asn Gln Cys Ala Ala Gly Cys Thr Gly Pro Arg Glu Ser Asp Cys
    210                 215                 220

Leu Val Cys Arg Lys Phe Arg Asp Glu Ala Thr Cys Lys Asp Thr Cys
225                 230                 235                 240

Pro Pro Leu Met Leu Tyr Asn Pro Thr Thr Tyr Gln Met Asp Val Asn
```

```
                245                 250                 255
Pro Glu Gly Lys Tyr Ser Phe Gly Ala Thr Cys Val Lys Lys Cys Pro
            260                 265                 270

Arg Asn Tyr Val Val Thr Asp His Gly Ser Cys Val Arg Ala Cys Gly
            275                 280                 285

Ala Asp Ser Tyr Glu Met Glu Glu Asp Gly Val Arg Lys Cys Lys Lys
        290                 295                 300

Cys Glu Gly Pro Cys Arg Lys Val Cys Asn Gly Ile Gly Ile Gly Glu
305                 310                 315                 320

Phe Lys Asp Ser Leu Ser Ile Asn Ala Thr Asn Ile Lys His Phe Lys
                325                 330                 335

Asn Cys Thr Ser Ile Ser Gly Asp Leu His Ile Leu Pro Val Ala Phe
            340                 345                 350

Arg Gly Asp Ser Phe Thr His Thr Pro Pro Leu Asp Pro Gln Glu Leu
            355                 360                 365

Asp Ile Leu Lys Thr Val Lys Glu Ile Thr Gly Phe Leu Leu Ile Gln
370                 375                 380

Ala Trp Pro Glu Asn Arg Thr Asp Leu His Ala Phe Glu Asn Leu Glu
385                 390                 395                 400

Ile Ile Arg Gly Arg Thr Lys Gln His Gly Gln Phe Ser Leu Ala Val
                405                 410                 415

Val Ser Leu Asn Ile Thr Ser Leu Gly Leu Arg Ser Leu Lys Glu Ile
            420                 425                 430

Ser Asp Gly Asp Val Ile Ile Ser Gly Asn Lys Asn Leu Cys Tyr Ala
            435                 440                 445

Asn Thr Ile Asn Trp Lys Lys Leu Phe Gly Thr Ser Gly Gln Lys Thr
        450                 455                 460

Lys Ile Ile Ser Asn Arg Gly Glu Asn Ser Cys Lys Ala Thr Gly Gln
465                 470                 475                 480

Val Cys His Ala Leu Cys Ser Pro Glu Gly Cys Trp Gly Pro Glu Pro
                485                 490                 495

Arg Asp Cys Val Ser Cys Arg Asn Val Ser Arg Gly Arg Glu Cys Val
            500                 505                 510

Asp Lys Cys Asn Leu Leu Glu Gly Glu Pro Arg Glu Phe Val Glu Asn
        515                 520                 525

Ser Glu Cys Ile Gln Cys His Pro Glu Cys Leu Pro Gln Ala Met Asn
    530                 535                 540

Ile Thr Cys Thr Gly Arg Gly Pro Asp Asn Cys Ile Gln Cys Ala His
545                 550                 555                 560

Tyr Ile Asp Gly Pro His Cys Val Lys Thr Cys Pro Ala Gly Val Met
                565                 570                 575

Gly Glu Asn Asn Thr Leu Val Trp Lys Tyr Ala Asp Ala Gly His Val
            580                 585                 590

Cys His Leu Cys His Pro Asn Cys Thr Tyr Gly Cys Thr Gly Pro Gly
            595                 600                 605

Leu Glu Gly Cys Pro Thr Asn Gly Pro Lys Ile Pro Ser
        610                 615                 620

<210> SEQ ID NO 51
<211> LENGTH: 630
<212> TYPE: PRT
<213> ORGANISM: Artificial Sequence
<220> FEATURE:
<223> OTHER INFORMATION: HER2/Neu ec domain
```

```
<400> SEQUENCE: 51

Thr Gln Val Cys Thr Gly Thr Asp Met Lys Leu Arg Leu Pro Ala Ser
  1               5                  10                  15

Pro Glu Thr His Leu Asp Met Leu Arg His Leu Tyr Gln Gly Cys Gln
             20                  25                  30

Val Val Gln Gly Asn Leu Glu Leu Thr Tyr Leu Pro Thr Asn Ala Ser
         35                  40                  45

Leu Ser Phe Leu Gln Asp Ile Gln Glu Val Gln Gly Tyr Val Leu Ile
     50                  55                  60

Ala His Asn Gln Val Arg Gln Val Pro Leu Gln Arg Leu Arg Ile Val
 65                  70                  75                  80

Arg Gly Thr Gln Leu Phe Glu Asp Asn Tyr Ala Leu Ala Val Leu Asp
                 85                  90                  95

Asn Gly Asp Pro Leu Asn Asn Thr Thr Pro Val Thr Gly Ala Ser Pro
             100                 105                 110

Gly Gly Leu Arg Glu Leu Gln Leu Arg Ser Leu Thr Glu Ile Leu Lys
             115                 120                 125

Gly Gly Val Leu Ile Gln Arg Asn Pro Gln Leu Cys Tyr Gln Asp Thr
         130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Met
                 165                 170                 175

Cys Lys Gly Ser Arg Cys Trp Gly Glu Ser Ser Glu Asp Cys Gln Ser
             180                 185                 190

Leu Thr Arg Thr Val Cys Ala Gly Gly Cys Ala Arg Cys Lys Gly Pro
         195                 200                 205

Leu Pro Thr Asp Cys Cys His Glu Gln Cys Ala Ala Gly Cys Thr Gly
         210                 215                 220

Pro Lys His Ser Asp Cys Leu Ala Cys Leu His Phe Asn His Ser Gly
225                 230                 235                 240

Ile Cys Glu Leu His Cys Pro Ala Leu Val Thr Tyr Asn Thr Asp Thr
                 245                 250                 255

Phe Glu Ser Met Pro Asn Pro Glu Gly Arg Tyr Thr Phe Gly Ala Ser
             260                 265                 270

Cys Val Thr Ala Cys Pro Tyr Asn Tyr Leu Ser Thr Asp Val Gly Ser
         275                 280                 285

Cys Thr Leu Val Cys Pro Leu His Asn Gln Glu Val Thr Ala Glu Asp
         290                 295                 300

Gly Thr Gln Arg Cys Glu Lys Cys Ser Lys Pro Cys Ala Arg Val Cys
305                 310                 315                 320

Tyr Gly Leu Gly Met Glu His Leu Arg Glu Val Arg Ala Val Thr Ser
                 325                 330                 335

Ala Asn Ile Gln Glu Phe Ala Gly Cys Lys Lys Ile Phe Gly Ser Leu
             340                 345                 350

Ala Phe Leu Pro Glu Ser Phe Asp Gly Asp Pro Ala Ser Asn Thr Ala
         355                 360                 365

Pro Leu Gln Pro Glu Gln Leu Gln Val Phe Glu Thr Leu Glu Glu Ile
         370                 375                 380

Thr Gly Tyr Leu Tyr Ile Ser Ala Trp Pro Asp Ser Leu Pro Asp Leu
385                 390                 395                 400

Ser Val Phe Gln Asn Leu Gln Val Ile Arg Gly Arg Ile Leu His Asn
                 405                 410                 415
```

```
Gly Ala Tyr Ser Leu Thr Leu Gln Gly Leu Gly Ile Ser Trp Leu Gly
            420                 425                 430

Leu Arg Ser Leu Arg Glu Leu Gly Ser Gly Leu Ala Leu Ile His His
        435                 440                 445

Asn Thr His Leu Cys Phe Val His Thr Val Pro Trp Asp Gln Leu Phe
    450                 455                 460

Arg Asn Pro His Gln Ala Leu Leu His Thr Ala Asn Arg Pro Glu Asp
465                 470                 475                 480

Glu Cys Val Gly Glu Gly Leu Ala Cys His Gln Leu Cys Ala Arg Gly
                485                 490                 495

His Cys Trp Gly Pro Gly Pro Thr Gln Cys Val Asn Cys Ser Gln Phe
            500                 505                 510

Leu Arg Gly Gln Glu Cys Val Glu Glu Cys Arg Val Leu Gln Gly Leu
        515                 520                 525

Pro Arg Glu Tyr Val Asn Ala Arg His Cys Leu Pro Cys His Pro Glu
    530                 535                 540

Cys Gln Pro Gln Asn Gly Ser Val Thr Cys Phe Gly Pro Glu Ala Asp
545                 550                 555                 560

Gln Cys Val Ala Cys Ala His Tyr Lys Asp Pro Pro Phe Cys Val Ala
                565                 570                 575

Arg Cys Pro Ser Gly Val Lys Pro Asp Leu Ser Tyr Met Pro Ile Trp
            580                 585                 590

Lys Phe Pro Asp Glu Glu Gly Ala Cys Gln Pro Cys Pro Ile Asn Cys
        595                 600                 605

Thr His Ser Cys Val Asp Leu Asp Asp Lys Gly Cys Pro Ala Glu Gln
    610                 615                 620

Arg Ala Ser Pro Leu Thr
625                 630

<210> SEQ ID NO 52
<211> LENGTH: 44
<212> TYPE: PRT
<213> ORGANISM: Artificial Sequence
<220> FEATURE:
<223> OTHER INFORMATION: CD20 large ec loop

<400> SEQUENCE: 52

Ile Ser His Phe Leu Lys Met Glu Ser Leu Asn Phe Ile Arg Ala His
1               5                   10                  15

Thr Pro Tyr Ile Asn Ile Tyr Asn Cys Glu Pro Ala Asn Pro Ser Glu
            20                  25                  30

Lys Asn Ser Pro Ser Thr Gln Tyr Cys Tyr Ser Ile
        35                  40

<210> SEQ ID NO 53
<211> LENGTH: 206
<212> TYPE: PRT
<213> ORGANISM: Artificial Sequence
<220> FEATURE:
<223> OTHER INFORMATION: VEGF-A

<400> SEQUENCE: 53

Ala Pro Met Ala Glu Gly Gly Gln Asn His His Glu Val Val Lys
1               5                   10                  15

Phe Met Asp Val Tyr Gln Arg Ser Tyr Cys His Pro Ile Glu Thr Leu
            20                  25                  30

Val Asp Ile Phe Gln Glu Tyr Pro Asp Glu Ile Glu Tyr Ile Phe Lys
```

```
            35                  40                  45
Pro Ser Cys Val Pro Leu Met Arg Cys Gly Gly Cys Cys Asn Asp Glu
 50                  55                  60

Gly Leu Glu Cys Val Pro Thr Glu Glu Ser Asn Ile Thr Met Gln Ile
 65                  70                  75                  80

Met Arg Ile Lys Pro His Gln Gly Gln His Ile Gly Glu Met Ser Phe
                 85                  90                  95

Leu Gln His Asn Lys Cys Glu Cys Arg Pro Lys Lys Asp Arg Ala Arg
                100                 105                 110

Gln Glu Lys Lys Ser Val Arg Gly Lys Gly Lys Gly Gln Lys Arg Lys
                115                 120                 125

Arg Lys Lys Ser Arg Tyr Lys Ser Trp Ser Val Tyr Val Gly Ala Arg
            130                 135                 140

Cys Cys Leu Met Pro Trp Ser Leu Pro Gly Pro His Pro Cys Gly Pro
145                 150                 155                 160

Cys Ser Glu Arg Arg Lys His Leu Phe Val Gln Asp Pro Gln Thr Cys
                165                 170                 175

Lys Cys Ser Cys Lys Asn Thr Asp Ser Arg Cys Lys Ala Arg Gln Leu
            180                 185                 190

Glu Leu Asn Glu Arg Thr Cys Arg Cys Asp Lys Pro Arg Arg
            195                 200                 205

<210> SEQ ID NO 54
<211> LENGTH: 12
<212> TYPE: PRT
<213> ORGANISM: Artificial Sequence
<220> FEATURE:
<223> OTHER INFORMATION: CD52

<400> SEQUENCE: 54

Gly Gln Asn Asp Thr Ser Gln Thr Ser Ser Pro Ser
 1               5                  10

<210> SEQ ID NO 55
<211> LENGTH: 242
<212> TYPE: PRT
<213> ORGANISM: Artificial Sequence
<220> FEATURE:
<223> OTHER INFORMATION: EpCAM ec domain

<400> SEQUENCE: 55

Gln Glu Glu Cys Val Cys Glu Asn Tyr Lys Leu Ala Val Asn Cys Phe
 1               5                  10                  15

Val Asn Asn Asn Arg Gln Cys Gln Cys Thr Ser Val Gly Ala Gln Asn
                 20                  25                  30

Thr Val Ile Cys Ser Lys Leu Ala Ala Lys Cys Leu Val Met Lys Ala
             35                  40                  45

Glu Met Asn Gly Ser Lys Leu Gly Arg Arg Ala Lys Pro Glu Gly Ala
 50                  55                  60

Leu Gln Asn Asn Asp Gly Leu Tyr Asp Pro Asp Cys Asp Glu Ser Gly
 65                  70                  75                  80

Leu Phe Lys Ala Lys Gln Cys Asn Gly Thr Ser Met Cys Trp Cys Val
                 85                  90                  95

Asn Thr Ala Gly Val Arg Arg Thr Asp Lys Asp Thr Glu Ile Thr Cys
                100                 105                 110

Ser Glu Arg Val Arg Thr Tyr Trp Ile Ile Ile Glu Leu Lys His Lys
            115                 120                 125
```

```
Ala Arg Glu Lys Pro Tyr Asp Ser Lys Ser Leu Arg Thr Ala Leu Gln
    130                 135                 140

Lys Glu Ile Thr Thr Arg Tyr Gln Leu Asp Pro Lys Phe Ile Thr Ser
145                 150                 155                 160

Ile Leu Tyr Glu Asn Asn Val Ile Thr Ile Asp Leu Val Gln Asn Ser
                165                 170                 175

Ser Gln Lys Thr Gln Asn Asp Val Asp Ile Ala Asp Val Ala Tyr Tyr
            180                 185                 190

Phe Glu Lys Asp Val Lys Gly Glu Ser Leu Phe His Ser Lys Lys Met
            195                 200                 205

Asp Leu Thr Val Asn Gly Glu Gln Leu Asp Leu Asp Pro Gly Gln Thr
    210                 215                 220

Leu Ile Tyr Tyr Val Asp Glu Lys Ala Pro Glu Phe Ser Met Gln Gly
225                 230                 235                 240

Leu Lys
```

<210> SEQ ID NO 56
<211> LENGTH: 94
<212> TYPE: PRT
<213> ORGANISM: Artificial Sequence
<220> FEATURE:
<223> OTHER INFORMATION: CD3 gamma chain ec domain

<400> SEQUENCE: 56

```
Gln Ser Ile Lys Gly Asn His Leu Val Lys Val Tyr Asp Tyr Gln Glu
1               5                   10                  15

Asp Gly Ser Val Leu Leu Thr Cys Asp Ala Glu Ala Lys Asn Ile Thr
            20                  25                  30

Trp Phe Lys Asp Gly Lys Met Ile Gly Phe Leu Thr Glu Asp Lys Lys
        35                  40                  45

Lys Trp Asn Leu Gly Ser Asn Ala Lys Asp Pro Arg Gly Met Tyr Gln
    50                  55                  60

Cys Lys Gly Ser Gln Asn Lys Ser Lys Pro Leu Gln Val Tyr Tyr Arg
65                  70                  75                  80

Met Cys Gln Asn Cys Ile Glu Leu Asn Ala Ala Thr Ile Ser
                85                  90
```

<210> SEQ ID NO 57
<211> LENGTH: 84
<212> TYPE: PRT
<213> ORGANISM: Artificial Sequence
<220> FEATURE:
<223> OTHER INFORMATION: CD3 delta chain ec domain

<400> SEQUENCE: 57

```
Phe Lys Ile Pro Ile Glu Glu Leu Glu Asp Arg Val Phe Val Asn Cys
1               5                   10                  15

Asn Thr Ser Ile Thr Trp Val Glu Gly Thr Val Gly Thr Leu Leu Ser
            20                  25                  30

Asp Ile Thr Arg Leu Asp Leu Gly Lys Arg Ile Leu Asp Pro Arg Gly
        35                  40                  45

Ile Tyr Arg Cys Asn Gly Thr Asp Ile Tyr Lys Asp Lys Glu Ser Thr
    50                  55                  60

Val Gln Val His Tyr Arg Met Cys Gln Ser Cys Val Glu Leu Asp Pro
65                  70                  75                  80

Ala Thr Val Ala
```

-continued

```
<210> SEQ ID NO 58
<211> LENGTH: 104
<212> TYPE: PRT
<213> ORGANISM: Artificial Sequence
<220> FEATURE:
<223> OTHER INFORMATION: CD3 epsilon chain ec domain

<400> SEQUENCE: 58

Asp Gly Asn Glu Glu Met Gly Gly Ile Thr Gln Thr Pro Tyr Lys Val
 1               5                  10                  15

Ser Ile Ser Gly Thr Thr Val Ile Leu Thr Cys Pro Gln Tyr Pro Gly
            20                  25                  30

Ser Glu Ile Leu Trp Gln His Asn Asp Lys Asn Ile Gly Gly Asp Glu
        35                  40                  45

Asp Asp Lys Asn Ile Gly Ser Asp Glu Asp His Leu Ser Leu Lys Glu
    50                  55                  60

Phe Ser Glu Leu Glu Gln Ser Gly Tyr Tyr Val Cys Tyr Pro Arg Gly
65                  70                  75                  80

Ser Lys Pro Glu Asp Ala Asn Phe Tyr Leu Tyr Leu Arg Ala Arg Val
                85                  90                  95

Cys Glu Asn Cys Met Glu Met Asp
                100

<210> SEQ ID NO 59
<211> LENGTH: 242
<212> TYPE: PRT
<213> ORGANISM: Artificial Sequence
<220> FEATURE:
<223> OTHER INFORMATION: CD33 ec domain

<400> SEQUENCE: 59

Asp Pro Asn Phe Trp Leu Gln Val Gln Glu Ser Val Thr Val Gln Glu
 1               5                  10                  15

Gly Leu Cys Val Leu Val Pro Cys Thr Phe Phe His Pro Ile Pro Tyr
            20                  25                  30

Tyr Asp Lys Asn Ser Pro Val His Gly Tyr Trp Phe Arg Glu Gly Ala
        35                  40                  45

Ile Ile Ser Arg Asp Ser Pro Val Ala Thr Asn Lys Leu Asp Gln Glu
    50                  55                  60

Val Gln Glu Glu Thr Gln Gly Arg Phe Arg Leu Leu Gly Asp Pro Ser
65                  70                  75                  80

Arg Asn Asn Cys Ser Leu Ser Ile Val Asp Ala Arg Arg Arg Asp Asn
                85                  90                  95

Gly Ser Tyr Phe Phe Arg Met Glu Arg Gly Ser Thr Lys Tyr Ser Tyr
                100                 105                 110

Lys Ser Pro Gln Leu Ser Val His Val Thr Asp Leu Thr His Arg Pro
            115                 120                 125

Lys Ile Leu Ile Pro Gly Thr Leu Glu Pro Gly His Ser Lys Asn Leu
        130                 135                 140

Thr Cys Ser Val Ser Trp Ala Cys Glu Gln Gly Thr Pro Pro Ile Phe
145                 150                 155                 160

Ser Trp Leu Ser Ala Ala Pro Thr Ser Leu Gly Pro Arg Thr Thr His
                165                 170                 175

Ser Ser Val Leu Ile Ile Thr Pro Arg Pro Gln Asp His Gly Thr Asn
                180                 185                 190

Leu Thr Cys Gln Val Lys Phe Ala Gly Ala Gly Val Thr Thr Glu Arg
            195                 200                 205
```

```
Thr Ile Gln Leu Asn Val Thr Tyr Val Pro Gln Asn Pro Thr Thr Gly
    210                 215                 220

Ile Phe Pro Gly Asp Gly Ser Gly Lys Gln Glu Thr Arg Ala Gly Val
225                 230                 235                 240

Val His

<210> SEQ ID NO 60
<211> LENGTH: 208
<212> TYPE: PRT
<213> ORGANISM: Artificial Sequence
<220> FEATURE:
<223> OTHER INFORMATION: CD80 ec domain

<400> SEQUENCE: 60

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
                20                  25                  30

Gln Lys Glu Lys Lys Met Val Leu Thr Met Met Ser Gly Asp Met Asn
            35                  40                  45

Ile Trp Pro Glu Tyr Lys Asn Arg Thr Ile Phe Asp Ile Thr Asn Asn
50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205

<210> SEQ ID NO 61
<211> LENGTH: 224
<212> TYPE: PRT
<213> ORGANISM: Artificial Sequence
<220> FEATURE:
<223> OTHER INFORMATION: CD86 ec domain

<400> SEQUENCE: 61

Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
                20                  25                  30

Phe Trp Gln Asp Gln Glu Asn Leu Val Leu Asn Glu Val Tyr Leu Gly
            35                  40                  45

Lys Glu Lys Phe Asp Ser Val His Ser Lys Tyr Met Gly Arg Thr Ser
50                  55                  60
```

Phe Asp Ser Asp Ser Trp Thr Leu Arg Leu His Asn Leu Gln Ile Lys
65                  70                  75                  80

Asp Lys Gly Leu Tyr Gln Cys Ile Ile His His Lys Lys Pro Thr Gly
                85                  90                  95

Met Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Ile Met Gln Lys Ser Gln Asp Asn Val Thr Glu Leu Tyr Asp Val
                165                 170                 175

Ser Ile Ser Leu Ser Val Ser Phe Pro Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Asp His Ile Pro
    210                 215                 220

<210> SEQ ID NO 62
<211> LENGTH: 126
<212> TYPE: PRT
<213> ORGANISM: Artificial Sequence
<220> FEATURE:
<223> OTHER INFORMATION: CTLA-4 ec domain

<400> SEQUENCE: 62

Lys Ala Met His Val Ala Gln Pro Ala Val Leu Ala Ser Ser Arg
1               5                   10                  15

Gly Ile Ala Ser Phe Val Cys Glu Tyr Ala Ser Pro Gly Lys Ala Thr
                20                  25                  30

Glu Val Arg Val Thr Val Leu Arg Gln Ala Asp Ser Gln Val Thr Glu
            35                  40                  45

Val Cys Ala Ala Thr Tyr Met Met Gly Asn Glu Leu Thr Phe Leu Asp
    50                  55                  60

Asp Ser Ile Cys Thr Gly Thr Ser Ser Gly Asn Gln Val Asn Leu Thr
65                  70                  75                  80

Ile Gln Gly Leu Arg Ala Met Asp Thr Gly Leu Tyr Ile Cys Lys Val
                85                  90                  95

Glu Leu Met Tyr Pro Pro Pro Tyr Tyr Leu Gly Ile Gly Asn Gly Thr
            100                 105                 110

Gln Ile Tyr Val Ile Asp Pro Glu Pro Cys Pro Asp Ser Asp
        115                 120                 125

<210> SEQ ID NO 63
<211> LENGTH: 203
<212> TYPE: PRT
<213> ORGANISM: Artificial Sequence
<220> FEATURE:
<223> OTHER INFORMATION: PLGF

<400> SEQUENCE: 63

Leu Pro Ala Val Pro Pro Gln Gln Trp Ala Leu Ser Ala Gly Asn Gly
1               5                   10                  15

Ser Ser Glu Val Glu Val Val Pro Phe Gln Glu Val Trp Gly Arg Ser
                20                  25                  30

-continued

Tyr Cys Arg Ala Leu Glu Arg Leu Val Asp Val Val Ser Glu Tyr Pro
            35                  40                  45

Ser Glu Val Glu His Met Phe Ser Pro Ser Cys Val Ser Leu Leu Arg
 50                  55                  60

Cys Thr Gly Cys Cys Gly Asp Glu Asn Leu His Cys Val Pro Val Glu
 65                  70                  75                  80

Thr Ala Asn Val Thr Met Gln Leu Leu Lys Ile Arg Ser Gly Asp Arg
                85                  90                  95

Pro Ser Tyr Val Glu Leu Thr Phe Ser Gln His Val Arg Cys Glu Cys
            100                 105                 110

Arg His Ser Pro Gly Arg Gln Ser Pro Asp Met Pro Gly Asp Phe Arg
            115                 120                 125

Ala Asp Ala Pro Ser Phe Leu Pro Pro Arg Arg Ser Leu Pro Met Leu
130                 135                 140

Phe Arg Met Glu Trp Gly Cys Ala Leu Thr Gly Ser Gln Ser Ala Val
145                 150                 155                 160

Trp Pro Ser Ser Pro Val Pro Glu Glu Ile Pro Arg Met His Pro Gly
                165                 170                 175

Arg Asn Gly Lys Lys Gln Gln Arg Lys Pro Leu Arg Glu Lys Met Lys
            180                 185                 190

Pro Glu Arg Cys Gly Asp Ala Val Pro Arg Arg
            195                 200

<210> SEQ ID NO 64
<211> LENGTH: 962
<212> TYPE: PRT
<213> ORGANISM: Artificial Sequence
<220> FEATURE:
<223> OTHER INFORMATION: alpha 1 integrin (ec domain)

<400> SEQUENCE: 64

Phe Asn Leu Asp Val Asp Ser Pro Ala Glu Tyr Ser Gly Pro Glu Gly
 1               5                  10                  15

Ser Tyr Phe Gly Phe Ala Val Asp Phe Phe Val Pro Ser Ala Ser Ser
            20                  25                  30

Arg Met Phe Leu Leu Val Gly Ala Pro Lys Ala Asn Thr Thr Gln Pro
            35                  40                  45

Gly Ile Val Glu Gly Gly Gln Val Leu Lys Cys Asp Trp Ser Ser Thr
 50                  55                  60

Arg Arg Cys Gln Pro Ile Glu Phe Asp Ala Thr Gly Asn Arg Asp Tyr
 65                  70                  75                  80

Ala Lys Asp Asp Pro Leu Glu Phe Lys Ser His Gln Trp Phe Gly Ala
                85                  90                  95

Ser Val Arg Ser Lys Gln Asp Lys Ile Leu Ala Cys Ala Pro Leu Tyr
            100                 105                 110

His Trp Arg Thr Glu Met Lys Gln Glu Arg Glu Pro Val Gly Thr Cys
            115                 120                 125

Phe Leu Gln Asp Gly Thr Lys Thr Val Glu Tyr Ala Pro Cys Arg Ser
130                 135                 140

Gln Asp Ile Asp Ala Asp Gly Gln Gly Phe Cys Gln Gly Gly Phe Ser
145                 150                 155                 160

Ile Asp Phe Thr Lys Ala Asp Arg Val Leu Leu Gly Gly Pro Gly Ser
                165                 170                 175

Phe Tyr Trp Gln Gly Gln Leu Ile Ser Asp Gln Val Ala Glu Ile Val
            180                 185                 190

```
Ser Lys Tyr Asp Pro Asn Val Tyr Ser Ile Lys Tyr Asn Asn Gln Leu
        195                 200                 205

Ala Thr Arg Thr Ala Gln Ala Ile Phe Asp Asp Ser Tyr Leu Gly Tyr
        210                 215                 220

Ser Val Ala Val Gly Asp Phe Asn Gly Asp Gly Ile Asp Asp Phe Val
225                 230                 235                 240

Ser Gly Val Pro Arg Ala Ala Arg Thr Leu Gly Met Val Tyr Ile Tyr
                245                 250                 255

Asp Gly Lys Asn Met Ser Ser Leu Tyr Asn Phe Thr Gly Glu Gln Met
                260                 265                 270

Ala Ala Tyr Phe Gly Phe Ser Val Ala Ala Thr Asp Ile Asn Gly Asp
                275                 280                 285

Asp Tyr Ala Asp Val Phe Ile Gly Ala Pro Leu Phe Met Asp Arg Gly
        290                 295                 300

Ser Asp Gly Lys Leu Gln Glu Val Gly Gln Val Ser Val Ser Leu Gln
305                 310                 315                 320

Arg Ala Ser Gly Asp Phe Gln Thr Thr Lys Leu Asn Gly Phe Glu Val
                325                 330                 335

Phe Ala Arg Phe Gly Ser Ala Ile Ala Pro Leu Gly Asp Leu Asp Gln
                340                 345                 350

Asp Gly Phe Asn Asp Ile Ala Ile Ala Ala Pro Tyr Gly Gly Glu Asp
                355                 360                 365

Lys Lys Gly Ile Val Tyr Ile Phe Asn Gly Arg Ser Thr Gly Leu Asn
        370                 375                 380

Ala Val Pro Ser Gln Ile Leu Glu Gly Gln Trp Ala Ala Arg Ser Met
385                 390                 395                 400

Pro Pro Ser Phe Gly Tyr Ser Met Lys Gly Ala Thr Asp Ile Asp Lys
                405                 410                 415

Asn Gly Tyr Pro Asp Leu Ile Val Gly Ala Phe Gly Val Asp Arg Ala
                420                 425                 430

Ile Leu Tyr Arg Ala Arg Pro Val Ile Thr Val Asn Ala Gly Leu Glu
        435                 440                 445

Val Tyr Pro Ser Ile Leu Asn Gln Asp Asn Lys Thr Cys Ser Leu Pro
        450                 455                 460

Gly Thr Ala Leu Lys Val Ser Cys Phe Asn Val Arg Phe Cys Leu Lys
465                 470                 475                 480

Ala Asp Gly Lys Gly Val Leu Pro Arg Lys Leu Asn Phe Gln Val Glu
                485                 490                 495

Leu Leu Leu Asp Lys Leu Lys Gln Lys Gly Ala Ile Arg Arg Ala Leu
                500                 505                 510

Phe Leu Tyr Ser Arg Ser Pro Ser His Ser Lys Asn Met Thr Ile Ser
        515                 520                 525

Arg Gly Gly Leu Met Gln Cys Glu Glu Leu Ile Ala Tyr Leu Arg Asp
        530                 535                 540

Glu Ser Glu Phe Arg Asp Lys Leu Thr Pro Ile Thr Ile Phe Met Glu
545                 550                 555                 560

Tyr Arg Leu Asp Tyr Arg Thr Ala Ala Asp Thr Thr Gly Leu Gln Pro
                565                 570                 575

Ile Leu Asn Gln Phe Thr Pro Ala Asn Ile Ser Arg Gln Ala His Ile
        580                 585                 590

Leu Leu Asp Cys Gly Glu Asp Asn Val Cys Lys Pro Lys Leu Glu Val
        595                 600                 605
```

Ser Val Asp Ser Asp Gln Lys Lys Ile Tyr Ile Gly Asp Asp Asn Pro
610                 615                 620

Leu Thr Leu Ile Val Lys Ala Gln Asn Gln Gly Glu Gly Ala Tyr Glu
625                 630                 635                 640

Ala Glu Leu Ile Val Ser Ile Pro Leu Gln Ala Asp Phe Ile Gly Val
                645                 650                 655

Val Arg Asn Asn Glu Ala Leu Ala Arg Leu Ser Cys Ala Phe Lys Thr
        660                 665                 670

Glu Asn Gln Thr Arg Gln Val Val Cys Asp Leu Gly Asn Pro Met Lys
            675                 680                 685

Ala Gly Thr Gln Leu Leu Ala Gly Leu Arg Phe Ser Val His Gln Gln
690                 695                 700

Ser Glu Met Asp Thr Ser Val Lys Phe Asp Leu Gln Ile Gln Ser Ser
705                 710                 715                 720

Asn Leu Phe Asp Lys Val Ser Pro Val Val Ser His Lys Val Asp Leu
                725                 730                 735

Ala Val Leu Ala Ala Val Glu Ile Arg Gly Val Ser Ser Pro Asp His
        740                 745                 750

Val Phe Leu Pro Ile Pro Asn Trp Glu His Lys Glu Asn Pro Glu Thr
    755                 760                 765

Glu Glu Asp Val Gly Pro Val Val Gln His Ile Tyr Glu Leu Arg Asn
770                 775                 780

Asn Gly Pro Ser Ser Phe Ser Lys Ala Met Leu His Leu Gln Trp Pro
785                 790                 795                 800

Tyr Lys Tyr Asn Asn Asn Thr Leu Leu Tyr Ile Leu His Tyr Asp Ile
                805                 810                 815

Asp Gly Pro Met Asn Cys Thr Ser Asp Met Glu Ile Asn Pro Leu Arg
        820                 825                 830

Ile Lys Ile Ser Ser Leu Gln Thr Thr Glu Lys Asn Asp Thr Val Ala
            835                 840                 845

Gly Gln Gly Glu Arg Asp His Leu Ile Thr Lys Arg Asp Leu Ala Leu
850                 855                 860

Ser Glu Gly Asp Ile His Thr Leu Gly Cys Gly Val Ala Gln Cys Leu
865                 870                 875                 880

Lys Ile Val Cys Gln Val Gly Arg Leu Asp Arg Gly Lys Ser Ala Ile
                885                 890                 895

Leu Tyr Val Lys Ser Leu Leu Trp Thr Glu Thr Phe Met Asn Lys Glu
        900                 905                 910

Asn Gln Asn His Ser Tyr Ser Leu Lys Ser Ser Ala Ser Phe Asn Val
            915                 920                 925

Ile Glu Phe Pro Tyr Lys Asn Leu Pro Ile Glu Asp Ile Thr Asn Ser
930                 935                 940

Thr Leu Val Thr Thr Asn Val Thr Trp Gly Ile Gln Pro Ala Pro Met
945                 950                 955                 960

Pro Val

<210> SEQ ID NO 65
<211> LENGTH: 708
<212> TYPE: PRT
<213> ORGANISM: Artificial Sequence
<220> FEATURE:
<223> OTHER INFORMATION: beta 5 integrin (ec domain)

<400> SEQUENCE: 65

Gln Thr Asp Glu Asn Arg Cys Leu Lys Ala Asn Ala Lys Ser Cys Gly

```
           1               5              10              15
         Glu Cys Ile Gln Ala Gly Pro Asn Cys Gly Trp Cys Thr Asn Ser Thr
                          20                  25                  30

Phe Leu Gln Glu Gly Met Pro Thr Ser Ala Arg Cys Asp Asp Leu Glu
                          35                  40                  45

Ala Leu Lys Lys Lys Gly Cys Pro Pro Asp Asp Ile Glu Asn Pro Arg
                          50                  55                  60

Gly Ser Lys Asp Ile Lys Lys Asn Lys Val Thr Asn Arg Ser Lys
         65                  70                  75                  80

Gly Thr Ala Glu Lys Leu Lys Pro Glu Asp Ile Thr Gln Ile Gln Pro
                              85                  90                  95

Gln Gln Leu Val Leu Arg Leu Arg Ser Gly Glu Pro Gln Thr Phe Thr
                         100                 105                 110

Leu Lys Phe Lys Arg Ala Glu Asp Tyr Pro Ile Asp Leu Tyr Tyr Leu
                         115                 120                 125

Met Asp Leu Ser Tyr Ser Met Lys Asp Asp Leu Glu Asn Val Lys Ser
                         130                 135                 140

Leu Gly Thr Asp Leu Met Asn Glu Met Arg Arg Ile Thr Ser Asp Phe
         145                 150                 155                 160

Arg Ile Gly Phe Gly Ser Phe Val Glu Lys Thr Val Met Pro Tyr Ile
                         165                 170                 175

Ser Thr Thr Pro Ala Lys Leu Arg Asn Pro Cys Thr Ser Glu Gln Asn
                         180                 185                 190

Cys Thr Ser Pro Phe Ser Tyr Lys Asn Val Leu Ser Leu Thr Asn Lys
                         195                 200                 205

Gly Glu Val Phe Asn Glu Leu Val Gly Lys Gln Arg Ile Ser Gly Asn
                         210                 215                 220

Leu Asp Ser Pro Glu Gly Gly Phe Asp Ala Ile Met Gln Val Ala Val
         225                 230                 235                 240

Cys Gly Ser Leu Ile Gly Trp Arg Asn Val Thr Arg Leu Leu Val Phe
                         245                 250                 255

Ser Thr Asp Ala Gly Phe His Phe Ala Gly Asp Gly Lys Leu Gly Gly
                         260                 265                 270

Ile Val Leu Pro Asn Asp Gly Gln Cys His Leu Glu Asn Asn Met Tyr
                         275                 280                 285

Thr Met Ser His Tyr Tyr Asp Tyr Pro Ser Ile Ala His Leu Val Gln
                         290                 295                 300

Lys Leu Ser Glu Asn Asn Ile Gln Thr Ile Phe Ala Val Thr Glu Glu
         305                 310                 315                 320

Phe Gln Pro Val Tyr Lys Glu Leu Lys Asn Leu Ile Pro Lys Ser Ala
                         325                 330                 335

Val Gly Thr Leu Ser Ala Asn Ser Ser Asn Val Ile Gln Leu Ile Ile
                         340                 345                 350

Asp Ala Tyr Asn Ser Leu Ser Ser Glu Val Ile Leu Glu Asn Gly Lys
                         355                 360                 365

Leu Ser Glu Gly Val Thr Ile Ser Tyr Lys Ser Tyr Cys Lys Asn Gly
                         370                 375                 380

Val Asn Gly Thr Gly Glu Asn Gly Arg Lys Cys Ser Asn Ile Ser Ile
         385                 390                 395                 400

Gly Asp Glu Val Gln Phe Glu Ile Ser Ile Thr Ser Asn Lys Cys Pro
                         405                 410                 415

Lys Lys Asp Ser Asp Ser Phe Lys Ile Arg Pro Leu Gly Phe Thr Glu
                         420                 425                 430
```

```
Glu Val Glu Val Ile Leu Gln Tyr Ile Cys Glu Cys Glu Cys Gln Ser
            435                 440                 445

Glu Gly Ile Pro Glu Ser Pro Lys Cys His Glu Gly Asn Gly Thr Phe
    450                 455                 460

Glu Cys Gly Ala Cys Arg Cys Asn Glu Gly Arg Val Gly Arg His Cys
465                 470                 475                 480

Glu Cys Ser Thr Asp Glu Val Asn Ser Glu Asp Met Asp Ala Tyr Cys
            485                 490                 495

Arg Lys Glu Asn Ser Ser Glu Ile Cys Ser Asn Asn Gly Glu Cys Val
            500                 505                 510

Cys Gly Gln Cys Val Cys Arg Lys Arg Asp Asn Thr Asn Glu Ile Tyr
            515                 520                 525

Ser Gly Lys Phe Cys Glu Cys Asp Asn Phe Asn Cys Asp Arg Ser Asn
            530                 535                 540

Gly Leu Ile Cys Gly Gly Asn Gly Val Cys Lys Cys Arg Val Cys Glu
545                 550                 555                 560

Cys Asn Pro Asn Tyr Thr Gly Ser Ala Cys Asp Cys Ser Leu Asp Thr
                565                 570                 575

Ser Thr Cys Glu Ala Ser Asn Gly Gln Ile Cys Asn Gly Arg Gly Ile
            580                 585                 590

Cys Glu Cys Gly Val Cys Lys Cys Thr Asp Pro Lys Phe Gln Gly Gln
            595                 600                 605

Thr Cys Glu Met Cys Gln Thr Cys Leu Gly Val Cys Ala Glu His Lys
            610                 615                 620

Glu Cys Val Gln Cys Arg Ala Phe Asn Lys Gly Glu Lys Lys Asp Thr
625                 630                 635                 640

Cys Thr Gln Glu Cys Ser Tyr Phe Asn Ile Thr Lys Val Glu Ser Arg
                645                 650                 655

Asp Lys Leu Pro Gln Pro Val Gln Pro Asp Pro Val Ser His Cys Lys
            660                 665                 670

Glu Lys Asp Val Asp Asp Cys Trp Phe Tyr Phe Thr Tyr Ser Val Asn
            675                 680                 685

Gly Asn Asn Glu Val Met Val His Val Val Glu Asn Pro Glu Cys Pro
    690                 695                 700

Thr Gly Pro Asp
705

<210> SEQ ID NO 66
<211> LENGTH: 286
<212> TYPE: PRT
<213> ORGANISM: Artificial Sequence
<220> FEATURE:
<223> OTHER INFORMATION: mesothelin (ec domain)

<400> SEQUENCE: 66

Glu Val Glu Lys Thr Ala Cys Pro Ser Gly Lys Lys Ala Arg Glu Ile
1               5                   10                  15

Asp Glu Ser Leu Ile Phe Tyr Lys Lys Trp Glu Leu Glu Ala Cys Val
            20                  25                  30

Asp Ala Ala Leu Leu Ala Thr Gln Met Asp Arg Val Asn Ala Ile Pro
        35                  40                  45

Phe Thr Tyr Glu Gln Leu Asp Val Leu Lys His Lys Leu Asp Glu Leu
    50                  55                  60

Tyr Pro Gln Gly Tyr Pro Glu Ser Val Ile Gln His Leu Gly Tyr Leu
65                  70                  75                  80
```

Phe Leu Lys Met Ser Pro Glu Asp Ile Arg Lys Trp Asn Val Thr Ser
                85                  90                  95

Leu Glu Thr Leu Lys Ala Leu Leu Glu Val Asn Lys Gly His Glu Met
            100                 105                 110

Ser Pro Gln Ala Pro Arg Arg Pro Leu Pro Gln Val Ala Thr Leu Ile
        115                 120                 125

Asp Arg Phe Val Lys Gly Arg Gly Gln Leu Asp Lys Asp Thr Leu Asp
    130                 135                 140

Thr Leu Thr Ala Phe Tyr Pro Gly Tyr Leu Cys Ser Leu Ser Pro Glu
145                 150                 155                 160

Glu Leu Ser Ser Val Pro Pro Ser Ser Ile Trp Ala Val Arg Pro Gln
                165                 170                 175

Asp Leu Asp Thr Cys Asp Pro Arg Gln Leu Asp Val Leu Tyr Pro Lys
            180                 185                 190

Ala Arg Leu Ala Phe Gln Asn Met Asn Gly Ser Glu Tyr Phe Val Lys
        195                 200                 205

Ile Gln Ser Phe Leu Gly Gly Ala Pro Thr Glu Asp Leu Lys Ala Leu
    210                 215                 220

Ser Gln Gln Asn Val Ser Met Asp Leu Ala Thr Phe Met Lys Leu Arg
225                 230                 235                 240

Thr Asp Ala Val Leu Pro Leu Thr Val Ala Glu Val Gln Lys Leu Leu
                245                 250                 255

Gly Pro His Val Glu Gly Leu Lys Ala Glu Glu Arg His Arg Pro Val
            260                 265                 270

Arg Asp Trp Ile Leu Arg Gln Arg Gln Asp Asp Leu Asp Thr
        275                 280                 285

<210> SEQ ID NO 67
<211> LENGTH: 195
<212> TYPE: PRT
<213> ORGANISM: Artificial Sequence
<220> FEATURE:
<223> OTHER INFORMATION: IGF1R ec domain

<400> SEQUENCE: 67

Asp Val Met Gln Val Ala Asn Thr Thr Met Ser Ser Arg Ser Arg Asn
1               5                   10                  15

Thr Thr Ala Ala Asp Thr Tyr Asn Ile Thr Asp Pro Glu Glu Leu Glu
            20                  25                  30

Thr Glu Tyr Pro Phe Phe Glu Ser Arg Val Asp Asn Lys Glu Arg Thr
        35                  40                  45

Val Ile Ser Asn Leu Arg Pro Phe Thr Leu Tyr Arg Ile Asp Ile His
    50                  55                  60

Ser Cys Asn His Glu Ala Glu Lys Leu Gly Cys Ser Ala Ser Asn Phe
65                  70                  75                  80

Val Phe Ala Arg Thr Met Pro Ala Glu Gly Ala Asp Asp Ile Pro Gly
                85                  90                  95

Pro Val Thr Trp Glu Pro Arg Pro Glu Asn Ser Ile Phe Leu Lys Trp
            100                 105                 110

Pro Glu Pro Glu Asn Pro Asn Gly Leu Ile Leu Met Tyr Glu Ile Lys
        115                 120                 125

Tyr Gly Ser Gln Val Glu Asp Gln Arg Glu Cys Val Ser Arg Gln Glu
    130                 135                 140

Tyr Arg Lys Tyr Gly Gly Ala Lys Leu Asn Arg Leu Asn Pro Gly Asn
145                 150                 155                 160

```
Tyr Thr Ala Arg Ile Gln Ala Thr Ser Leu Ser Gly Asn Gly Ser Trp
                165                 170                 175

Thr Asp Pro Val Phe Phe Tyr Val Gln Ala Lys Thr Gly Tyr Glu Asn
            180                 185                 190

Phe Ile His
        195

<210> SEQ ID NO 68
<211> LENGTH: 358
<212> TYPE: PRT
<213> ORGANISM: Artificial Sequence
<220> FEATURE:
<223> OTHER INFORMATION: CTLA4-IG

<400> SEQUENCE: 68

Ala Met His Val Ala Gln Pro Ala Val Val Leu Ala Ser Ser Arg Gly
  1               5                  10                  15

Ile Ala Ser Phe Val Cys Glu Tyr Ala Ser Pro Gly Lys Ala Thr Glu
             20                  25                  30

Val Arg Val Thr Val Leu Arg Gln Ala Asp Ser Gln Val Thr Glu Val
         35                  40                  45

Cys Ala Ala Thr Tyr Met Met Gly Asn Glu Leu Thr Phe Leu Asp Asp
 50                  55                  60

Ser Ile Cys Thr Gly Thr Ser Ser Gly Asn Gln Val Asn Leu Thr Ile
 65                  70                  75                  80

Gln Gly Leu Arg Ala Met Asp Thr Gly Leu Tyr Ile Cys Lys Val Glu
                 85                  90                  95

Leu Met Tyr Pro Pro Pro Tyr Tyr Leu Gly Ile Gly Asn Gly Thr Gln
            100                 105                 110

Ile Tyr Val Ile Asp Pro Glu Pro Cys Pro Asp Ser Asp Gln Glu Pro
        115                 120                 125

Lys Ser Ser Asp Lys Thr His Thr Ser Pro Pro Ser Pro Ala Pro Glu
130                 135                 140

Leu Leu Gly Gly Ser Ser Val Phe Leu Phe Pro Pro Lys Pro Lys Asp
145                 150                 155                 160

Thr Leu Met Ile Ser Arg Thr Pro Glu Val Thr Cys Val Val Val Asp
                165                 170                 175

Val Ser His Glu Asp Pro Glu Val Lys Phe Asn Trp Tyr Val Asp Gly
            180                 185                 190

Val Glu Val His Asn Ala Lys Thr Lys Pro Arg Glu Glu Gln Tyr Asn
        195                 200                 205

Ser Thr Tyr Arg Val Val Ser Val Leu Thr Val Leu His Gln Asp Trp
    210                 215                 220

Leu Asn Gly Lys Glu Tyr Lys Cys Lys Val Ser Asn Lys Ala Leu Pro
225                 230                 235                 240

Ala Pro Ile Glu Lys Thr Ile Ser Lys Ala Lys Gly Gln Pro Arg Glu
                245                 250                 255

Pro Gln Val Tyr Thr Leu Pro Pro Ser Arg Asp Glu Leu Thr Lys Asn
            260                 265                 270

Gln Val Ser Leu Thr Cys Leu Val Lys Gly Phe Tyr Pro Ser Asp Ile
        275                 280                 285

Ala Val Glu Trp Glu Ser Asn Gly Gln Pro Glu Asn Asn Tyr Lys Thr
    290                 295                 300

Thr Pro Pro Val Leu Asp Ser Asp Gly Ser Phe Phe Leu Tyr Ser Lys
305                 310                 315                 320
```

```
Leu Thr Val Asp Lys Ser Arg Trp Gln Gln Gly Asn Val Phe Ser Cys
            325                 330                 335

Ser Val Met His Glu Ala Leu His Asn His Tyr Thr Gln Lys Ser Leu
        340                 345                 350

Ser Leu Ser Pro Gly Lys
        355

<210> SEQ ID NO 69
<211> LENGTH: 358
<212> TYPE: PRT
<213> ORGANISM: Artificial Sequence
<220> FEATURE:
<223> OTHER INFORMATION: L104EA29YIg

<400> SEQUENCE: 69

Ala Met His Val Ala Gln Pro Ala Val Val Leu Ala Ser Ser Arg Gly
 1               5                  10                  15

Ile Ala Ser Phe Val Cys Glu Tyr Ala Ser Pro Gly Lys Tyr Thr Glu
            20                  25                  30

Val Arg Val Thr Val Leu Arg Gln Ala Asp Ser Gln Val Thr Glu Val
        35                  40                  45

Cys Ala Ala Thr Tyr Met Met Gly Asn Glu Leu Thr Phe Leu Asp Asp
    50                  55                  60

Ser Ile Cys Thr Gly Thr Ser Ser Gly Asn Gln Val Asn Leu Thr Ile
65                  70                  75                  80

Gln Gly Leu Arg Ala Met Asp Thr Gly Leu Tyr Ile Cys Lys Val Glu
                85                  90                  95

Leu Met Tyr Pro Pro Pro Tyr Tyr Glu Gly Ile Gly Asn Gly Thr Gln
            100                 105                 110

Ile Tyr Val Ile Asp Pro Glu Pro Cys Pro Asp Ser Asp Gln Glu Pro
        115                 120                 125

Lys Ser Ser Asp Lys Thr His Thr Ser Pro Pro Ser Pro Ala Pro Glu
    130                 135                 140

Leu Leu Gly Gly Ser Ser Val Phe Leu Phe Pro Pro Lys Pro Lys Asp
145                 150                 155                 160

Thr Leu Met Ile Ser Arg Thr Pro Glu Val Thr Cys Val Val Val Asp
                165                 170                 175

Val Ser His Glu Asp Pro Glu Val Lys Phe Asn Trp Tyr Val Asp Gly
            180                 185                 190

Val Glu Val His Asn Ala Lys Thr Lys Pro Arg Glu Glu Gln Tyr Asn
        195                 200                 205

Ser Thr Tyr Arg Val Val Ser Val Leu Thr Val Leu His Gln Asp Trp
    210                 215                 220

Leu Asn Gly Lys Glu Tyr Lys Cys Lys Val Ser Asn Lys Ala Leu Pro
225                 230                 235                 240

Ala Pro Ile Glu Lys Thr Ile Ser Lys Ala Lys Gly Gln Pro Arg Glu
                245                 250                 255

Pro Gln Val Tyr Thr Leu Pro Pro Ser Arg Asp Glu Leu Thr Lys Asn
            260                 265                 270

Gln Val Ser Leu Thr Cys Leu Val Lys Gly Phe Tyr Pro Ser Asp Ile
        275                 280                 285

Ala Val Glu Trp Glu Ser Asn Gly Gln Pro Glu Asn Asn Tyr Lys Thr
    290                 295                 300

Thr Pro Pro Val Leu Asp Ser Asp Gly Ser Phe Phe Leu Tyr Ser Lys
305                 310                 315                 320
```

```
Leu Thr Val Asp Lys Ser Arg Trp Gln Gln Gly Asn Val Phe Ser Cys
                325                 330                 335

Ser Val Met His Glu Ala Leu His Asn His Tyr Thr Gln Lys Ser Leu
            340                 345                 350

Ser Leu Ser Pro Gly Lys
        355

<210> SEQ ID NO 70
<211> LENGTH: 10
<212> TYPE: PRT
<213> ORGANISM: Artificial Sequence
<220> FEATURE:
<223> OTHER INFORMATION: (Gly4Ser)2 Linker

<400> SEQUENCE: 70

Gly Gly Gly Gly Ser Gly Gly Gly Gly Ser
1               5                   10

<210> SEQ ID NO 71
<211> LENGTH: 15
<212> TYPE: PRT
<213> ORGANISM: Artificial Sequence
<220> FEATURE:
<223> OTHER INFORMATION: (Gly4Ser)3 Linker

<400> SEQUENCE: 71

Gly Gly Gly Gly Ser Gly Gly Gly Gly Ser Gly Gly Gly Gly Ser
1               5                   10                  15

<210> SEQ ID NO 72
<211> LENGTH: 20
<212> TYPE: PRT
<213> ORGANISM: Artificial Sequence
<220> FEATURE:
<223> OTHER INFORMATION: (Gly4Ser)4 Linker

<400> SEQUENCE: 72

Gly Gly Gly Gly Ser Gly Gly Gly Gly Ser Gly Gly Gly Gly Ser Gly
1               5                   10                  15

Gly Gly Gly Ser
            20

<210> SEQ ID NO 73
<211> LENGTH: 25
<212> TYPE: PRT
<213> ORGANISM: Artificial Sequence
<220> FEATURE:
<223> OTHER INFORMATION: (Gly4Ser)5 Linker

<400> SEQUENCE: 73

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 74
<211> LENGTH: 451
<212> TYPE: PRT
<213> ORGANISM: Artificial Sequence
<220> FEATURE:
<223> OTHER INFORMATION: Trastuzumab HC

<400> SEQUENCE: 74

Glu Val Gln Leu Val Glu Ser Gly Gly Gly Leu Val Gln Pro Gly Gly
```

-continued

```
  1               5                  10                  15
Ser Leu Arg Leu Ser Cys Ala Ala Ser Gly Phe Asn Ile Lys Asp Thr
             20                  25                  30

Tyr Ile His Trp Val Arg Gln Ala Pro Gly Lys Gly Leu Glu Trp Val
             35                  40                  45

Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
             85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430
```

```
His Glu Ala Leu His Asn His Tyr Thr Gln Lys Ser Leu Ser Leu Ser
        435                 440                 445

Pro Gly Lys
    450

<210> SEQ ID NO 75
<211> LENGTH: 214
<212> TYPE: PRT
<213> ORGANISM: Artificial Sequence
<220> FEATURE:
<223> OTHER INFORMATION: Trastuzumab LC

<400> SEQUENCE: 75

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Val Asn Thr Ala
             20                  25                  30

Val Ala Trp Tyr Gln Gln Lys Pro Gly Lys Ala Pro Lys Leu Leu Ile
         35                  40                  45

Tyr Ser Ala Ser Phe Leu Tyr Ser Gly Val Pro Ser Arg Phe Ser Gly
     50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 76
<211> LENGTH: 451
<212> TYPE: PRT
<213> ORGANISM: Artificial Sequence
<220> FEATURE:
<223> OTHER INFORMATION: Rituximab HC

<400> SEQUENCE: 76

Gln Val Gln Leu Gln Gln Pro Gly Ala Glu Leu Val Lys Pro Gly Ala
  1               5                  10                  15

Ser Val Lys Met Ser Cys Lys Ala Ser Gly Tyr Thr Phe Thr Ser Tyr
             20                  25                  30

Asn Met His Trp Val Lys Gln Thr Pro Gly Arg Gly Leu Glu Trp Ile
         35                  40                  45

Gly Ala Ile Tyr Pro Gly Asn Gly Asp Thr Ser Tyr Asn Gln Lys Phe
```

```
                50                  55                  60
Lys Gly Lys Ala Thr Leu Thr Ala Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Ser Thr Tyr Tyr Gly Gly Asp Trp Tyr Phe Asn Val Trp Gly
             100                 105                 110

Ala Gly Thr Thr Val Thr Val Ser Ala Ala Ser Thr Lys Gly Pro Ser
         115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 77
```

<211> LENGTH: 213
<212> TYPE: PRT
<213> ORGANISM: Artificial Sequence
<220> FEATURE:
<223> OTHER INFORMATION: Rituximab LC

<400> SEQUENCE: 77

```
Gln Ile Val Leu Ser Gln Ser Pro Ala Ile Leu Ser Ala Ser Pro Gly
  1               5                  10                  15

Glu Lys Val Thr Met Thr Cys Arg Ala Ser Ser Val Ser Tyr Ile
             20                  25                  30

His Trp Phe Gln Gln Lys Pro Gly Ser Ser Pro Lys Pro Trp Ile Tyr
             35                  40                  45

Ala Thr Ser Asn Leu Ala Ser Gly Val Pro Val Arg Phe Ser Gly Ser
 50                  55                  60

Gly Ser Gly Thr Ser Tyr Ser Leu Thr Ile Ser Arg Val Glu Ala Glu
 65                  70                  75                  80

Asp Ala Ala Thr Tyr Tyr Cys Gln Gln Trp Thr Ser Asn Pro Pro Thr
                 85                  90                  95

Phe Gly Gly Gly Thr Lys Leu Glu Ile Lys Arg Thr Val Ala Ala Pro
             100                 105                 110

Ser Val Phe Ile Phe Pro Pro Ser Asp Glu Gln Leu Lys Ser Gly Thr
             115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
                195                 200                 205

Asn Arg Gly Glu Cys
        210
```

<210> SEQ ID NO 78
<211> LENGTH: 453
<212> TYPE: PRT
<213> ORGANISM: Artificial Sequence
<220> FEATURE:
<223> OTHER INFORMATION: Bevacizumab HC

<400> SEQUENCE: 78

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Tyr Thr Phe Thr Asn Tyr
             20                  25                  30

Gly Met Asn Trp Val Arg Gln Ala Pro Gly Lys Gly Leu Glu Trp Val
             35                  40                  45

Gly Trp Ile Asn Thr Tyr Thr Gly Glu Pro Tyr Ala Ala Asp Phe
 50                  55                  60

Lys Arg Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ala Lys Tyr Pro His Tyr Tyr Gly Ser Ser His Trp Tyr Phe Asp Val
```

```
            100                 105                 110
Trp Gly Gln Gly Thr Leu Val Thr Val Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 79
<211> LENGTH: 214
<212> TYPE: PRT
<213> ORGANISM: Artificial Sequence
<220> FEATURE:
<223> OTHER INFORMATION: Bevacizumab LC

<400> SEQUENCE: 79

Asp Ile Gln Met Thr Gln Ser Pro Ser Ser Leu Ser Ala Ser Val Gly
```

```
                1               5                  10                 15
Asp Arg Val Thr Ile Thr Cys Ser Ala Ser Gln Asp Ile Ser Asn Tyr
                        20                  25                 30
Leu Asn Trp Tyr Gln Gln Lys Pro Gly Lys Ala Pro Lys Val Leu Ile
                        35                  40                 45
Tyr Phe Thr Ser Ser Leu His Ser Gly Val Pro Ser Arg Phe Ser Gly
                50                  55                  60
Ser Gly Ser Gly Thr Asp Phe Thr Leu Thr Ile Ser Ser Leu Gln Pro
 65                     70                  75                 80
Glu Asp Phe Ala Thr Tyr Tyr Cys Gln Gln Tyr Ser Thr Val Pro Trp
                        85                  90                 95
Thr Phe Gly Gln Gly Thr Lys Val Glu Ile Lys Arg Thr Val Ala Ala
                        100                 105                110
Pro Ser Val Phe Ile Phe Pro Pro Ser Asp Glu Gln Leu Lys Ser Gly
                        115                 120                125
Thr Ala Ser Val Val Cys Leu Leu Asn Asn Phe Tyr Pro Arg Glu Ala
                130                 135                 140
Lys Val Gln Trp Lys Val Asp Asn Ala Leu Gln Ser Gly Asn Ser Gln
145                     150                 155                160
Glu Ser Val Thr Glu Gln Asp Ser Lys Asp Ser Thr Tyr Ser Leu Ser
                        165                 170                175
Ser Thr Leu Thr Leu Ser Lys Ala Asp Tyr Glu Lys His Lys Val Tyr
                180                 185                 190
Ala Cys Glu Val Thr His Gln Gly Leu Ser Ser Pro Val Thr Lys Ser
                        195                 200                205
Phe Asn Arg Gly Glu Cys
                210

<210> SEQ ID NO 80
<211> LENGTH: 451
<212> TYPE: PRT
<213> ORGANISM: Artificial Sequence
<220> FEATURE:
<223> OTHER INFORMATION: Alemtuzumab HC

<400> SEQUENCE: 80

Gln Val Gln Leu Gln Glu Ser Gly Pro Gly Leu Val Arg Pro Ser Gln
 1               5                  10                 15
Thr Leu Ser Leu Thr Cys Thr Val Ser Gly Phe Thr Phe Thr Asp Phe
                        20                  25                 30
Tyr Met Asn Trp Val Arg Gln Pro Pro Gly Arg Gly Leu Glu Trp Ile
                        35                  40                 45
Gly Phe Ile Arg Asp Lys Ala Lys Gly Tyr Thr Thr Glu Tyr Asn Pro
                50                  55                  60
Ser Val Lys Gly Arg Val Thr Met Leu Val Asp Thr Ser Lys Asn Gln
 65                     70                  75                 80
Phe Ser Leu Arg Leu Ser Ser Val Thr Ala Ala Asp Thr Ala Val Tyr
                        85                  90                 95
Tyr Cys Ala Arg Glu Gly His Thr Ala Ala Pro Phe Asp Tyr Trp Gly
                        100                 105                110
Gln Gly Ser Leu Val Thr Val Ser Ser Ala Ser Thr Lys Gly Pro Ser
                        115                 120                125
Val Phe Pro Leu Ala Pro Ser Ser Lys Ser Thr Ser Gly Gly Thr Ala
                130                 135                 140

Ala Leu Gly Cys Leu Val Lys Asp Tyr Phe Pro Glu Pro Val Thr Val
```

```
                145                 150                 155                 160
Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Leu Gly Thr Gln Thr Tyr Ile Cys Asn Val Asn His
                195                 200                 205

Lys Pro Ser Asn Thr Lys Val Asp Lys Lys Val Glu Pro Lys Ser Cys
                210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Asn Ser Thr Tyr
                290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
                355                 360                 365

Leu Thr Cys Leu Val Lys Gly Phe Tyr Pro Ser Asp Ile Ala Val Glu
                370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
    450

<210> SEQ ID NO 81
<211> LENGTH: 214
<212> TYPE: PRT
<213> ORGANISM: Artificial Sequence
<220> FEATURE:
<223> OTHER INFORMATION: Alemtuzumab LC

<400> SEQUENCE: 81

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asp Lys Tyr
                20                  25                  30

Leu Asn Trp Tyr Gln Gln Lys Pro Gly Lys Ala Pro Lys Leu Leu Ile
                35                  40                  45

Tyr Asn Thr Asn Asn Leu Gln Thr Gly Val Pro Ser Arg Phe Ser Gly
```

```
            50                  55                  60
Ser Gly Ser Gly Thr Asp Phe Thr Phe Thr Ile Ser Ser Leu Gln Pro
 65                  70                  75                  80

Glu Asp Ile Ala Thr Tyr Tyr Cys Leu Gln His Ile Ser Arg Pro Arg
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 82
<211> LENGTH: 444
<212> TYPE: PRT
<213> ORGANISM: Artificial Sequence
<220> FEATURE:
<223> OTHER INFORMATION: Panitumumab HC

<400> SEQUENCE: 82

Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Val Ser Ser Gly
             20                  25                  30

Asp Tyr Tyr Trp Thr Trp Ile Arg Gln Ser Pro Gly Lys Gly Leu Glu
         35                  40                  45

Trp Ile Gly His Ile Tyr Tyr Ser Gly Asn Thr Asn Tyr Asn Pro Ser
 50                  55                  60

Leu Lys Ser Arg Leu Thr Ile Ser Ile Asp Thr Ser Lys Thr Gln Phe
 65                  70                  75                  80

Ser Leu Lys Leu Ser Ser Val Thr Ala Ala Asp Thr Ala Ile Tyr Tyr
                 85                  90                  95

Cys Val Arg Asp Arg Val Thr Gly Ala Phe Asp Ile Trp Gly Gln Gly
            100                 105                 110

Thr Met Val Thr Ser Ser Ala Ser Thr Lys Gly Pro Ser Val Phe Pro
            115                 120                 125

Leu Ala Pro Cys Ser Arg Ser Thr Ser Glu Ser Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
```

-continued

```
                195                 200                 205
Asn Thr Lys Val Asp Lys Thr Val Glu Arg Lys Cys Cys Val Glu Cys
210                 215                 220

Pro Pro Cys Pro Ala Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
                260                 265                 270

Asn Trp Tyr Val Asp Gly Val Glu Val His Asn Ala Lys Thr Lys Pro
                275                 280                 285

Arg Glu Glu Gln Phe Asn Ser Thr Phe Arg Val Val Ser Val Leu Thr
290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
                325                 330                 335

Lys Gly Gln Pro Arg Glu Pro Gln Val Tyr Thr Leu Pro Pro Ser Arg
                340                 345                 350

Glu Glu Met Thr Lys Asn Gln Val Ser Leu Thr Cys Leu Val Lys Gly
                355                 360                 365

Phe Tyr Pro Ser Asp Ile Ser Val Glu Trp Glu Ser Asn Gly Gln Pro
370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
                420                 425                 430

Tyr Thr Gln Lys Ser Leu Ser Leu Ser Pro Gly Lys
                435                 440

<210> SEQ ID NO 83
<211> LENGTH: 214
<212> TYPE: PRT
<213> ORGANISM: Artificial Sequence
<220> FEATURE:
<223> OTHER INFORMATION: Panitumumab LC

<400> SEQUENCE: 83

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Phe Asp His Leu Pro Leu
                85                  90                  95

Ala Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
```

```
                    115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
            195                 200                 205
Phe Asn Arg Gly Glu Cys
    210

<210> SEQ ID NO 84
<211> LENGTH: 218
<212> TYPE: PRT
<213> ORGANISM: Artificial Sequence
<220> FEATURE:
<223> OTHER INFORMATION: Ranibizumab HC

<400> SEQUENCE: 84

Glu Val Gln Leu Val Glu Ser Gly Gly Gly Leu Val Gln Pro Gly Gly
1               5                   10                  15
Ser Leu Arg Leu Ser Cys Ala Ala Ser Gly Tyr Asp Phe Thr His Tyr
            20                  25                  30
Gly Met Asn Trp Val Arg Gln Ala Pro Gly Lys Gly Leu Glu Trp Val
        35                  40                  45
Gly Trp Ile Asn Thr Tyr Thr Gly Glu Pro Thr Tyr Ala Ala Asp Phe
    50                  55                  60
Lys Arg Arg Phe Thr Phe Ser Leu Asp Thr Ser Lys Ser Thr Ala Tyr
65                  70                  75                  80
Leu Gln Met Asn Ser Leu Arg Ala Glu Asp Thr Ala Val Tyr Tyr Cys
                85                  90                  95
Ala Lys Tyr Pro Tyr Tyr Tyr Gly Thr Ser His Trp Tyr Phe Asp Val
            100                 105                 110
Trp Gly Gln Gly Thr Leu Val Thr Val Ser Ser Ala Ser Thr Lys Gly
        115                 120                 125
Pro Ser Val Phe Pro Leu Ala Pro Ser Gly Thr Ala Ala Leu Gly Cys
    130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
        195                 200                 205
Thr Lys Val Asp Lys Lys Val Glu Pro Lys
    210                 215

<210> SEQ ID NO 85
<211> LENGTH: 213
<212> TYPE: PRT
<213> ORGANISM: Artificial Sequence
<220> FEATURE:
<223> OTHER INFORMATION: Ranibizumab LC
```

```
<400> SEQUENCE: 85

Asp Ile Gln Leu Thr Gln Ser Pro Ser Ser Leu Ser Ala Ser Val Gly
 1               5                  10                  15

Asp Arg Val Thr Ile Thr Cys Ser Ala Ser Gln Asp Ile Ser Asn Tyr
             20                  25                  30

Leu Asn Trp Tyr Gln Gln Lys Pro Gly Lys Ala Pro Lys Val Leu Ile
         35                  40                  45

Tyr Phe Thr Ser Ser Leu His Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Thr Val Pro Trp
                 85                  90                  95

Thr Phe Gly Gln Gly Thr Lys Val Glu Ile Lys Arg Thr Val Ala Ala
             100                 105                 110

Pro Ser Val Phe Ile Phe Pro Pro Ser Asp Glu Gln Leu Lys Ser Gly
             115                 120                 125

Thr Ala Ser Val Val Cys Leu Leu Asn Asn Phe Tyr Pro Arg Glu Ala
         130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                 165                 170                 175

Ser Thr Leu Thr Leu Ser Lys Ala Asp Tyr Glu Lys His Lys Val Tyr
             180                 185                 190

Ala Cys Glu Val Thr His Gln Gly Leu Ser Ser Pro Val Thr Lys Ser
         195                 200                 205

Phe Asn Arg Gly Glu
210
```